(12) United States Patent
Sverdlik et al.

(10) Patent No.: US 10,933,259 B2
(45) Date of Patent: Mar. 2, 2021

(54) DEVICES AND METHODS FOR RENAL DENERVATION AND ASSESSMENT THEREOF

(71) Applicant: CardioSonic Ltd., Tel-Aviv (IL)

(72) Inventors: Ariel Sverdlik, Tel-Aviv (IL); Or Shabtay, Kibbutz Farod (IL); Ronen Neeman, Givataim (IL); Giora Beit-Yaakov, Jerusalem (IL); Lilah Marziano, Ganei-Tikva (IL); Avital Schauder, Lod (IL); Marina Dubinsky, Herzlia (IL); Yehuda Zadok, Holon (IL); Jonathan Yalom, Gedera (IL)

(73) Assignee: CardioSonic Ltd., Tel-Aviv (IL)

( * ) Notice: Subject to any disclaimer, the term of this patent is extended or adjusted under 35 U.S.C. 154(b) by 877 days.

(21) Appl. No.: 14/889,890

(22) PCT Filed: May 22, 2014

(86) PCT No.: PCT/IL2014/050457
§ 371 (c)(1),
(2) Date: Nov. 9, 2015

(87) PCT Pub. No.: WO2014/188430
PCT Pub. Date: Nov. 27, 2014

(65) Prior Publication Data
US 2016/0113699 A1    Apr. 28, 2016

Related U.S. Application Data

(60) Provisional application No. 61/931,890, filed on Jan. 27, 2014, provisional application No. 61/931,838, (Continued)

(51) Int. Cl.
*A61B 18/04*    (2006.01)
*A61N 7/00*    (2006.01)
(Continued)

(52) U.S. Cl.
CPC .............. *A61N 7/022* (2013.01); *A61B 18/04* (2013.01); *A61B 18/1492* (2013.01); *A61N 7/00* (2013.01);
(Continued)

(58) Field of Classification Search
CPC ....................................................... A61N 7/02
See application file for complete search history.

(56) References Cited

U.S. PATENT DOCUMENTS

| 4,319,580 A | 3/1982 | Colley et al. |
| 5,038,789 A | 8/1991 | Frazin |

(Continued)

FOREIGN PATENT DOCUMENTS

| CN | 1279595 | 1/2001 |
| CN | 101610735 | 12/2009 |

(Continued)

OTHER PUBLICATIONS

Advisory Action Before the Filing of an Appeal Brief dated Feb. 4, 2019 From the US Patent and Trademark Office Re. U.S. Appl. No. 14/190,113. (6 pages).

(Continued)

*Primary Examiner* — Ronald Hupczey, Jr.

(57) ABSTRACT

The present invention, in some embodiments thereof, relates to a devices and methods for intravascular denervation and assessment thereof and, more particularly, but not exclusively, to devices and methods for renal denervation. Some embodiments of the invention relate to an intravascular catheter configured for ultrasonic ablation of the tissue, comprising a plurality of piezoelectric transceivers. In some embodiments, an intravascular distancing device is provided, the device adapted for obtaining at least a minimal distance between an ultrasound emitting element and a tissue, such as the blood vessel wall. Some embodiments of (Continued)

the invention relate to assessment of renal sympathetic denervation (RSD) treatment effectiveness. Some embodiments of the invention relate to processing echo of signals, such as processing of signals to characterize physical and/or mechanical properties of the blood vessel.

28 Claims, 119 Drawing Sheets
(72 of 119 Drawing Sheet(s) Filed in Color)

Related U.S. Application Data filed on Jan. 27, 2014, provisional application No. 61/924,848, filed on Jan. 8, 2014, provisional application No. 61/924,778, filed on Jan. 8, 2014, provisional application No. 61/826,583, filed on May 23, 2013.

(51) Int. Cl.
| | | |
|---|---|---|
| *A61B 18/14* | (2006.01) | |
| *A61B 8/12* | (2006.01) | |
| *A61B 8/06* | (2006.01) | |
| *A61B 17/00* | (2006.01) | |
| *A61N 7/02* | (2006.01) | |
| *A61B 18/00* | (2006.01) | |

(52) U.S. Cl.
CPC . *A61B 8/06* (2013.01); *A61B 8/12* (2013.01); *A61B 2017/0011* (2013.01); *A61B 2017/00084* (2013.01); *A61B 2017/00106* (2013.01); *A61B 2017/00292* (2013.01); *A61B 2018/00011* (2013.01); *A61B 2018/0016* (2013.01); *A61B 2018/00178* (2013.01); *A61B 2018/00267* (2013.01); *A61B 2018/00279* (2013.01); *A61B 2018/00434* (2013.01); *A61B 2018/00511* (2013.01); *A61B 2018/00577* (2013.01); *A61N 2007/003* (2013.01); *A61N 2007/0043* (2013.01)

(56) References Cited

U.S. PATENT DOCUMENTS

| | | | |
|---|---|---|---|
| 5,226,847 | A | 7/1993 | Thomas, III et al. |
| 5,421,338 | A | 6/1995 | Crowley et al. |
| 5,467,251 | A | 11/1995 | Katchmar |
| 5,471,988 | A | 12/1995 | Fujio et al. |
| 5,524,630 | A | 6/1996 | Crowley |
| 5,590,653 | A | 1/1997 | Aida et al. |
| 5,620,417 | A | 4/1997 | Jang et al. |
| 5,620,479 | A * | 4/1997 | Diederich .............. A61B 18/18 601/3 |
| 5,657,760 | A | 8/1997 | Ying et al. |
| 5,699,804 | A | 12/1997 | Rattner |
| 5,707,367 | A | 1/1998 | Nilsson |
| 5,735,280 | A | 4/1998 | Sherman et al. |
| 5,762,066 | A | 6/1998 | Law et al. |
| 5,772,642 | A | 6/1998 | Ciamacco, Jr. et al. |
| 5,895,355 | A | 4/1999 | Schaer |
| 5,895,356 | A | 4/1999 | Andrus et al. |
| 5,971,949 | A | 10/1999 | Levin et al. |
| 6,007,499 | A | 12/1999 | Martin et al. |
| 6,042,556 | A | 3/2000 | Beach et al. |
| 6,073,048 | A | 6/2000 | Kieval et al. |
| 6,077,225 | A | 6/2000 | Brock-Fisher |
| 6,117,101 | A | 9/2000 | Diederich et al. |
| 6,119,041 | A | 9/2000 | Pomeranz et al. |
| 6,165,127 | A | 12/2000 | Crowley |
| 6,210,393 | B1 | 4/2001 | Brisken |
| 6,216,041 | B1 | 4/2001 | Tierney et al. |
| 6,235,024 | B1 | 5/2001 | Tu |
| 6,261,233 | B1 | 7/2001 | Kantorovich |
| 6,296,619 | B1 | 10/2001 | Brisken et al. |
| 6,379,320 | B1 | 4/2002 | Lafon et al. |
| 6,428,477 | B1 | 8/2002 | Mason |
| 6,451,013 | B1 | 9/2002 | Bays et al. |
| 6,500,121 | B1 | 12/2002 | Slayton et al. |
| 6,511,428 | B1 | 1/2003 | Azuma et al. |
| 6,511,436 | B1 | 1/2003 | Asmar |
| 6,514,249 | B1 * | 2/2003 | Maguire ................ A61B 18/00 606/37 |
| 6,524,271 | B2 * | 2/2003 | Brisken .............. A61B 17/2202 600/466 |
| 6,527,759 | B1 | 3/2003 | Tachibana et al. |
| 6,547,788 | B1 | 4/2003 | Maguire et al. |
| 6,599,288 | B2 | 7/2003 | Maguire et al. |
| 6,607,502 | B1 | 8/2003 | Maguire et al. |
| 6,645,147 | B1 | 11/2003 | Jackson et al. |
| 6,740,040 | B1 | 5/2004 | Mandrusov et al. |
| 6,752,805 | B2 | 6/2004 | Maguire et al. |
| 6,953,460 | B2 | 10/2005 | Maguire et al. |
| 6,955,173 | B2 | 10/2005 | Lesh |
| 6,978,174 | B2 | 12/2005 | Gelfand et al. |
| 7,001,336 | B2 | 2/2006 | Mandrusov et al. |
| 7,037,271 | B2 | 5/2006 | Crowley |
| 7,084,004 | B2 | 8/2006 | Vaiyapuri et al. |
| 7,156,816 | B2 | 1/2007 | Schwartz et al. |
| 7,162,303 | B2 | 1/2007 | Levin et al. |
| 7,166,098 | B1 | 1/2007 | Steward et al. |
| 7,220,233 | B2 | 5/2007 | Nita et al. |
| 7,220,258 | B2 | 5/2007 | Myhr |
| 7,220,261 | B2 | 5/2007 | Truckai et al. |
| 7,285,116 | B2 | 10/2007 | De la Rama et al. |
| 7,326,201 | B2 | 2/2008 | Fjield et al. |
| 7,341,583 | B2 | 3/2008 | Shiono et al. |
| 7,344,529 | B2 | 3/2008 | Torchia et al. |
| 7,347,859 | B2 | 3/2008 | Garabedian et al. |
| 7,410,486 | B2 | 8/2008 | Fuimaono et al. |
| 7,460,369 | B1 | 12/2008 | Blish, II |
| 7,470,241 | B2 | 12/2008 | Weng et al. |
| 7,479,106 | B2 | 1/2009 | Banik et al. |
| 7,510,536 | B2 | 3/2009 | Foley et al. |
| 7,538,425 | B2 | 5/2009 | Myers et al. |
| RE40,815 | E | 6/2009 | Kudaravalli et al. |
| 7,540,846 | B2 | 6/2009 | Harhen et al. |
| 7,540,870 | B2 | 6/2009 | Babaev |
| 7,563,260 | B2 | 7/2009 | Whitmore et al. |
| 7,617,005 | B2 | 11/2009 | Demarais et al. |
| 7,620,451 | B2 | 11/2009 | Demarais et al. |
| 7,621,929 | B2 | 11/2009 | Nita et al. |
| 7,647,115 | B2 | 1/2010 | Levin et al. |
| 7,653,438 | B2 | 1/2010 | Deem et al. |
| 7,655,005 | B2 | 2/2010 | Bhola |
| 7,678,104 | B2 | 3/2010 | Keidar |
| 7,704,212 | B2 | 4/2010 | Wekell et al. |
| 7,713,210 | B2 | 5/2010 | Byrd et al. |
| 7,717,948 | B2 | 5/2010 | Demarais et al. |
| 7,727,228 | B2 | 6/2010 | Abboud et al. |
| 7,736,317 | B2 | 6/2010 | Stephens et al. |
| 7,756,583 | B2 | 7/2010 | Demarais et al. |
| 7,762,954 | B2 | 7/2010 | Nix et al. |
| 7,771,372 | B2 | 8/2010 | Wilson |
| 7,819,868 | B2 | 10/2010 | Cao et al. |
| 7,824,348 | B2 | 11/2010 | Barthe et al. |
| 7,850,683 | B2 | 12/2010 | Elkins et al. |
| 7,850,685 | B2 | 12/2010 | Kunis et al. |
| 7,853,333 | B2 | 12/2010 | Demarais |
| 7,854,733 | B2 | 12/2010 | Govari |
| 7,883,506 | B2 | 2/2011 | McIntyre et al. |
| 7,940,969 | B2 | 5/2011 | Nair et al. |
| 8,216,216 | B2 | 7/2012 | Warnking et al. |
| 8,221,402 | B2 | 7/2012 | Francischelli et al. |
| 8,401,667 | B2 | 3/2013 | Gustus et al. |
| 8,419,729 | B2 | 4/2013 | Ibrahim et al. |
| 8,540,662 | B2 | 9/2013 | Stehr et al. |
| 8,568,403 | B2 | 10/2013 | Soltesz et al. |
| 8,585,695 | B2 | 11/2013 | Shih |
| 8,974,446 | B2 | 3/2015 | Nguyen et al. |
| 2001/0007940 | A1 | 7/2001 | Tu et al. |
| 2001/0014780 | A1 | 8/2001 | Martin et al. |

(56) References Cited

U.S. PATENT DOCUMENTS

| | | |
|---|---|---|
| 2001/0053885 A1 | 12/2001 | Gielen et al. |
| 2002/0002371 A1 | 1/2002 | Acker et al. |
| 2002/0016624 A1 | 2/2002 | Patterson et al. |
| 2002/0019627 A1 | 2/2002 | Maguire et al. |
| 2002/0022833 A1 | 2/2002 | Maguire et al. |
| 2002/0026127 A1 | 2/2002 | Balbierz et al. |
| 2002/0048310 A1 | 4/2002 | Heuser |
| 2002/0055754 A1 | 5/2002 | Ranucci et al. |
| 2002/0065512 A1 | 5/2002 | Fjield et al. |
| 2002/0077643 A1 | 6/2002 | Rabiner et al. |
| 2002/0169394 A1 | 11/2002 | Eppstein et al. |
| 2002/0188218 A1 | 12/2002 | Lipman |
| 2003/0013968 A1 | 1/2003 | Fjield et al. |
| 2003/0092667 A1 | 5/2003 | Tachibana et al. |
| 2003/0125726 A1 | 7/2003 | Maguire et al. |
| 2003/0151417 A1 | 8/2003 | Koen |
| 2003/0163190 A1 | 8/2003 | LaFont et al. |
| 2003/0181901 A1 | 9/2003 | Maguire et al. |
| 2003/0195496 A1 | 10/2003 | Maguire et al. |
| 2003/0199747 A1 | 10/2003 | Michlitsch et al. |
| 2003/0199768 A1 | 10/2003 | Cespededs et al. |
| 2004/0006333 A1 | 1/2004 | Arnold et al. |
| 2004/0019687 A1 | 1/2004 | Ozawa et al. |
| 2004/0073660 A1 | 4/2004 | Toomey |
| 2004/0082859 A1* | 4/2004 | Schaer ............... A61B 8/4281 600/459 |
| 2004/0102361 A1 | 5/2004 | Bodin |
| 2004/0102769 A1 | 5/2004 | Schwartz et al. |
| 2005/0015079 A1 | 1/2005 | Keider |
| 2005/0020967 A1 | 1/2005 | Ono |
| 2005/0096542 A1 | 5/2005 | Weng et al. |
| 2005/0096647 A1 | 5/2005 | Steinke et al. |
| 2005/0215946 A1 | 9/2005 | Hansmann et al. |
| 2005/0240170 A1 | 10/2005 | Zhang et al. |
| 2005/0288730 A1 | 12/2005 | Deem et al. |
| 2006/0009753 A1 | 1/2006 | Fjield et al. |
| 2006/0052774 A1 | 3/2006 | Garrison et al. |
| 2006/0058711 A1 | 3/2006 | Harhen et al. |
| 2006/0079816 A1 | 4/2006 | Barthe et al. |
| 2006/0084966 A1 | 4/2006 | Maguire et al. |
| 2006/0173387 A1 | 8/2006 | Hansmann et al. |
| 2006/0229594 A1 | 10/2006 | Francischelli et al. |
| 2006/0241442 A1 | 10/2006 | Barthe et al. |
| 2006/0241739 A1 | 10/2006 | Besselink et al. |
| 2006/0264809 A1 | 11/2006 | Hansmann et al. |
| 2007/0043297 A1 | 2/2007 | Miyazawa |
| 2007/0088346 A1 | 4/2007 | Mirizzi et al. |
| 2007/0142831 A1 | 6/2007 | Shadduck |
| 2007/0142879 A1 | 6/2007 | Greenberg et al. |
| 2007/0167824 A1 | 7/2007 | Lee et al. |
| 2007/0203479 A1 | 8/2007 | Auth et al. |
| 2007/0222339 A1 | 9/2007 | Lukacs et al. |
| 2007/0225619 A1 | 9/2007 | Rabiner et al. |
| 2007/0233057 A1 | 10/2007 | Konishi |
| 2007/0249997 A1 | 10/2007 | Goodson, IV et al. |
| 2007/0282407 A1 | 12/2007 | Demarais et al. |
| 2008/0039745 A1 | 2/2008 | Babaev |
| 2008/0077202 A1 | 3/2008 | Levinson |
| 2008/0086073 A1 | 4/2008 | McDaniel |
| 2008/0114354 A1 | 5/2008 | Whayne et al. |
| 2008/0125829 A1 | 5/2008 | Velasco et al. |
| 2008/0139971 A1 | 6/2008 | Lockhart |
| 2008/0146924 A1 | 6/2008 | Smith et al. |
| 2008/0171934 A1 | 7/2008 | Greenan et al. |
| 2008/0179736 A1 | 7/2008 | Hartwell et al. |
| 2008/0183110 A1 | 7/2008 | Davenport et al. |
| 2008/0195000 A1 | 8/2008 | Spooner et al. |
| 2008/0214966 A1 | 9/2008 | Slayton et al. |
| 2008/0215039 A1 | 9/2008 | Slatkine et al. |
| 2008/0228111 A1 | 9/2008 | Nita |
| 2008/0249518 A1 | 10/2008 | Warnking et al. |
| 2008/0281297 A1 | 11/2008 | Pesach et al. |
| 2008/0300571 A1 | 12/2008 | LePivert |
| 2008/0300655 A1 | 12/2008 | Cholette |
| 2008/0312643 A1 | 12/2008 | Kania et al. |
| 2009/0018446 A1 | 1/2009 | Medan et al. |
| 2009/0036914 A1 | 2/2009 | Houser |
| 2009/0093737 A1 | 4/2009 | Chomas et al. |
| 2009/0131930 A1 | 5/2009 | Gelbart et al. |
| 2009/0149782 A1 | 6/2009 | Cohen et al. |
| 2009/0163807 A1 | 6/2009 | Sliwa |
| 2009/0216246 A1 | 8/2009 | Nita et al. |
| 2009/0221939 A1 | 9/2009 | Demarais et al. |
| 2009/0221955 A1 | 9/2009 | Babaev |
| 2009/0254078 A1 | 10/2009 | Just et al. |
| 2009/0281478 A1 | 11/2009 | Duke |
| 2009/0299360 A1 | 12/2009 | Ormsby |
| 2010/0036293 A1 | 2/2010 | Isola et al. |
| 2010/0081933 A1 | 4/2010 | Sverdlik et al. |
| 2010/0091112 A1 | 4/2010 | Veeser et al. |
| 2010/0114082 A1 | 5/2010 | Sharma |
| 2010/0125198 A1 | 5/2010 | Thapliyal et al. |
| 2010/0130892 A1 | 5/2010 | Warnking |
| 2010/0137860 A1 | 6/2010 | Demarais et al. |
| 2010/0152625 A1 | 6/2010 | Milo |
| 2010/0168624 A1 | 7/2010 | Sliwa |
| 2010/0168649 A1 | 7/2010 | Schwartz et al. |
| 2010/0191112 A1 | 7/2010 | Demarais et al. |
| 2010/0198040 A1 | 8/2010 | Friedman et al. |
| 2010/0210946 A1 | 8/2010 | Harada et al. |
| 2010/0222851 A1 | 9/2010 | Deem et al. |
| 2010/0228162 A1* | 9/2010 | Sliwa ..................... A61N 7/02 601/2 |
| 2010/0262014 A1* | 10/2010 | Huang ................... A61B 8/12 600/466 |
| 2010/0331686 A1 | 12/2010 | Hossack et al. |
| 2010/0331950 A1 | 12/2010 | Strommer |
| 2011/0009779 A1 | 1/2011 | Romano et al. |
| 2011/0028962 A1 | 2/2011 | Werneth et al. |
| 2011/0034809 A1 | 2/2011 | Eberle et al. |
| 2011/0066217 A1 | 3/2011 | Diller et al. |
| 2011/0092781 A1 | 4/2011 | Gertner |
| 2011/0092880 A1 | 4/2011 | Gertner |
| 2011/0106132 A1 | 5/2011 | Barbut et al. |
| 2011/0112400 A1 | 5/2011 | Eatery et al. |
| 2011/0178441 A1 | 7/2011 | Tyler |
| 2011/0201973 A1 | 8/2011 | Stephens et al. |
| 2011/0257563 A1 | 10/2011 | Thapliyal et al. |
| 2011/0264086 A1 | 10/2011 | Ingle |
| 2011/0270247 A1 | 11/2011 | Sherman |
| 2011/0282203 A1 | 11/2011 | Tsoref et al. |
| 2011/0282249 A1 | 11/2011 | Tsoref et al. |
| 2011/0319765 A1 | 12/2011 | Gertner et al. |
| 2012/0016273 A1 | 1/2012 | Diederich |
| 2012/0053577 A1 | 3/2012 | Lee et al. |
| 2012/0065494 A1 | 3/2012 | Gertner et al. |
| 2012/0095335 A1 | 4/2012 | Sverdlik et al. |
| 2012/0095371 A1 | 4/2012 | Sverdlik et al. |
| 2012/0095372 A1* | 4/2012 | Sverdlik ............ A61B 17/2202 601/2 |
| 2012/0123243 A1* | 5/2012 | Hastings ............... A61B 8/0841 600/411 |
| 2012/0123270 A1 | 5/2012 | Klee et al. |
| 2012/0209116 A1 | 8/2012 | Hossack et al. |
| 2012/0215106 A1 | 8/2012 | Sverdlik et al. |
| 2012/0232409 A1 | 9/2012 | Stahmann et al. |
| 2012/0232436 A1 | 9/2012 | Warnking |
| 2012/0265227 A1 | 10/2012 | Sverdlik et al. |
| 2012/0268886 A1 | 10/2012 | Leontiev et al. |
| 2012/0283605 A1 | 11/2012 | Lewis, Jr. |
| 2012/0310233 A1 | 12/2012 | Dimmer et al. |
| 2012/0316559 A1 | 12/2012 | Mayse et al. |
| 2013/0072928 A1 | 3/2013 | Schaer |
| 2013/0131668 A1 | 5/2013 | Schaer |
| 2013/0197555 A1 | 8/2013 | Schaer |
| 2013/0204068 A1 | 8/2013 | Gnanashanmugam et al. |
| 2013/0204167 A1 | 8/2013 | Sverdlik et al. |
| 2013/0204242 A1 | 8/2013 | Sverdlik et al. |
| 2013/0207519 A1 | 8/2013 | Chaggares et al. |
| 2013/0211292 A1 | 8/2013 | Sverdlik et al. |
| 2013/0211396 A1 | 8/2013 | Sverdlik et al. |
| 2013/0211437 A1 | 8/2013 | Sverdlik et al. |
| 2013/0218054 A1 | 8/2013 | Sverdlik et al. |
| 2013/0218068 A1 | 8/2013 | Sverdlik et al. |

(56) References Cited

U.S. PATENT DOCUMENTS

| | | | |
|---|---|---|---|
| 2013/0225595 A1 | 8/2013 | Gillies et al. | |
| 2013/0226040 A1* | 8/2013 | Michael | A61B 8/12 601/2 |
| 2013/0267875 A1 | 10/2013 | Thapliyal et al. | |
| 2013/0296836 A1 | 11/2013 | Barbut et al. | |
| 2013/0310822 A1 | 11/2013 | Mayse et al. | |
| 2014/0012133 A1 | 1/2014 | Sverdlik et al. | |
| 2014/0024975 A1* | 1/2014 | Little | A61N 7/02 601/3 |
| 2014/0039286 A1 | 2/2014 | Hoffer | |
| 2014/0039477 A1 | 2/2014 | Sverdlik et al. | |
| 2014/0074076 A1 | 3/2014 | Gertner | |
| 2014/0088585 A1 | 3/2014 | Hill et al. | |
| 2014/0163540 A1* | 6/2014 | Iyer | A61N 7/022 606/27 |
| 2014/0180197 A1 | 6/2014 | Sverdlik et al. | |
| 2014/0180277 A1 | 6/2014 | Chen | |
| 2014/0194866 A1 | 7/2014 | Wang | |
| 2014/0257262 A1* | 9/2014 | Carpentier | A61N 7/02 606/28 |
| 2014/0276135 A1 | 9/2014 | Agah et al. | |
| 2014/0359111 A1 | 12/2014 | Hilmo et al. | |
| 2015/0057599 A1 | 2/2015 | Chen | |
| 2015/0073400 A1 | 3/2015 | Sverdlik et al. | |
| 2015/0112234 A1 | 4/2015 | McCaffrey et al. | |
| 2015/0272668 A1 | 10/2015 | Chen | |
| 2016/0059044 A1 | 3/2016 | Gertner | |
| 2016/0374710 A1 | 12/2016 | Sinelnikov et al. | |
| 2017/0027645 A1 | 2/2017 | Ben Oren et al. | |
| 2018/0326227 A1 | 11/2018 | Sverdlik et al. | |
| 2019/0366130 A1 | 12/2019 | Sverdlik et al. | |

FOREIGN PATENT DOCUMENTS

| | | |
|---|---|---|
| CN | 101820820 | 9/2010 |
| EP | 1384445 | 1/2004 |
| EP | 1424100 | 6/2004 |
| EP | 1799302 | 3/2006 |
| EP | 1769759 | 4/2007 |
| EP | 1802370 | 7/2007 |
| EP | 2092957 | 8/2009 |
| EP | 2218479 | 8/2010 |
| EP | 2455133 | 5/2012 |
| JP | 07-227394 | 8/1995 |
| JP | 09-122139 | 5/1997 |
| JP | 10-248854 | 9/1998 |
| JP | 2008-536562 | 9/2008 |
| JP | 2010-517695 | 5/2010 |
| WO | WO 91/10405 | 7/1991 |
| WO | WO 99/16366 | 4/1999 |
| WO | WO 00/67648 | 10/2000 |
| WO | WO 01/45550 | 6/2001 |
| WO | WO 02/096501 | 12/2002 |
| WO | WO 2004/054448 | 7/2004 |
| WO | WO 2006/022790 | 3/2006 |
| WO | WO 2006/041847 | 4/2006 |
| WO | WO 2006/041881 | 4/2006 |
| WO | WO 2006/042163 | 4/2006 |
| WO | WO 2007/001981 | 1/2007 |
| WO | WO 2007/078997 | 7/2007 |
| WO | WO 2007/115307 | 10/2007 |
| WO | WO 2007/127176 | 11/2007 |
| WO | WO 2008/003058 | 1/2008 |
| WO | WO 2008/098101 | 8/2008 |
| WO | WO 2008/102363 | 8/2008 |
| WO | WO 2010/009473 | 1/2010 |
| WO | WO 2010/118307 | 10/2010 |
| WO | WO 2011/053757 | 5/2011 |
| WO | WO 2011/060200 | 5/2011 |
| WO | WO 2012/052920 | 4/2012 |
| WO | WO 2012/052921 | 4/2012 |
| WO | WO 2012/052922 | 4/2012 |
| WO | WO 2012/052924 | 4/2012 |
| WO | WO 2012/052925 | 4/2012 |
| WO | WO 2012/052926 | 4/2012 |
| WO | WO 2012/052927 | 4/2012 |
| WO | WO 2012/061713 | 5/2012 |
| WO | WO 2013/030743 | 3/2013 |
| WO | WO 2013/111136 | 8/2013 |
| WO | WO 2013/134479 | 9/2013 |
| WO | WO 2013/157009 | 10/2013 |
| WO | WO 2013/157011 | 10/2013 |
| WO | WO 2013/162694 | 10/2013 |
| WO | WO 2014/141052 | 9/2014 |
| WO | WO 2014/188430 | 11/2014 |
| WO | WO 2016/084081 | 6/2016 |
| WO | WO 2016/084081 A8 | 6/2017 |
| WO | WO 2018/173052 | 9/2018 |
| WO | WO 2018/173053 | 9/2018 |

OTHER PUBLICATIONS

Applicant-Initiated Interview Summary dated Apr. 2, 2019 From the US Patent and Trademark Office Re. U.S. Appl. No. 13/905,224. (3 pages).

Applicant-Initiated Interview Summary dated Jan. 4, 2016 From the US Patent and Trademark Office Re. U.S. Appl. No. 13/449,539.

Applicant-Initiated Interview Summary dated Jul. 14, 2016 From the US Patent and Trademark Office Re. U.S. Appl. No. 13/449,539.

Applicant-Initiated Interview Summary dated Nov. 14, 2018 From the US Patent and Trademark Office Re. U.S. Appl. No. 13/449,539. (3 pages).

Applicant-Initiated Interview Summary dated Jan. 21, 2015 From the US Patent and Trademark Office Re. U.S. Appl. No. 13/449,539.

Applicant-Initiated Interview Summary dated Feb. 22, 2016 From the US Patent and Trademark Office Re. U.S. Appl. No. 13/880,066.

Applicant-Initiated Interview Summary dated Jan. 24, 2014 From the US Patent and Trademark Office Re. U.S. Appl. No. 13/449,539.

Applicant-Initiated Interview Summary dated Apr. 25, 2018 From the US Patent and Trademark Office Re. U.S. Appl. No. 14/394,276. (3 pages).

Applicant-Initiated Interview Summary dated Sep. 28, 2016 From the US Patent and Trademark Office Re. U.S. Appl. No. 13/905,224.

Communication Pursuant to Article 94(3) EPC dated Nov. 4, 2014 From the European Patent Office Re. Application No. 11833950.6.

Communication Pursuant to Article 94(3) EPC dated Feb. 8, 2016 From the European Patent Office Re. Application No. 11833950.6.

Communication Pursuant to Article 94(3) EPC dated Apr. 10, 2015 From the European Patent Office Re. Application No. 11782222.1.

Communication Pursuant to Article 94(3) EPC dated Jun. 10, 2014 From the European Patent Office Re. Application No. 117822476.3.

Communication Pursuant to Article 94(3) EPC dated Jun. 10, 2014 From the European Patent Office Re. Application No. 11784782.2.

Communication Pursuant to Article 94(3) EPC dated Apr. 14, 2014 From the European Patent Office Re. Application No. 11782221.3.

Communication Pursuant to Article 94(3) EPC dated Jul. 20, 2016 From the European Patent Office Re. Application No. 11782221.3.

Communication Pursuant to Article 94(3) EPC dated Sep. 26, 2014 From the European Patent Office Re. Application No. 11782222.1.

Communication Pursuant to Article 94(3) EPC dated Jul. 27, 2016 From the European Patent Office Re. Application No. 11782222.1.

Communication Pursuant to Article 94(3) EPC dated Oct. 30, 2014 From the European Patent Office Re. Application No. 11782221.3.

Communication Pursuant to Rule 164(1) EPC: Supplementary Partial European Search Report and the European Provisional Opinion dated May 18, 2018 From the European Patent Office Re. Application No. 15862313.2. (15 pages).

Decision of Rejection dated Apr. 28, 2016 From the Japanese Patent Office Re. Application No. 2013-534435 and Its Machine Translation in English.

International Preliminary Report on Patentability dated May 2, 2013 From the International Bureau of WIPO Re. Application No. PCT/IB2011/054634.

International Preliminary Report on Patentability dated May 2, 2013 From the International Bureau of WIPO Re. Application No. PCT/IB2011/054635.

(56) References Cited

OTHER PUBLICATIONS

International Preliminary Report on Patentability dated May 2, 2013 From the International Bureau of WIPO Re. Application No. PCT/IB2011/054636.
International Preliminary Report on Patentability dated May 2, 2013 From the International Bureau of WIPO Re. Application No. PCT/IB2011/054638.
International Preliminary Report on Patentability dated May 2, 2013 From the International Bureau of WIPO Re. Application No. PCT/IB2011/054639.
International Preliminary Report on Patentability dated May 2, 2013 From the International Bureau of WIPO Re. Application No. PCT/IB2011/054640.
International Preliminary Report on Patentability dated May 2, 2013 From the International Bureau of WIPO Re. Application No. PCT/IB2011/054641.
International Preliminary Report on Patentability dated Dec. 3, 2015 From the International Bureau of WIPO Re. Application No. PCT/IL2014/050457.
International Preliminary Report on Patentability dated Aug. 7, 2014 From the International Bureau of WIPO Re. Application No. PCT/IL2013/050068.
International Preliminary Report on Patentability dated Jun. 8, 2017 From the International Bureau of WIPO Re. Application No. PCT/IL2015/051145. (16 Pages).
International Preliminary Report on Patentability dated Oct. 30, 2014 From the International Bureau of WIPO Re. Application No. PCT/IL2013/050339.
International Preliminary Report on Patentability dated Oct. 30, 2014 From the International Bureau of WIPO Re. Application No. PCT/IL2013/050341.
International Search Report and the Written Opinion dated May 2, 2016 From the International Searching Authority Re. Application No. PCT/IL2015/051145.
International Search Report and the Written Opinion dated Feb. 7, 2012 From the International Searching Authority Re. Application No. PCT/IB2011/054641.
International Search Report and the Written Opinion dated Oct. 11, 2013 From the International Searching Authority Re. Application No. PCT/IL2013/050341.
International Search Report and the Written Opinion dated Sep. 19, 2013 From the International Searching Authority Re. Application No. PCT/IL2013/050068.
International Search Report and the Written Opinion dated Nov. 20, 2014 From the International Searching Authority Re. Application No. PCT/IL2014/050457.
International Search Report and the Written Opinion dated Jun. 22, 2012 From the International Searching Authority Re. Application No. PCT/IB2011/054640.
International Search Report and the Written Opinion dated Jan. 23, 2012 From the International Searching Authority Re. Application No. PCT/IB2011/054635.
International Search Report and the Written Opinion dated Jan. 25, 2012 From the International Searching Authority Re. Application No. PCT/IB2011/054636.
International Search Report and the Written Opinion dated Jan. 27, 2012 From the International Searching Authority Re. Application No. PCT/IB2011/054634.
International Search Report and the Written Opinion dated Jan. 27, 2012 From the International Searching Authority Re. Application No. PCT/IB2011/054638.
International Search Report and the Written Opinion dated Aug. 28, 2018 From the International Searching Authority Re. Application No. PCT/IL2018/050322. (40 Pages).
International Search Report and the Written Opinion dated Aug. 29, 2018 From the International Searching Authority Re. Application No. PCT/IL2018/050321. (16 Pages).
International Search Report and the Written Opinion dated Oct. 29, 2013 From the International Searching Authority Re. Application No. PCT/IL2013/050339.
International Search Report and the Written Opinion dated Jan. 31, 2012 From the International Searching Authority Re. Application No. PCT/IB2011/054639.
Invitation Pursuant to Rule 137(4) EPC dated Apr. 4, 2014 From the European Patent Office Re. Application No. 11785792.0.
Invitation Pursuant to Rule 137(4) EPC dated Apr. 8, 2014 From the European Patent Office Re. Application No. 11782222.1.
Invitation Pursuant to Rule 137(4) EPC dated Apr. 10, 2014 From the European Patent Office Re. Application No. 11782476.3.
Invitation Pursuant to Rule 137(4) EPC dated Mar. 21, 2016 From the European Patent Office Re. Application No. 11782222.1.
Invitation to Pay Additional Fees dated Sep. 3, 2013 From the International Searching Authority Re. Application No. PCT/IL2013/050339.
Invitation To Pay Additional Fees dated Mar. 4, 2016 From the International Searching Authority Re. Application No. PCT/IL2015/051145.
Invitation to Pay Additional Fees dated Sep. 4, 2014 From the International Searching Authority Re. Application No. PCT/IL2014/050457.
Invitation to Pay Additional Fees dated Aug. 5, 2013 From the International Searching Authority Re. Application No. PCT/IL2013/050341.
Invitation to Pay Additional Fees dated Apr. 17, 2012 From the International Searching Authority Re. Application No. PCT/IB2011/054640.
Invitation to Pay Additional Fees dated Jun. 21, 2018 From the International Searching Authority Re. Application No. PCT/IL2018/050322. (3 Pages).
Invitation to Pay Additional Fees dated Jul. 24, 2013 From the International Searching Authority Re. Application No. PCT/IL2013/050068.
Invitation to Pay Additional Fees dated Jun. 25, 2018 From the International Searching Authority Re. Application No. PCT/IL2018/050321. (2 Pages).
Notice of Non-Compliant Amendment dated Sep. 23, 2015 From the US Patent and Trademark Office Re. U.S. Appl. No. 13/880,124.
Notice of Reason for Rejection dated Aug. 25, 2015 From the Japanese Patent Office Re. Application No. 2013-534435.
Notification of Office Action and Search Report dated Dec. 1, 2014 From the State Intellectual Property Office of the People's Republic of China Re. Application No. 201180060862.8.
Office Action dated Jul. 30, 2014 From the State Intellectual Property Office of the People's Republic of China Re. Application No. 201180060741.3 and Its Summary in English.
Official Action dated Jul. 20, 2015 From the US Patent and Trademark Office Re. U.S. Appl. No. 13/879,400.
Official Action dated Dec. 3, 2014 From the US Patent and Trademark Office Re. U.S. Appl. No. 13/462,956.
Official Action dated Jun. 3, 2016 From the US Patent and Trademark Office Re. U.S. Appl. No. 13/880,066.
Official Action dated Jun. 3, 2019 From the US Patent and Trademark Office Re. U.S. Appl. No. 13/449,539. (13 Pages).
Official Action dated Nov. 3, 2017 From the US Patent and Trademark Office Re. U.S. Appl. No. 14/394,276. (11 pages).
Official Action dated Nov. 4, 2014 From the US Patent and Trademark Office Re. U.S. Appl. No. 13/879,400.
Official Action dated Aug. 5, 2015 From the US Patent and Trademark Office Re. U.S. Appl. No. 13/905,224.
Official Action dated Jan. 5, 2016 From the US Patent and Trademark Office Re. U.S. Appl. No. 13/880,124.
Official Action dated Jun. 5, 2015 From the US Patent and Trademark Office Re. U.S. Appl. No. 14/049,238.
Official Action dated Nov. 5, 2014 From the US Patent and Trademark Office Re. U.S. Appl. No. 13/049,022.
Official Action dated Feb. 6, 2015 From the US Patent and Trademark Office Re. U.S. Appl. No. 14/190,113.
Official Action dated Jan. 6, 2017 From the US Patent and Trademark Office Re. U.S. Appl. No. 14/190,113. (11 pages).
Official Action dated Oct. 7, 2014 From the US Patent and Trademark Office Re. U.S. Appl. No. 13/880,109.
Official Action dated May 8, 2013 From the US Patent and Trademark Office Re. U.S. Appl. No. 13/462,956.

(56) References Cited

OTHER PUBLICATIONS

Official Action dated Aug. 10, 2018 From the US Patent and Trademark Office Re. U.S. Appl. No. 14/190,113. (11 pages).
Official Action dated Jun. 10, 2016 From the US Patent and Trademark Office Re. U.S. Appl. No. 14/190,113.
Official Action dated Mar. 10, 2016 From the US Patent and Trademark Office Re. U.S. Appl. No. 13/449,539.
Official Action dated Sep. 10, 2014 From the US Patent and Trademark Office Re. U.S. Appl. No. 14/049,238.
Official Action dated Oct. 11, 2018 From the US Patent and Trademark Office Re. U.S. Appl. No. 14/394,276. (200 Pages).
Official Action dated Sep. 11, 2015 From the US Patent and Trademark Office Re. U.S. Appl. No. 13/880,066.
Official Action dated Apr. 14, 2014 From the US Patent and Trademark Office Re. U.S. Appl. No. 13/879,400.
Official Action dated Aug. 14, 2015 From the US Patent and Trademark Office Re. U.S. Appl. No. 13/449,539.
Official Action dated May 16, 2019 From the US Patent and Trademark Office Re. U.S. Appl. No. 15/529,137. (11 pages).
Official Action dated Jul. 17, 2013 From the US Patent and Trademark Office Re. U.S. Appl. No. 13/049,013.
Official Action dated Nov. 17, 2017 From the US Patent and Trademark Office Re. U.S. Appl. No. 13/905,224. (19 pages).
Official Action dated Dec. 19, 2013 From the US Patent and Trademark Office Re. U.S. Appl. No. 13/049,022.
Official Action dated Mar. 20, 2014 From the US Patent and Trademark Office Re. U.S. Appl. No. 13/449,539.
Official Action dated Oct. 20, 2017 From the US Patent and Trademark Office Re. U.S. Appl. No. 14/190,113. (7 pages).
Official Action dated Apr. 21, 2017 From the US Patent and Trademark Office Re. U.S. Appl. No. 14/394,276. (13 pages).
Official Action dated Jun. 21, 2018 From the US Patent and Trademark Office Re. U.S. Appl. No. 13/449,539. (8 pages).
Official Action dated Apr. 23, 2014 From the US Patent and Trademark Office Re. U.S. Appl. No. 13/880,061.
Official Action dated Oct. 24, 2012 From the US Patent and Trademark Office Re. U.S. Appl. No. 13/049,013.
Official Action dated Sep. 25, 2013 From the US Patent and Trademark Office Re. U.S. Appl. No. 13/462,956.
Official Action dated Sep. 25, 2015 From the US Patent and Trademark Office Re. U.S. Appl. No. 14/190,113.
Official Action dated Jul. 26, 2016 From the US Patent and Trademark Office Re. U.S. Appl. No. 13/880,124.
Official Action dated Dec. 27, 2016 From the US Patent and Trademark Office Re. U.S. Appl. No. 13/449,539. (13 pages).
Official Action dated Apr. 29, 2016 From the US Patent and Trademark Office Re. U.S. Appl. No. 13/905,224.
Official Action dated Aug. 29, 2013 From the US Patent and Trademark Office Re. U.S. Appl. No. 13/449,539.
Official Action dated Jan. 29, 2013 From the US Patent and Trademark Office Re. U.S. Appl. No. 13/049,151.
Official Action dated Oct. 31, 2018 From the US Patent and Trademark Office Re. U.S. Appl. No. 13/905,224. (23 pages).
Restriction Official Action dated Jan. 4, 2019 From the US Patent and Trademark Office Re. U.S. Appl. No. 15/529,137. (8 pages).
Restriction Official Action dated Oct. 5, 2012 From the US Patent and Trademark Office Re. U.S. Appl. No. 13/049,151.
Restriction Official Action dated Jul. 7, 2014 From the US Patent and Trademark Office Re. U.S. Appl. No. 14/049,238.
Restriction Official Action dated Apr. 14, 2015 From the US Patent and Trademark Office Re. U.S. Appl. No. 13/880,124.
Restriction Official Action dated Nov. 17, 2014 From the US Patent and Trademark Office Re. U.S. Appl. No. 13/880,066.
Restriction Official Action dated Feb. 27, 2015 From the US Patent and Trademark Office Re. U.S. Appl. No. 13/905,224.
Restriction Official Action dated Mar. 27, 2015 From the US Patent and Trademark Office Re. U.S. Appl. No. 13/880,095.
Restriction Official Action dated Oct. 27, 2016 From the US Patent and Trademark Office Re. U.S. Appl. No. 14/394,276.
Restriction Official Action dated Jun. 28, 2013 From the US Patent and Trademark Office Re. U.S. Appl. No. 13/449,539.
Restriction Official Action dated Aug. 30, 2012 From the US Patent and Trademark Office Re. U.S. Appl. No. 13/049,013.
Restriction Official Action dated Oct. 30, 2014 From the US Patent and Trademark Office Re. U.S. Appl. No. 13/880,083.
Search Report dated Jul. 17, 2014 From the State Intellectual Property Office of the People's Republic of China Re. Application No. 201180060741.3 and Its Machine Translation in English.
Supplementary European Search Report and the European Search Opinion dated Sep. 5, 2018 From the European Patent Office Re. Application No. 15862313.2. (13 Pages).
Supplementary European Search Report and the European Search Opinion dated Dec. 22, 2016 From the European Patent Office Re. Application No. 14801877.3. (9 Pages).
Supplementary European Search Report dated Mar. 12, 2014 From the European Patent Office Re. Application No. 11833950.6.
Translation Dated Mar. 12, 2015 of Notification of Office Action and Search Report dated Dec. 1, 2014 From the State Intellectual Property Office of the People's Republic of China Re. Application No. 201180060862.8.
Translation Dated Nov. 18, 2015 of Notice of Reason for Rejection dated Aug. 25, 2015 From the Japanese Patent Office Re. Application No. 2013-534435.
Ahmed et al. "Renal Sympathetic Denervation Using an Irrigated Radiofrequency Ablation Catheter for the Management of Drug-Resistant Hypertension", Journal of the American College of Cardiology: Cardiovascular Interventions, JACC, 5(7): 758-765, 2012.
Ali et al. "Signal Processing Overview of Ultrasound Systems for Medical Imaging", Texas Instruments White Paper, SPRAB12: 1-27, Nov. 2008.
Anonymus "Indication for and Results of Sympathectomy in Patients With Peripheral Vascular Disease", Lumbar Sympathectomy, Poster, 34 P., 2009.
Aoyama et al. "Comparison of Cryothermia and Radiofrequency Current in Safety and Efficacy of Catheter Ablation Within the Canine Coronary Sinus Close to the Left Circumflex Coronary Artery", Journal of Cardiovascular Electrophysiology, 16: 1218-1226, Nov. 2005.
Atherton et al. "Micro-Anatomy of the Renal Sympathetic Nervous System: A Human Postmortem Histologic Study", Clinical Anatomy, p. 1-6, Oct. 4, 2011.
Bailey et al. "Cavitation Detection During Shock-Wave Lithotripsy", Ultrasound in Medicine and Biology, XP027605630, 31(9): 1245-1256, Sep. 1, 2005. Abstract, Fig.1, p. 1246, p. 1247, r-h col., p. 1249, r-h col.
Baker et al. "Operative Lumbar Sympathectomy for Severe Lower Limb Ischaemia: Still a Valuable Treatment Option", Annals of the Royal College of Surgeons of England, 76(1): 50-53, Jan. 1994.
Bambi et al. "Real-Time Digital Processing of Doppler Ultrasound Signals", IEEE International Conference on Acoustics, Speech, and Signal Processing, Proceedings, (ICASSP '05), (5): v/977-v/980, Mar. 23-23, 2005.
Bandyopadhyay et al. "Outcomes of Beta-Blocker Use in Pulmonary Arterial Hypertension: A Propensity-Matched Analysis", European Respiratory Journal, 46(3): 750-760, Published Online May 28, 2015.
Bharat et al. "Monitoring Stiffness Changes in Lesions After Radiofrequency Ablation at Different Temperatures and Durations of Ablation", Ultrasound in Medicine & Biology, 31(3): 415-422, 2005.
Bhatt et al. "A Controlled Trial of Renal Denervation for Resistant Hypertension", The New England Journal of Medicine, 270(15): 1393-1401, Published Online Mar. 29, 2014.
Blankestijn et al. "Renal Denervation: Potential Impact on Hypertension in Kidney Disease?", Nephrology, Dialysis, Transplantation, 26(9): 2732-2734, Apr. 19, 2011.
Brandt et al. "Effects of Renal Sympathetic Denervation on Arterial Stiffness and Central Hemodynamics in Patients With Resistant Hypertension", Journal of the American College of Cardiology, 60(19): 1956-1965, 2012.
Brandt et al. "Renal Sympathetic Denervation Reduces Left Ventricular Hypertrophy and Improves Cardiac Function in Patients

(56) References Cited

OTHER PUBLICATIONS

With Resistant Hypertension", Journal of the American College of Cardiology, 59(10): 901-909, 2012.
Brasselet et al. "Effect of Local Heating on Restenosis and In-Stent Neointimal Hyperplasia in the Atherosclerotic Rabbit Model: A Dose-Ranging Study", European Heart Journal, 29: 402-412, 2008.
Brinton et al. "Externally Focused Ultrasound for Sympathetic Renal Denervation", WAVE I First-In-Man Study, Kona Medical Inc., PowerPont Presentation, TCT 2012, 15 P., 2012.
Campese et al. "Renal Afferent Denervation Prevents the Progression of Renal Disease in the Renal Ablation Model of Chronic Renal Failure in the Rat", American Journal of Kidney Diseases, 26(5): 861-865, Nov. 1995. Abstract.
Campese et al. "Sympathetic Renal Innervation and Resistant Hypertension", International Journal of Hypertension, 2011(Art.ID 814354): 1-6, 2011.
Cardiosonic "Cardiosonic New Applications", Cardiosonic, p. 1-20, Mar. 2014.
Cardiosonic "Histological Map of Swine Pulmonary Arteries", Cardiosonic, Animal #223, Mar. 26, 2014.
Cardiosonic "Histological Map of Swine Pulmonary Arteries", Cardiosonic, Animal #234, Mar. 18, 2014.
Cardiosonic "Histological Map of Swine Pulmonary Arteries", Cardiosonic, Animal #234, Mar. 26, 2014.
Cardiosonic "Histopathology Report", Cardiosonic, 2 P., Dec. 26, 2013.
Cardiosonic "PA/Trachea—Feedback Provisional", Cardiosonic, 5 P, Jun. 9, 2014.
Cardiosonic "PAH Preliminary Development Meeting Minutes", Cardiosonic, 2 P., Mar. 23, 2014.
Chen et al. "Artery Denervation to Treat Pulmonary Arterial Hypertension. The Single-Center, Prospective, First-in-Man PADN-1 Study (First-in-Man Pulmonary Artery Denervation for Treatment of Pulmonary Artery Hypertension)", Journal of the American College of Cardiology, JACC, 62(12): 1092-1100, Sep. 17, 2013.
Chen et al. "Hemodynamic, Functional, and Clinical Responses to Pulmonary Artery Denervation in Patients With Pulmonary Arterial Hypertension of Different Causes: Phase II Results From the Pulmonary Artery Denervation-1 Study", Circulation: Cardiovascular Interventions, 8(11): e002837-1-e002837-10, Nov. 9, 2015.
Chen et al. "Percutaneous Pulmonary Artery Denervation Completely Abolishes Experimental Pulmonary Arterial Hypertension In Vivo", EuroIntervention, 9(2): 269-276, Jun. 22, 2013.
Ciarka et al. "Prognostic Significance of Sympathetic Nervous System Activation in Pulmonary Arterial Hypertension", American Journal of Respiratory and Critical Care Medicine, 181(11): 1269-1275, Published Online Mar. 1, 2010.
CIBIS-II Investigators and Committees "The Cardiac Insufficiency Bisoprolol Study II (CIBIS-II): A Randomised Trial", The Lancet, 353(9146): 9-13, Jan. 2, 1999.
Cohn et al. "A Comparison of Enalapril With Hydralazine-Isosorbide Dinitrate in the Treatment of Chronic Congestive Heart Failure", The New England Journal of Medicine, 325(5): 303-310, Aug. 1, 1991.
CONSENSUS Trial Study Group "Effects of Enalapril on Mortality in severe Congestive Heart Failure. Results of the Cooperative North Scandinavian Enalapril Survival Study (CONSENSUS)", The New England Journal of Medicine, 316(23): 1429-1435, Jun. 4, 1987.
Copty et al. "Localized Heating of Biological Media Using A 1-W Microwave Near-Field Probe", IEEE Transactions on Microwave Theory and Techniques, 52(8): 1957-1963, Aug. 2004.
Copty et al. "Low-Power Near-Field Microwave Applicator for Localized Heating of Soft Matter", Applied Physics Letters, 84(25): 5109-5111, Jun. 21, 2004.
Damianou et al. "Dependence of Ultrasonic Attenuation and Absorpteion in Dog Soft Tissues on Temperature and Thermal Dose", Journal of the Acoustical Society of America, 102(1): 628-634, Jul. 1997.

Davies et al. "First-in-Man Safety Evaluation of Renal Denervation for Chronic Systolic Heart Failure: Primary Outcome From Reach—Pilot Study", International Journal of Cardiology, 162: 189-192, 2013.
De Man et al. "Bisoprolol Delays Progression Towards Right Heart Failure in Experimental Pulmonary Hypertension", Circulation Heart Failure, 5(1): 97-105, Published Online Dec. 9, 2011.
De Man et al. "Neurohormonal Axis in Patients With Pulmonary Arterial Hypertension. Friend or Foe?", American Journal of Respiratory and Critical Care Medicine, 187(1): 14-19, Published Online Nov. 9, 2012.
Deneke et al. "Histopathology of Intraoperatively Induced Linear Radiofrequency Ablation Lesions in Patients With Chronic Atrial Fibrillation", European Heart Journal, 26: 1797-1803, 2005.
Dewhirst et al. "Basic Principles of Thermal Dosimetry and Thermal Thresholds for Tissue Damage From Hyperthermia", International Journal of Hyperthermia, 19(3): 267-294, May-Jun. 2003.
DiBona "Neural Control of Renal Function: Cardiovascular Implications", Hypertension, 13: 539-548, 1989.
DiBona "Neural Control of the Kidney: Past, Present, and Future", Hypertension, 41: 621-624, Dec. 16, 2002.
DiBona "Physiology in Perspective: The Wisdom of the Body. Neural Control of the Kidney", American Journal of Physiology, Regulatory, Integrative and Comparative Physiology, 289(3): R633-R641, Sep. 2005.
DiBona et al. "Differentiated Sympathetic Neural Control of the Kidney", American Journal of Physiology, 271: R84-R90, 1996.
DiBona et al. "Translational Medicine: The Antihypertensive Effect of Renal Denervation", American Journal of Physiology, Regulatory, Integrative and Comparative Physiology, 298(2): R245-R253, Feb. 2010.
Diederich et al. "Catheter-Based Ultrasound Applicators for Selective Thermal Ablation: Progress Towards MRI-Guided Applications in Prostate", International Journal of Hyperthermia, 20(7): 739-756, Nov. 2004.
Diederich et al. "Catheter-Based Ultrasound Devices and MR Thermal Monitoring for Conformal Prostate Thermal Therapy", 30th Annual International IEEE EMBS Conference, Vancouver, British Columbia, Canada, Aug. 20-24, 2008, p. 3664-3668, 2008.
Diederich et al. "Induction of Hyperthermia Using an Intracavitary Multielement Ultrasonic Applicator", IEEE Transactions on Biomedical Engineering, 36(4): 432-438, Apr. 1989.
Diederich et al. "Ultrasound Technology for Hyperthermia", Ultrasound in Medicine & Biology, 25(6): 871-887, 1999.
Donoho et al. "Stable Recovery of Sparse Overcomplete Representations in the Presence of Noise", IEEE Transactions on Information Theory, 52(1): 1-42, Jan. 2006.
Drake et al. "Problematic Anatomical Sites Around the Pulmonary Artery", Gray's Anatomy for Students, 9 P., 2004.
Esler "The 2009 Carl Ludwig Lecture: Pathophysiology of the Human Sympathetic Nervous System in Cardiovascular Diseases: The Transition From Mechanisms to Medical Management", Journal of Applied Physiology, 108: 227-237, 2010.
Esler et al. "Measurement of Total and Organ-Specific Norepinephrine Kinetics in Humans", American Journal of Physiology—Endocrinology Metabolism 10, 247(1/Pt.1): E21-E28, Jul. 1984.
Esler et al. "Renal Sympathetic Denervation for Treatment of Drug-Resistant Hypertension: One-Year Results From the Symplicity HTN-2 Randomized, Controlled Trial", Circulation, 126: 2976-2982, 2012.
Failla et al. "Sympathetic Tone Restrains Arterial Distensibility of Healthy and Atherosclerotic Subjects", Journal of Hypertension, 17: 1117-1123, 1999.
Fischell PeriVascular Renal Denervation (PVRD™), Ablative Solutions Inc., TransCatheter Therapeutics Meeting, Miami, FL, USA, Oct. 24, 2012, PowerPoint Presentation, 14 P., Oct. 2012.
Fort Wayne Metals "HHS Tube", Fort Wayne Metals Research Products Corporation, 2 P., 2009.
Fujikura et al. "Effects of Ultrasonic Exposure Parameters on Myocardial Lesions Induced by High-Intensity Focused Ultrasound", Journal of Ultrasound Medicine, 25: 1375-1386, 2006.
Galie et al. "2015 ESC/ERS Guidelines for the Diagnosis and Treatment of Pulonary Hypertension. The Joint Task Force for the

(56) References Cited

OTHER PUBLICATIONS

Diagnosis and Treatment of Pulmonary Hypertension of the European Society of Cardiology (ESC) and the European Respiratory Society (ERS). Endorsed by: Association for European Paediatric and Congenital Cardiology (AEPC), International Society for Heart and Lung Transplantation (ISHLT)", European Heart Journal, 37(1): 67-119, Published Online Aug. 29, 2015.
Galie et al. "New Treatment Stategies for Pulmonary Arterial Hypertension. Hopes or Hypes?", Journal of the American College of Cardiology, 62(12): 1101-1102, Sep. 17, 2013.
Galie et al. "Updated Treatment Algorithm of Pulmonary Arterial Hypertension", Journal of the American College of Cardiology, 62(25/Suppl.D): D60-D72, 2013.
Gander et al. "Least-Squares Fitting of Circles and Ellipses", BIT Numerical Mathematics, 34(4): 558-578, Dec. 1994.
Giering et al. "Determination of the Specific Heat Capacity of Healthy and Tumorous Human Tissue", Thermochimica Acta, 251: 199-205, Mar. 1995.
Glazier et al. "Laser Balloon Angioplasty Combined With Local Intrcoronary Heparin Therapy: Immediate and Short-Term Follow-Up Results", American Heart Journal, 134: 266-273, 1997.
Goswami "Renal Denervation: A Percutaneous Therapy for HTN", Prairie Heart Institute, Synvacor, The VEINS: Venous Endovascular Interventions Strategies, Chicago, USA, 42 P., 2012.
Granada et al. "A Translational Overview for the Evaluation of Peri-Renal Denervation Technologies", Cardiovascular Research Foundation, Columbai University Medical Center, New York, USA, Alizee Pathology, 25 P., 2011.
Grassi et al. "Sympathetic Mechanisms, Organ Damage, and Antihypertensive Treatment", Current Hypertension Report, 13: 303-308, 2011.
Griffiths et al. "Thoraco-Lumbar Splanchnicectomy and Sympathectomy. Anaesthetic Procedure", Anaesthesia, 3(4): 134-146, Oct. 1948.
Grimson et al. "Total Thoracic and Partial to Total Lumbar Sympathectomy, Splanchnicectomy and Celiac Ganglionectomy for Hypertension", Annals of Surgery, 138(4): 532-547, Oct. 1953.
Heath et al. "The Structure of the Pulmonary Trunk at Different Ages and in Cases of Pulmonary Hypertension and Pulmonary Stenosis", The Journal of Pathology and Bacteriology, 77(2): 443-456, Apr. 1959.
Hering et al. "Renal Denervation in Moderate to Severe CKD", Journal of the American Society of Nephrology, 23: 1250-1257, 2012.
Hering et al. "Substantial Reduction in Single Sympathetic Nerve Firing After Renal Denervation in Patients With rRsistant Hypertension", Hypertension, 61: 1-14, Nov. 19, 2012.
Holdaas et al. "Modulation of Reflex Renal Vasoconstriction by increased Endogenous Renal Prostaglandin Synthesis", The Journal of Pharmacology and Experimental Therapeutics, 232(3): 725-731, 1985.
Janssen et al. "Role of Afferent Renal Nerves in Spontaneous Hypertension in Rats", Hypertension, 13: 327-333, 1989.
Joner "Histopathological Characterization of Renal Arteries After Radiofrequency Catheter Based Sympathetic Denervation in a Healthy Porcine Model", Deutsches Herzzentrum M'?nchen, Technische Universit?t M?nchen, PowerPoint Presentation, TCT 2012, 15 P., 2012.
Katholi "Renal Nerves in the Pathogenesis of Hypertension in Experimental Animals and Humans", American Journal of Physiology, 245: F1-F14, 1983.
Katholi et al. "Intrarenal Adenosine Produces Hypertension by Activating the Sympathetic Nervous System via the Renal Nerves in the Dog", Journal of Hypertension, 2: 349-359, 1984.
Katholi et al. "Renal Nerves in the Maintenance of Hypertension: A Potential Therapeutic Target", Current Hypertension Reports, 12(3): 196-204, Jun. 2010.
Kleinlogel et al. "A Gene-Fusion Strategy for Stoichiometric and Co-Localized Expression of Light-Gated Membrane Proteins", Nature Methods, 8(12): 1083-1091, Dec. 2011.

Kline et al. "Functional Reinnervation and Development of Supersensitivity to NE After Renal Denervation in Rats", American Journal of Physiology, 238: R353-R358, 1980.
Kolh "Carotid Denervation by Adventitial Stripping: A Promising Treatment of Carotid Sinus Syndrome?", European Journal of Vascular and Endovascular Surgery, 39(2): 153-154, Feb. 2010.
Krum et al. "Catheter-Based Renal Sympathetic Denervation for Resistant Hypertension: A Multicentre Safety and Proof-of-Principle Cohort Study", The Lancet, 373: 1275-1281, Apr. 11, 2009.
Krum et al. "Catheter-Based Renal Sympathetic Denervation for Resistant Hypertension: A Multicentre Safety and Proof-of-Principle Cohort Study", The Lancet, 373: 1275-1281, Mar. 30, 2009.
Kummer "Pulmonary Vascular Innervation and Its Role in Responses to Hypoxia: Size Matters!", Proceedings of the American Thoracic Society, 8(6): 471-476, Nov. 1, 2011.
Lafon "Miniature Devices for Minimally Invasive Thermal Ablation by High Intensity Ultrasound", Cargese Workshop 2009, University of Lyon, France, INSERM U556, Presentation, 39 P., 2009.
Lambert et al. "Redo of Percutaneous Renal Denervation in a Patient With Recurrent Resistant Hypertension After Primary Treatment Success", Catheterization and Cardiovascular Interventions, p. 1-11, 2012.
Lele "Effects of Focused Ultrasonic Radiation on Peripheral Nerve, With Observations on Local Heating", Experimental Neurology, 8: 47-83, 1963.
Lemoine et al. "Amputations and Sympathectomy in Peripheral Vascular Disease of the Lower Extremity. Experience With 180 Patients", Journal of the National Medical Association, 61(3): 219-221, May 1969.
Li et al. "Acoustic Proximity Ranging in the Presence of Secondary Echoes", IEEE Transactions on Instrumentation and Measurement, XP011102759, 52(5): 1593-1605, Oct. 1, 2003. p. 1593.
Lin et al. "Utility of the PlasmaKinetic™ Bipolar Forceps® for Control of the Renal Artery in a Porcine Model", JTUA, 14(3): 118-121, Sep. 2003.
Liu et al. "A Helical Microwave Antenna for Welding Plaque During Balloon Angioplasty", IEEE Transactions on Microwave Theory and Techniques, 44(10): 1819-1831, Oct. 1996.
Liu et al. "Pulmonary Artery Denervation improves Pulmonary Arterial Hypertension Induced Right Ventricular Dysfunction by Modulating the Local Renin-Angiotensin-Aldosterone System", BMC Cardiovascular Disorders, 16(1): 192-1-192-10, Oct. 10, 2016.
Lopez et al. "Effects of Sympathetic Nerves on Collateral Vessels in the Limb of Atherosclerosis Primates", Atherosclerosis, 90: 183-188, 1991.
Mabin et al. "First Experience With Endovascular Ultrasound Renal Denervation for the Treatment of Resistant Hypertension", EuroIntervention, 8: 57-61, 2012.
Mahfoud et al. "Effect of Renal Sympathetic Denervation on Glucose Metabolism in Patients With Resistant Hypertension: A Pilot Study", Circulation, 123: 1940-1946, 2011.
Mahfoud et al. "Is There a Role for Renal Sympathetic Denervation in the Future Treatment of Resistant Hypertension?", Future Cardiology, 7(5): 591-594, 2011.
Mahfoud et al. "Renal Hemodynamics and Renal Function After Catheter-Based Renal Sympathetic Denervation in Patients With Resistant Hypertension", Hypertension, 60: 419-424, 2012.
Makris et al. "Resistant Hypertension Workup and Approach to Treatment", International Journal of Hypertension, 2011(Art. ID598694): 1-10, 2011.
Manasse et al. "Clinical Histopathology and Ultrstructural Analysis of Myocardium Following Microwave Energy Ablation", European Journal of Cardio-Thoracic Surgery, 23: 573-577, 2003.
Mangoni et al. "Effect of Sympathectomy on Mechanical Properties of Common Carotid and Femoral Arteries", Hypertension, 30: 1085-1088, 1997.
Martin et al. "Premise, Promise, and Potential Limitations of Invasive Devices to Treat Hypertension", Current Cardiology Reports, 13(1): 86-92, Feb. 2011.

(56) References Cited

OTHER PUBLICATIONS

Mazor "Efficacy of Renal Denervation is Positively Impacted by Longitudinal Treatments", Vessix Vascular Inc., PowerPoint Presentation, TCT 2012, 20 P., 2012.
MERIT-HF Study Group "Effect of Metaprolol CR/XL in Chronic Heart Failure: Metoprolol CR/XL Randomised Intervention Trial in Congestive Heart Failure (MERIT-HF)", The Lancet, 353(9169): 2001-2007, Jun. 12, 1999.
Mogil et al. "Renal Innervation and Renin Activity in Salt Metabolism and Hypertension", American Journal of Physiology, 216(4): 693-697, Apr. 1969.
Moretti et al. "Beta Blocker for Patients With Pulmonary Arterial Hypertension: A Single Center Experience", International Journal of Cardiology, 184(1): 528-532, Available Online Feb. 24, 2015.
Mortensen et al. "Catheter-Based Renal Sympathetic Denervation Improves Central Hemodynamics and Arterial Stiffness: A Pilot Study", The Journal of Clinical Hypertension, 14(12): 861-870, Dec. 2012.
Nootens et al. "Neurohormonal Activation in Patients With Right Ventricular Failure From Pulmonary Hypertension: Relation to Hemodynamic Variables and Endothelin Levels", Journal of the American College of Cardiology, JACC, 26(7): 1581-1585, Dec. 1995.
Ohkubo et al. "Histological Findings After Angioplasty Using Conventional Balloon, Radiofrequency Thermal Balloon, and Stent for Experimental Aortic Coarctation", Pediatrics International, 46: 39-47, 2004.
Olafsson et al. "Ultrasound Current Source Density Imaging", IEEE Transactions on Biomedical Engineering, 55(7): 1840-1848, Jul. 2008.
Ong et al. "Successful Treatment of Resistant Hypertension With Percutaneous Renal Denervation Therapy", Heart, 98(23): 1754-1755, Dec. 2012.
Ormiston "OneShot (Covidien)", Maya Medical, Auckland, New Zealand, PowerPoint Presentation.
Ormiston et al. "First-in-Human Use of the OneShot™ Renal Denervation System From Covidien", EuroIntervention, 8: 1090-1094, 2013.
Packer et al. "Effect of Carvedilol on Survival in Severe Chronic Heart Failure", The New England Journal of Medicine, 344(22): 1651-1658, May 31, 2001.
Page et al. "The Effect of Renal Denervation on Patients Suffering From Nephritis", The Journal of Clinical Investigation, 14(4): 443-458, Jul. 1935.
Papademetriou et al. "Renal Sympathetic Denervation for the Treatment of Difficult-to-Control or Resistant Hypertension", International Journal of Hypertension, 2011(Art.ID196518): 1-8, Jan. 2011.
Para Tech Coating "Parylene Properties", Para Tech Coating Inc., 1 P., 2010.
Perros et al. "Nebivolol for Improving Endothelial Dysfunction, Pulmonary Vascular Remodeling, and Right Heart Function in Pulmonary Hypertension", Journal of the American College of Cardiology, JACC, 65(7): 668-680, Feb. 24, 2015.
Pokushalov et al. "A Randomized Comparison of Pulmonary Vein Isolation With Versus Without Concomitant Renal Artery Denervation in Patients With Refractory Symptomatic Atrial Fibrillation and Resistant Hypertension", Journal of the American College of Cardiology, 60(13): 1163-1170, 2012.
Prapa et al. "Histopathology of the Great Vessels in Patients With Pulmonary Arterial Hypertension in Association With Congenital Heart Disease: Large Pulmonary Arteries Matter Too", international Journal of Cardiology, 168: 2248-2254, Available Online Feb. 28, 2013.
Prochnau et al. "Catheter-Based Renal Denervation for Drug-Resistant Hypertension by Using a Standard Electrophysiology Catheter", EuroIntervention, 7: 1077-1080, 2012.
Prochnau et al. "Efficacy of Renal Denervation With a Standard EP Catheter in the 24-h Ambulatory Blood Pressure Monitoring—Long-Term Follow-Up", International Journal of Cardiology, 157(3): 447-448, 14 Jun. 2012.
Quinn "Pre-Eclampsia and Partial Uterine Denervation", Medical Hypotheses, 64(3): 449-454, 2005. Abstract.
Rappaport "Treating Cardiac Disease With Catheter-Based Tissue Heating", IEEE Microwave Magazine, p. 57-64, Mar. 2002.
Reddy "Sound Intervention", Mount Sinai School of Medicine, MSSM, Presentation, 19 P., 2012.
Roehl et al. "Comparison of 3 Methods to Induce Acute Pulmonary Hypertension in Pigs", Comparative Medicine, 59(3): 280-286, Jun. 2009.
Rothman "FIM Evaluation of a New, Multi-Electrode RF System for Renal Denervation (Medtronic)", Medtronic Inc., PowerPoint Presentation, 8 P., 2012.
Rothman et al. "Pulmonary Artery Denervation Reduces Pulmonary Artery Pressure and Induces Histological Changes in an Acute Porcine Model of Pulmonary Hypertension", Circulation: Cardiovascular Interventions, 8(11): e002569-1-e002569-7, Published Online Nov. 17, 2015.
Rousselle "Experimental Pathways for the Evaluation of Extrinsic Renal Nerve Distribution, Density, and Quantification (Swine Model)", Alizee Pathology in Collaboration With Jack Skirkball Center for Cardiovascular Research, TCT, 20 P., Nov. 8, 2011.
Rousselle "Renal Artery Dervation: Experimental Pathways for the Evaluation of Extrinsic Renal Nerve Distribution, Density, and Quantification (Swine Model)", Alizee Pathology, Cardiovascular Research Foundation, Nov. 8, 2011.
Sakakura et al. "Methodological Standardization for the Pre-Clinical Evaluation of Renal Sympathetic Denervation", JACC: Cardiovascular Interventions. 7(10): 1184-1193, Published Online Sep. 14, 2014.
Sangiorgi et al. "Histo-Morphometric Evaluation of 2D Characteristics and 3D Sympatetic Renal Nerve Distribution in Hypertensive Vs. Normotensive Patients", Department of Pathology, Department of Cardiology, University of Rome Tor Vergata, Department of Cardiology University of Modena and Reggio Emilia, Medtronic Cardiovascular, PowerPoint Presentation, TCT 2012, 22 P., 2012.
Sanni et al. "Is Sympathectomy of Benefit in Critical Leg Ischaemia Not Amenable to Revascularisation?", Interactive CardioVascular and Thoracic Surgery, 4: 478-483, 2005.
Scheinert "Cardiosonic TIVUS™ Technology: An Intra-Vascular Ultrasonic Catheter for Targeted Renal Denervation", Center for Vascular Medicine, Park Hospital Leipzig, Germany, PowerPoint Presentation, TCT 2012, 16 P., 2012.
Schelegle et al. "Vagal Afferents Contribute to Exacerbates Airway Responses Following Ozone and Allergen Challenge", Respiratory Physiology & Neurobiology, 181(3): 277-285, May 31, 2012.
Schlaich "Long-Term Follow Up of Catheter-Based Renal Denervation for Resistant Hypertension Confirms Durable Blood Pressure Reduction", Hypertension & Kidney Disease Laboratory, Baker IDI Heart & Diabetes Institute, Melbourne VIC, Australia, PowerPoint Presentation, TCT 2012, 22 P., 2012.
Schlaich et al. "Renal Sympathetic-Nerve Ablation for Uncontrolled Hypertension", New England Journal of Medicine, 361(9): 932-934, Aug. 27, 2009.
Schnyder et al. "Common Femoral Artery Anatomy is Influenced by Demographics and Comorbidity: Implications for Cardiac and Peripherial Invasive Studies", Catheterization and Cardiovascular Interventions, 53(3): 289-295, Jul. 2001.
Schwartz "Strategies to Model Efficacy of Hypertension Devices", EuroPCR 2013, The Leading Cardiovascular Course, 24 P., 2013.
Shelton Jr. et al. "A Nondestructive Technique to Measure Pulmonary Artery Diameter and Its Pulsatile Variations", Journal of Applied Physiology, 33(4): 542-544, Oct. 1972.
Shung "Doppler Flow Measurements", Diagnostic Ultrasound—Imaging and Blood Flow Measurements, Chap.5:103-104, 2006.
Sievert et al. "Catheter-Based Technology Alternatives for Renal Denervation", CardioVascular Center Frankfurt, Germany, TCT 2012, Miami, FL, USA, Oct. 22-26, 2012, PowerPoint Presentation, 35 P., Oct. 2012.
Simonneau et al. "Updated Clinical Classification of Pulmonary Hypertension", Journal of the American College of Cardiology, 54(1/Suppl.S): S43-S54, Jun. 30, 2009.

(56) References Cited

OTHER PUBLICATIONS

Sitbon et al. "Beyond a Single Pathway: Combination Therapy in Pulmonary Arterial Hypertension", European Respiratory Review, 25(142): 408-417, Dec. 2016.
SOLVD Investigators "Effect of Enalapril on Survival in Patients With Reduced Left Ventricular Ejection Fractions and Congestive Heart Failure", The New England Journal of Medicine, 325(5): 293-302, Aug. 1, 1991.
Souchon et al. "Monitoring the Formation of Thermal Lesions With Heat-Induced Echo-Strain Imaging: A Feasibility Study", Ultrasound in Medicine & Biology, 31(2): 251-259, 2005.
Stefanadis "Vincristine Local Delivery for Renal Artery Denervation", Athens, Greece, PowerPoint Presentation, TCT 2012, 21 P., 2012.
Steigerwald et al. "Morphological Assessment of Renal Arteries After Radiofrequency Catheter-Based Sympathetic Denervation in a Porcine Model", Journal of Hypertension, 30(11): 2230-2239, Nov. 2012.
Swierblewska et al. "An Independent Relationship Between Muscle Sympathetic Nerve Activity and Pulse Wave Velocity in Normal Humans", Journal of Hypertension, 28: 979-984, 2010.
Symplicity HTN-1 Investigators "Catheter-Based Renal Sympathetic Denervation for Resistant Hypertension: Durability of Blood Pressure Reduction Out to 24 Months", Hypertension, 57: 911-917, Mar. 14, 2011.
Symplicity HTN-2 Investigators "Renal Sympathetic Denervation in Patients With Treatment-Resistant Hypertension (The Symplicity HTN-2 Trial): A Randomised Controlled Trial", The Lancet, 376(9756): 1903-1909, Published Online Nov. 17, 2010.
Symplicity HTN-2 Investigators "Renal Sympathetic Denervation in Patients With Treatment-Resistant Hypertension (The Symplicity HTN-2 Trial): A Randomised Controlled Trial", The Lancet, 376: 1903-1909, Dec. 4, 2010.
Szabo "Diagnostic Ultrasound Imaging Inside Out", Academic Press Series in Biomedical Engineering, 2004.
Techavipoo et al. "Temperature Dependence of Ultrasonic Propagation Speed and Attenuation in Excised Canine Liver Tissue Measured Using Transmitted and Reflected Pulses", Journal of the Acoustical Society of America, 115(6): 2859-2865, Jun. 2004.
Thenappan et al. "Beta-Blocker Therapy Is Not Associated With Adverse Outcomes in Patients With Pulmonary Arterial Hypertension. A Propensity Score Analysis", Circulation Heart Failure, 7(6): 903-910, Published Online Oct. 2, 2014.
Tibshirani "Regression Shrinkage and Selction via the Lasso: A Retrospective", Journal of the Royal Statistical Society, Series B: Statistical Methodology, 73(Pt.3): 273-282, 2011.
Tibshirani "Regression Shrinkage and Selection via the Lasso", Journal of the Royal Statistical Society, Series B: Methodological, 58(1): 267-288, 1996.
Toorop et al. "Clinical Results of Carotid Denervation by Adventitial Stripping in Caotid Sinus Syndrome", Europan Journal of Vascular and Endovascular Syndrome, 39: 146-152, 2010.
Tyreus et al. "Two-Dimensional Acoustic Attenuation Mapping of High-Temperature Interstitial Ultrasound Lesions", Physics in Medicine and Biology, 49: 533-546, 2004.
Van Albada et al. "Biological Serum Markers in the Managment of Pediatric Pulmonary Arterial Hypertension", Pediatric Research, 63(3): 321-327, Mar. 2008.
Van Campen et al. "Bisoprolol in Idiopathic Pulmonary Arterial Hypertension: an Explorative Study", European Respiratory Journal, 48: 787-796, 2016.
Velez-Roa et al. "Increased Sympathetic Nerve Activity in Pulmonary Artery Hypertension", Circulation, 110(10): 1308-1312, Sep. 7, 2004.
Verloop et al. "The Effects of Renal Denervation on Renal Haemodynamics", Interventions for Hypertenison & Heart Failure, Abstracts of EuroPCR & AsiaPCR/SingLIVE 2013, May 21, 2013.
Virmani "Translation Medicine and Renal Denervation: Pre-Clinical Animal Models and Histoanatomy", CVPath Institute, Gaithersburg, MD, USA, PowerPoint Presentation.
Voskuil et al. "Percutaneous Renal Denervation for the Treatment of Resistant Essential Hypertension; The First Dutch Experience", Netherlands Heart Journal, 19(7-8): 319-323, Aug. 2011.
Warwick et al. "Trackless Lesions in Nervous Tissues Produced by High Intensity Focused Ultrasound (High-Frequency Mechanical Waves)", Journal of Anatomy, 102(3): 387-405, 1968.
Wikswo Jr. et al. "Magnetic Field of a Nerve Impulse: First Measurements", Science, 208: 53-55, Apr. 4, 1980.
Wilcox "Resistant Hypertension and the Role of the Sympathetic Nervous System", Medtronic, 30 P.
Williams et al. "Laser Energy Source in Surgical Atrial Fibrillation Ablation: Preclinical Experience", The Annals of Thoracic Surgery, 82: 2260-2264, 2006.
Witkowski "Future Perspective in Renal Denervation: Congestive Heart Failure, Insulin Resistance and Sleep Apnea", Innovations in Cardiovascular Interventions, ICI Meeting 2011, Tel Aviv, Israel, Dec. 4-6, 2011, 23 P., 2011.
Witkowski et al. "Effects of Renal Sympathetic Denervation on Blood Pressure, Sleep Apnea Course, and Glycemic Control in Patients With Resistant Hypertension and Sleep Apnea", Hypertension, 58(4): 559-565, Oct. 2011.
Witkowski et al. "Effects of Renal Sympathetic Denervation on Blood Pressure, Sleep Apnea Course, and Glycemic Control in Patients With Resistant Hypertension and Sleep Apnea", Hypertension, 58: 559-565, Aug. 15, 2011.
Witte et al. "Imaging Current Flow in Lobster Nerve Cord Using the Acoustoelectric Effect", Applied Physics Letters, 90: 163902-1-163902-3, 2007.
Wolf-De Jonge et al. "25 Years of Laser Assisted Vascular Anastomosis (LAVA): What Have We Learned?", European Journal of Vascular and Endovascular Surgery, 27(5): 466-476, May 2004.
Worthington et al. "Changes in Ultrasound Properties of Porcine Kidney Tissue During Heating", Ultrasound in Medicine & Biology, 27(5): 673-682, 2001.
Worthington et al. "Ultrasound Properties of Human Prostate Tissue During Heating", Ultrsound in Medicine & Biology, 28(10): 1311-1318, 2002.
Wright "On a Relationship Between the Arrhenius Parameters From Thermal Damage Studies", Transactions of the ASME, Technical Brief, Journal of Biomechanical Engineering, 125(2): 300-304, Apr. 9, 2003.
Wu et al. "A Quality Control Program for MR-Guided Focused Ultrasound Ablation Therapy", Journal of Applied Clinical Medical Physics, 3(2): 162-167, Spring 2002.
Wu et al. "Noninvasive Cardiac Arrhythmia Therapy Using High-Intensity Focused Ultrasound (HIFU) Ablation", International Journal of Cardiology, 166(2): e28-e30, Available Online Feb. 26, 2013.
Xu et al. "Experimental Nerve Thermal Injury", Brain, 117: 375-384, 1994.
Zeller "Percutaneous Renal Denervation System. The New Ultrasound Solution for the Mangament of Hypertension", Paradise Ultrasound Denervation System, ReCor Medical, 27 P., 2013.
Zhou et al. "Pulmonary Artery Denervation Attenuates Pulmonary Arterial Remodeling in Dogs With Pulmonary Arterial Hypertension Induced by Dehydrogenized Monocrotaline", JACC: Cardiovascular Interventions, 8(15): 2013-2023, Dec. 28, 2015.

\* cited by examiner

FIG. 19A
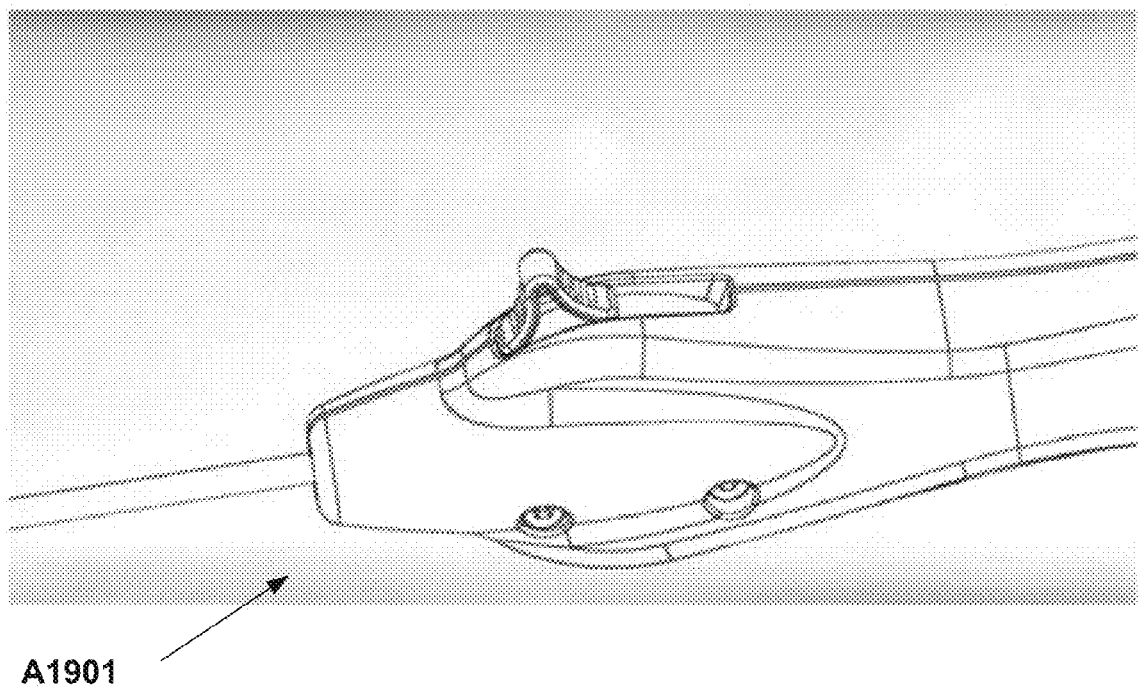
A1901
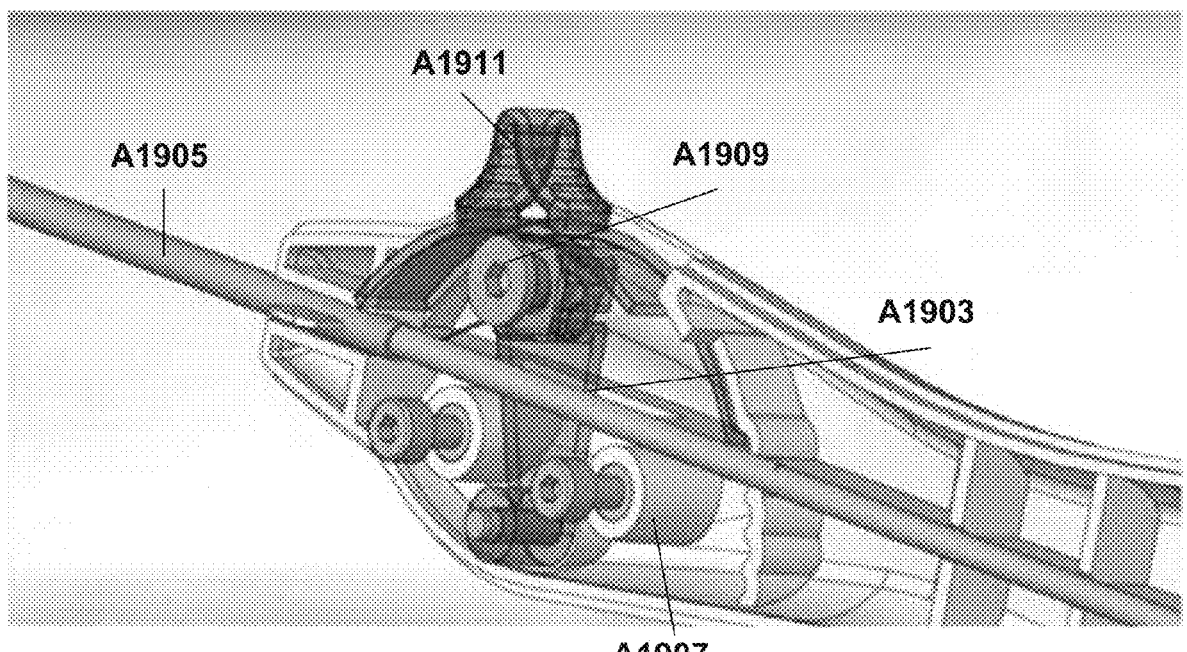
FIG. 19B

FIG. 34A
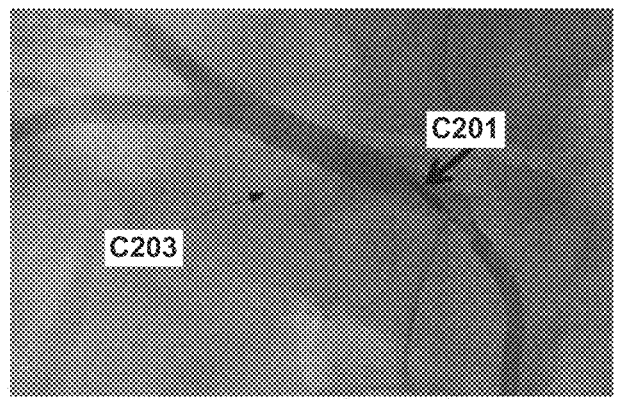
FIG. 34B
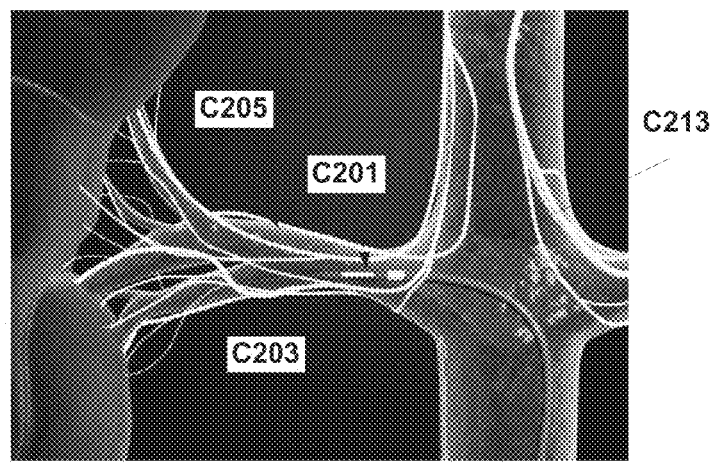
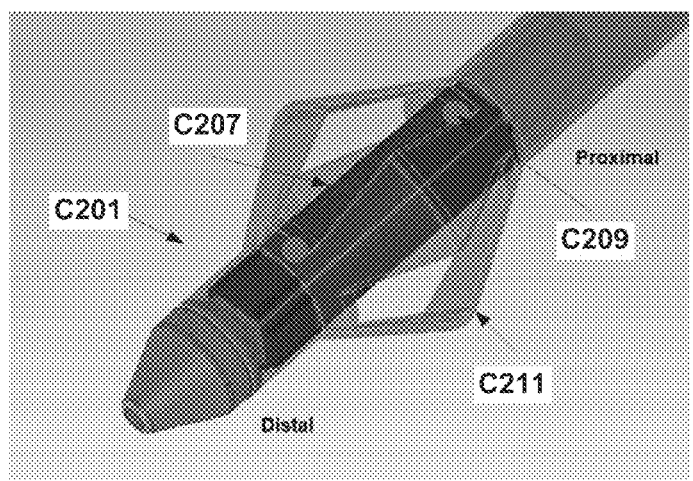
FIG. 34C
FIG. 34D
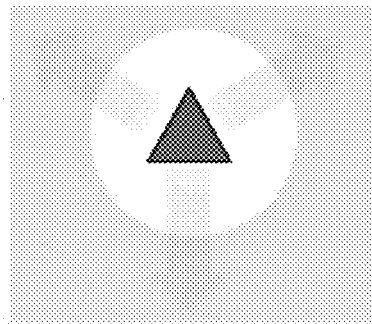
FIG. 34E
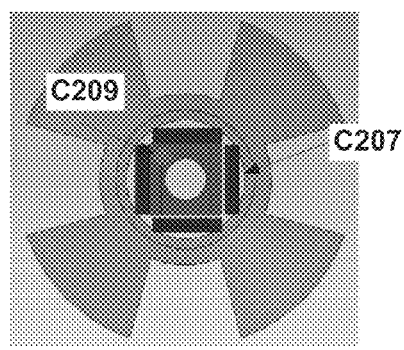

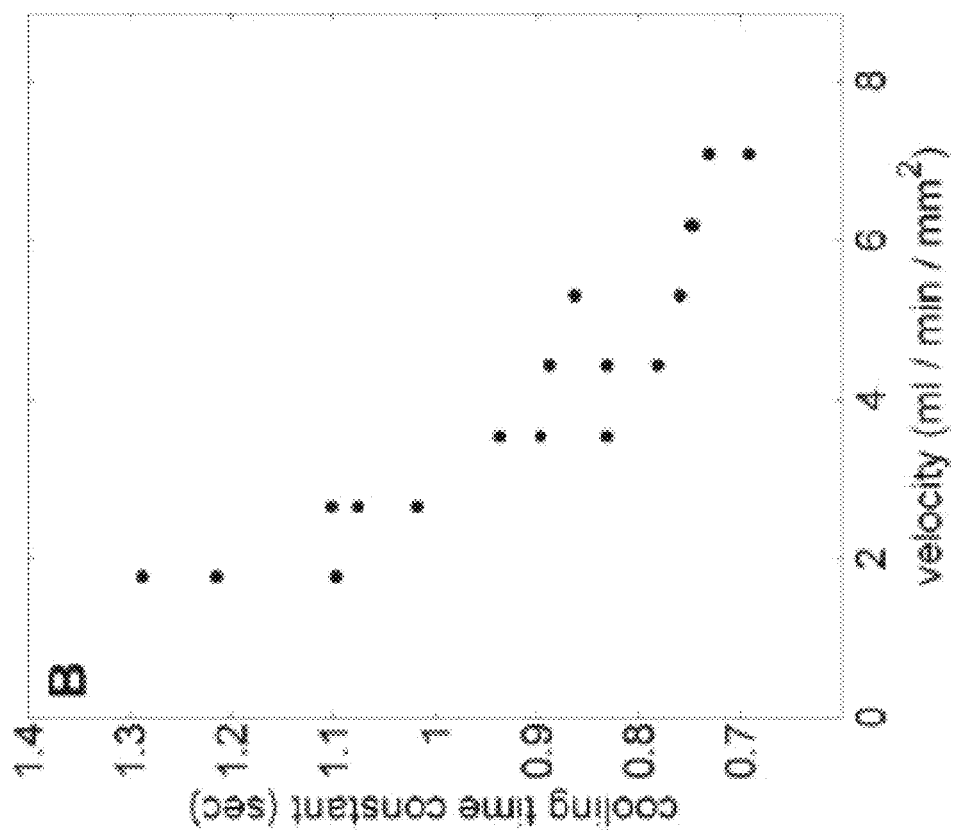
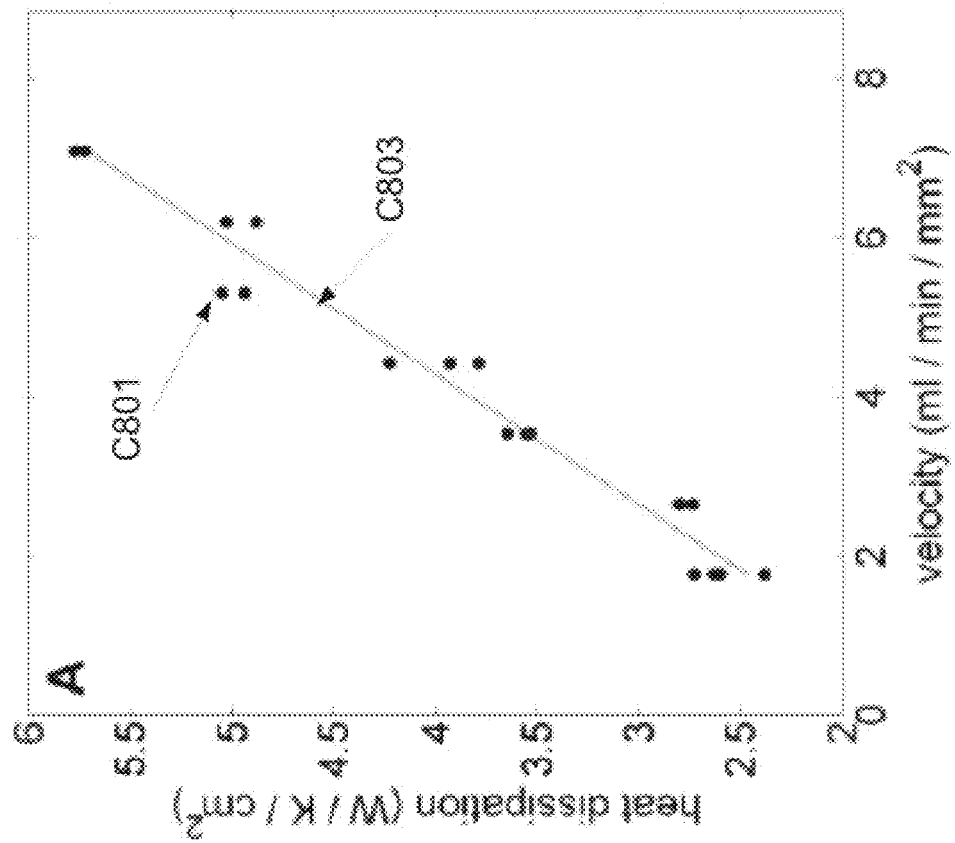
FIG. 40B
FIG. 40A

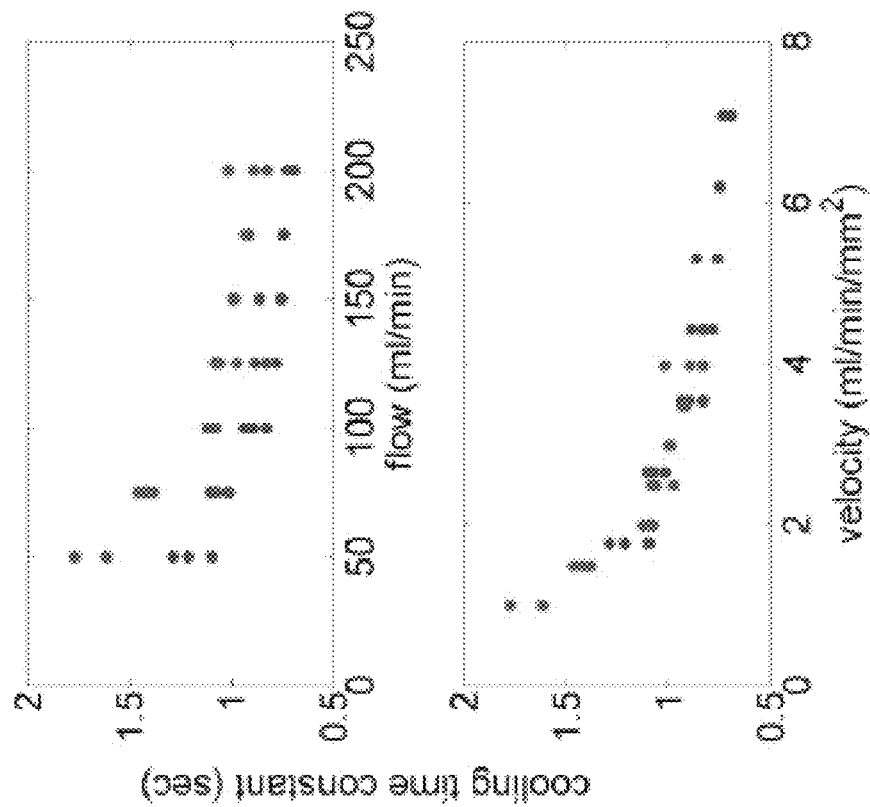
FIG. 41B
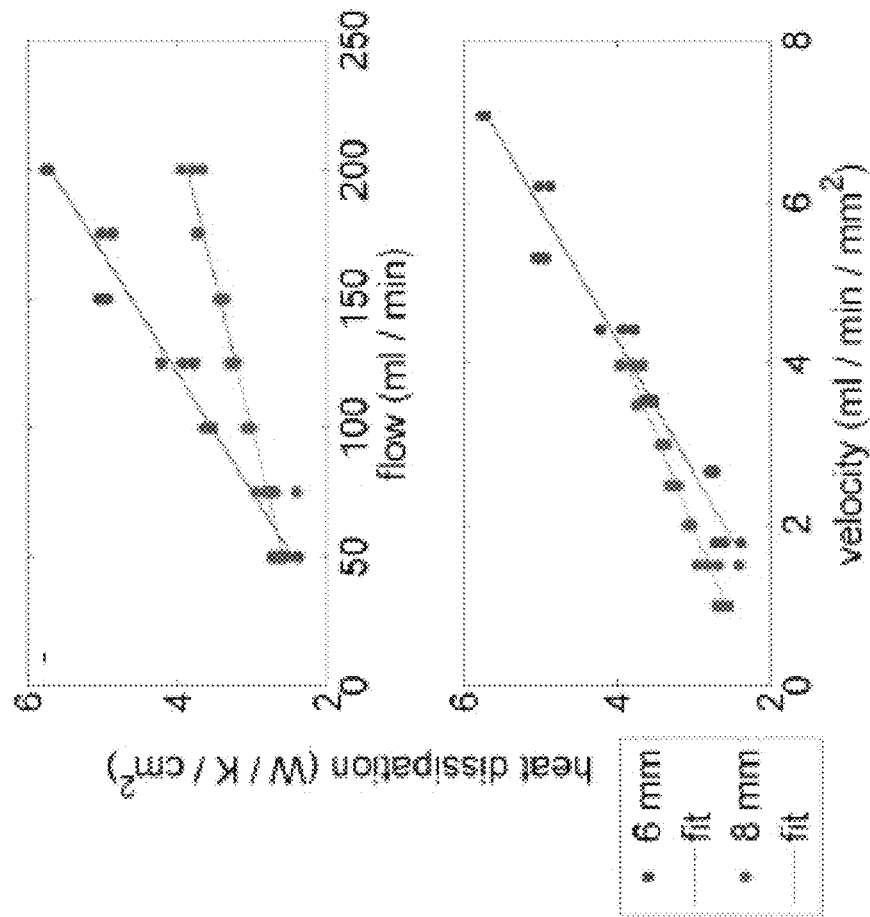
FIG. 41A
FIG. 41D
FIG. 41C

FIG. 54A
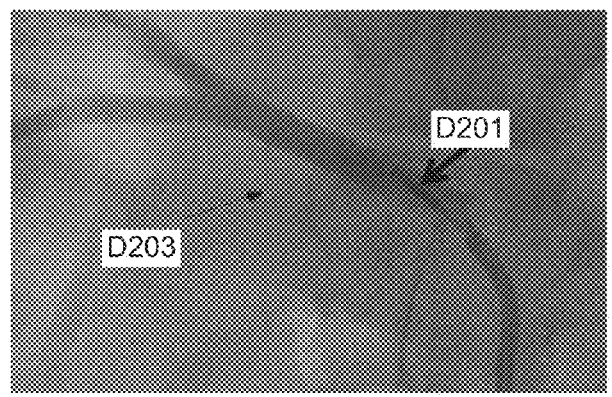
FIG. 54B
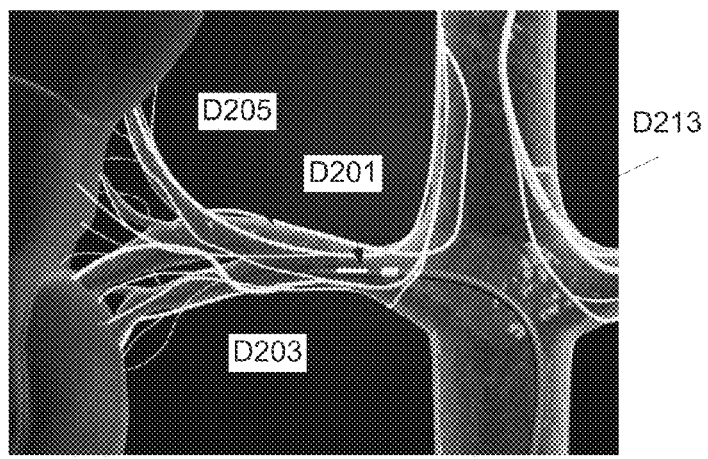
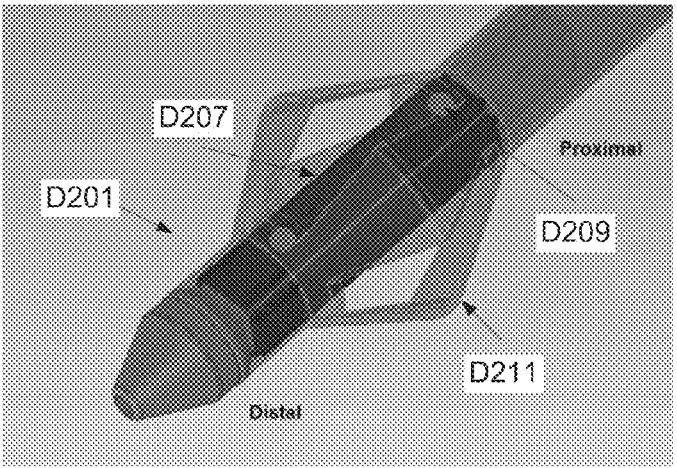
FIG. 54C
FIG. 54D
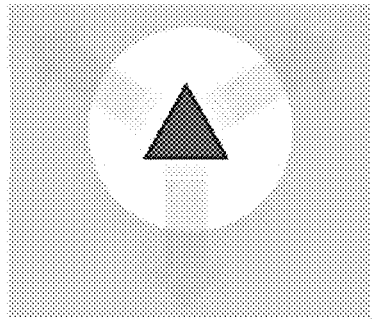
FIG. 54E
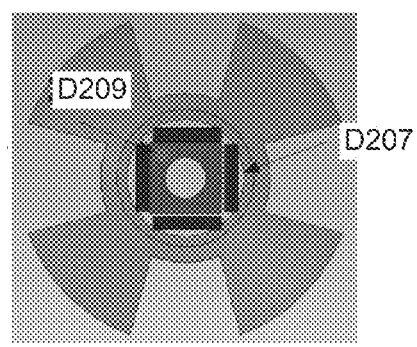

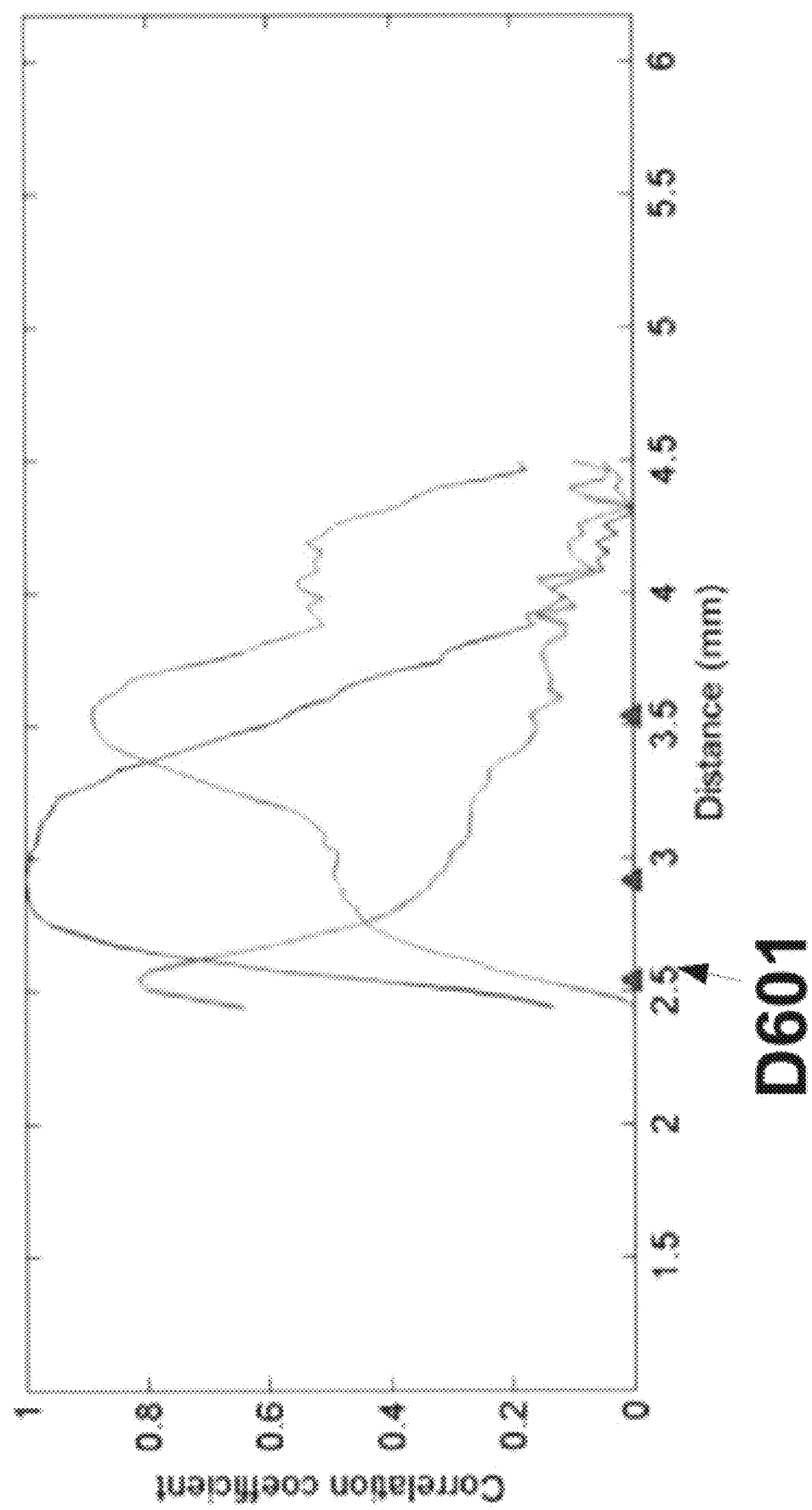

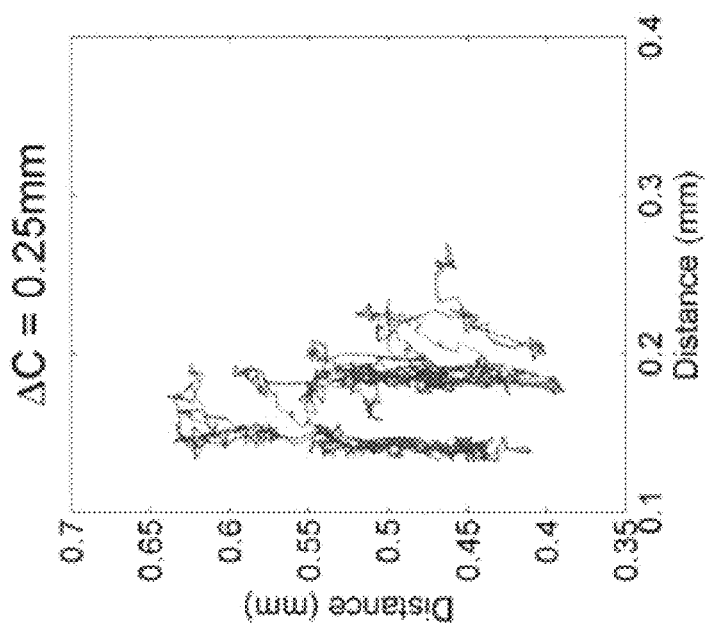
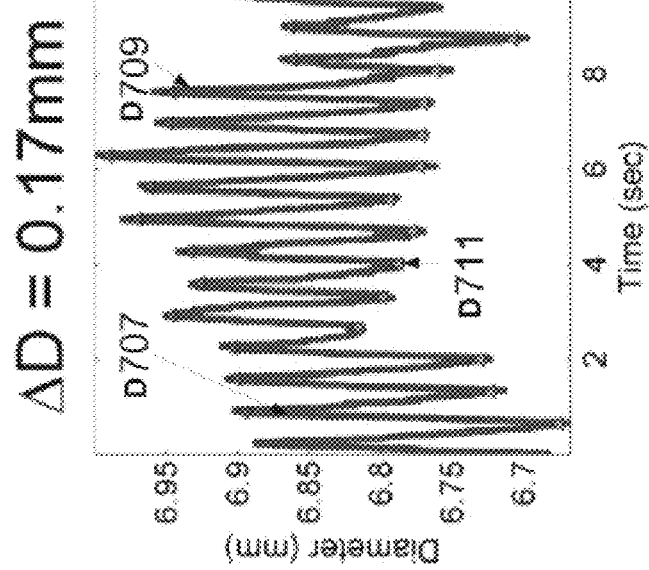
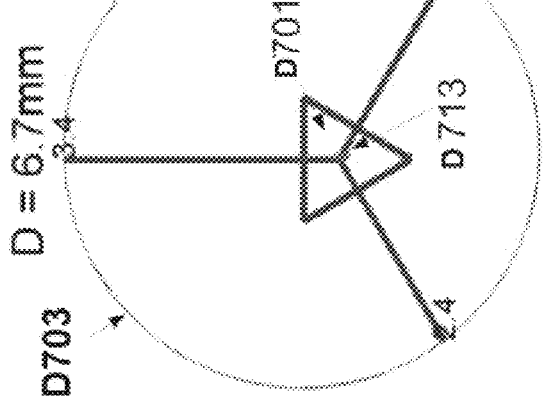

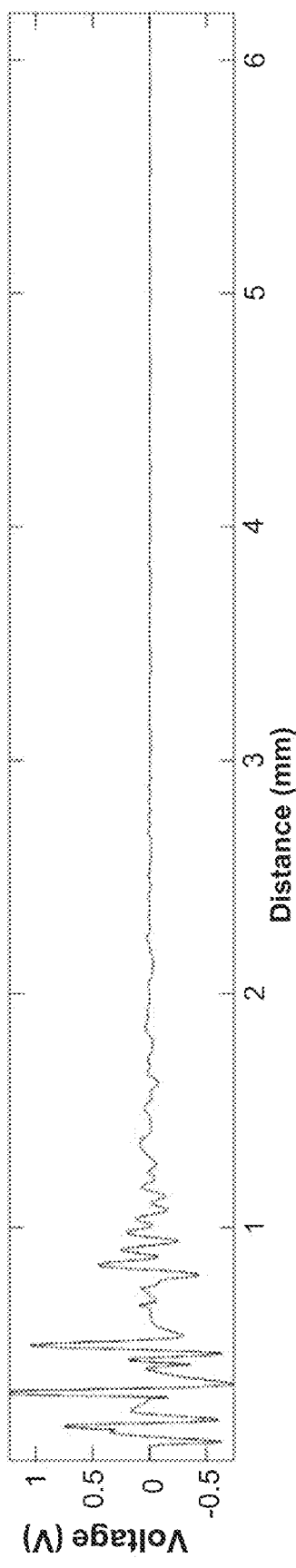
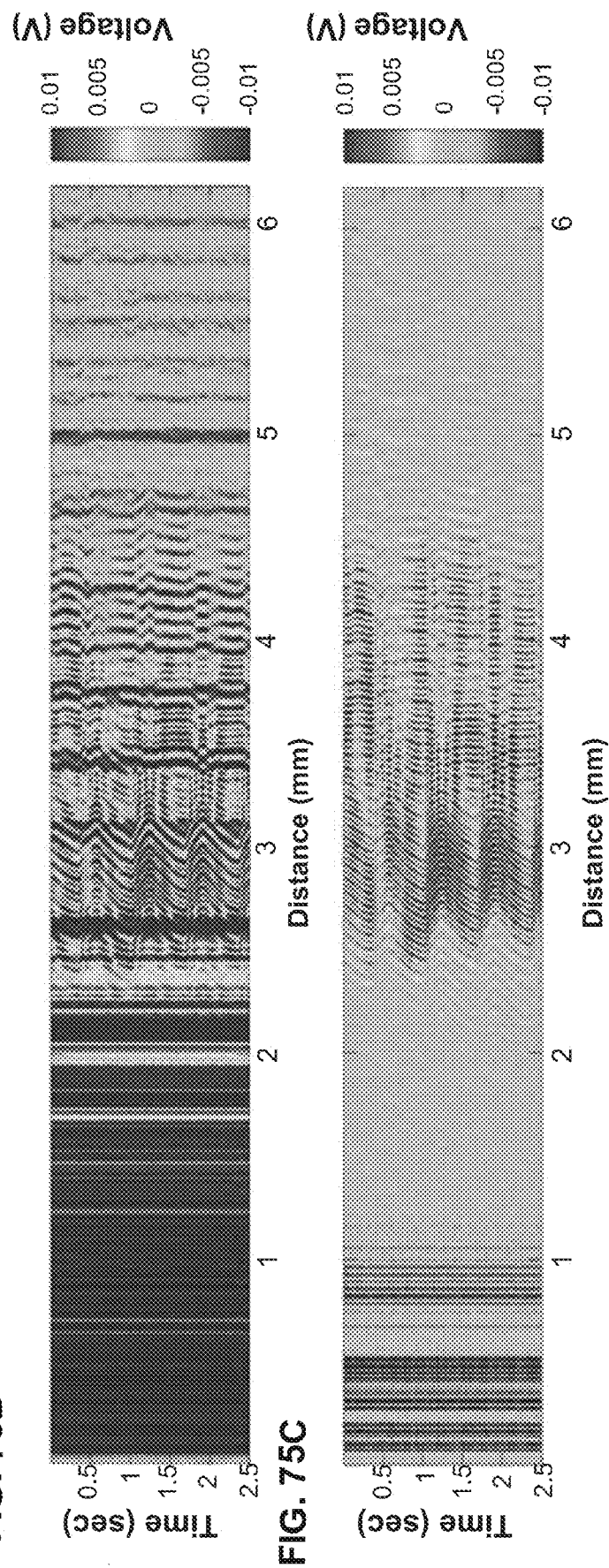
FIG. 75A
FIG. 75B
FIG. 75C

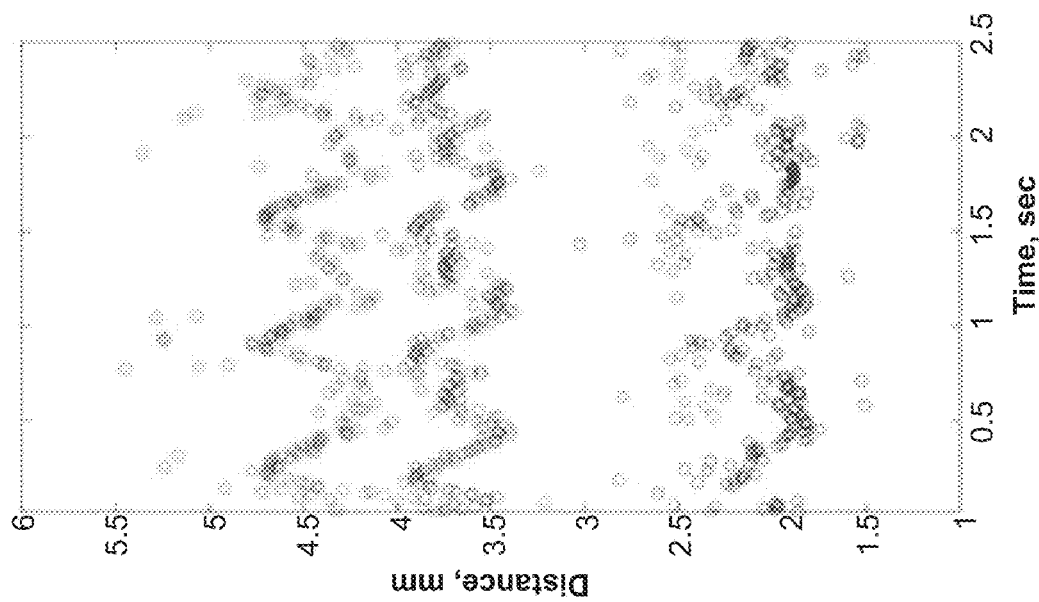
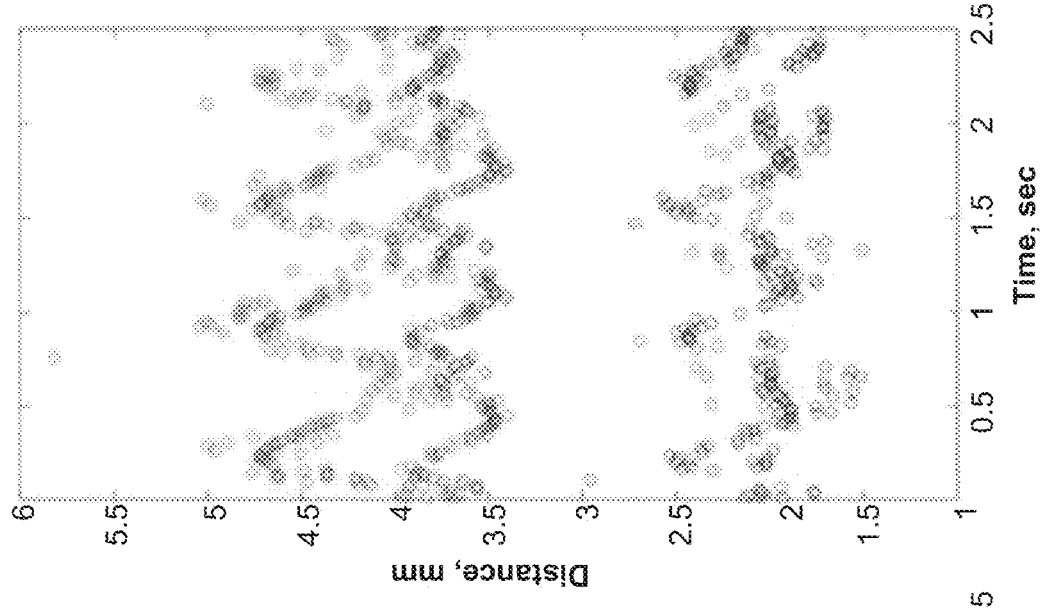
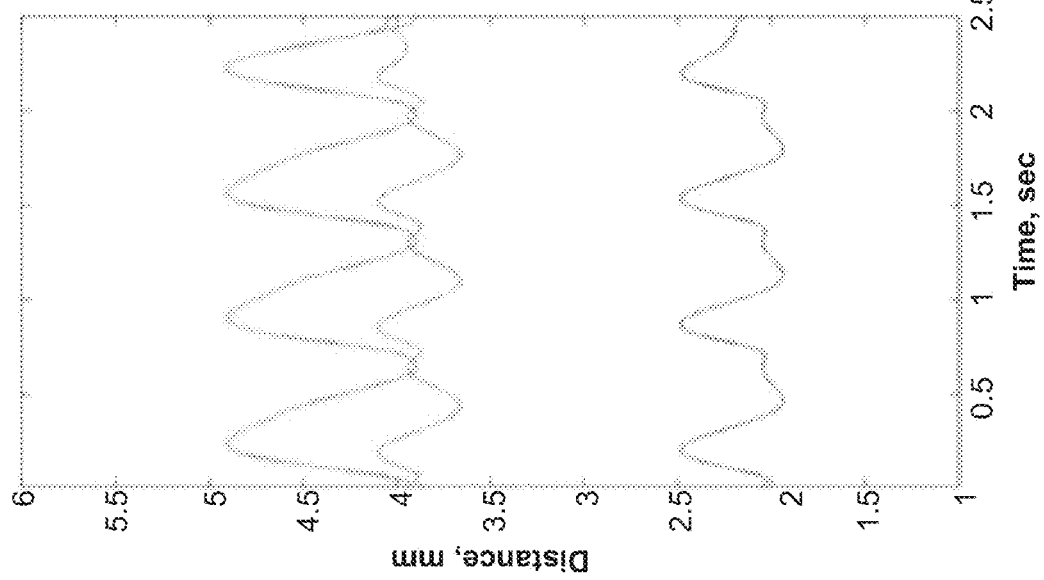

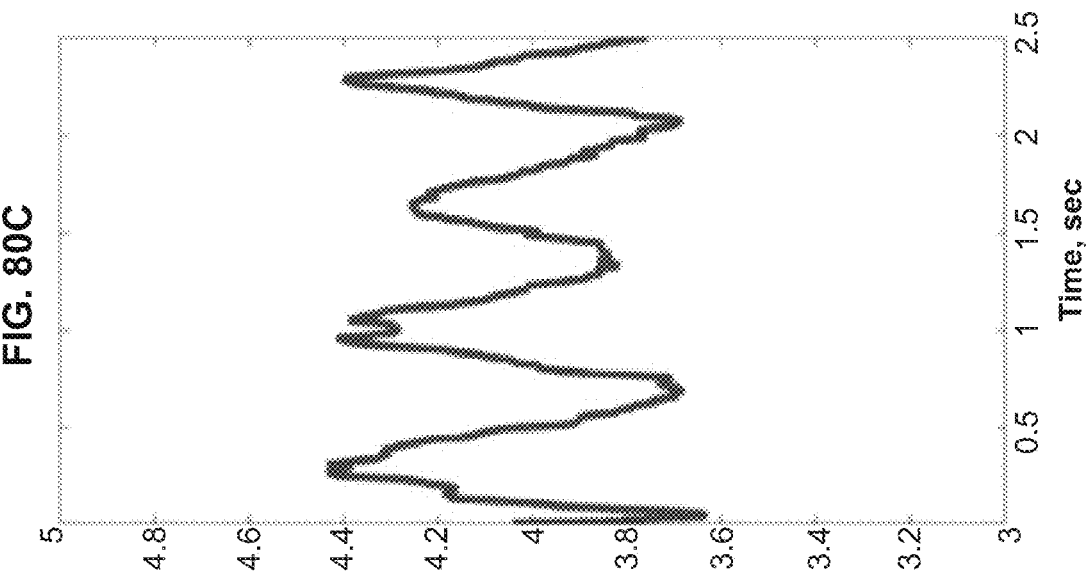
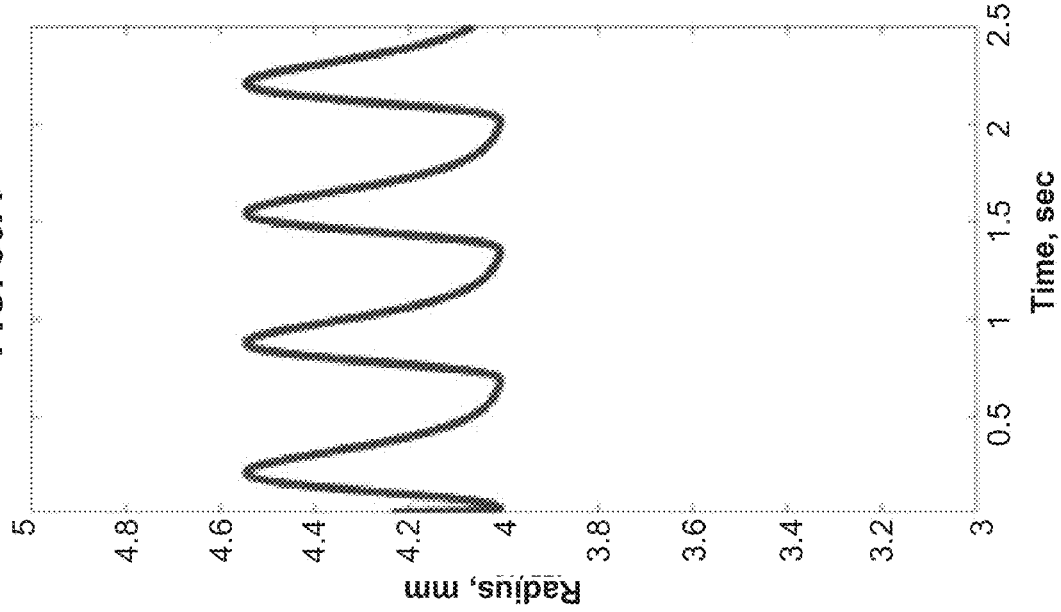
FIG. 80A
FIG. 80B
FIG. 80C

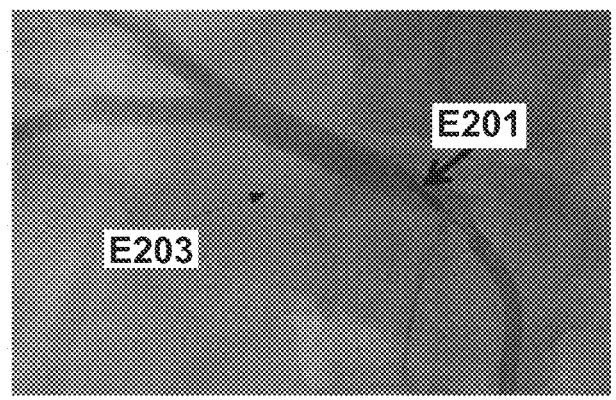
FIG. 82A
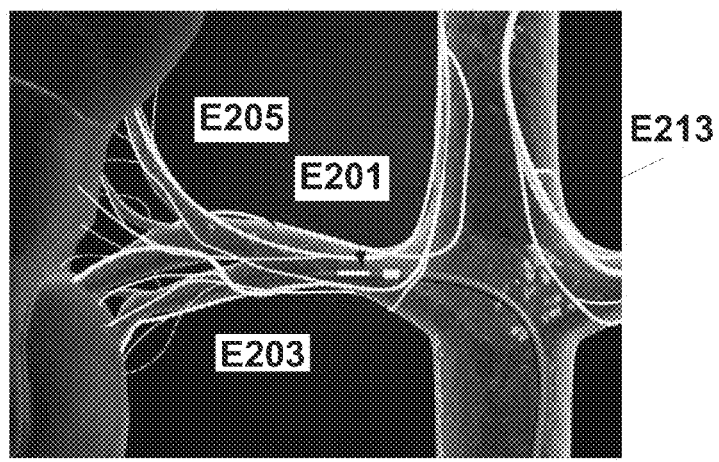
FIG. 82B
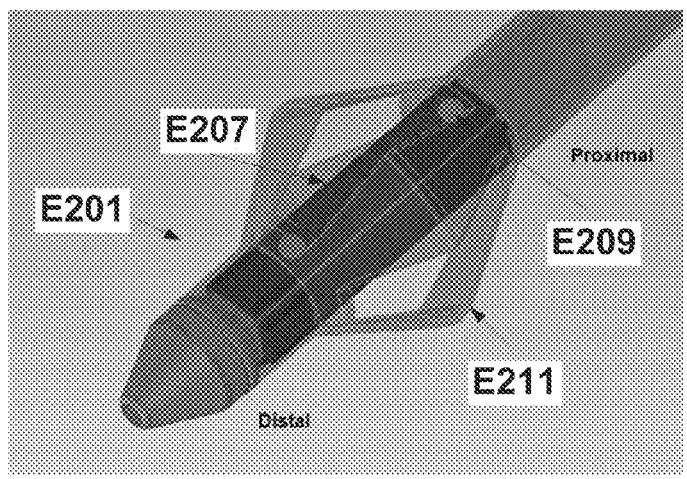
FIG. 82C
FIG. 82D
FIG. 82E
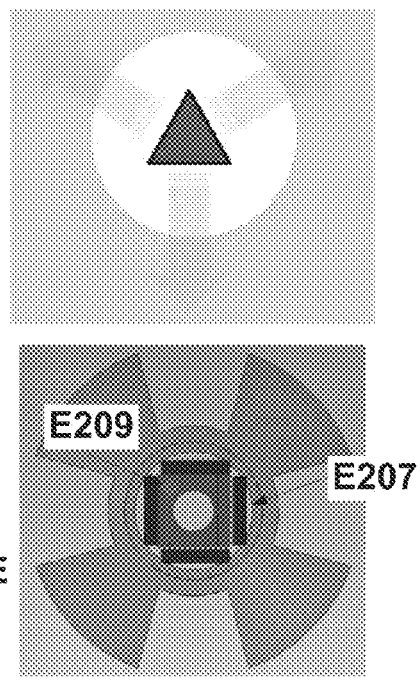

Pre

Post

E601 → Locating thermistors at two distal points along the artery

E603 → Injecting a cold liquid into the artery

E605 → Continuously recording the temperatures of both thermistors

E607 → Detecting changes in recorded temperatures

E609 → Calculating the flow rate

FIG. 86

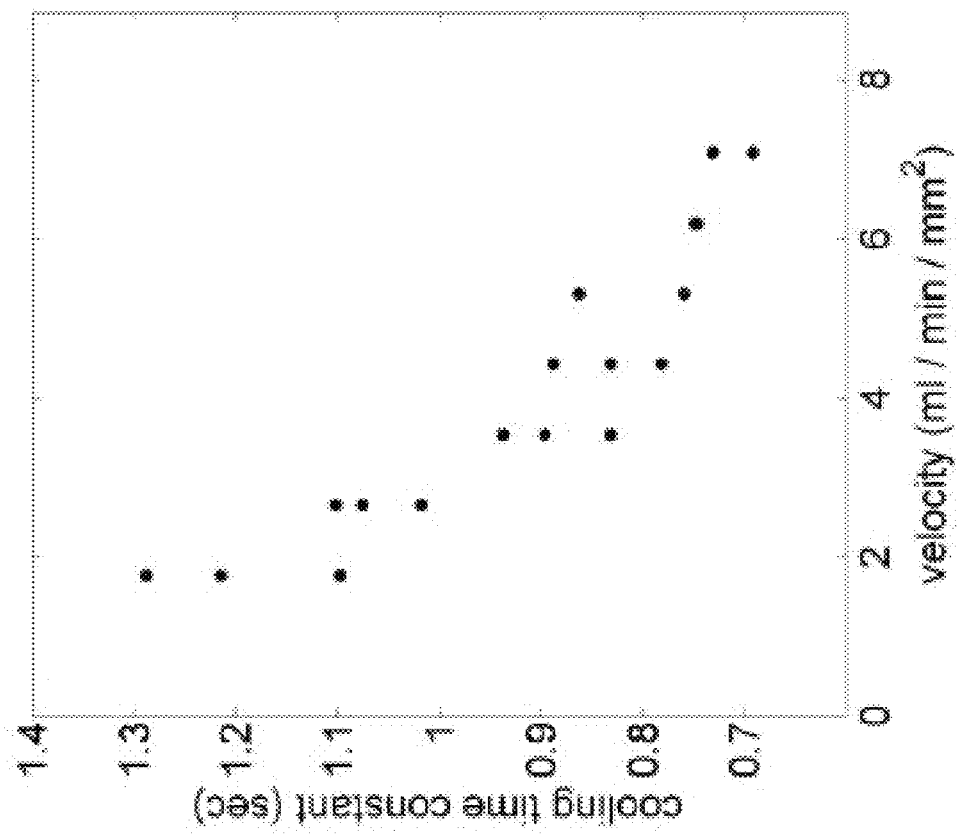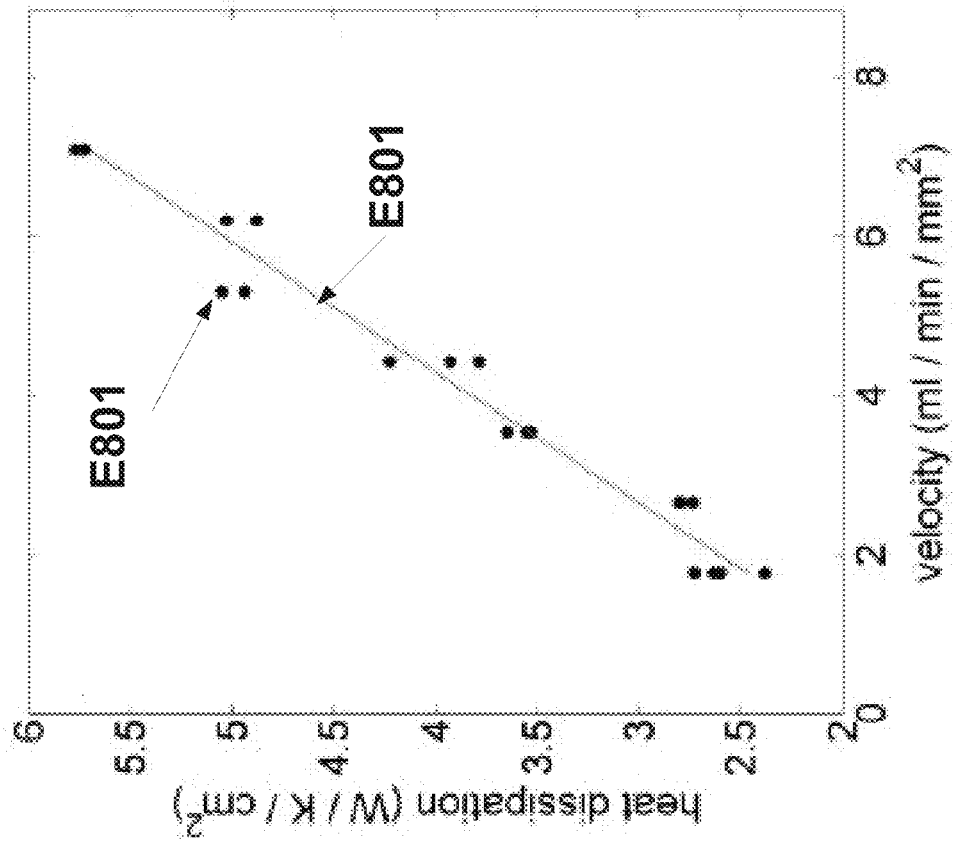

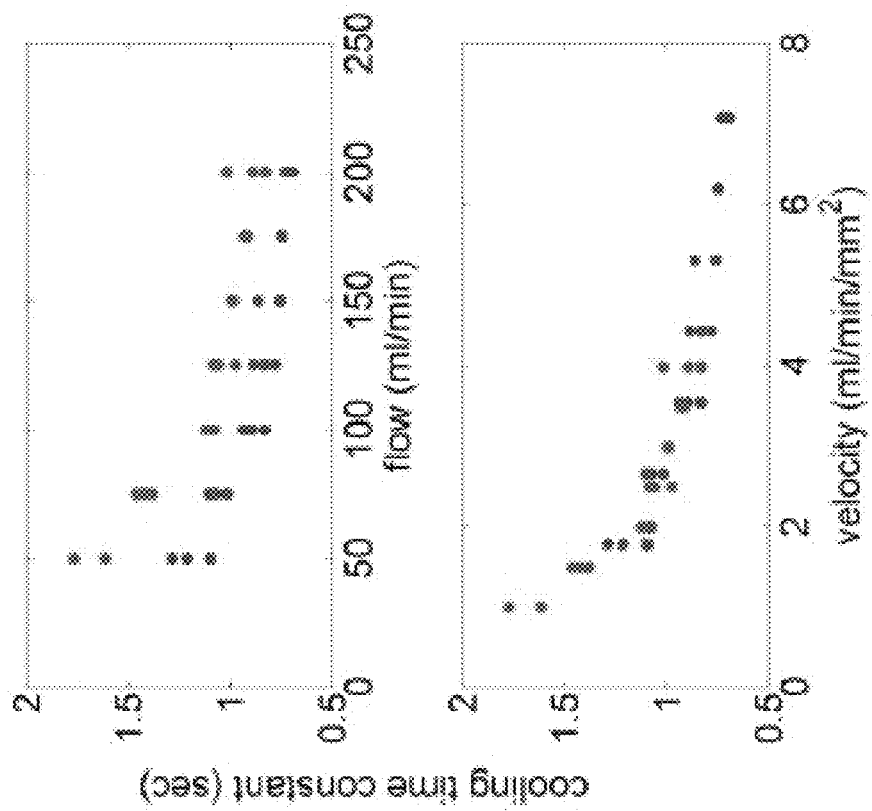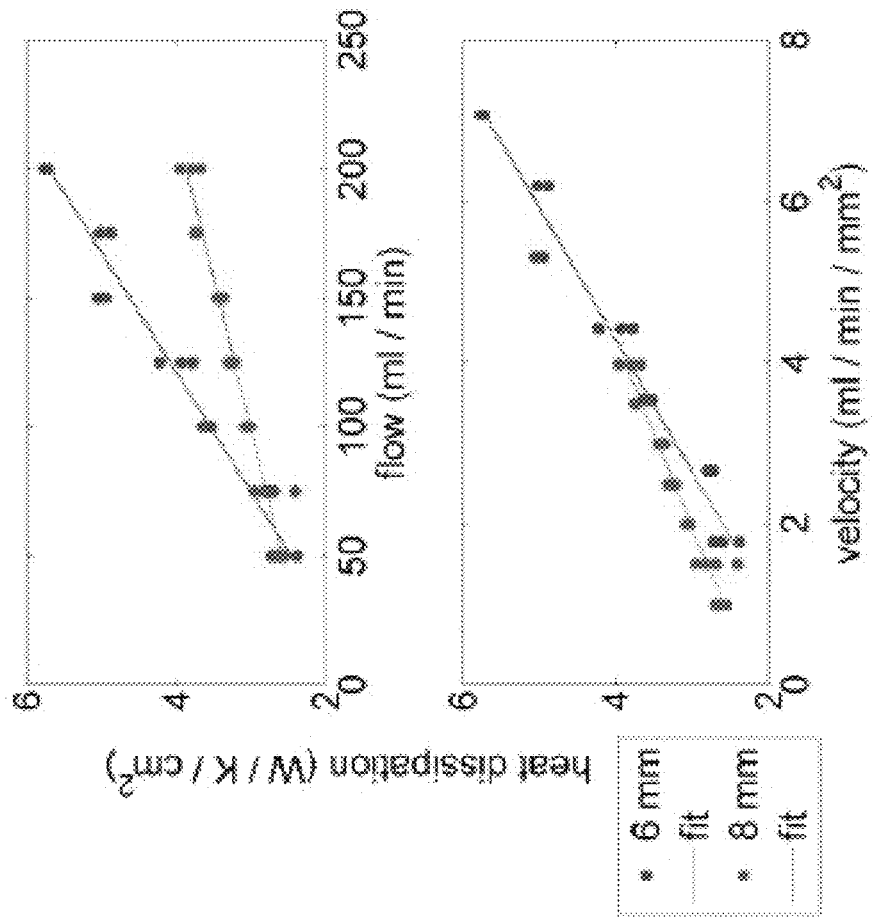

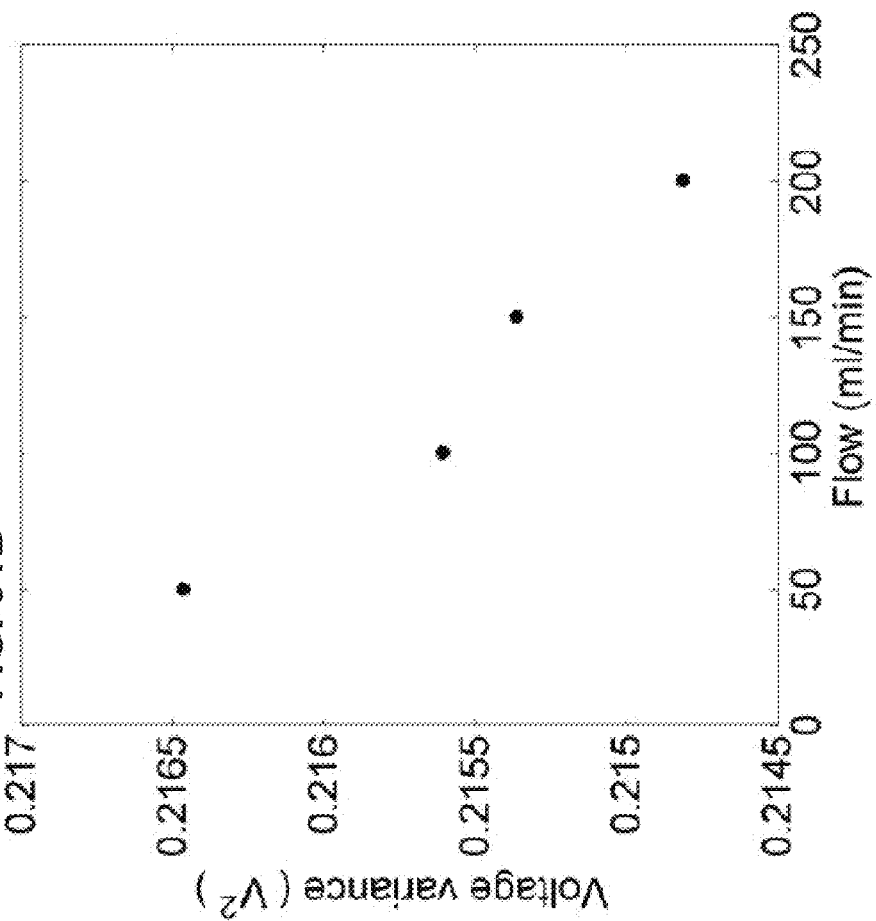
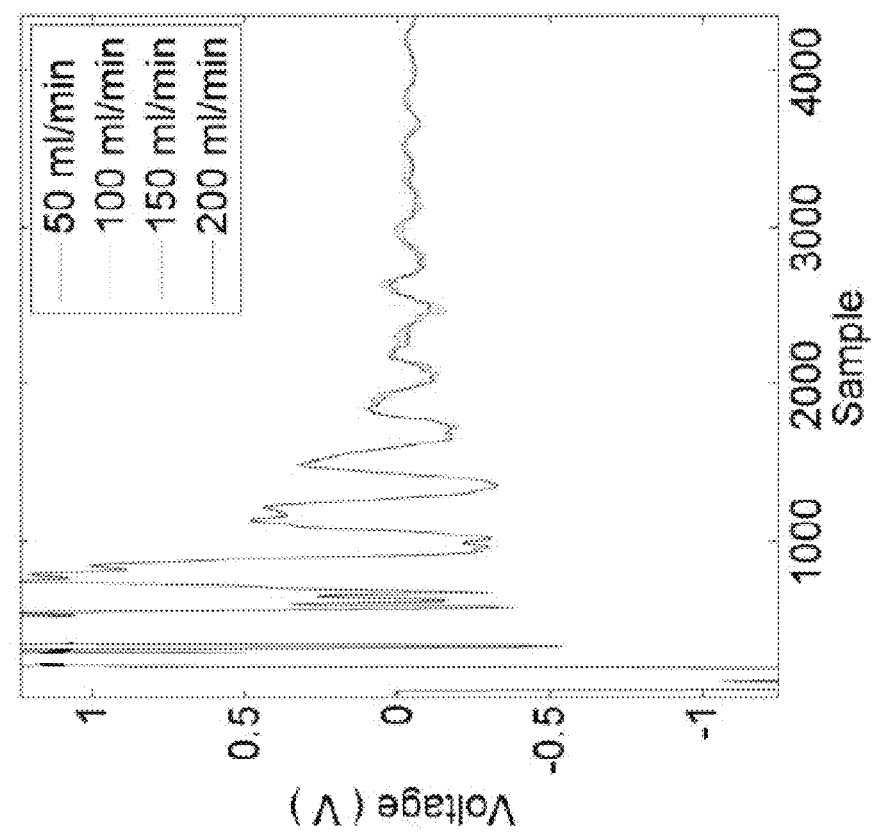
FIG. 91B
FIG. 91A

E1301 — Inserting a catheter connected to a pressure transducer into the artery

E1303 — Measuring arterial blood pressure

FIG. 93

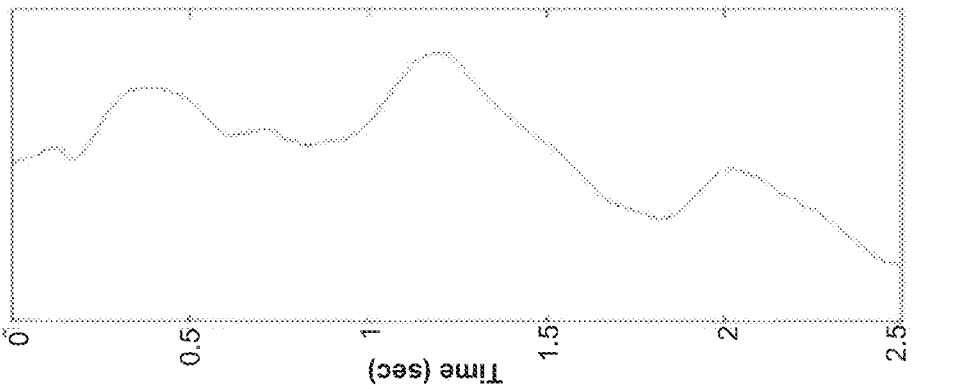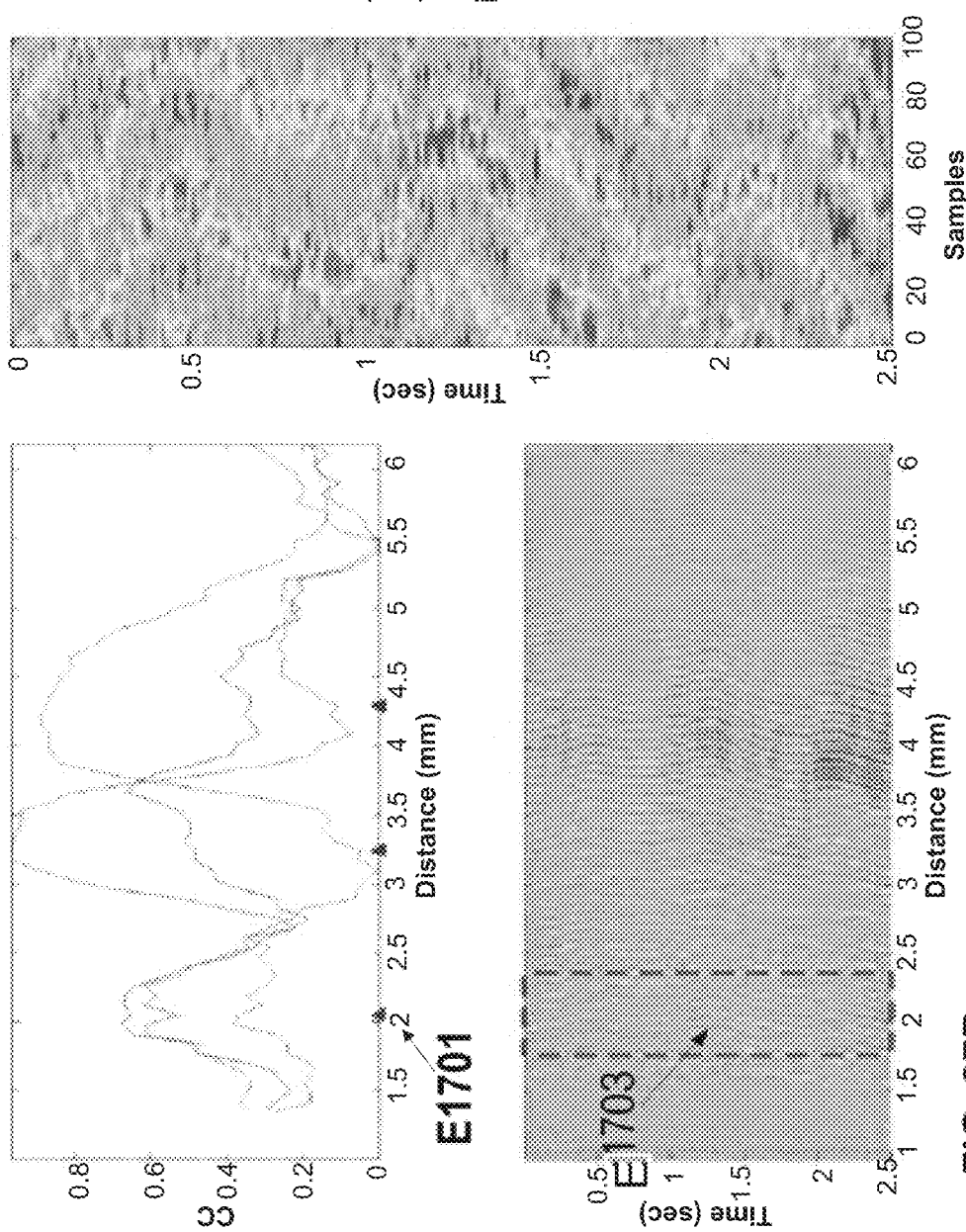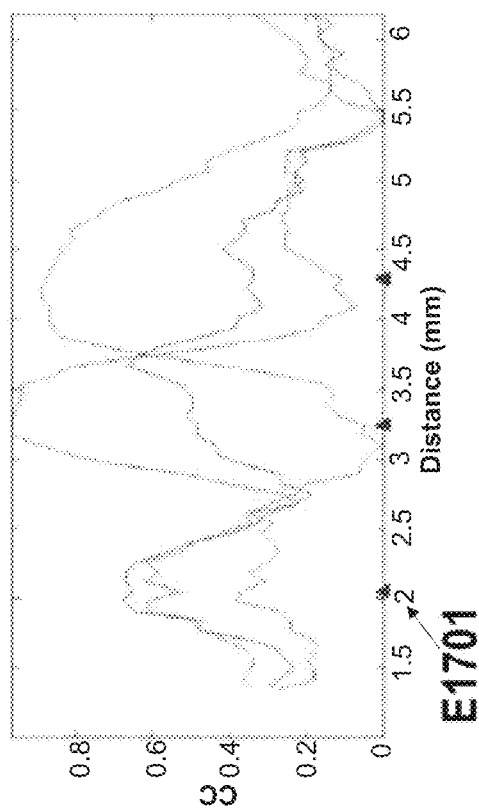
FIG. 97A  FIG. 97B  FIG. 97C  FIG. 97D

DEVICES AND METHODS FOR RENAL DENERVATION AND ASSESSMENT THEREOF

RELATED APPLICATIONS

This application is National Phase of PCT Patent Application No. PCT/IL2014/050457 having International filing date of May 22, 2014, which claims the benefit of priority under 35 USC § 119(e) of U.S. Provisional Application Nos. 61/931,890 filed on Jan. 27, 2014, 61/931,838 filed on Jan. 27, 2014, 61/924,848 filed on Jan. 8, 2014, 61/924,778 filed on Jan. 8, 2014 and 61/826,583 filed on May 23, 2013. The contents of the above applications are all incorporated by reference as if fully set forth herein in their entirely.

FIELD AND BACKGROUND OF THE INVENTION

EP publication number EP2455133 A1 to Dekker et al. discloses "A catheter (700, 800, 1206) comprising: a shaft with distal (808, 906, 1004, 1208) and proximal ends (1006), wherein the distal end comprises at least one array of capacitive micromachined ultrasound transducers (308, 402, 404, 500, 512, 600, 604, 802, 1008) with an adjustable focus for controllably heating a target zone (806, 1014, 1210); and a connector (1012) at the proximal end for supplying the at least one array of capacitive micromachined ultrasound transducers with electrical power and for controlling the adjustable focus."

U.S. Pat. No. 5,938,582 to Ciamacco et al. discloses "An apparatus for centering a radiation delivery device at a selected location in a body vessel such as a coronary artery. An elongated catheter is insertable into the body vessel until the catheter head is in the desired position. The catheter has a guidewire lumen, inflation lumen and treatment lumen running lengthwise. The catheter head includes an expandable mechanism for engaging the vessel internal wall with the treatment lumen centered in the vessel. At least one channel is provided extending past the expandable mechanism so that a fluid, such as blood, can perfuse past the catheter head. A radiation delivery device, such as a wire having a radiation source at the distal end can be inserted into the treatment lumen to uniformly irradiate the vessel wall at the selected location."

Modulation and inhibition of renal sympathetic afferent and/or efferent nerve activity has been proven to contribute to the treatment of hypertension and related disorders. Renal denervation treatment has been shown, for example, to reduce sympathetic activation of the kidney, reduce renin release, and/or change vasodilatation properties of the renal artery, thereby modulating the patient's blood pressure. The denervation treatment may affect one or more physiological parameters, assessment of which may indicate an effectiveness of the treatment.

U.S. patent application Ser. No. 13/327,161 to Stahmann et al. discloses "A catheter includes a flexible shaft having a length sufficient to access a patient's renal artery relative to a percutaneous access location. A treatment arrangement is provided at a distal end of the shaft and configured for deployment in the renal artery. The treatment arrangement includes an ablation arrangement configured to deliver renal denervation therapy. An occlusion arrangement is configured for deployment in the renal artery and for altering blood flow through the renal artery during or subsequent to renal denervation therapy delivery. A monitoring unit is configured for monitoring for a change in one or more physiologic parameters influenced by the renal denervation therapy. The monitoring unit is configured to produce data useful in assessing effectiveness of the renal denervation therapy based on the physiologic parameter monitoring".

PCT Publication No. 2012/033974 A2 to Smith discloses "A transducer arrangement causes target tissue of the body to vibrate and senses resulting vibration of the target tissue. Changes in one or more mechanical properties of the target tissue are measured based on the sensed vibration. Changes in one or more electromechanical properties of the target tissue can also be measured based on the sensed vibration and various electrical parameters. An output indicative of the measured changes in the one or more mechanical and/or electromechanical properties of the target tissue is generated. Changes in elasticity of the target tissue, for example, can be measured based on the sensed vibration, such as changes resulting from ablation of the target tissue".

PCT Patent Publication No. WO1994023652 to Talhami et al. titled "Tissue characterization using intravascular echoscopy" discloses: An intravascular transducer (10) at a location within an artery (15) is used to obtain frames of ultrasound during at least one cardiac cycle of a subject. The ultrasound data obtained is processed to produce an indication of the elasticity of the artery wall (12), namely the average fractional deformation of each region of the arterial tissue. This 'elasticity' data is displayed simultaneously with an image of the artery wall. The presence of degenerative plaque is determined using intravascular echoscopy and monitoring the frequency content of echoes produced by backscatter from the tissue in the artery wall. The parameter known as the 'attenuation slope' of the ultrasound echoes is used as a measure of their frequency content. The values of this parameter are displayed on the conventional grey scale image of the artery cross section at the point of measurement."

WO Patent Publication No. 2013030743 to Jie Wang discloses "System and method for locating and identifying nerves innervating the wall of arteries such as the renal artery are disclosed. The present invention identifies areas on vessel walls that are innervated with nerves; provides indication on whether energy is delivered accurately to a targeted nerve; and provides immediate post-procedural assessment of the effect of energy delivered to the nerve. The method includes at least the steps to evaluate a change in physiological parameters after energy is delivered to an arterial wall; and to determine the type of nerve that the energy was directed to (none, sympathetic or parasympathetic) based on the evaluated results. The system includes at least a device for delivering energy to the wall of blood vessel; sensors for detecting physiological signals from a subject; and indicators to display results obtained using said method. Also provided are catheters for performing the mapping and ablating functions."

U.S. Patent Publication No. 20120296329 to Kok-Hwee Ng discloses "A catheter apparatus for assessing denervation comprises: an elongated catheter body; a deployable structure coupled to the catheter body, the deployable structure being deployable outwardly from and contractible inwardly toward the longitudinal axis of the catheter body; one or more ablation elements disposed on the deployable structure to move outwardly and inwardly with the deployable structure; one or more stimulation elements spaced from each other and disposed on the deployable structure to move with the deployable structure, the stimulation elements being powered to supply nerve stimulating signals to the vessel; and one or more recording elements spaced from each other and from the stimulation elements, the recording elements being disposed on the deployable structure to move with the deployable structure, the recording elements configured to record response of the vessel to the nerve stimulating signals."

SUMMARY OF THE INVENTION

According to an aspect of some embodiments of the invention there is provided an intravascular catheter comprising an elongated shaft and a head for ultrasonic transmission, said head comprising a chassis comprising at least three facets, each facet sized to receive a piezoelectric transceiver; a plurality of piezoelectric transceivers peripherally mounted onto the facets of the chassis, the transceivers electrically activated for emitting ultrasound energy suitable for tissue ablation, and for receiving echo signals. In some embodiments, the chassis is cannulated. In some embodiments, the chassis comprises a substantially polygonal cross section profile. In some embodiments, the cross section profile is triangular, and 3 transceivers are mounted onto the facets of the chassis.

In some embodiments, a diameter of a circumscribing circle of the head is 2.2 mm or smaller. In some embodiments, a summed area of radially outward facing surfaces of the transceivers covers at least 70% of the radially outward facing facets of the chassis. In some embodiments, the summed area of radially outward facing surfaces of the transceivers covers no more than 95% of the radially outward facing facets of the chassis. In some embodiments, radially outward facing surfaces of the transceivers are flat.

In some embodiments, the chassis is shaped to align said transceivers with respect to a longitudinal axis of the chassis. In some embodiments, the catheter further comprises a PCB configured between the chassis and at least one of the transceivers.

In some embodiments, the PCB comprises one or more bendable extensions in contact with transceivers different than the transceiver mounted on top of the PCB. In some embodiments, the transceiver is mounted onto the PCB by an array of contact nodes, the nodes small enough to provide the transceiver with low damping.

In some embodiments, the contact nodes are electrically conductive. In some embodiments, the PCB comprises one or more vias for at least one of electrically and mechanically coupling between the PCB and the chassis.

In some embodiments, an electrically conductive strip surrounding an exterior surface of the catheter head serves as a current conducting electrode for activation of the transceivers. In some embodiments, the strip is folded so that it does not protrude beyond a periphery of the head in the radial direction. In some embodiments, the chassis is electrically conductive. In some embodiments, the transceivers are rectangular.

In some embodiments, an energy beam emitted by a transceiver diverges at an angle ranging between 5-20 degrees. In some embodiments, when said catheter is positioned within a vessel, the one or more transceivers are configured to emit ultrasound energy suitable for ablating tissue when the transceivers are positioned a distance away from a vessel wall. Optionally, the distance is large enough to permit blood to flow between a transceiver and the wall to cool the wall.

In some embodiments, a distancing device is assembled onto the catheter head for pushing the one or more transceivers away from the vessel wall. In some embodiments, the ultrasound is unfocused. In some embodiments, a lumen of the cannulated chassis comprises wiring connections.

In some embodiments, the blood vessel is the renal artery and the tissue comprises nerve tissue. In some embodiments, a lumen of the cannulated chassis is sized to receive a guide wire for delivering the catheter over a guide wire.

In some embodiments, a shaft of the catheter comprises two or more portions having different degrees of stiffness. In some embodiments, the catheter comprises one or more temperature sensors positioned in proximity to the transceivers. Optionally, the temperature sensors are connected in parallel. In some embodiments, the chassis is formed of metal. In some embodiments, the echo signals are signals reflected by walls of the blood vessel.

According to an aspect of some embodiments of the invention there is provided a PCB configured for mechanically and electrically connecting between a non-flat chassis and a piezoelectric transceiver, the PCB comprising one or more bendable extensions for fitting closely around the chassis. In some embodiments, the extensions connect between the PCB and one or more piezoelectric transceivers different from the piezoelectric transceiver mounted onto the PCB.

According to an aspect of some embodiments of the invention there is provided a system for operating an intravascular ultrasonic catheter by a physician, comprising: a console connected on one end to the catheter; a software installed on the console, the software configured for analyzing echo signals received by the plurality of piezoelectric transceivers, and a foot pedal activated by the physician for producing excitation of the transceivers.

In some embodiments, the console is configured for providing an excitation having a sinusoidal waveform at a duration and power suitable to ablate tissue using the catheter. In some embodiments, the software is configured for implementing signal processing algorithms for monitoring the ultrasound emission. Optionally, monitoring comprises estimating a distance between a transceiver and an artery wall using the reflected echo signals.

According to an aspect of some embodiments of the invention there is provided a method for operating a catheter comprising a plurality of transceivers, comprising: exciting the plurality of transceivers at an operating frequency that is in the range of ±10% from an average resonant frequency of the transceivers, the operating frequency different from the resonant frequency of any of the plurality of transceivers.

In some embodiments, the plurality of transceivers are pre-selected with resonant frequencies that are in the range of ±0.5% from each other. In some embodiments, the transceivers are excited at a frequency ranging between 8-13 MHz. Optionally, the transceivers are excited with a sinusoidal waveform. Optionally, the transceivers are excited with a similar frequency. In some embodiments, the transceivers are excited simultaneously to emit ultrasound energy towards multiple tissue regions located circumferentially around the blood vessel.

According to an aspect of some embodiments of the intravascular catheter comprising an elongated shaft and a head for ultrasonic transmission, the head comprising a chassis comprising a plurality of facets, each facet sized to receive a piezoelectric transceiver; a plurality of piezoelectric transceivers peripherally mounted onto the facets of the chassis, the mounting comprising an array of electrically conductive glue drops. Optionally, the glue drops are equally distributed on each of the facets. In some embodiments, a diameter of a glue drop ranges between 100-250 µm. In some embodiments, the array comprises 4-12 glue drops.

According to an aspect of some embodiments of the invention there is provided an apparatus for positioning at least one ultrasound transceiver of a catheter away from a wall of a body lumen, the apparatus comprising one or more leaflets which are radially collapsible to provide for insertion or removal of the catheter to and from the lumen; the apparatus comprising an open configuration in which the one or more leaflets position the catheter relative to two opposing walls of the lumen; wherein an area between the ultrasound transceiver and the wall defined by the one or more leaflets in the open configuration is large enough to permit a sufficient amount of blood to flow through to cool at least one of the transceiver and the lumen wall enough to prevent thermal damage to the inner wall. In some embodiments, the bendable leaflet is formed of at least two layers having different stiffness properties, a first layer rigid enough to maintain the open configuration, and a second layer soft enough to reduce mechanical damage to the lumen wall.

In some embodiments, the one or more leaflets are collapsible by a structural transformation or by being elastic enough to be pushed in the radial direction. In some embodiments, a distance between the transceiver and the wall is at least 0.5 mm. In some embodiments, at least a portion of the leaflet is bendable into a curved configuration having a curvature radius ranging between 0.1-0.5 mm.

In some embodiments, the apparatus is formed as a hollow slotted cylinder, and the at least one leaflet is a portion of the cylinder wall configured between two of the slots. In some embodiments, the apparatus comprises at least three bendable leaflets distributed circumferentially around the catheter. In some embodiments, the slots are arranged to expose at least a portion of a surface of the ultrasound transceivers. In some embodiments, at least one of a shape and size of a slot is determined according to at least one of a shape and size of a transceiver surface being exposed through the slot.

In some embodiments, the apparatus does not interfere with a beam of ultrasound emitted by the transceiver. In some embodiments, the apparatus does not interfere with echo signals from the vessel wall received by the transceivers. In some embodiments, the leaflet defines a slanted surface which funnels blood towards the vessel wall to cool the wall. In some embodiments, one or more of a curvature of the leaflet in the open configuration, an elasticity of a material of the leaflet facing the lumen wall, and/or one or more edges of the leaflets are selected not to cause substantial mechanical damage to the vessel wall.

In some embodiments, in a closed (collapsed) configuration, a diameter of the apparatus is 2.2 mm or smaller. In some embodiments, a bend of a leaflet is centered with respect to a longitudinal axis of the transceiver. Additionally or alternatively, a bend of a leaflet is configured in proximity to a proximal end or to a distal end of the transceiver. In some embodiments, the leaflet bends into a trapezoidal configuration. In some embodiments, the apparatus is coupled to an element extending to a proximal end of the catheter, the element operable from externally to a human body to remotely cause the distancing apparatus to open or close.

Optionally, the element is a guide wire tube extending within the catheter. In some embodiments, the apparatus is marked by a radiopaque marker for visualization under fluoroscopy. In some embodiments, a width of a leaflet ranges between 0.2 mm to 2 mm to reduce mechanical damage to the wall. In some embodiments, the apparatus further comprises one or more holes large enough to permit blood to flow through.

According to an aspect of some embodiments of the invention there is provided an apparatus for distancing at least one ultrasound transceiver of an intravascular catheter away from a blood vessel wall, the apparatus comprising at least one bendable leaflet; the leaflet formed of at least two layers having different stiffness properties. In some embodiments, a material from which the leaflet is formed of that faces the vessel wall is softer than a material facing the catheter.

According to an aspect of some embodiments of the invention there is provided a method for treating a blood vessel wall, comprising: inserting a catheter comprising one or more ultrasonic transceivers and a distancing apparatus into a blood vessel; remotely transferring the distancing apparatus to an open configuration for distancing the transceivers away from the wall; and activating the transceivers to emit ultrasound for treating the blood vessel wall. In some embodiments, distancing comprises centering the apparatus with respect to the blood vessel walls. In some embodiments, treating comprises thermally damaging nerve tissue using non-focused ultrasound. In some embodiments, transferring the apparatus to an open configuration comprises pulling a distal tip of the catheter in a proximal direction.

According to an aspect of some embodiments of the invention there is provided a method for assessing effectiveness of a renal denervation treatment, comprising analyzing at least one of echo signals reflected by an artery wall, and data acquired by at least one measurement device positioned within a renal artery, and assessing an effectiveness of a renal denervation treatment based on at least one of physical characteristics of the artery, and hemodynamic properties of blood flowing in the artery.

In some embodiments, assessing comprises estimating a change in the physical characteristics and hemodynamic properties which indicates a behavioral change of the wall tissue following neural modulation, carried out by the denervation. In some embodiments, the physical characteristics include artery wall stiffness. In some embodiments, hemodynamic properties include renal blood flow rate. In some embodiments, the measurement device is a temperature sensor. Optionally, blood flow rate is estimated according to a cross section area of said artery, estimated by analyzing the reflected echo signals, and according to blood flow velocity, indicated by temperature changes measured by the temperature sensor.

In some embodiments, the method further comprises emitting ultrasound energy towards the artery wall using at least one ultrasonic transceiver. Optionally, the transceiver is configured on a catheter adapted for insertion into the artery, the catheter further comprising at least one measurement device. In some embodiments, a plurality of transceivers are excited simultaneously to emit ultrasound towards the artery walls.

In some embodiments, analyzing comprises estimating a diameter of the artery based on signals reflected by the walls following emission of ultrasound. In some embodiments, two temperature sensors are positioned along a segment of the artery with a distance of at least 1 cm between them; and the method further comprises injecting cold liquid into the artery, and estimating flow rate based on a time in which a temperature drop is detected by at least one sensor, and a distance between the sensors. In some embodiments, at least one of the temperature sensors is positioned in proximity to the renal artery ostium. Optionally, a temperature of the cold liquid ranges between 4-25° C. In some embodiments, a sampling rate of the temperature sensors is determined according to a predefined estimation of flow velocity. In some embodiments, the hemodynamic property is blood flow velocity, estimated by exciting the transceiver with at least one excitation. Optionally, the when the transceiver is excited with at least one excitation, the method further comprises measuring a temperature of the transceiver; and estimating the velocity according to a heat dissipation rate of the transceiver.

In some embodiments, a power-law relation exists between the heat dissipation rate of the transceiver and the blood flow velocity. Optionally, a temperature of the transceiver is measured during the excitation. Optionally, the temperature is measured following the excitation, and the flow velocity is estimated according to a cooling time constant of the transceiver.

In some embodiments, the method further comprises estimating the flow velocity according to an impulse response of the transceiver following an excitation.

In some embodiments, blood flow velocity is estimated according to a damping of the transceiver. Optionally, a correlation exists between the impulse response of the transceiver and the blood flow velocity.

In some embodiments, a change in stiffness is estimated according to a Young's modulus of the artery wall, by determining a diameter of the artery over time by analyzing echo signals, measuring arterial blood pressure over time, and estimating the Young's modulus according to differences in diameter and differences in blood pressure over time. Optionally, the method is performed before and/or after a renal denervation treatment. Optionally, the method further comprises comparing an estimation of a Young's modulus before and after denervation to determine a change in stiffness, indicating the effectiveness of the denervation treatment. In some embodiments, a cross section area of the artery is calculated according to a diameter of the artery, the diameter is estimated by analyzing reflected echo signals, and the velocity is estimated using one or more of the methods described herein.

According to an aspect of some embodiments of the invention there is provided a method for assessing renal denervation effectiveness using neural stimulation, comprising: measuring a physiological parameter being at least one of an artery diameter, arterial blood pressure, blood flow velocity, catecholamine levels, and heart rate over a predefined period of time to deduce a baseline, stimulating at least one of efferent and afferent renal nerves during measuring, recording a pre-denervation response of the physiological parameter to stimulation, performing a renal denervation treatment, re-measuring the physiological parameter for a predefined period of time to deduce a post denervation baseline, stimulating at least one of efferent and afferent renal nerves during measuring, recording a post-denervation response of the physiological parameter to the stimulation, and comparing the pre denervation and post denervation responses to the stimuli to assess effectiveness of the denervation treatment. In some embodiments, nerve stimulation comprises applying a cold pressor test to activate sympathetic nerve activity. In some embodiments, nerve stimulation comprises injecting bradykynin and/or adenosine to the kidney to activate afferent nerve activity. In some embodiments, a norepineperine spillover procedure is applied, and nerve activity before and after denervation treatment is determined according to norepinepherine clearance level. In some embodiments, the method further comprises acquiring a first set of elastograms of a renal artery wall at systolic and diastolic stages before performing the renal denervation treatment, acquiring a second set of elastograms of the renal artery wall at systolic and diastolic stages after the renal denervation treatment, comparing the first set to and the second set to determine a change in artery wall stiffness.

According to an aspect of some embodiments of the invention there is provided a method for determining blood flow rate using cold liquid, comprising: positioning at least two temperature sensors having a distance of at least 1 cm between them along a segment of an artery, injecting cold liquid into the artery, estimating the flow rate based on a time in which a temperature drop is detected by at least one sensor, and a distance between the sensors.

According to an aspect of some embodiments of the invention there is provided a method for determining blood flow velocity based on a heat dissipation rate of a transceiver, comprising: exciting a transceiver with at least one low power excitation, measuring a temperature of the transceiver; and estimating blood flow velocity according to a heat dissipation rate of the transceiver.

According to an aspect of some embodiments of the invention there is provided a method for determining blood flow velocity based on an impulse response, comprising: exciting the transceiver by at least one pulse; and estimating blood flow velocity according to an impulse response of the transceiver.

According to an aspect of some embodiments of the invention there is provided an intravascular catheter device comprising: one or more transceivers adapted for at least one of emitting and receiving ultrasonic energy, at least one measurement device, a processor configured for analyzing signals received by the transceivers and data acquired by the measurement device, to estimate a physiological change in a vessel into which the catheter device is inserted. In some embodiments, the measurement device is a temperature sensor.

According to an aspect of some embodiments there is provided a method for separating a plurality of ultrasonic signals which were reflected by a number of locations and recorded through a single channel, comprising: identifying, out of a plurality of reflections recorded in response to different pulses, correlative behavior between at least some portions of the reflections; clustering, based on the correlative behavior, the portions of the reflections into a number of groups, the number of groups determined according to the number of locations; and associating between each of the groups and one of the locations. In some embodiments, a set of pulses is emitted over time by emitters directed towards said number of locations. In some embodiments, a reflection comprises a set of voltage values received following emission of a pulse. In some embodiments, portions of reflections include segments of the reflections having a similar time delay from emission of a pulse. In some embodiments, the reflections are received by a plurality of receivers. In some embodiments, a reflection includes mixed signals reflected by the number of locations. In some embodiments, each of the groups represents one of the locations. In some embodiments, a plurality of transceivers are used for emitting and receiving the ultrasound. In some embodiments, the locations are walls of a blood vessel, and said transceivers are positioned within a lumen of the vessel. In some embodiments, the method further comprises determining, for each of the groups, a characteristic reflection portion which represents the group. In some embodiments, the reflection portion is a vector of values, and wherein a maximal value of the vector and time information associated with the group are used for estimating a distance between one of the locations and a receiver of the reflection portions belonging to that group.

According to an aspect of some embodiments there is provided a method for separating a plurality of ultrasonic signals which were reflected by a number of locations and recorded through a single channel over a time in which energy is emitted in pulses towards said locations, comprising: selecting a plurality of segments of the single channel recording; identifying patterns, each pattern including portions of the segments having a similar time delay from emission of a pulse; calculating correlations between the patterns; clustering the determined correlations to a number of groups, the number of groups determined according to the number of locations; and estimating a distance between at least one of the groups and one of the locations. In some embodiments, estimating a distance comprises determining, for each group, a characterizing pattern which represents the group. In some embodiments, the characterizing pattern is a centroid vector, and the distance is estimated based on a maximal value of the vector and time information associated with the group. In some embodiments, each of said segments of the single channel recording comprises a reflection received following emission of a pulse. In some embodiments, a reflection comprises a set of voltage values. In some embodiments, a reflection includes mixed signals reflected by said number of locations. In some embodiments, a set of 1000 pulses is emitted over a time period ranging between 1-5 seconds, and 4000 samples are recorded following each pulse over a time period ranging between 5-50 microseconds. In some embodiments, segments of the single channel recording are arranged in a matrix, wherein a first dimension of the matrix includes the reflections recorded in between the pulses, and a second dimension of the matrix includes the patterns. In some embodiments, calculating correlations between the patterns comprises assigning correlation coefficients ranging between −1 for patterns with a negative correlation, and 1 for highly correlated patterns, and arranging them is a symmetric matrix. In some embodiments, correlation coefficients are represented as points in a multidimensional space. In some embodiments, clustering comprises applying a K-means algorithm to cluster the points to a predefined number of groups, the number of groups comprising the known number of locations and an additional group for noise. In some embodiments, energy is emitted from a plurality of ultrasonic transceivers. In some embodiments, the multiple locations are walls of a blood vessel. In some embodiments, the method further comprises determining a diameter of the blood vessel using at least three estimated distances. In some embodiments, the multiple locations are walls of a blood vessel and the method further comprises determining vessel wall movement by tracking distance over time. Optionally, distance is tracked over at least one cardiac cycle. In some embodiments, the method further comprises positioning an intravascular catheter comprising a plurality of ultrasonic transceivers in a blood vessel, emitting energy towards vessel walls, and receiving energy reflected by the vessel walls using the transceivers. In some embodiments, the transceivers are configured to emit energy suitable for ablating nerves. Optionally, the blood vessel is the renal artery.

According to an aspect of some embodiments of the invention there is provided a method for monitoring a distance to a vessel wall, comprising: evaluating a spectral statistic of at least one recorded echo signal received from a vessel wall; determining an intensity of the signal according to the spectral statistic; and estimating a distance to the vessel wall based on the intensity. In some embodiments, the spectral statistic is a spectral density of the signal. In some embodiments, estimating comprises detecting an onset of the intensity. In some embodiments, the method further comprises filtering noise using at least one noise filter constructed according to at least one region of the spectral density. Optionally, the noise is a ringing artifact caused by an undamped or partially damped transceiver. Optionally, the noise is sampling noise caused by a mistimed sampling. In some embodiments, the onset is detected by thresholding a first derivative of the intensity of the signal. In some embodiments, a difference in a relative location of the vessel wall due to heart pulsation is used for differentiating between a signature of the echo signals reflected by the vessel wall and the noise. In some embodiments, the method further comprises thresholding the calculated distance to determine a safe distance for renal nerve ablation. In some embodiments, the spectral density region on the basis of which a noise filter is constructed is a high frequency segment above 40 Hz, where the echo signal component is expected to be negligible. In some embodiments, the method is adapted for detecting a distance higher than 1 mm from the vessel wall.

According to an aspect of some embodiments of the invention there is provided a method for monitoring a minimal distance to a blood vessel wall, comprising: exciting an intravascular ultrasonic transceiver with a train of distance monitoring excitations having a frequency ranging between 100-250 Hz; analyzing echo signals reflected by the vessel wall to detect a distance between the transceiver and the wall. In some embodiments, the transceiver is adapted for ablating renal nerves, and the blood vessel is a renal artery. In some embodiments, the method further comprises exciting the transceiver for ablating the nerves if the distance to the wall is at least 1 mm. In some embodiments, ablating excitations are applied at a frequency ranging between 10-12 MHz. In some embodiments, distance monitoring excitations are applied in between the ablating excitations. In some embodiments, the method further comprises adjusting a location of the ultrasonic transceiver within the blood vessel according to the detected distance. In some embodiments, the train of distance monitoring excitations comprises 256 pulses at a frequency of 200 Hz.

According to an aspect of some embodiments of the invention there is provided a method for decomposing a signal to a base set of echo signals for determining a distance between one or more ultrasonic transceivers and the vessel wall, comprising using a dictionary of probable reflections; matching the base echo signals with the probable reflections; and determining a distance between the one or more ultrasonic transceivers and a vessel wall. In some embodiments, each of the probable reflections is characterized by at least a distance to a vessel wall, and a shape of an excitation pulse causing the echo signals. In some embodiments, the shape comprises a width of the excitation pulse. In some embodiments, the method is repeated for a successive one or more signals. In some embodiments, the dictionary of probable reflections is reduced according to an analysis of a first and/or preceding signal. In some embodiments, the dictionary of probable reflections is reduced to include a range of distances corresponding with distances obtained by analyzing the first and/or preceding signal. In some embodiments, the method further comprises estimating a diameter of the vessel according to the distance. In some embodiments, the method further comprises estimating a change in diameter over time. In some embodiments, the dictionary of probable reflections is a set of Gabor functions. In some embodiments, matching comprises applying a matching pursuit algorithm. In some embodiments, a center of each of the Gabor functions indicates a distance to a vessel wall, and a variance of the Gabor function indicates a width of the excitation pulse. In some embodiments, the dictionary of probable functions is defined for a selected intravascular ultrasonic catheter comprising one or more transceivers. In some embodiments, dictionary of probable functions is defined according to a resonant frequency of the one or more transceivers. In some embodiments, the method further comprises changing the dictionary, for example reducing a size of the dictionary, according to the data to be analyzed. In some embodiments, the dictionary is trained according to the data by applying a Least Absolute Shrinkage and Selection Operator algorithm and clustering according to one or both distance and phase to determine a different set of possible base signals.

According to an aspect of some embodiments there is provided a method for estimating a diameter or a change in diameter of a blood vessel, comprising emitting ultrasound energy in at least three directions towards the vessel walls; acquiring, over time, reflections of energy reflected back by the vessel walls; analyzing the reflections to estimate a diameter or a change in diameter of the vessel. In some embodiments, energy is emitted as a set of pulses, and the reflections are acquired in between pulses. In some embodiments, analyzing comprises calculating correlations between patterns, each pattern comprising portions of the reflections having a similar time delay from emission of a pulse. In some embodiments, analyzing comprises clustering correlations between the patterns into at least three groups representing the at least three directions. In some embodiments, analyzing comprises determining, for each of the groups, a characterizing pattern which represents the group, and estimating, for the three groups, a distance between a group and a vessel wall located in one of the three directions. In some embodiments, analyzing comprises estimating a diameter using three estimated distances.

According to an aspect of some embodiments of the invention there is provided an intravascular catheter system comprising: a head comprising a plurality of transceivers configured for emitting ultrasound energy towards the walls of a vessel and for receiving signals reflected by the vessel walls; a processor in communication with the head, the processor configured for analyzing the reflected signals to estimate a distance within the vessel. In some embodiments, the distance includes a diameter of the vessel. In some embodiments, the distance includes a distance between a transceiver and the vessel wall.

According to an aspect of some embodiments there is provided a method for immediate assessment of renal sympathetic denervation, comprising:
inserting a catheter into an artery, the catheter comprising at least one of an ultrasound transceiver and a measurement device; recording data received by the transceiver and measurement device; and analyzing the data for determining at least one of renal blood flow rate and arterial restraint.

According to an aspect of some embodiments there is provided a method for determining blood flow rate using contrast liquid, comprising:
injecting contrast liquid into an artery; continuously imaging the flow of the liquid;
analyzing the recorded images by detecting pixels comprising an intensity value that is at least 10% higher than a baseline intensity value in at least two regions of interest along the artery, and comparing a time in which the pixel intensities surpassed the baseline at each of the two regions; and calculating the flow rate based on the time difference and the distance between the regions of interest.

According to an aspect of some embodiments there is provided a method for determining blood flow rate using cold liquid, comprising:
placing at least two temperature sensors having a distance of at least 1 cm between them along a segment of an artery; injecting cold liquid into the artery; continuously recording the temperatures of the temperature sensors; analyzing the recorded data to detect variations in temperatures; calculating the flow rate based on a time of descent in temperatures in each of the temperature sensors, and a distance between the temperature sensors.

According to an aspect of some embodiments there is provided a method for determining blood flow velocity based on a heat dissipation rate, comprising:
inserting a transceiver equipped with a temperature sensor into an artery, the temperature sensor positioned in a vicinity of the transceiver; exciting the transceiver with a set of low power excitations; continuously recording a temperature of the transceiver as measured by the temperature sensor; analyzing the recorded data to detect variations in the recorded temperature of said transceiver; calculating a heat dissipation rate of the transceiver; determining blood flow velocity according to the heat dissipation rate.

According to an aspect of some embodiments there is provided a method for determining blood flow velocity based on an impulse response, comprising:
inserting a transceiver into an artery; exciting the transceiver with one or more impulses; recording an impulse response of the transceiver; analyzing the recorded voltage trace to detect a damping of the transceiver; determining the blood flow velocity according to the damping of said transceiver.

According to an aspect of some embodiments there is provided a method for analyzing a sequence of signals received from multiple sources and recorded through a single channel, comprising: recording signals received from multiple sources through a single channel, the signals received by a receiver in some distance from their sources; separating the signals to determine their sources by clustering the signals to groups according to an interference pattern of each of the signals.

In some embodiments, the method comprises determining a distance of each of said sources from said receiver. In some embodiments, the sources are periodically moving sources.

According to an aspect of some embodiments there is provided a method for estimating a diameter of an artery in real time, comprising: inserting one or more ultrasonic transceivers into an artery; emitting ultrasound energy towards the walls of the artery; recording echo signals reflected from said walls of the artery;
analyzing the recorded echo signals to determine their source artery wall according to an interference pattern of each of the signals; determining a distance of the artery walls from the one or more transceivers according to the interference pattern; estimating a diameter of the artery.

In some embodiments, the method comprises estimating a current location of the one or more transceivers with respect to the artery walls. In some embodiments, the method comprises estimating a current location of said one or more transceivers with respect the artery center. In some embodiments, the method comprises estimating a movement profile of the artery walls.

In some embodiments, any of the above methods comprises detecting physical changes of an artery wall to assess renal denervation.

In some embodiments, a signal processor is connected to the one or more transceivers for analyzing the recorded echo signals.

According to an aspect of some embodiments there is provided an apparatus comprising one or more undamped ultrasonic transceivers, wherein the transceivers are configured for emitting ultrasonic energy towards periodically-moving sources, and configured for receiving a plurality of returning echo signals from the sources; and a signal processor connected to the one more transceivers, the signal processor configured for implementing an algorithm which separates between the received echo signals and estimating a distance at least one of the sources.

According to an aspect of some embodiments there is provided an apparatus for renal denervation treatment and measurement comprising one or more ultrasonic transceivers configured for emitting and/or receiving ultrasonic energy; and at least one of a temperature sensor, a pressure sensor, and a flow sensor.

According to an aspect of some embodiments of the invention there is provided an intravascular catheter comprising an elongated shaft and a head for ultrasonic transmission, the head comprising a chassis comprising at least three facets, each facet sized to receive a piezoelectric transceiver; a plurality of piezoelectric transceivers peripherally mounted onto the facets of the chassis, the transceivers electrically activated for emitting ultrasound energy suitable for tissue ablation, and for receiving echo signals. In some embodiments, the chassis is cannulated. In some embodiments, chassis comprises a substantially polygonal cross section profile.

In some embodiments, a cross section profile of the chassis is triangular, and 3 transceivers are mounted onto the facets of the chassis. In some embodiments, a diameter of a circumscribing circle of the head is 2.2 mm or smaller. In some embodiments, a summed area of radially outward facing surfaces of the transceivers covers at least 70% of the radially outward facing facets of the chassis. In some embodiments, a summed area of radially outward facing surfaces of the transceivers covers no more than 95% of the radially outward facing facets of the chassis. In some embodiments, radially outward facing surfaces of the transceivers are flat. In some embodiments, the catheter further comprises a PCB configured between the chassis and at least one of the transceivers. In some embodiments, the PCB comprises one or more bendable extensions in contact with transceivers different than the transceiver mounted on top of the PCB. In some embodiments, the PCB comprises one or more vias for at least one of electrically and mechanically coupling between the PCB and the chassis. In some embodiments, an electrically conductive strip folded to surround an exterior surface of the catheter head serves as a current conducting electrode for activation of the transceivers. In some embodiments, the chassis is electrically conductive. In some embodiments, when the catheter is positioned within a vessel, the one or more transceivers are configured to emit unfocused ultrasound energy suitable for ablating tissue when the transceivers are positioned a distance away from a vessel wall. In some embodiments, the distance is large enough to permit blood to flow between a transceiver and the wall to cool the wall. In some embodiments, the blood vessel is the renal artery and the tissue comprises nerve tissue.

In some embodiments, the catheter comprises one or more temperature sensors positioned in proximity to the transceivers. In some embodiments, the temperature sensors are connected in parallel.

In some embodiments, the transceivers are mounted onto the facets of the chassis using an array of electrically conductive glue points. In some embodiments, the glue drops are equally distributed on each of the facets. Optionally, a diameter of a glue drop ranges between 100-250 µm. In some embodiments, the array comprises 4-12 glue drops.

In some embodiments, there is provided a system for operating an intravascular ultrasonic catheter by a physician, comprising: a catheter; a console connected on one end to the catheter; a software installed on the console, the software configured for analyzing echo signals received by the plurality of piezoelectric transceivers; and a foot pedal activated by the physician for producing excitation of the transceivers. In some embodiments, the console is configured for reading frequency and impedance data which characterizes the transceivers. In some embodiments, the console is configured for providing an excitation having a sinusoidal waveform having a duration and power suitable to ablate tissue using the catheter.

According to an aspect of some embodiments there is provided a PCB configured for mechanically and electrically connecting between a non-flat chassis of an intravascular catheter and at least one piezoelectric transceiver, the PCB comprising one or more bendable extensions for fitting closely around the non-flat chassis.

According to an aspect of some embodiments of the invention there is provided a method for operating a catheter comprising a plurality of transceivers, comprising; exciting the plurality of transceivers at an operating frequency that is in the range of ±10% from an average resonant frequency of the transceivers, the operating frequency different from the resonant frequency of any of the plurality of transceivers. In some embodiments, the plurality of transceivers are preselected with resonant frequencies that are in the range of ±0.5% from each other. In some embodiments, the transceivers are excited simultaneously to emit ultrasound energy towards multiple tissue regions located circumferentially around the blood vessel.

According to an aspect of some embodiments of the invention there is provided an apparatus for positioning at least one ultrasound transceiver of a catheter away from a wall of a body lumen, the apparatus comprising one or more leaflets which are radially collapsible to provide for insertion or removal of the catheter to and from the lumen; the apparatus comprising an open configuration in which the one or more leaflets position the catheter relative to two opposing walls of the lumen; wherein an area between the ultrasound transceiver and the wall defined by the one or more leaflets in the open configuration is large enough to permit a sufficient amount of blood to flow through to cool at least one of the transceiver and the lumen wall enough to prevent thermal damage to the inner wall. In some embodiments, the bendable leaflet is formed of at least two layers having different stiffness properties, a first layer rigid enough to maintain the open configuration, and a second layer soft enough to reduce mechanical damage to the lumen wall. In some embodiments, a distance between the transceiver and the wall is at least 0.5 mm. In some embodiments, the bendable leaflets define slots in between the leaflets; the slots arranged to expose at least a portion of a surface of the ultrasound transceivers. In some embodiments, a collapsed configuration the positioning apparatus comprises a diameter of 2.2 mm or smaller. In some embodiments, the leaflet defines a slanted surface which funnels blood towards the wall to cool the wall. In some embodiments, one or more of a curvature of the leaflet in an open configuration, an elasticity of a material of the leaflet facing the lumen wall, and one or more edges of the leaflets are selected not cause substantial mechanical damage to the lumen wall in the open configuration. In some embodiments, a width of the leaflet ranges between 0.2 mm to 2 mm to reduce mechanical damage to the wall.

According to an aspect of some embodiments of the invention there is provided a method for assessing effectiveness of a renal denervation treatment, comprising: analyzing at least one of echo signals reflected by an artery wall, and data acquired by at least one measurement device positioned within a renal artery; and assessing an effectiveness of a renal denervation treatment based on at least one of physical characteristics of the artery, and hemodynamic properties of blood flowing in the artery.

In some embodiments, the measurement device is a temperature sensor; and wherein the assessing comprises estimating, using the temperature sensor, a change in the physical characteristics and hemodynamic properties, which indicates a behavioral change of the wall tissue following neural modulation carried out by the denervation. In some embodiments, the physical characteristics include artery wall stiffness, and the hemodynamic properties include renal blood flow rate. In some embodiments, the measurement device is a temperature sensor; and wherein the blood flow rate is estimated according to a cross section area of the artery, estimated by analyzing the reflected echo signals, and according to blood flow velocity, indicated by temperature changes measured by the temperature sensor. In some embodiments, the transceiver is excited with at least one excitation; the method further comprising: measuring a temperature of the transceiver; and estimating the velocity according to a heat dissipation rate of the transceiver.

According to an aspect of some embodiments of the invention there is provided a method for separating a plurality of ultrasonic signals which were reflected by a number of locations and recorded through a single channel, comprising: identifying, out of a plurality of reflections recorded in response to different pulses, correlative behavior between at least some portions of the reflections; clustering, based on the correlative behavior, the portions of the reflections into a number of groups, the number of groups determined according to the number of locations; and associating between each of the groups and one of the locations. In some embodiments, a set of pulses is emitted over time by emitters directed towards the number of locations, and wherein a reflection comprises a set of voltage values received following emission of a pulse. In some embodiments, the portions of the reflections include segments of the reflections having a similar time delay from emission of a pulse. In some embodiments, a reflection includes mixed signals reflected by the number of locations, wherein each of the groups represents one of the locations. In some embodiments, a plurality of transceivers are used for emitting and receiving the ultrasound. In some embodiments, the locations are walls of a blood vessel, and the transceivers are positioned within a lumen of the vessel. In some embodiments, the method further comprises selecting, for each of the groups, a characteristic reflection portion which represents the group. In some embodiments, the reflection portion is a vector of values, and wherein a maximal value of the vector and time information associated with the group are used for estimating a distance between one of the locations and a receiver of the reflection portions belonging to that group.

According to an aspect of some embodiments of the invention there is provided a method for separating a plurality of ultrasonic signals which were reflected by a number of locations and recorded through a single channel over a time in which energy is emitted in pulses towards the locations, comprising: selecting a plurality of segments of the single channel recording; identifying patterns, each pattern including portions of the segments having a similar time delay from emission of a pulse; calculating correlations between the patterns; clustering the determined correlations to a number of groups, the number of groups determined according to the number of locations; and estimating a distance between at least one of the groups and one of the locations. In some embodiments, estimating a distance comprises determining, for each group, a characterizing pattern which represents the group. In some embodiments, the characterizing pattern is a centroid vector, and wherein the distance is estimated based on a maximal value of the vector and time information associated with the group. In some embodiments, a set of 1000 pulses is emitted over a time period ranging between 1-5 seconds, and 4000 samples are recorded following each pulse over a time period ranging between 5-50 microseconds. In some embodiments, the method further comprises determining a diameter of the blood vessel using at least three estimated distances. In some embodiments, the multiple locations are walls of a blood vessel and wherein the method further comprises determining vessel wall movement by tracking the distance over time.

According to an aspect of some embodiments of the invention there is provided a method for decomposing a signal to a base set of echo signals for determining a distance between one or more ultrasonic transceivers and the vessel wall, comprising: using a dictionary of probable reflections; matching between the base echo signals with the probable reflections; and determining a distance between the one or more ultrasonic transceivers and a vessel wall. In some embodiments, each of the probable reflections is characterized by at least a distance to a vessel wall, and a shape of an excitation pulse causing the echo signals. In some embodiments, the method further comprises estimating a diameter of the vessel according to the distance.

According to an aspect of some embodiments of the invention there is provided a method for estimating a diameter or a change in diameter of a blood vessel, comprising: emitting ultrasound energy in at least three directions towards the vessel walls; acquiring, over time, reflections of energy reflected back by the vessel walls; analyzing the reflections to estimate a diameter or a change in diameter of the vessel.

In some embodiments, energy is emitted as a set of pulses, and the reflections are acquired in between pulses. In some embodiments, analyzing comprises calculating correlations between patterns, each pattern comprising portions of the reflections having a similar time delay from emission of a pulse, and clustering correlations between the patterns into at least three groups representing the at least three directions. In some embodiments, analyzing comprises determining, for each of the groups, a characterizing pattern which represents the group, and estimating, for the three groups, a distance between a group and a vessel wall located in one of the three directions. In some embodiments, analyzing comprises estimating a diameter using three estimated distances.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
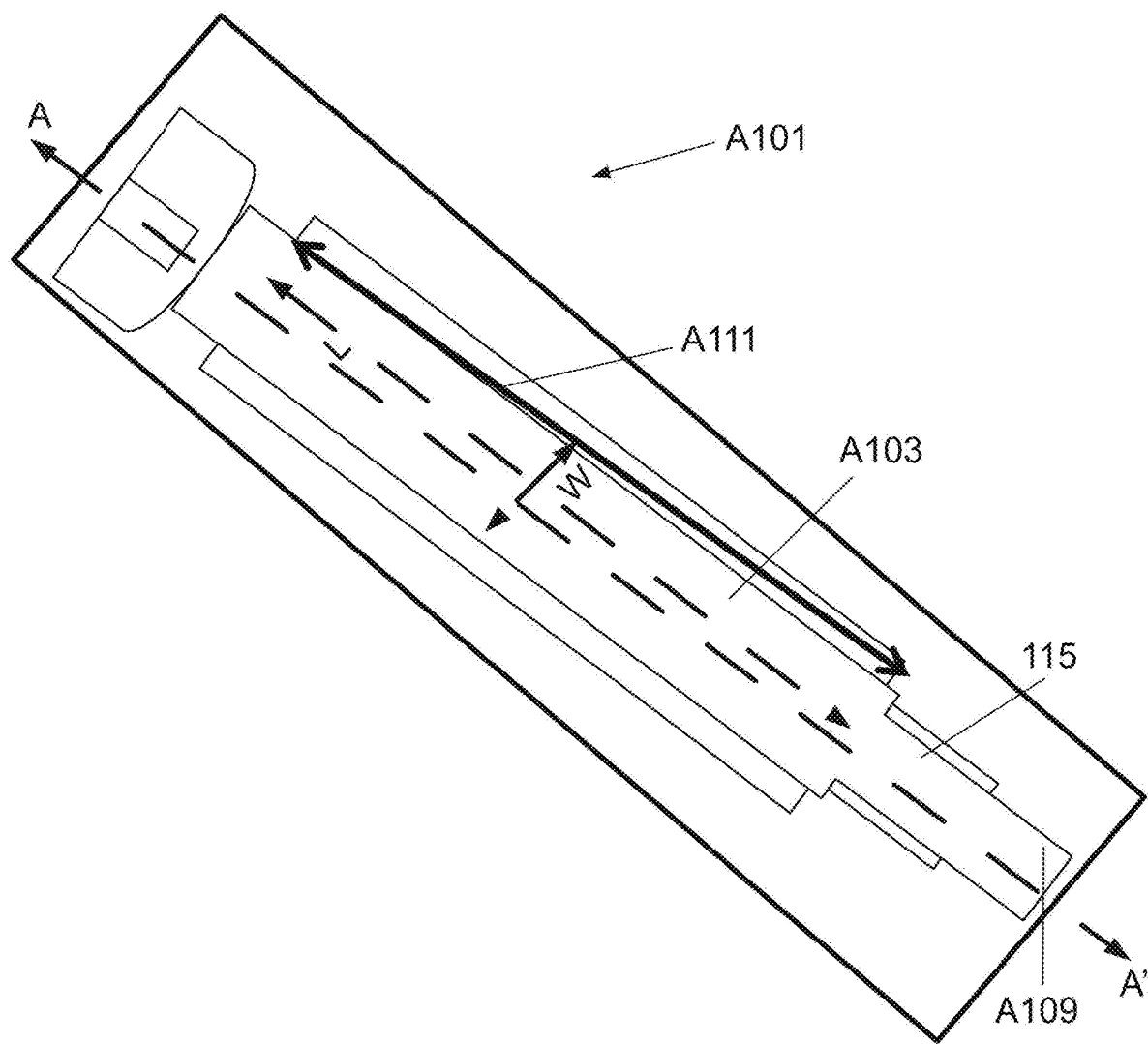
Figure 1B:
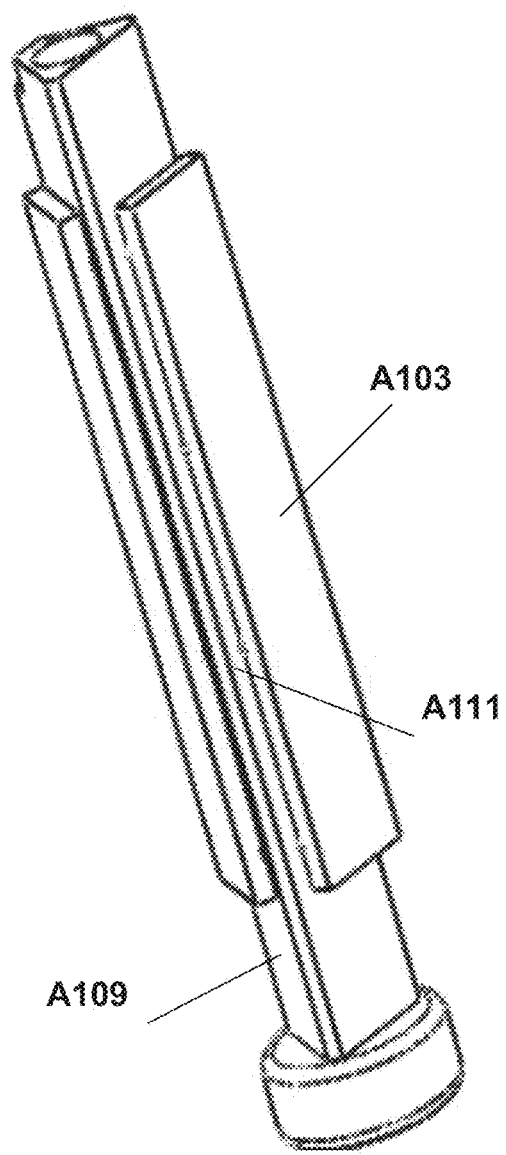
Figure 1C:
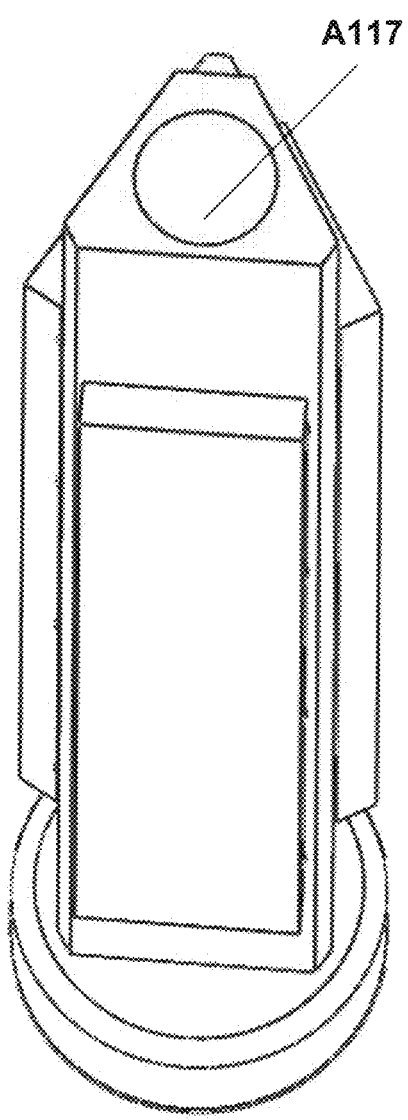
Figure 2A:
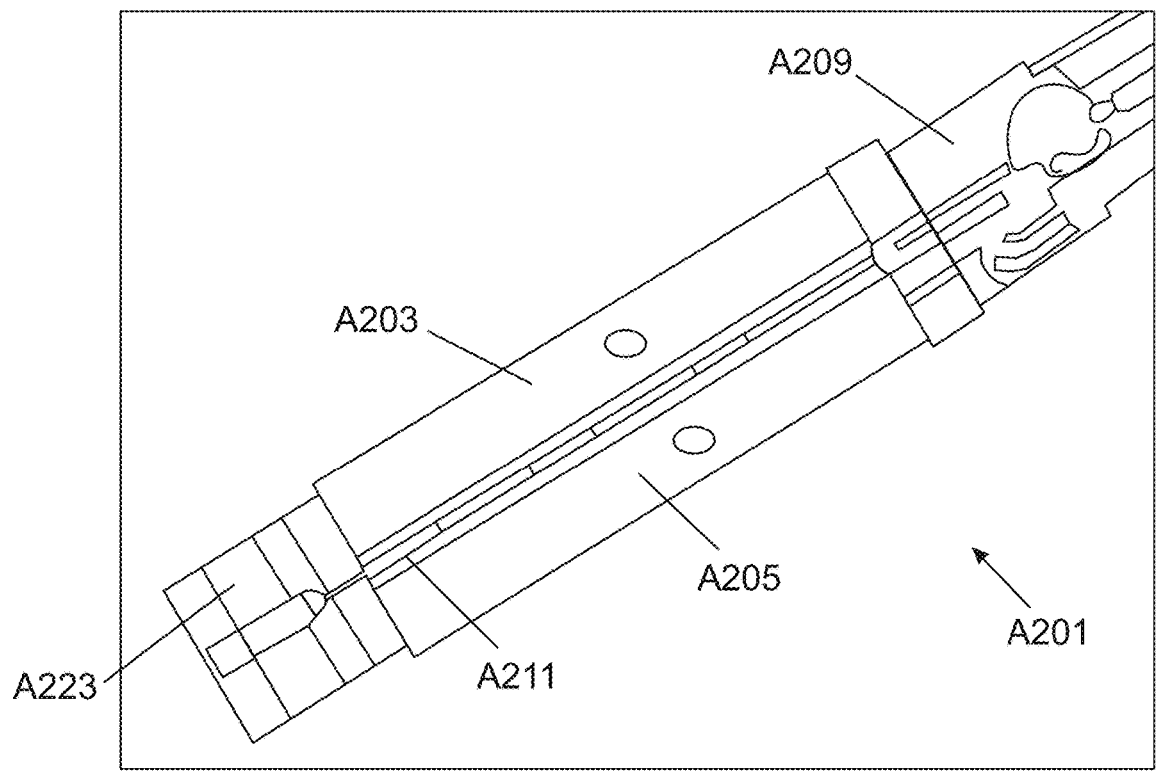
Figure 2B:
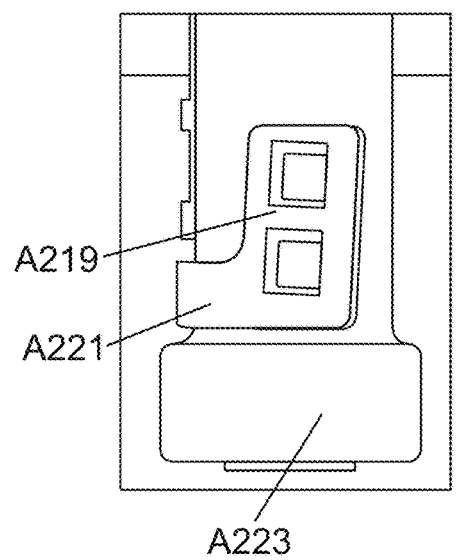
Figure 2C:
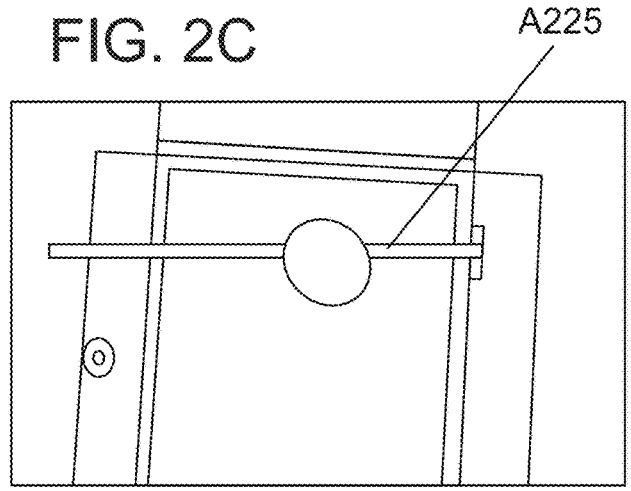
Figure 3:
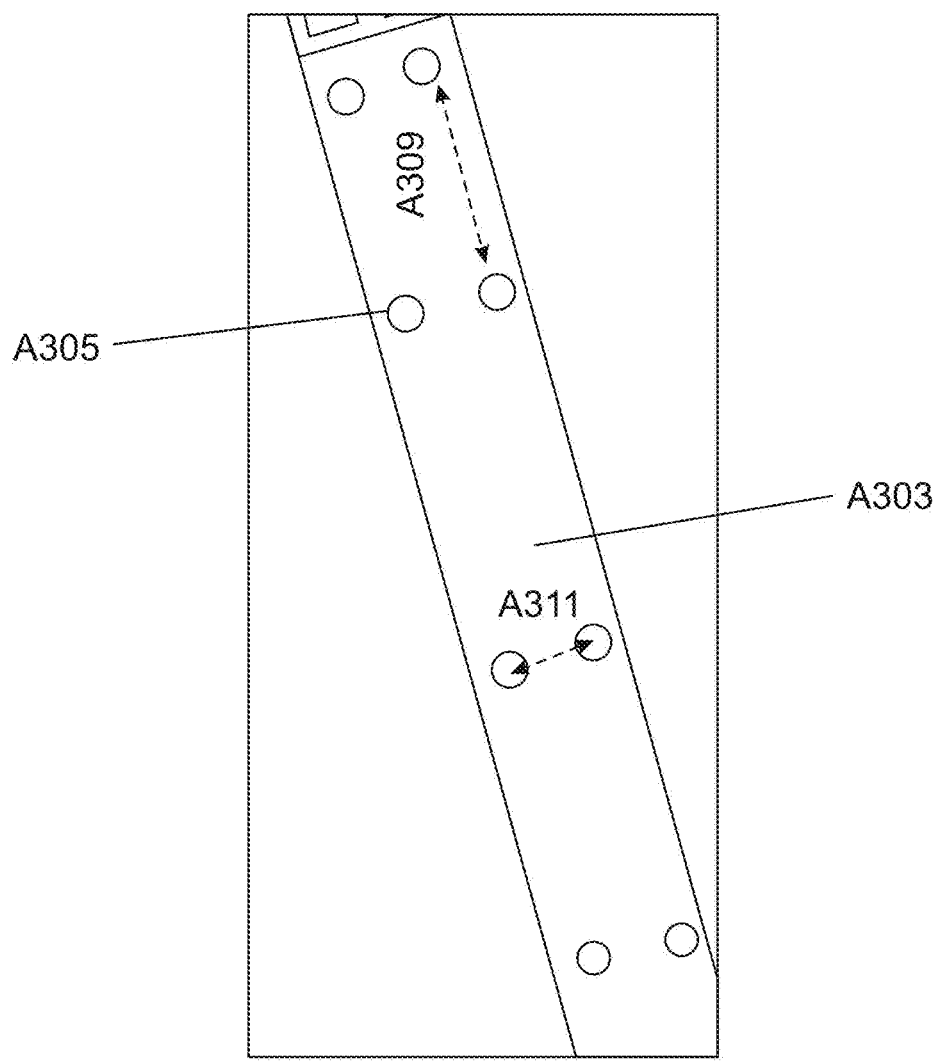
Figure 4A:
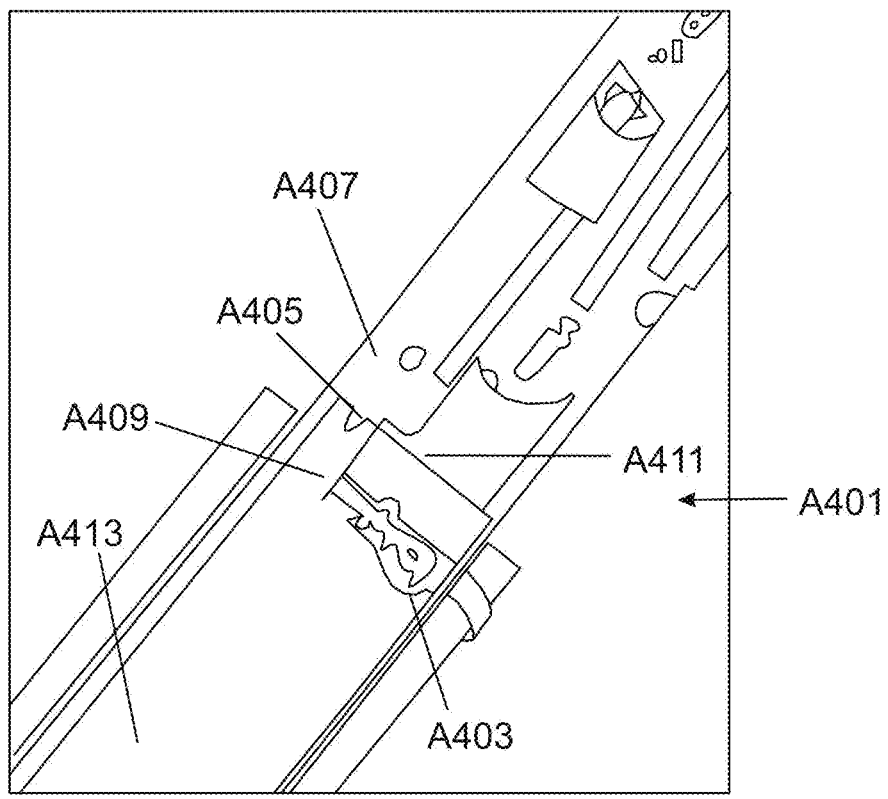
Figure 4C:
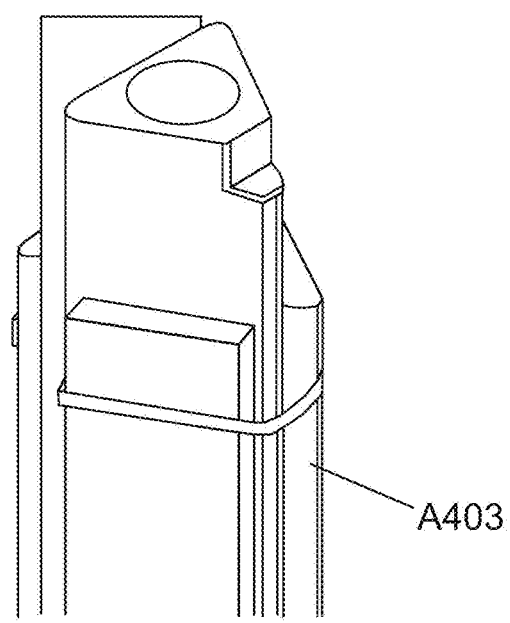
Figure 4B:
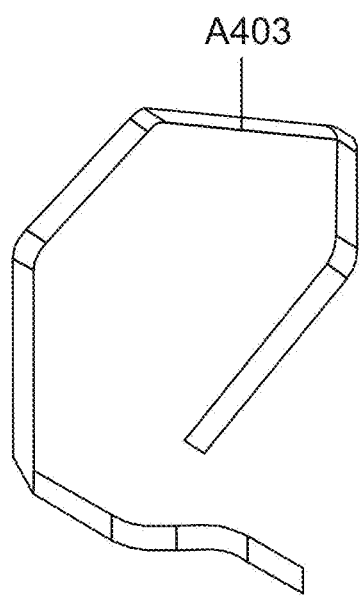
Figure 5:
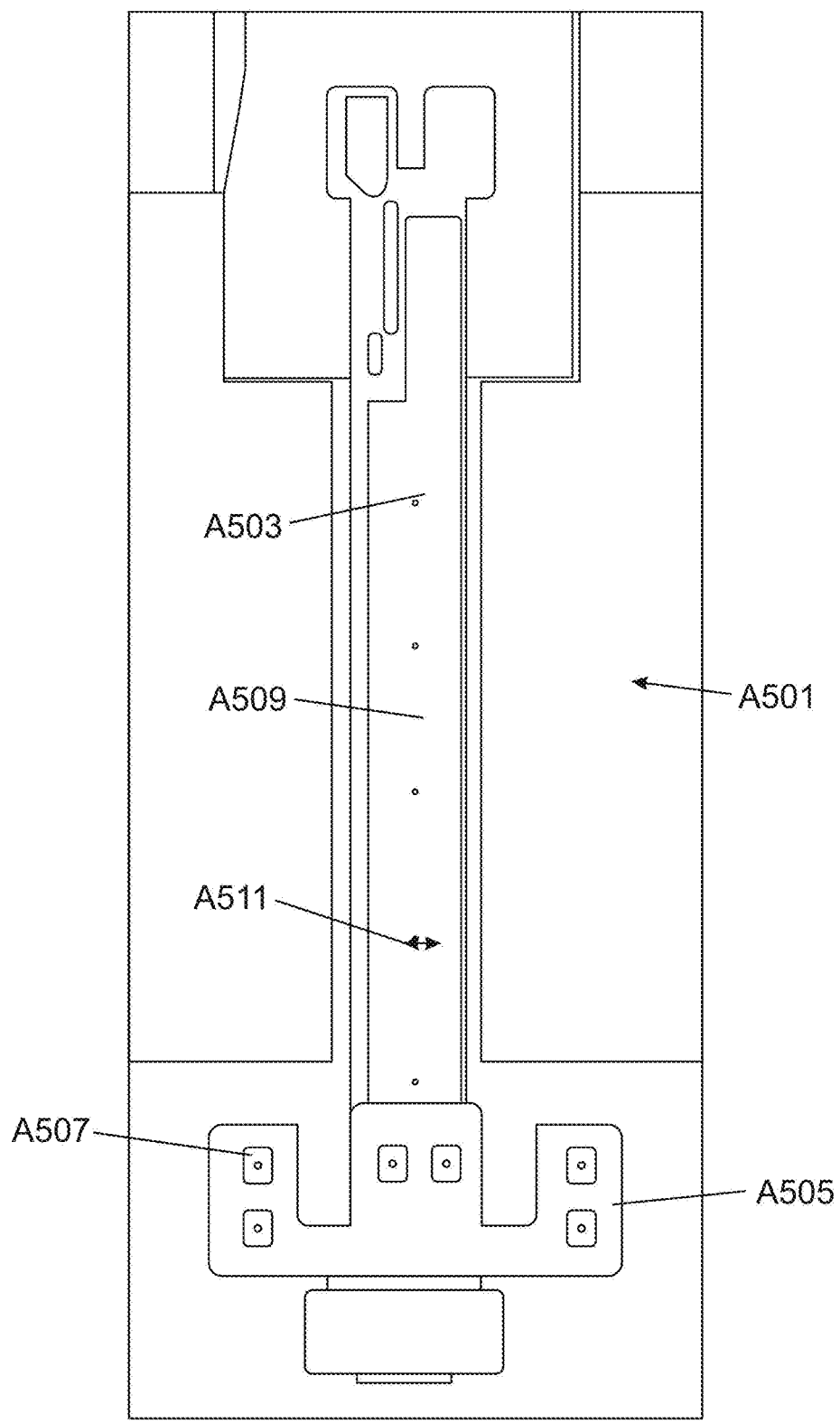
Figure 6A:
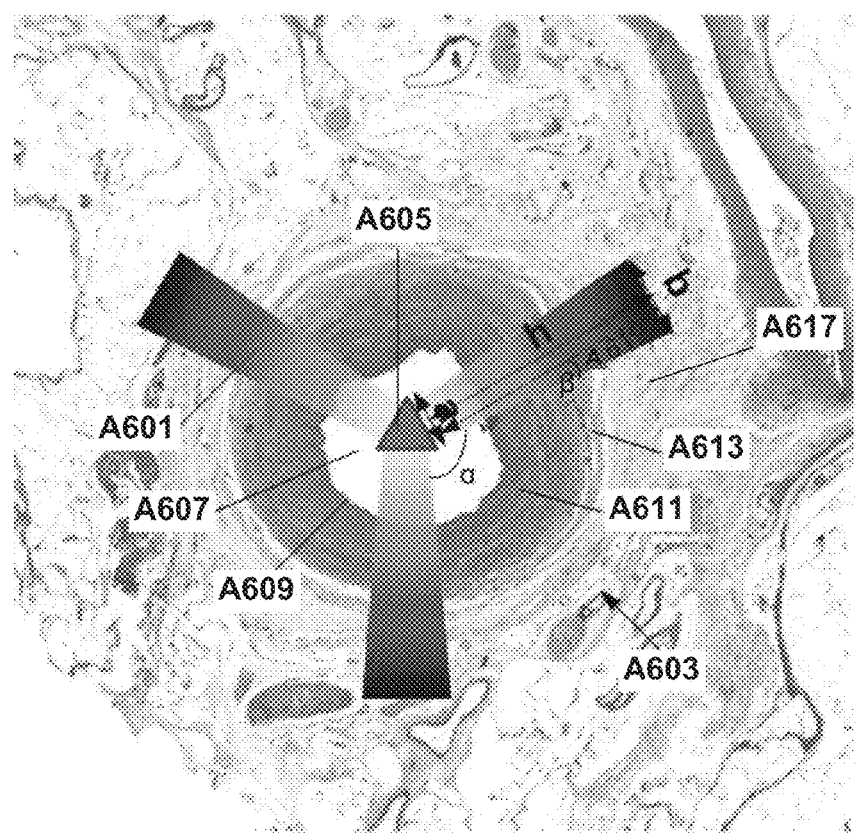
Figure 6B:
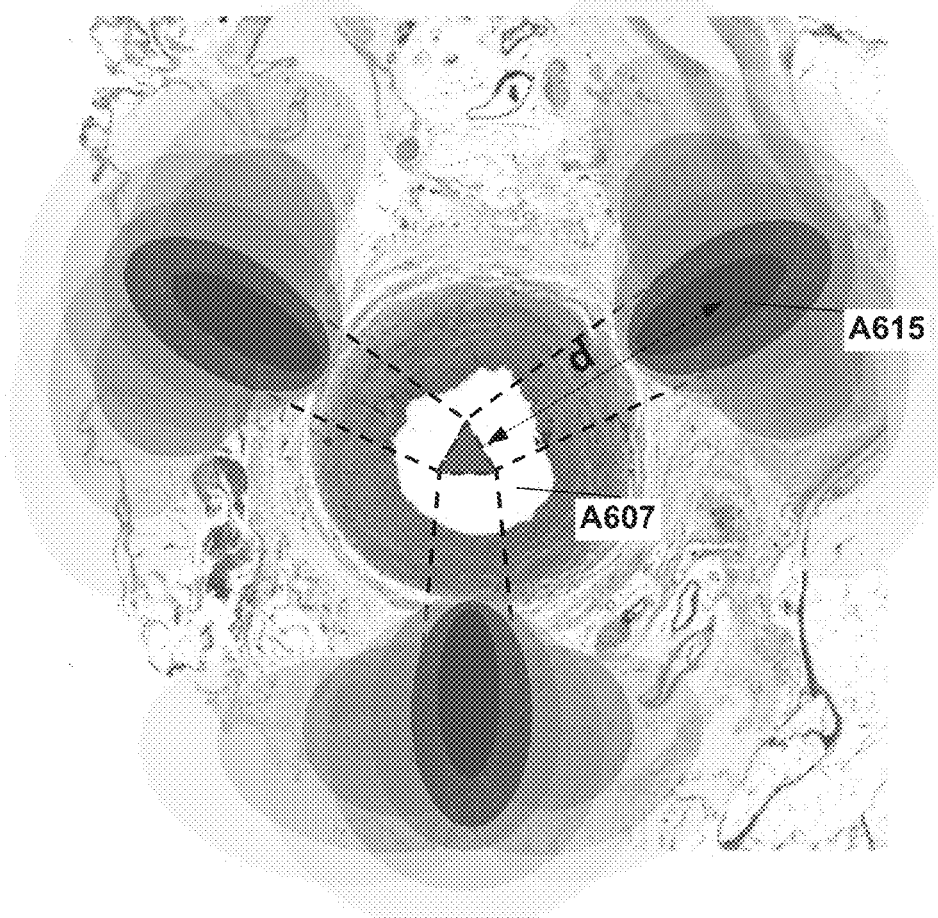
Figure 7A:
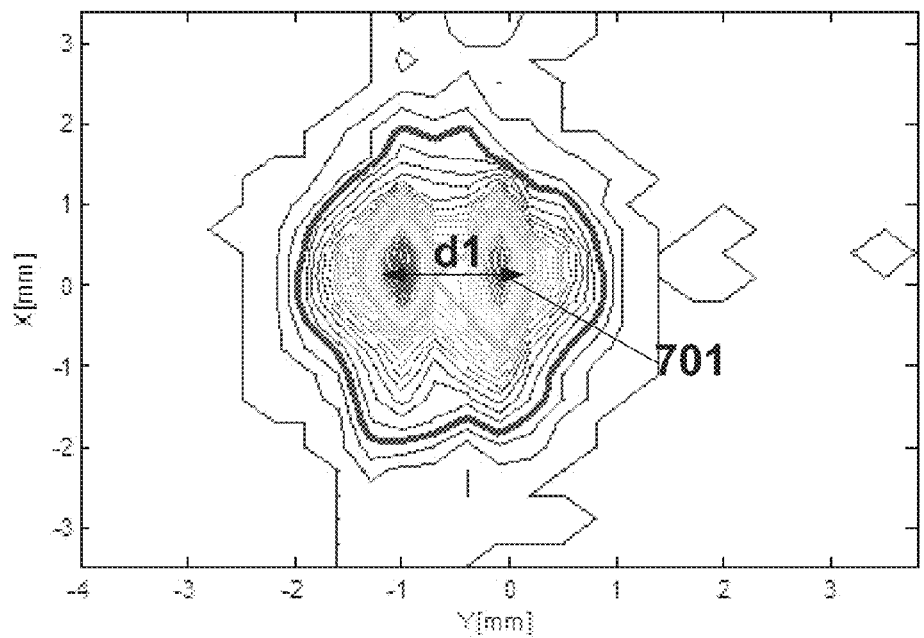
Figure 7B:
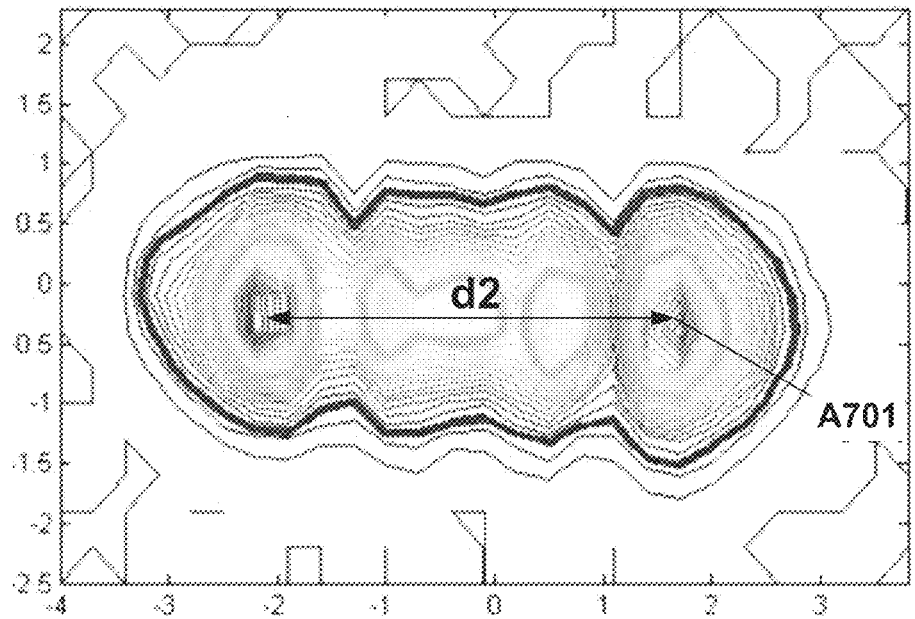
Figure 8:
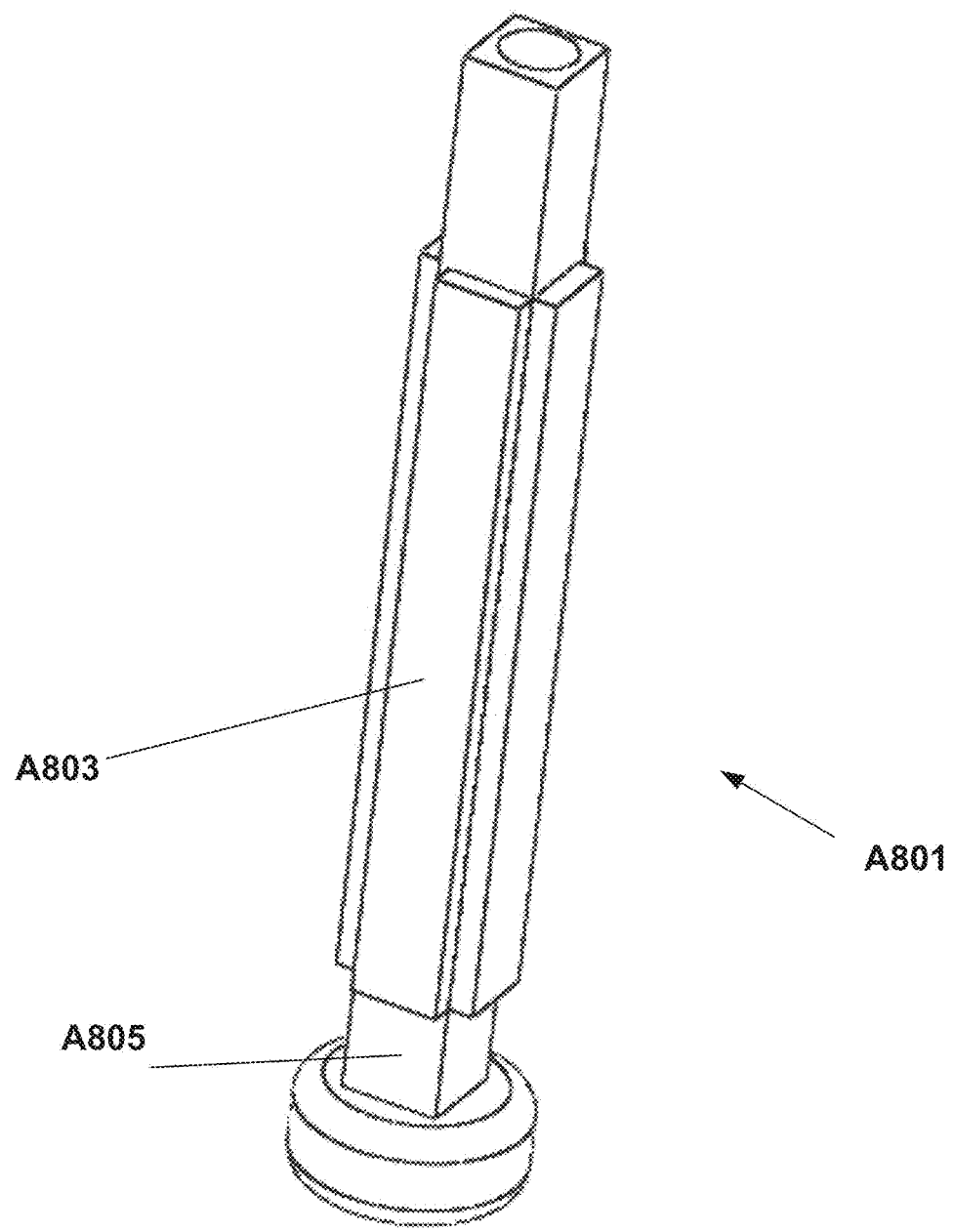
Figure 9A:
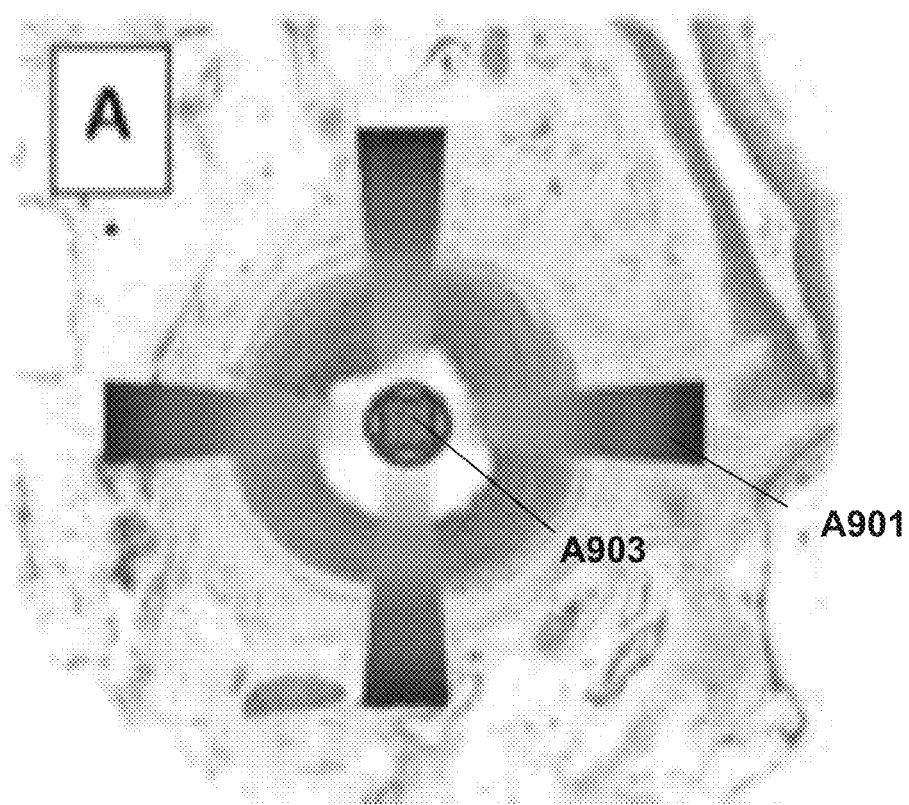
Figure 9B:
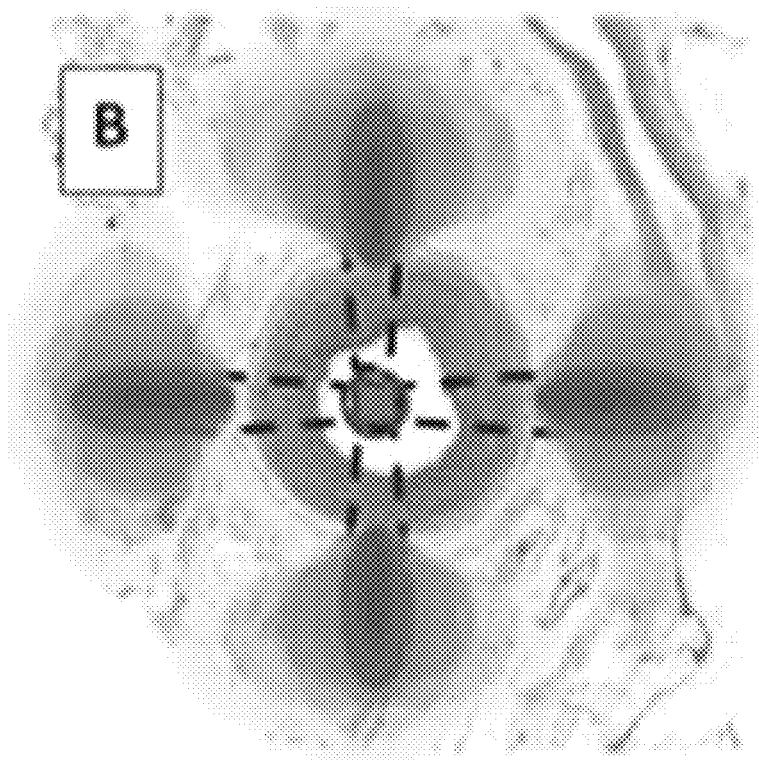
Figure 10:
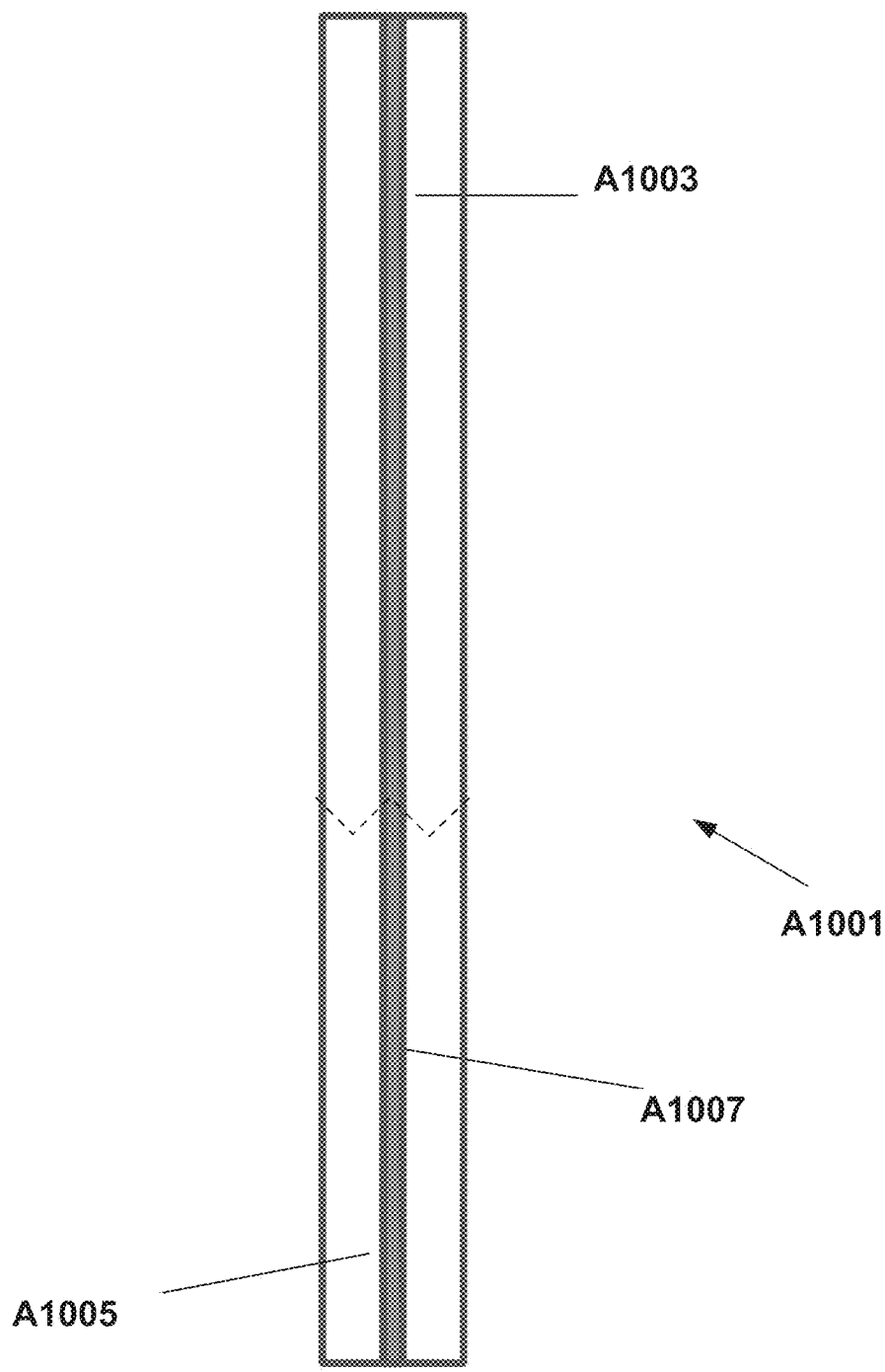
Figure 11:
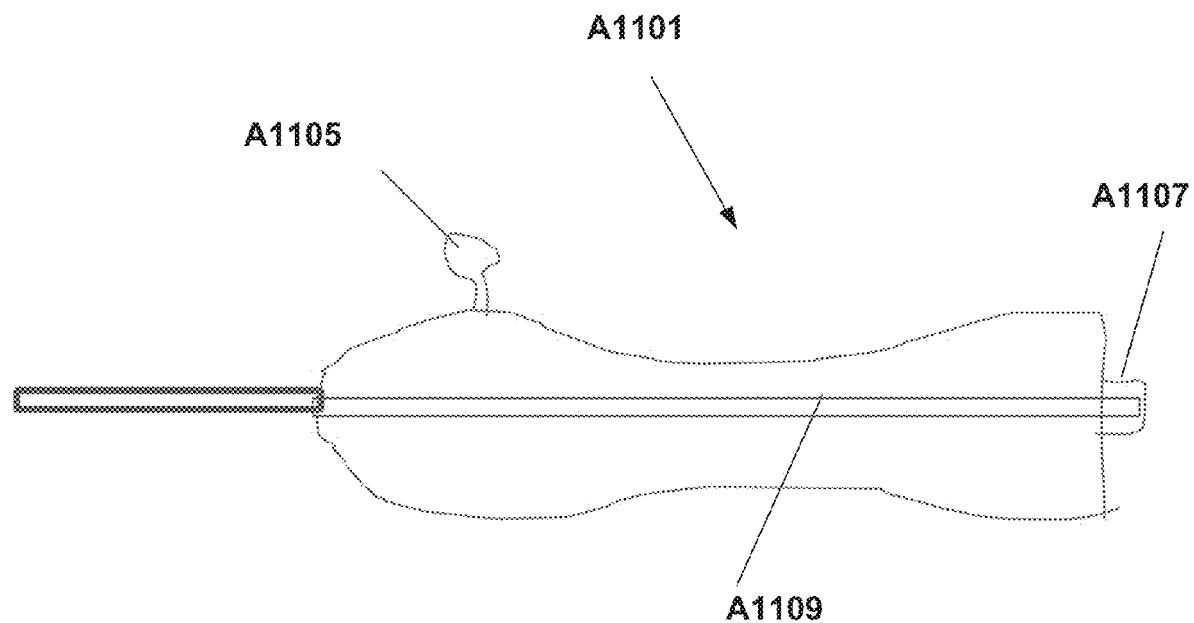
Figure 12:
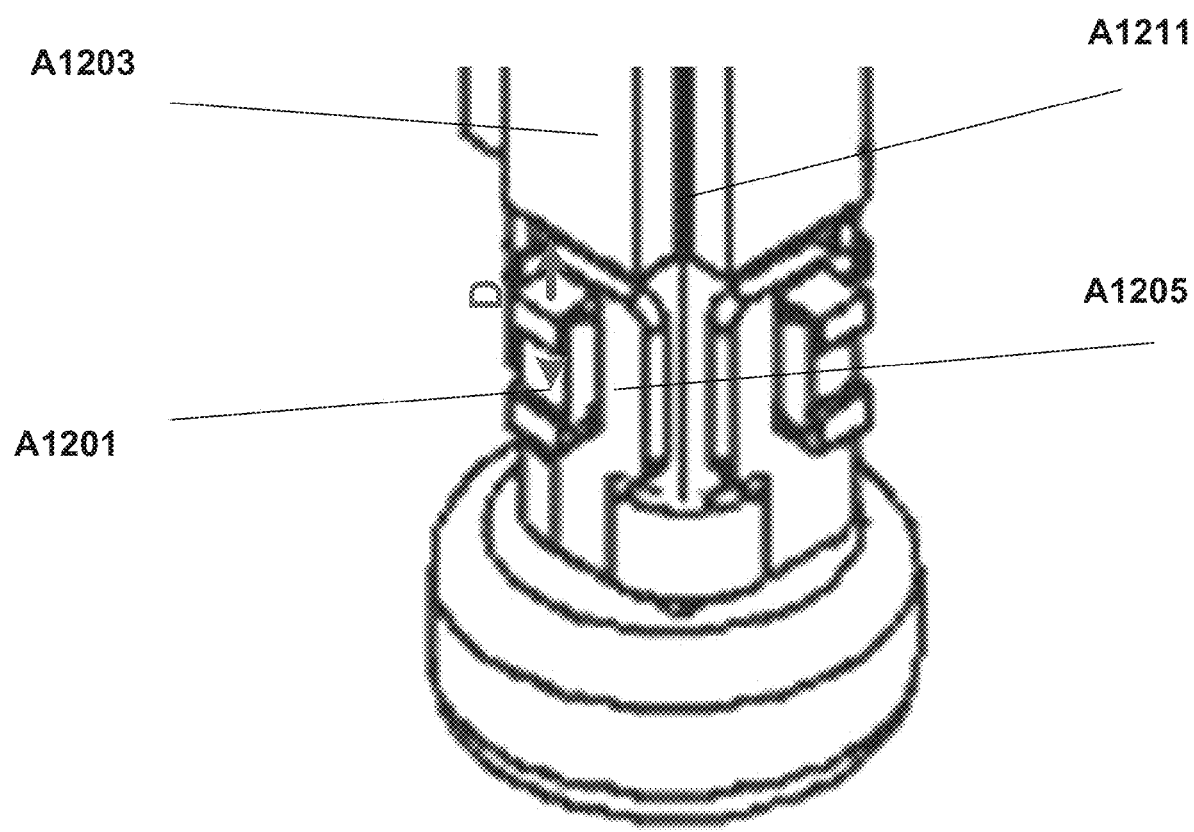
Figure 13A:
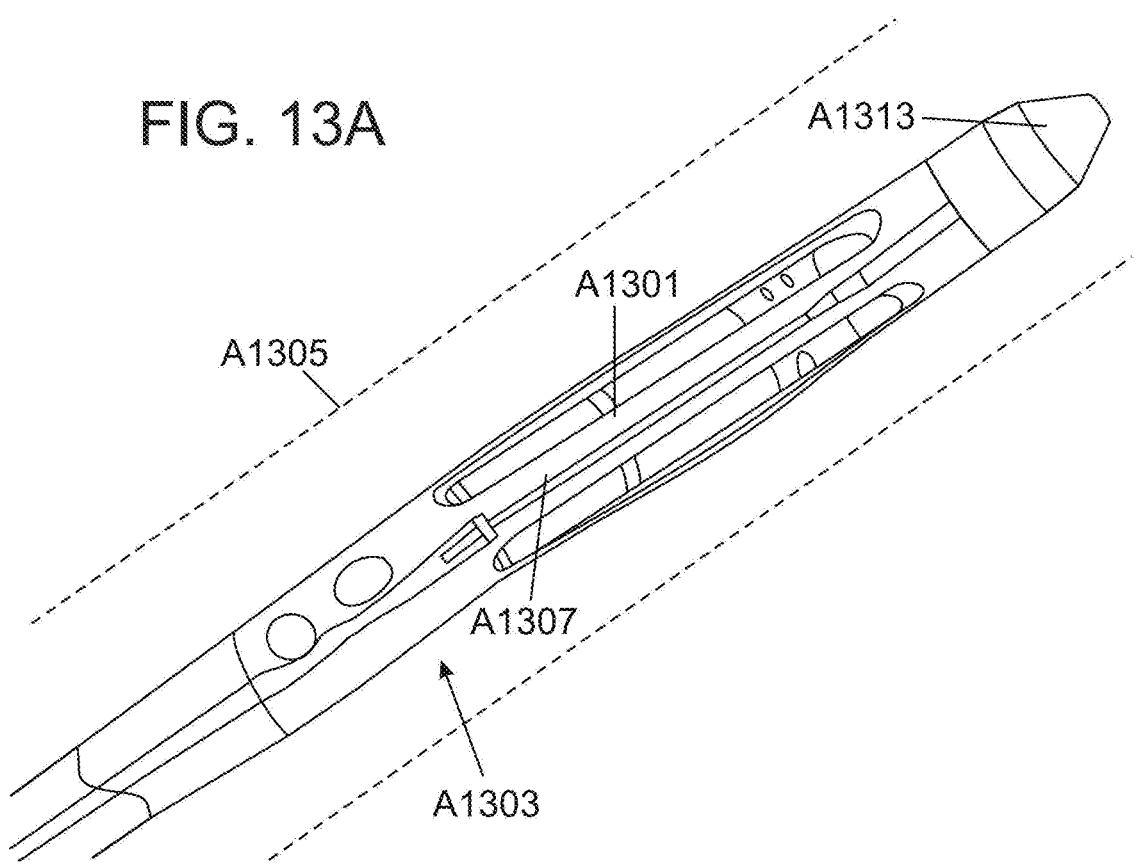
Figure 13B:
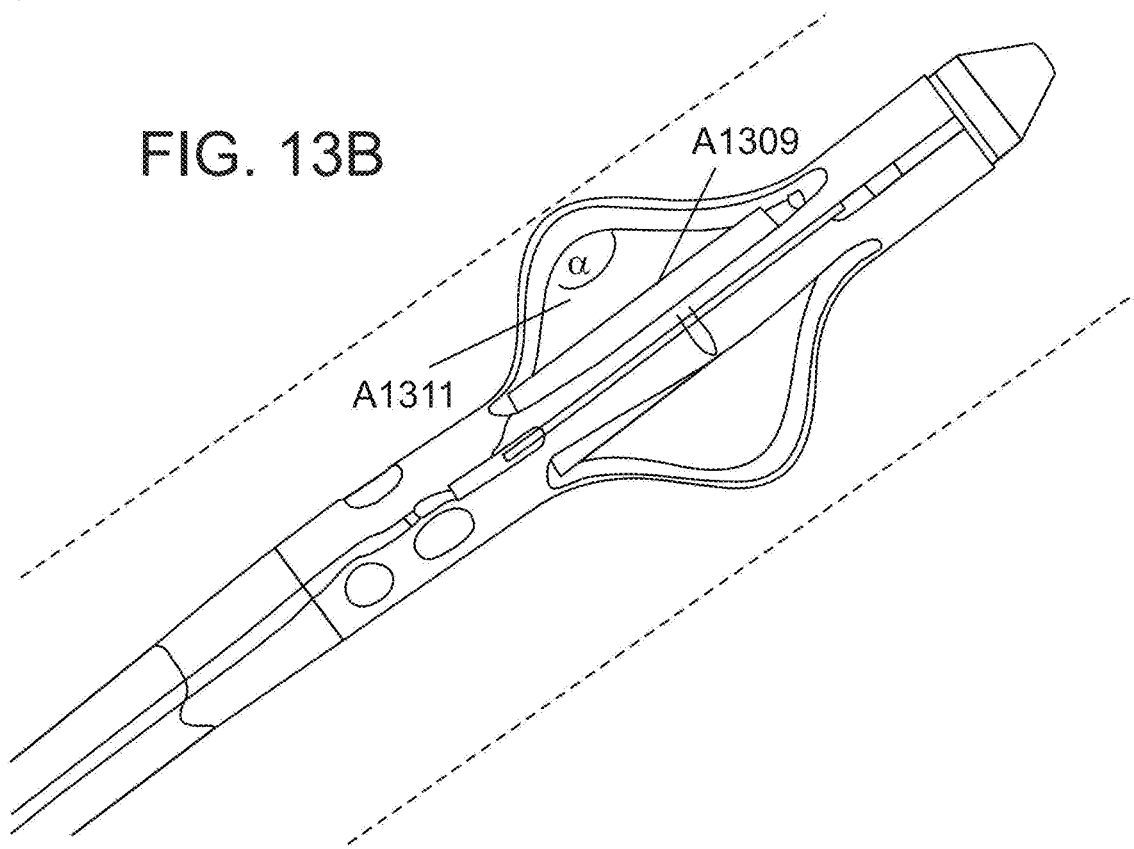
Figure 14:
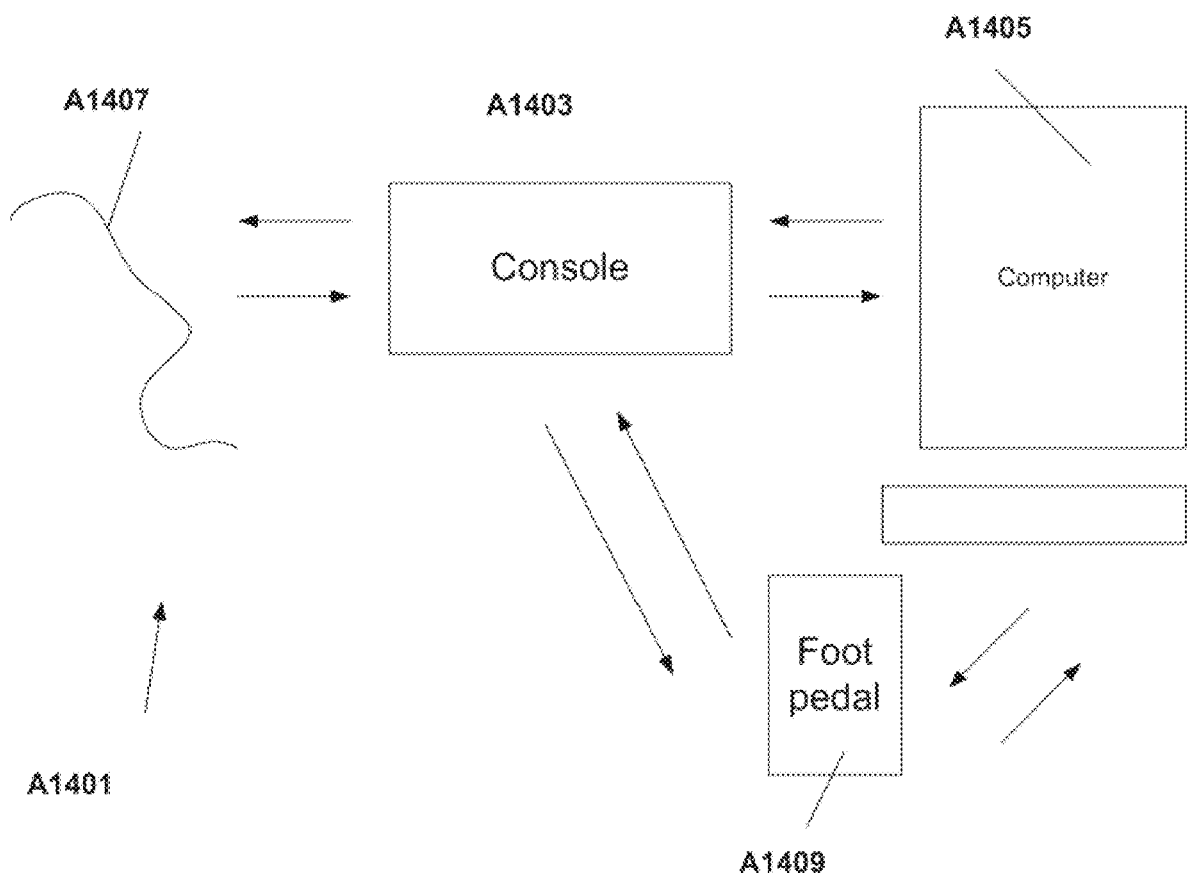
Figure 16:
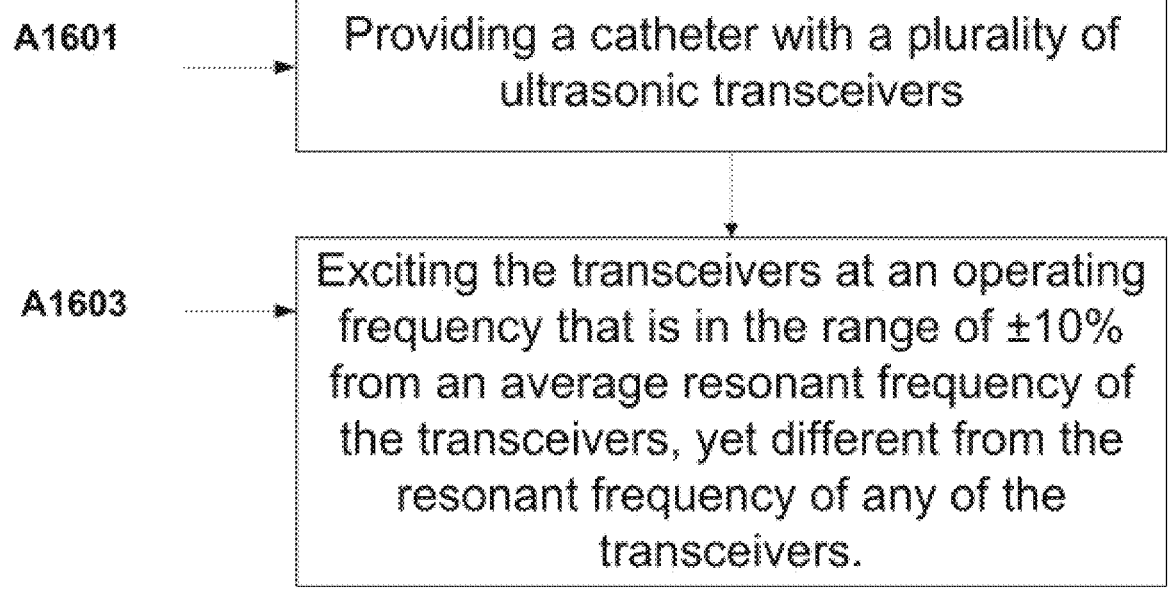
Figure 17:
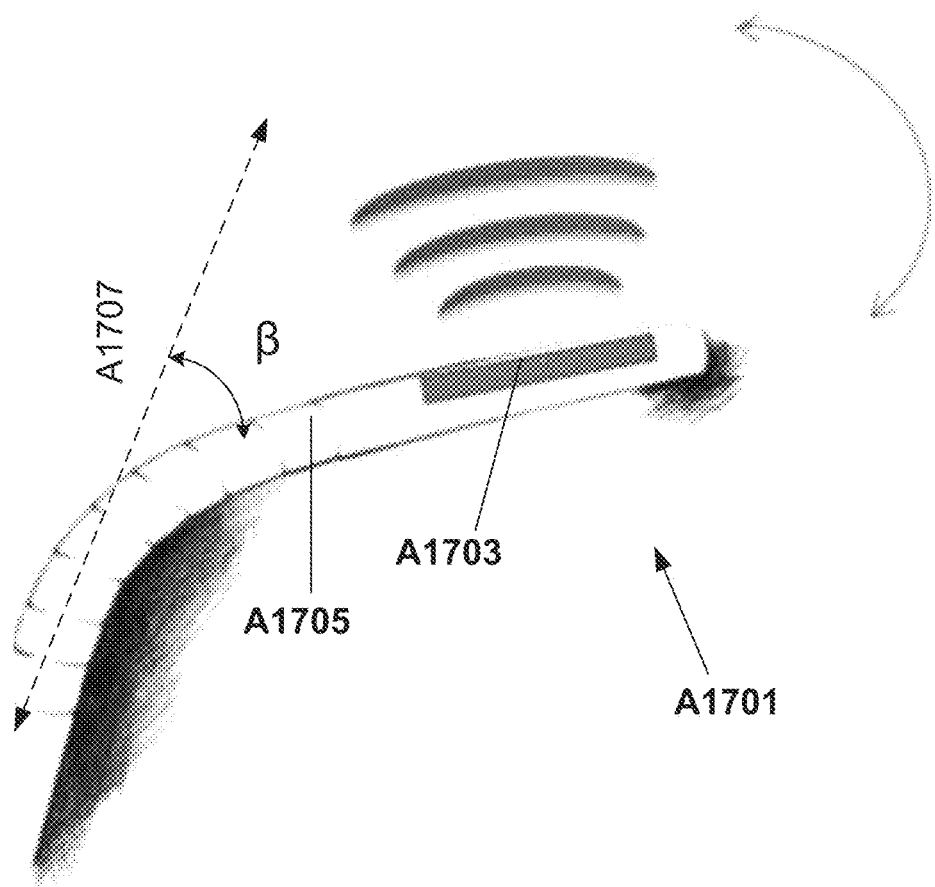
Figure 18A:
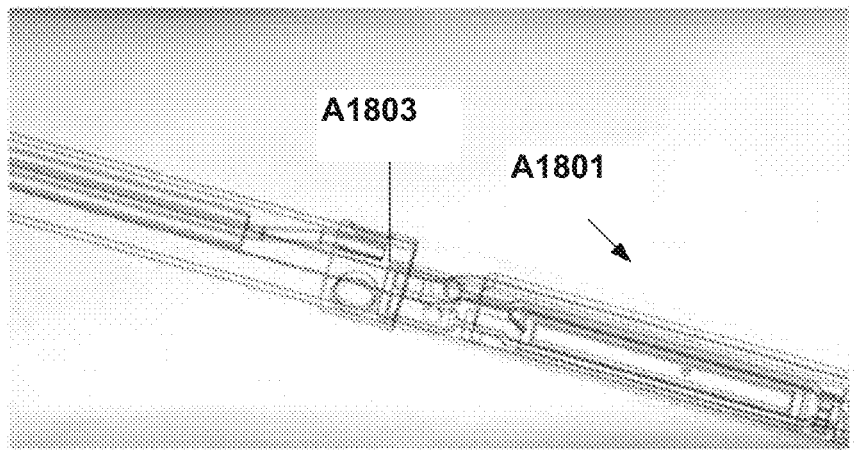
Figure 18B:
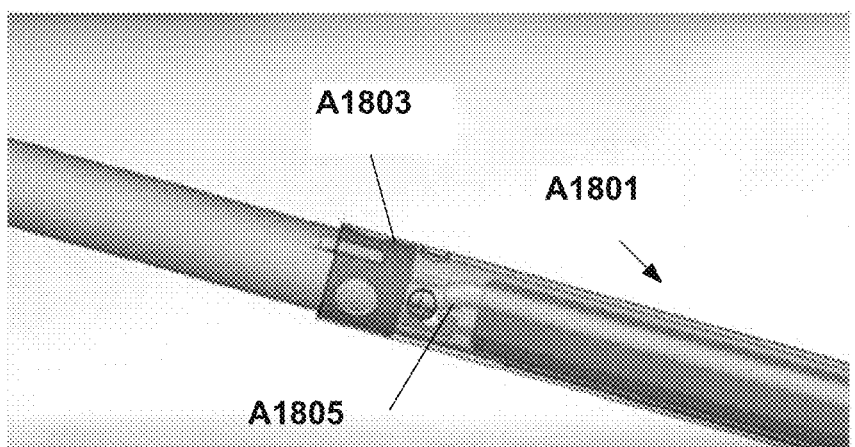
Figure 18C:
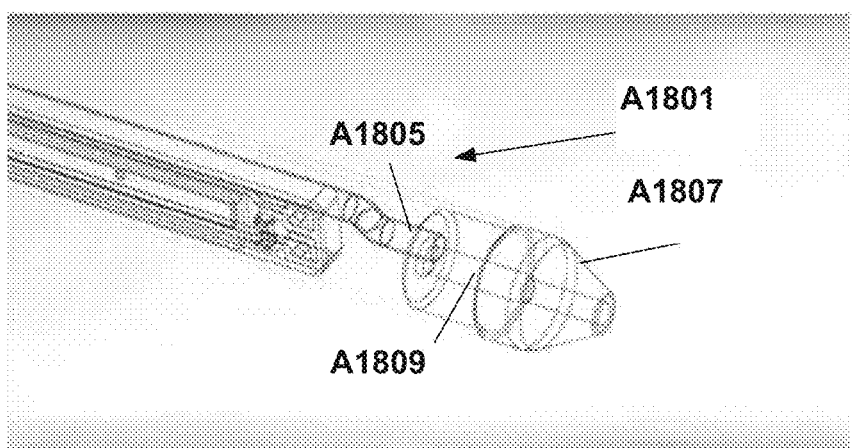

FIGS. 1A-C are a photo (FIG. 1A) and isometric views (FIGS. 1B and 1C) of a catheter head comprising a chassis and a plurality of ultrasonic transceivers, according to some embodiments of the invention;

FIGS. 2A-C are photos of a catheter head, according to some embodiments of the invention;

FIG. 3 is a photo of an exemplary mounting configuration of a transceiver on a chassis, according to some embodiments of the invention;

FIGS. 4A-C are a photo (FIG. 4A) and drawings (FIGS. 4B and 4C) of an electrical connection configuration encircling the catheter head, according to some embodiments of the invention;

FIG. 5 is a photo of a PCB comprising one or more vias, according to some embodiments of the invention;

FIGS. 6A-B are schematic representations of an acoustic field (FIG. 6A) and a heat distribution map (FIG. 6B) obtained by a triangular configuration of ultrasound transceivers, according to some embodiments of the invention;

FIGS. 7A-B are measurements of an acoustic energy field irradiated by a single ultrasonic transceiver, according to some embodiments of the invention;

FIG. 8 is an isometric view of a catheter head comprising a square configuration of transceivers mounted onto a square shaped chassis, according to some embodiments of the invention;

FIGS. 9A-B are schematic representations of an acoustic field (FIG. 9A) and a heat distribution map (FIG. 9B) obtained by using a square configuration of ultrasound transceivers, according to some embodiments of the invention;

FIG. 10 is a schematic cross section of a shaft of an intravascular catheter, according to some embodiments of the invention;

FIG. 11 is a drawing of an exemplary catheter handle, according to some embodiments of the invention;

FIG. 12 is a drawing of a catheter head portion comprising one or more temperature sensors, according to some embodiments of the invention;

FIGS. 13A-B are photos of a distancing device of a catheter in a closed configuration (FIG. 13A) and an expanded configuration (FIG. 13B), according to some embodiments of the invention;

FIG. 14 is a diagram of an intravascular catheter system, according to some embodiments of the invention;

FIGS. 15A-G are exemplary print screens of a user interface of the catheter system, according to some embodiments of the invention;

FIG. 16 is a flowchart of a method for controlling a catheter comprising a plurality of ultrasonic transceivers, according to some embodiments of the invention;

FIG. 17 shows a steerable catheter, according to some embodiments of the invention;

FIGS. 18A-C show an exemplary mechanism for deflecting a distal portion of a steerable catheter, according to some embodiments of the invention; and FIGS. 19A-B are a side view (FIG. 19A) and a longitudinal cross section (FIG. 19B) of a handle A1901 of a steerable catheter, according to some embodiments of the invention.

Figure 20A:
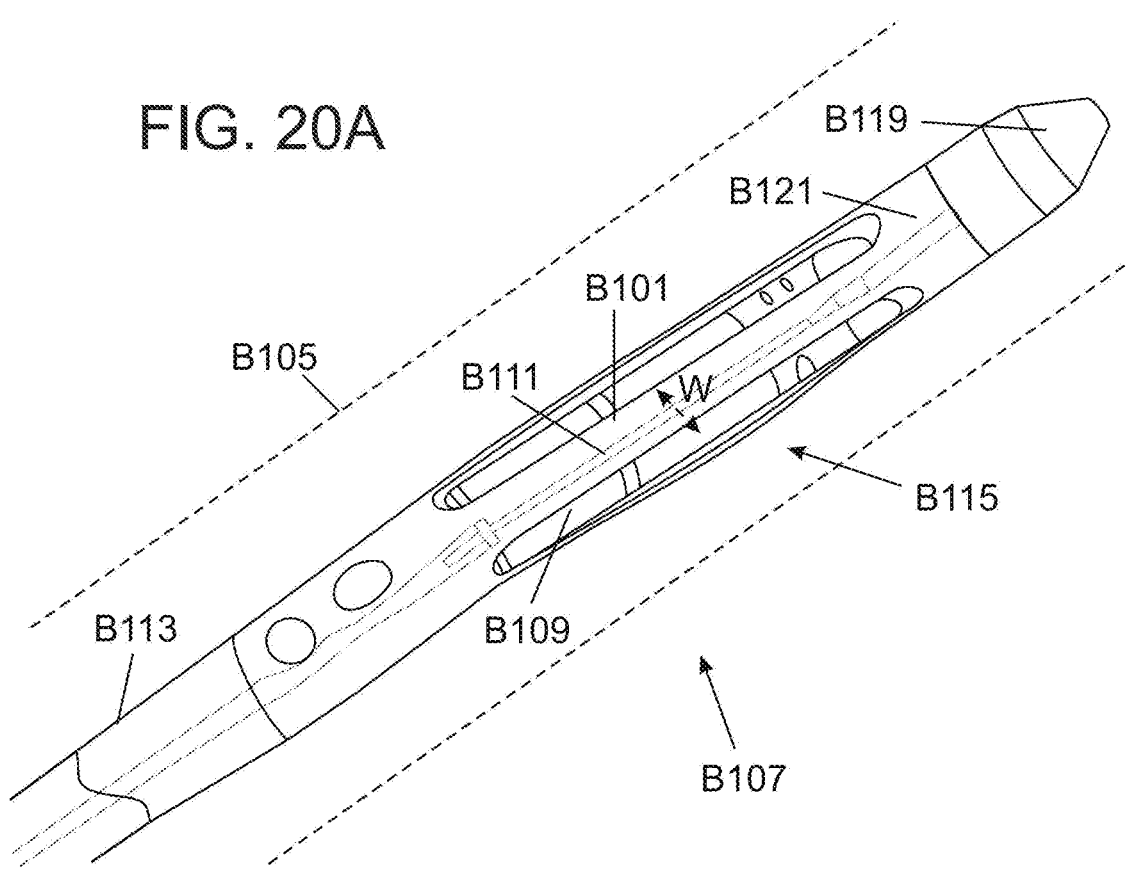
Figure 20B:
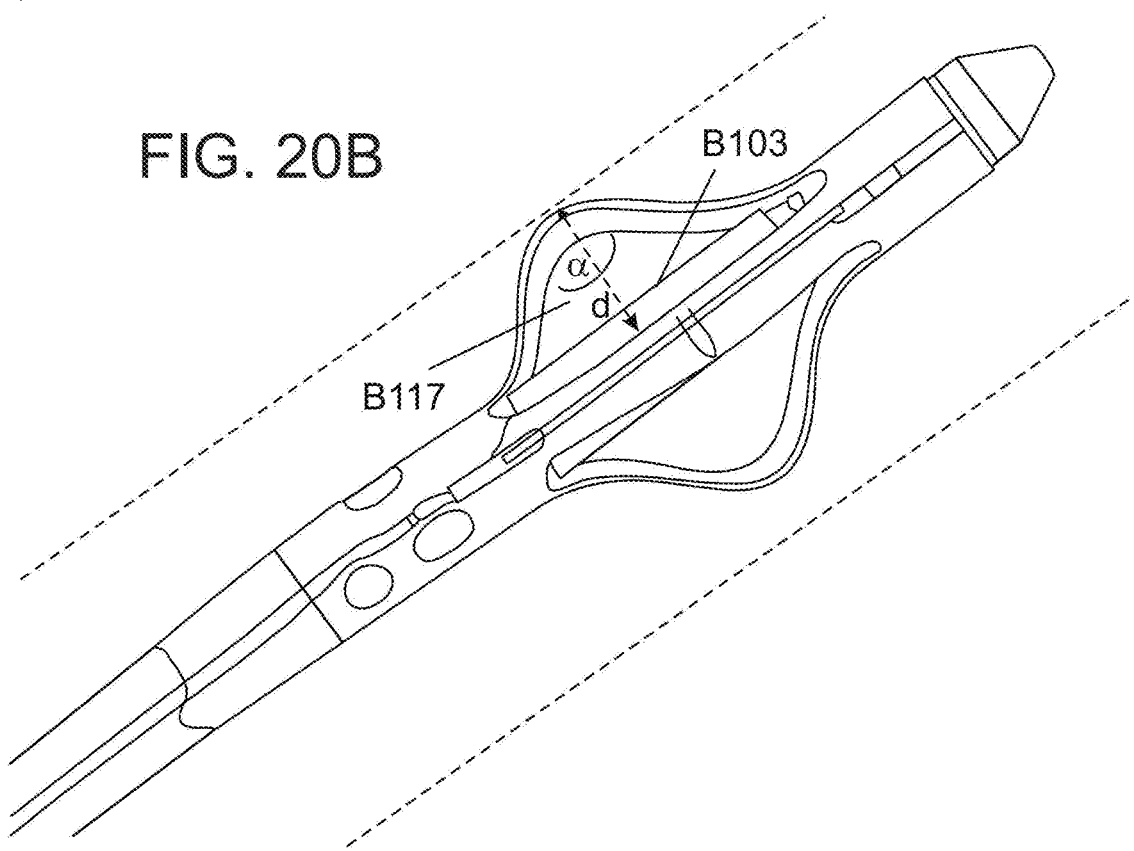
Figure 21A:
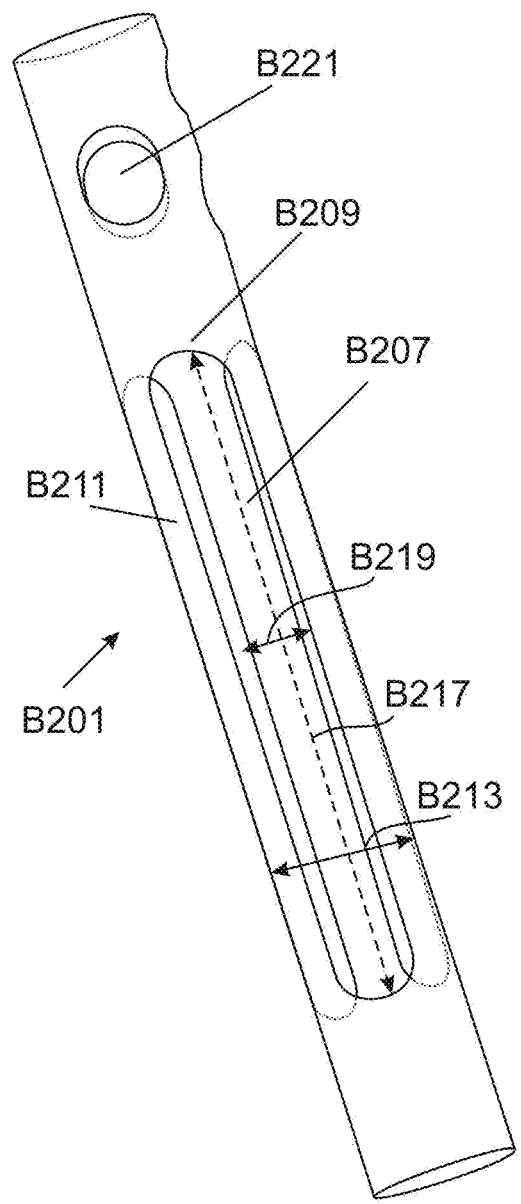
Figure 21B:
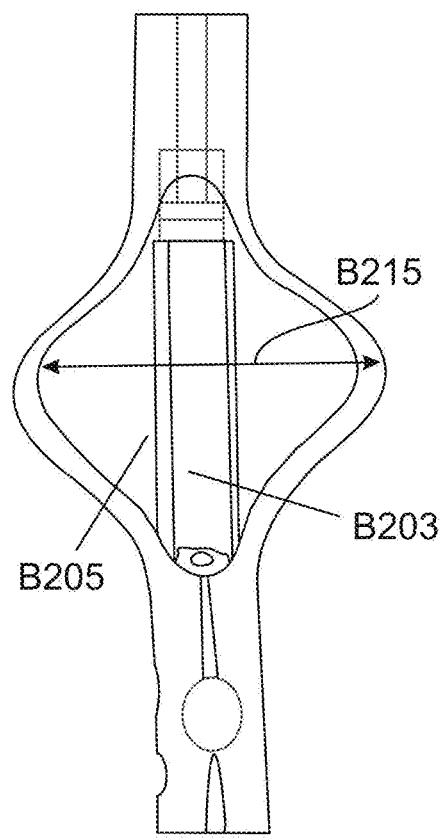
Figure 21C:
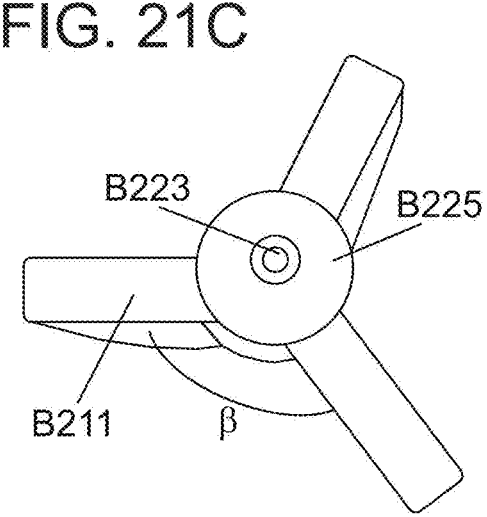
Figure 22:
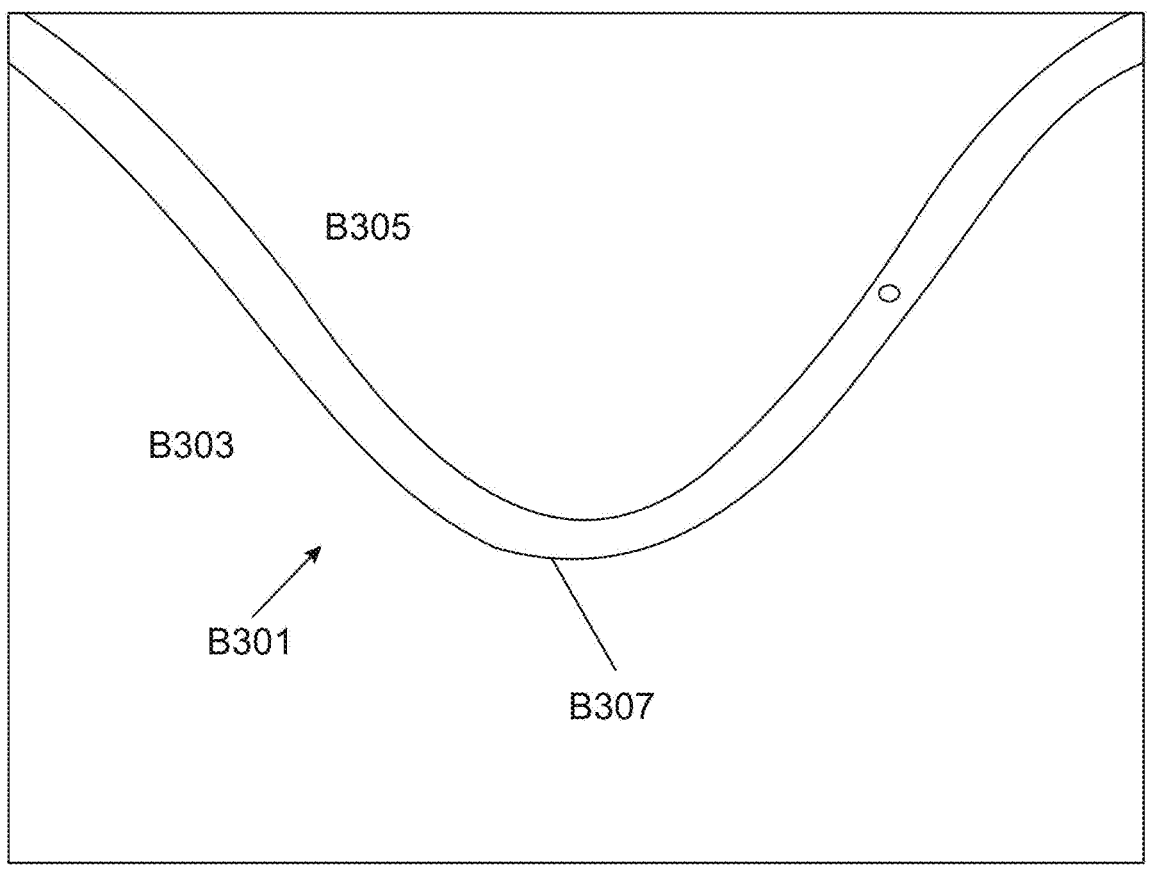
Figure 23A:
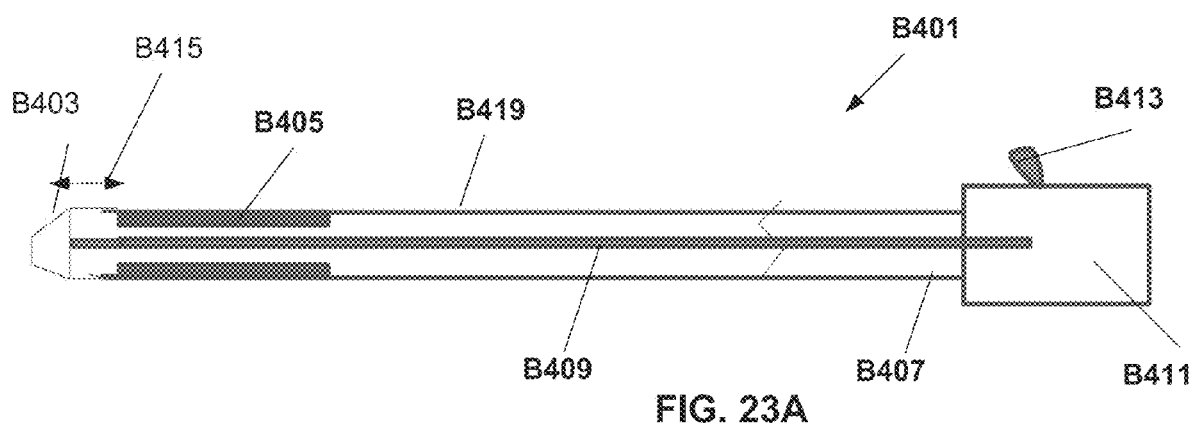
Figure 23B:
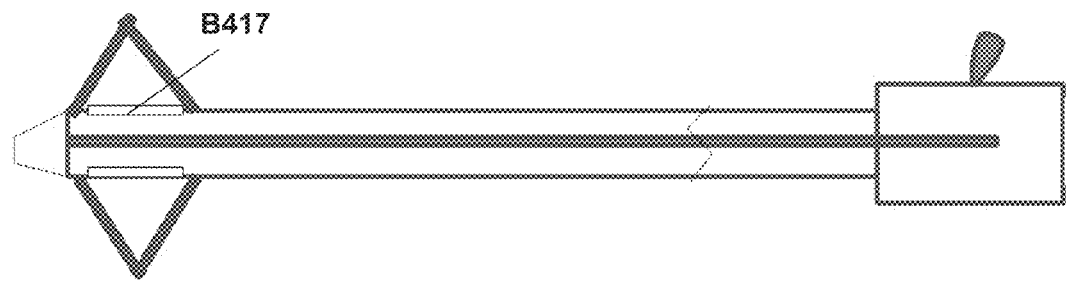
Figure 24:
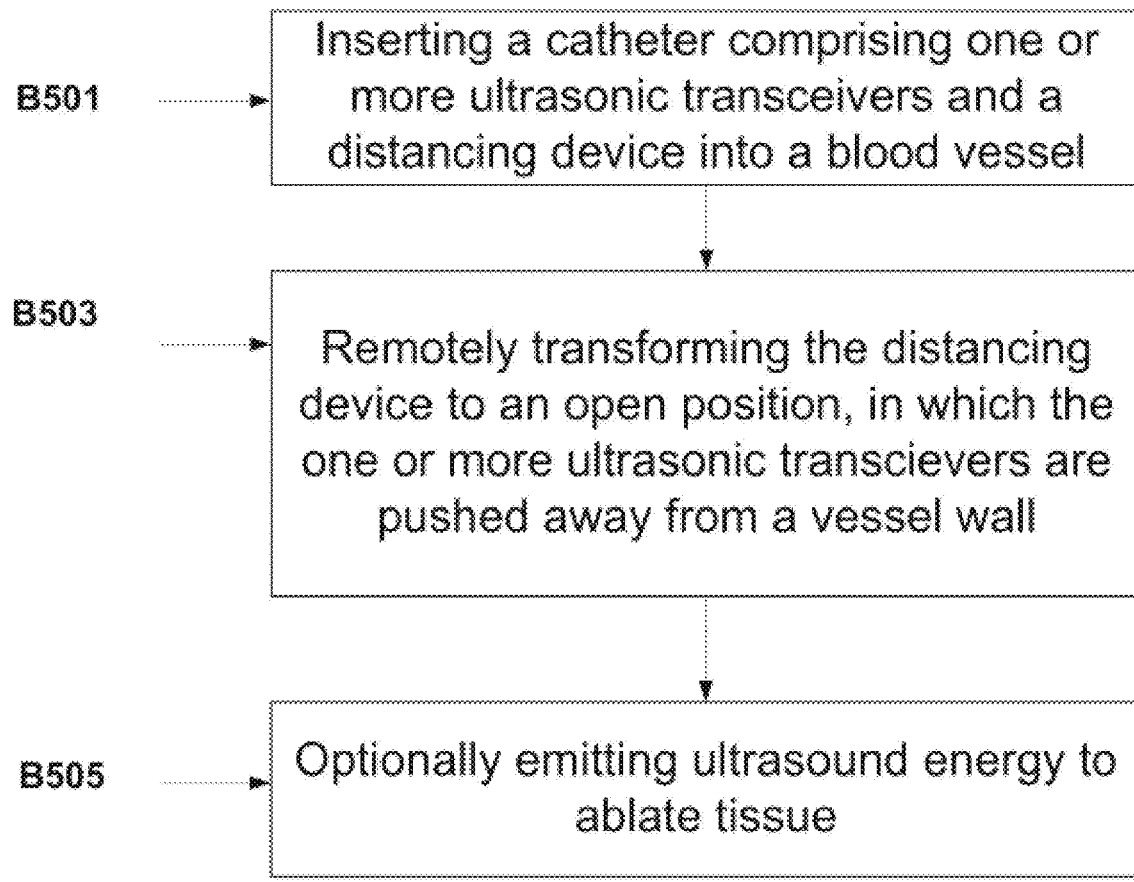
Figure 26:
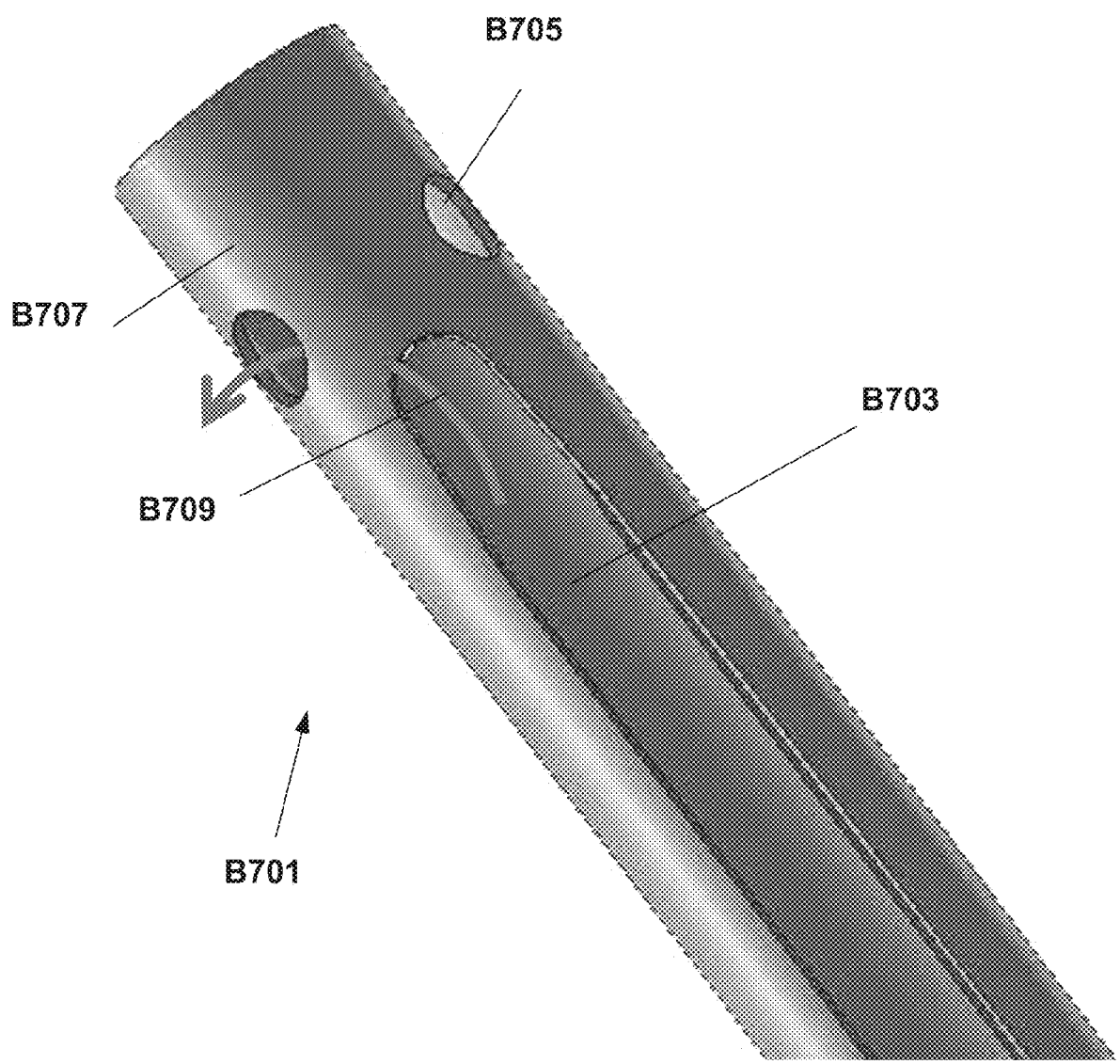
Figure 27A:
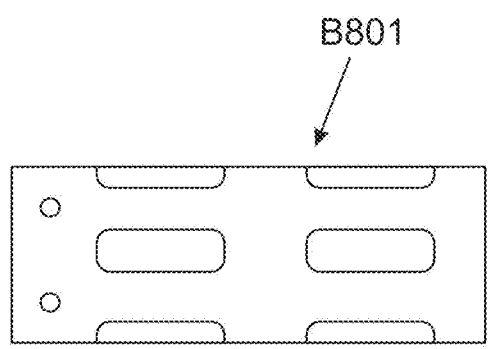
Figure 27B:
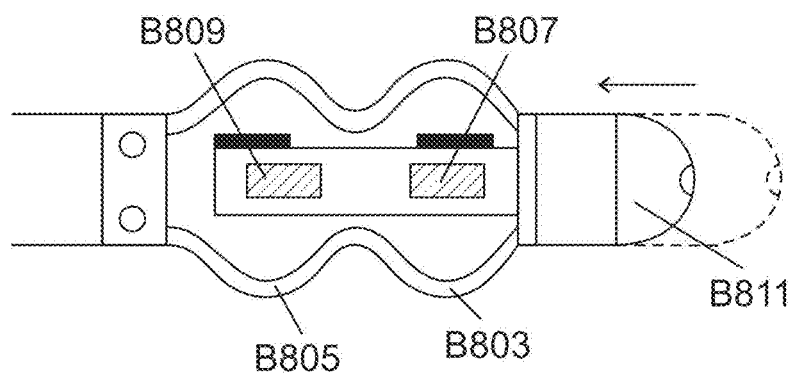
Figure 29A:
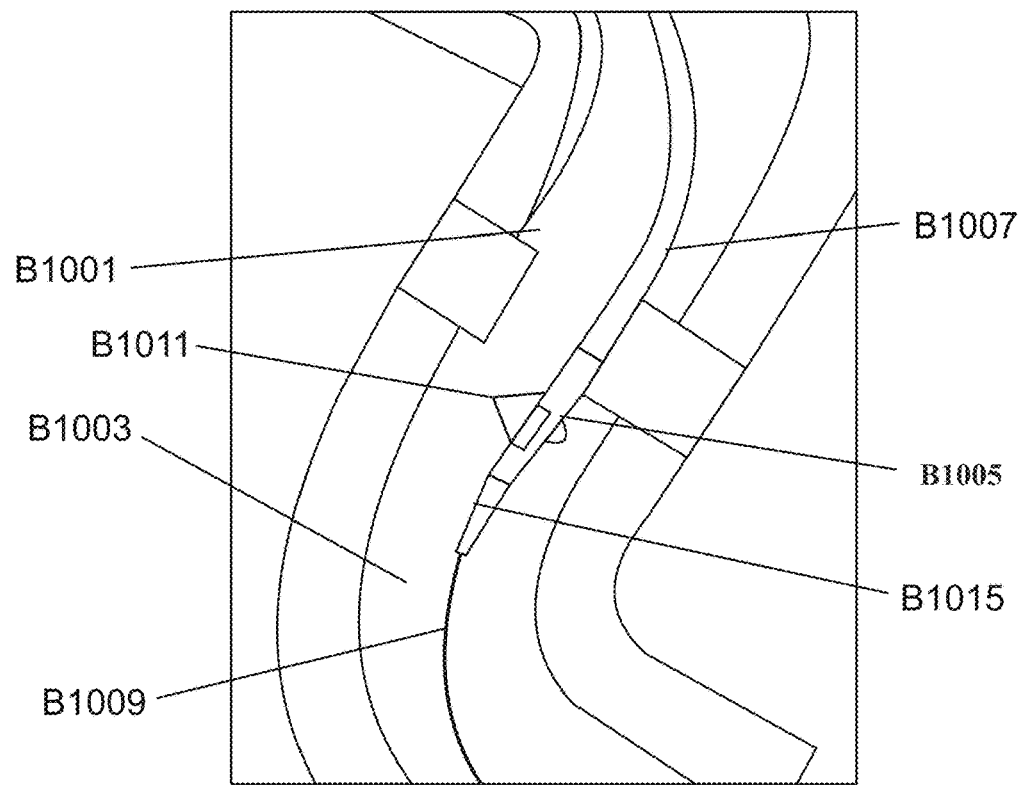
Figure 29B:
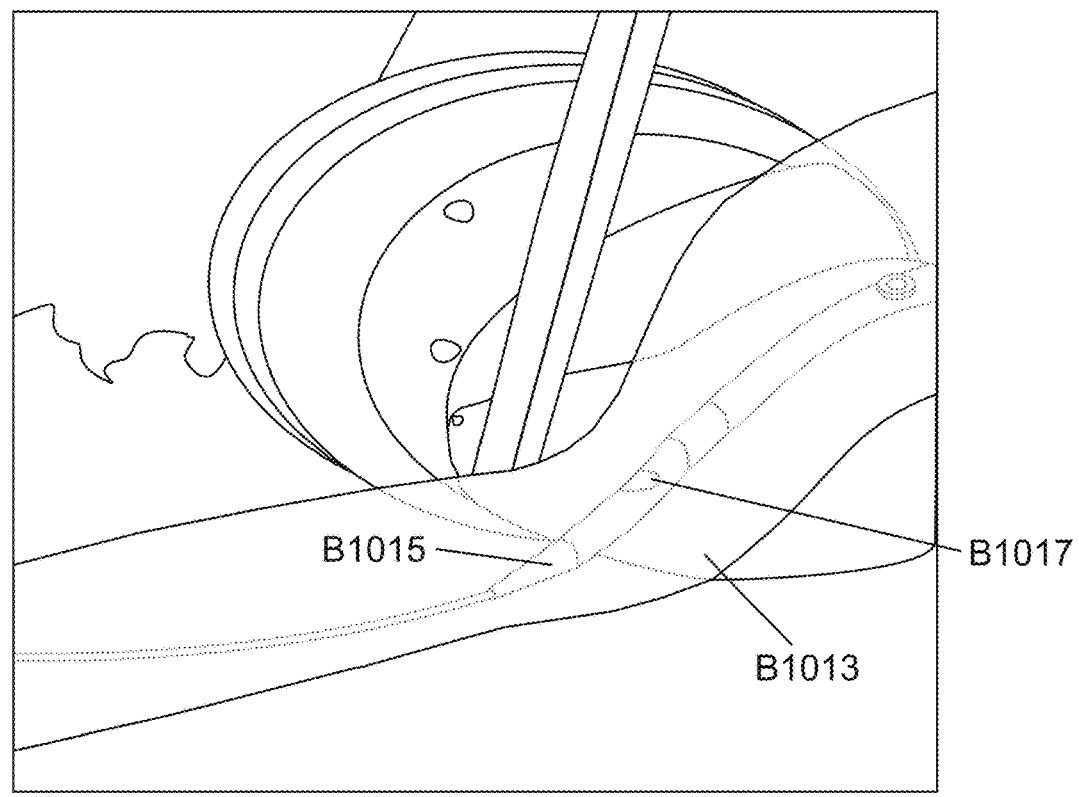
Figure 30A:
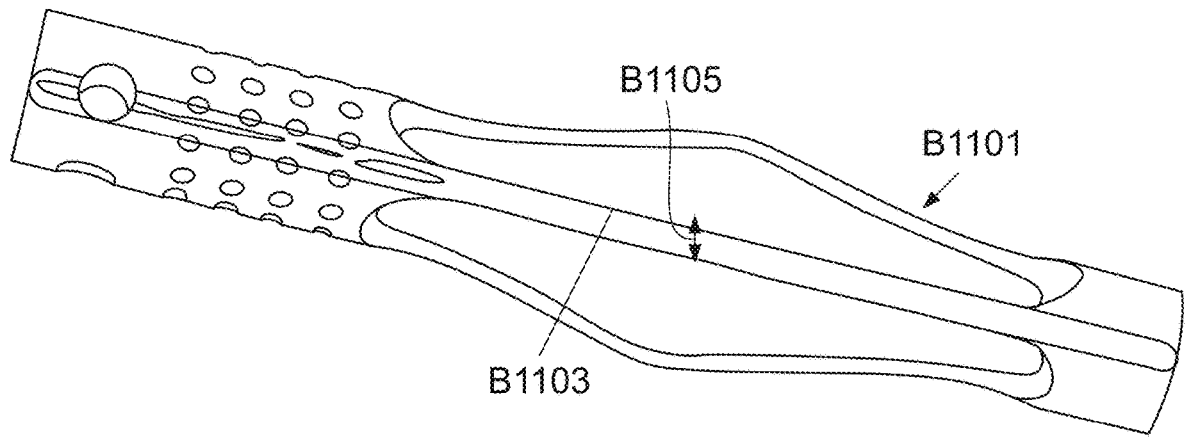
Figure 30B:
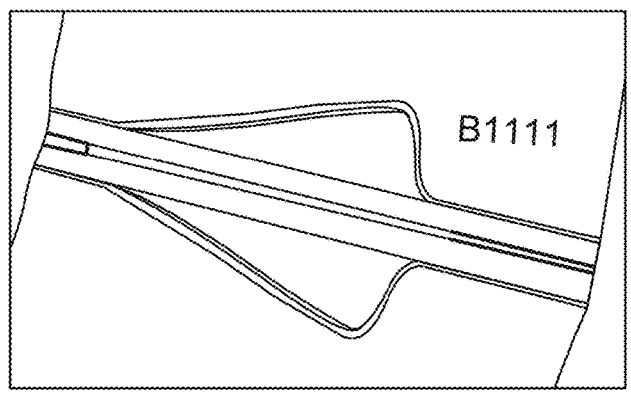
Figure 30C:
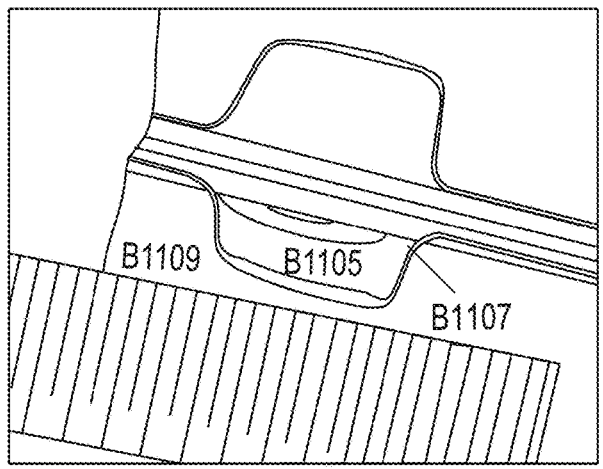
Figure 31A:
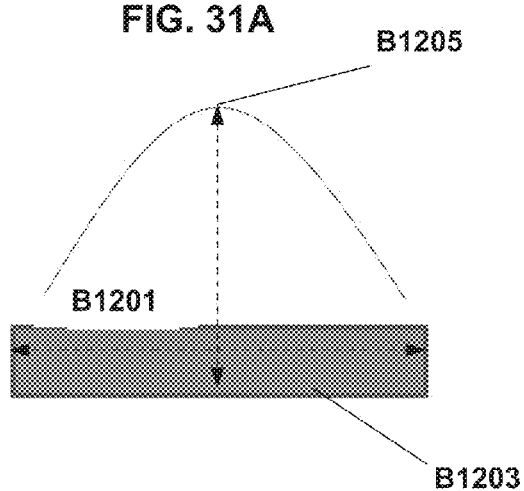
Figure 31B:
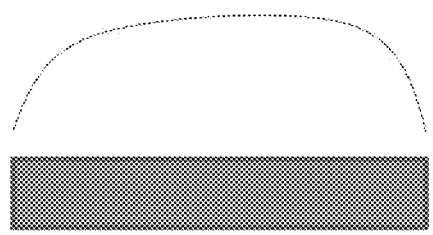
Figure 31C:
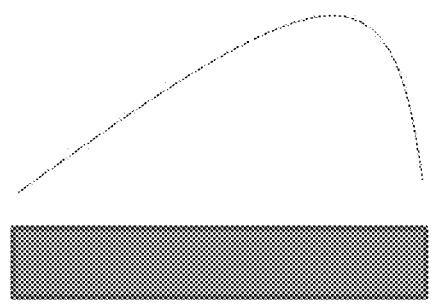
Figure 31D:
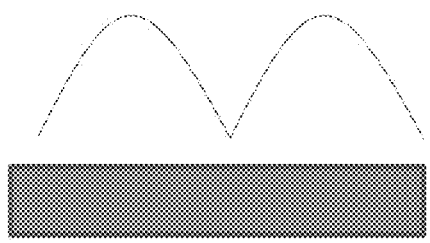
Figure 32A:
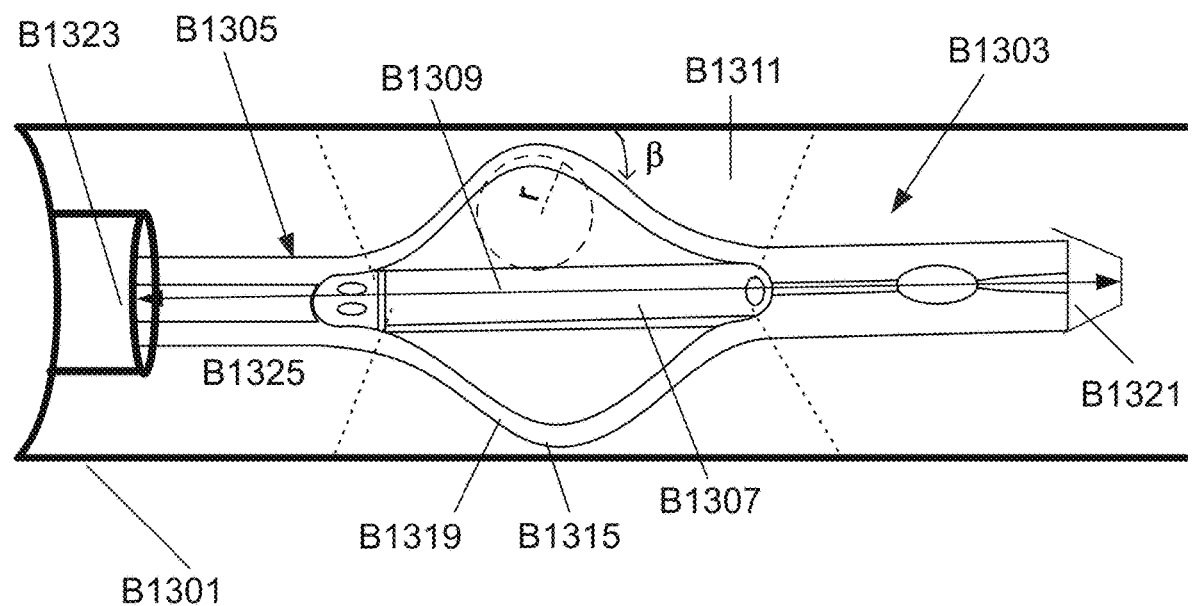
Figure 32B:
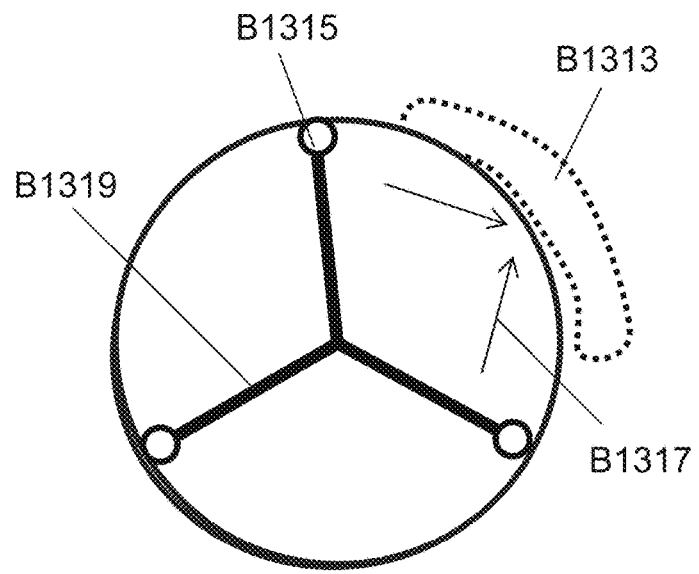

FIGS. 20A-B are photos of a distancing device configured for providing a distance between one or more ultrasonic transceivers and one or more walls of a blood vessel (represented by the dashed lines), according to some embodiments of the invention;

FIGS. 21A-C are a photo of an intravascular distancing device shown separately from a catheter (FIG. 21A); a photo of a distancing device configured on a catheter head and shown in an open configuration (FIG. 21B); and a front view photo of the distal end of the catheter, with the distancing device in an open configuration (FIG. 21C);

FIG. 22 is a side view photo of a leaflet of a distancing device in an open configuration, according to some embodiments of the invention;

FIGS. 23A-B are schematic illustrations of an exemplary mechanism for operating a distancing device, according to some embodiments of the invention;

FIG. 24 is a flowchart of an exemplary mechanism for operating a distancing device when treating a blood vessel wall, according to some embodiments of the invention;

FIGS. 25A-D are photos of an exemplary handle of a catheter, comprising a lever assembly for operating a distancing device, according to some embodiments of the invention;

FIG. 26 is a schematic illustration of flow through openings of a distancing device, according to some embodiments of the invention;

FIGS. 27A-B show an exemplary configuration of a distancing device comprising two sets of leaflets, according to some embodiments of the invention;

FIGS. 28A-D are photos of a catheter comprising a distancing device which is gradually transformed into a fully open position, according to some embodiments of the invention;

FIGS. 29A-B are photos of an experiment for passing a catheter device comprising a distancing device through a pipe model simulating a renal artery, according to some embodiments of the invention;

FIGS. 30A-C are photos of a distancing device comprising metal, according to some embodiments of the invention;

FIGS. 31A-D are exemplary configurations of an open leaflet of a distancing device, according to some embodiments of the invention; and FIGS. 32A-B are a schematic illustration (FIG. 32A) and a cross section (FIG. 32B) of a catheter comprising a distancing device positioned within a blood vessel, according to some embodiments of the invention.

Figure 33:
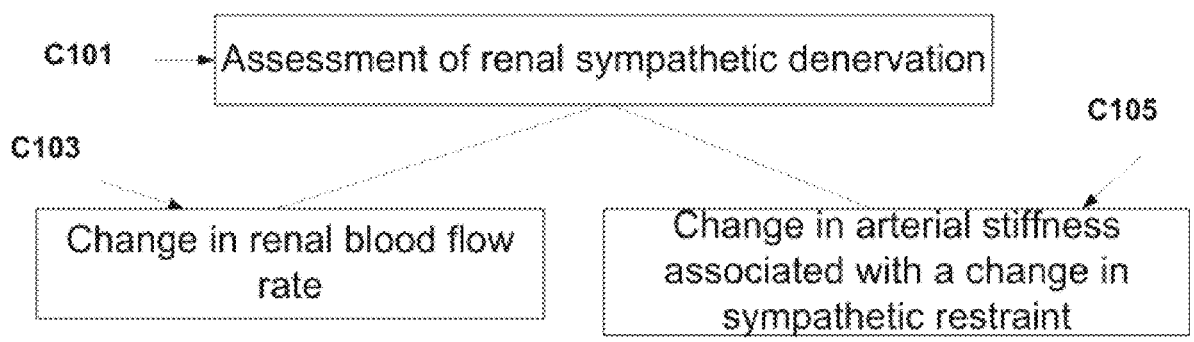
Figure 35:
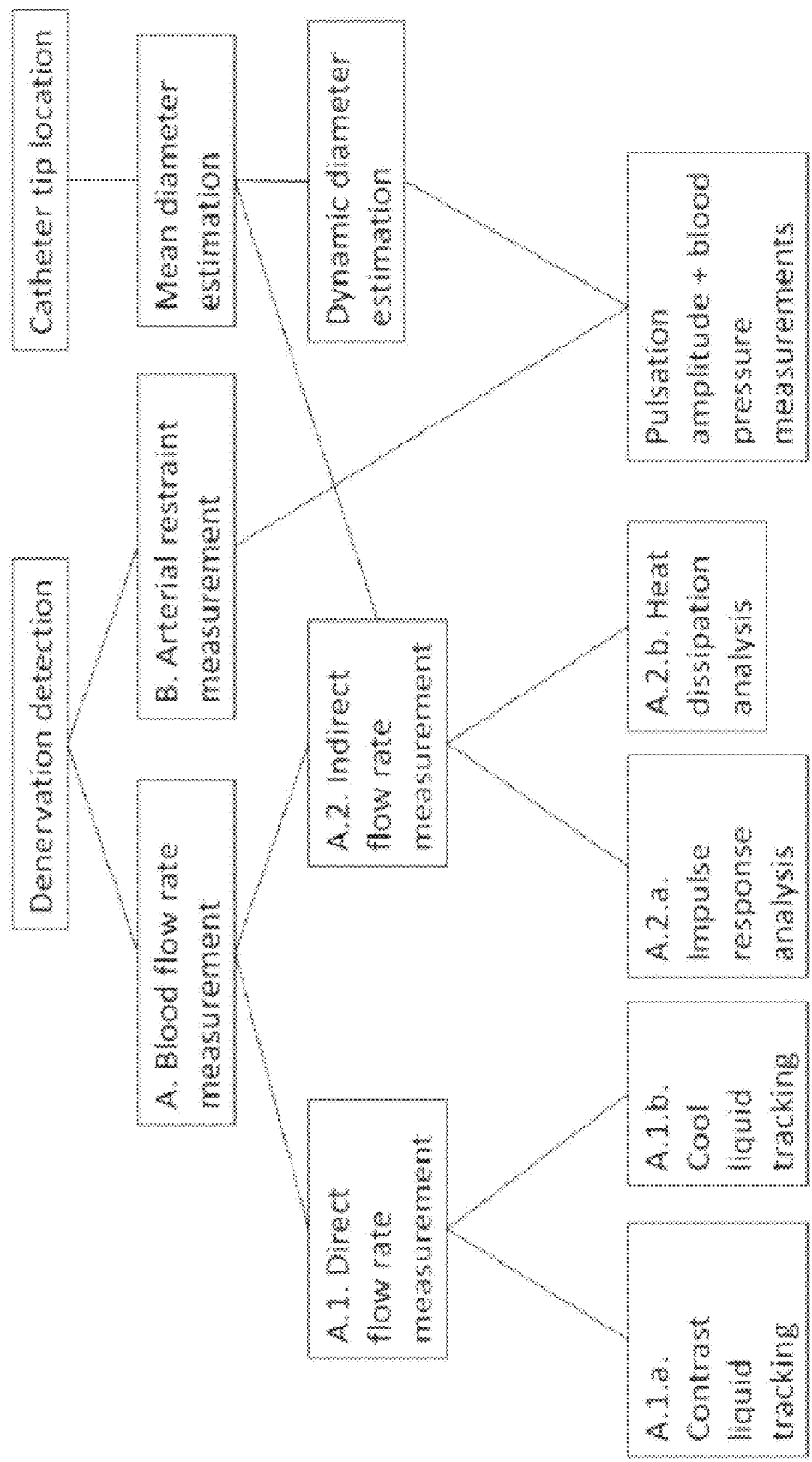
Figure 36:
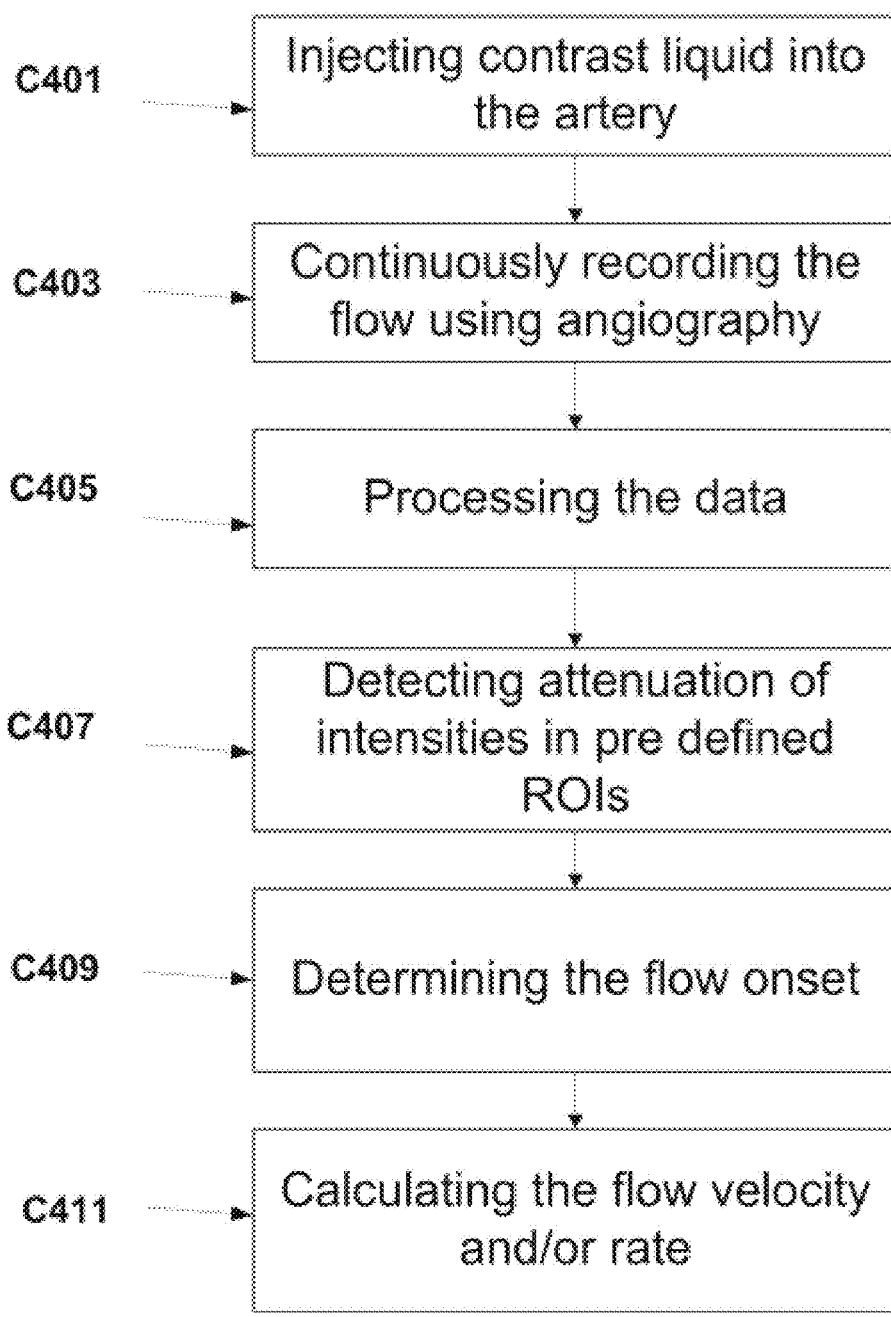
Figure 37A:
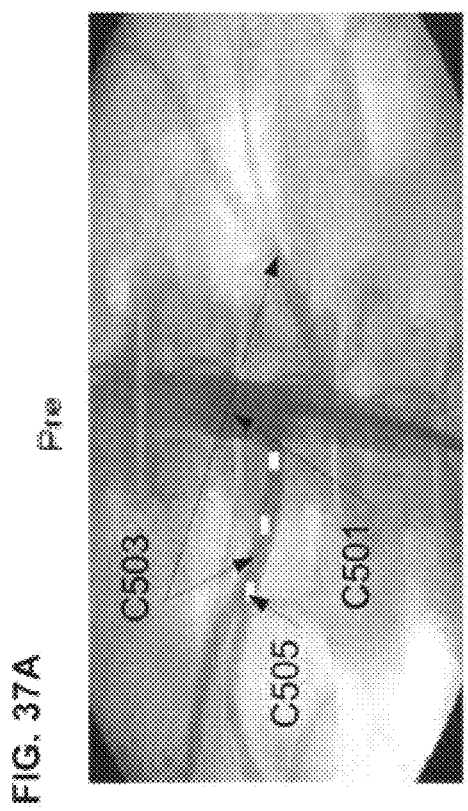
Figure 37B:
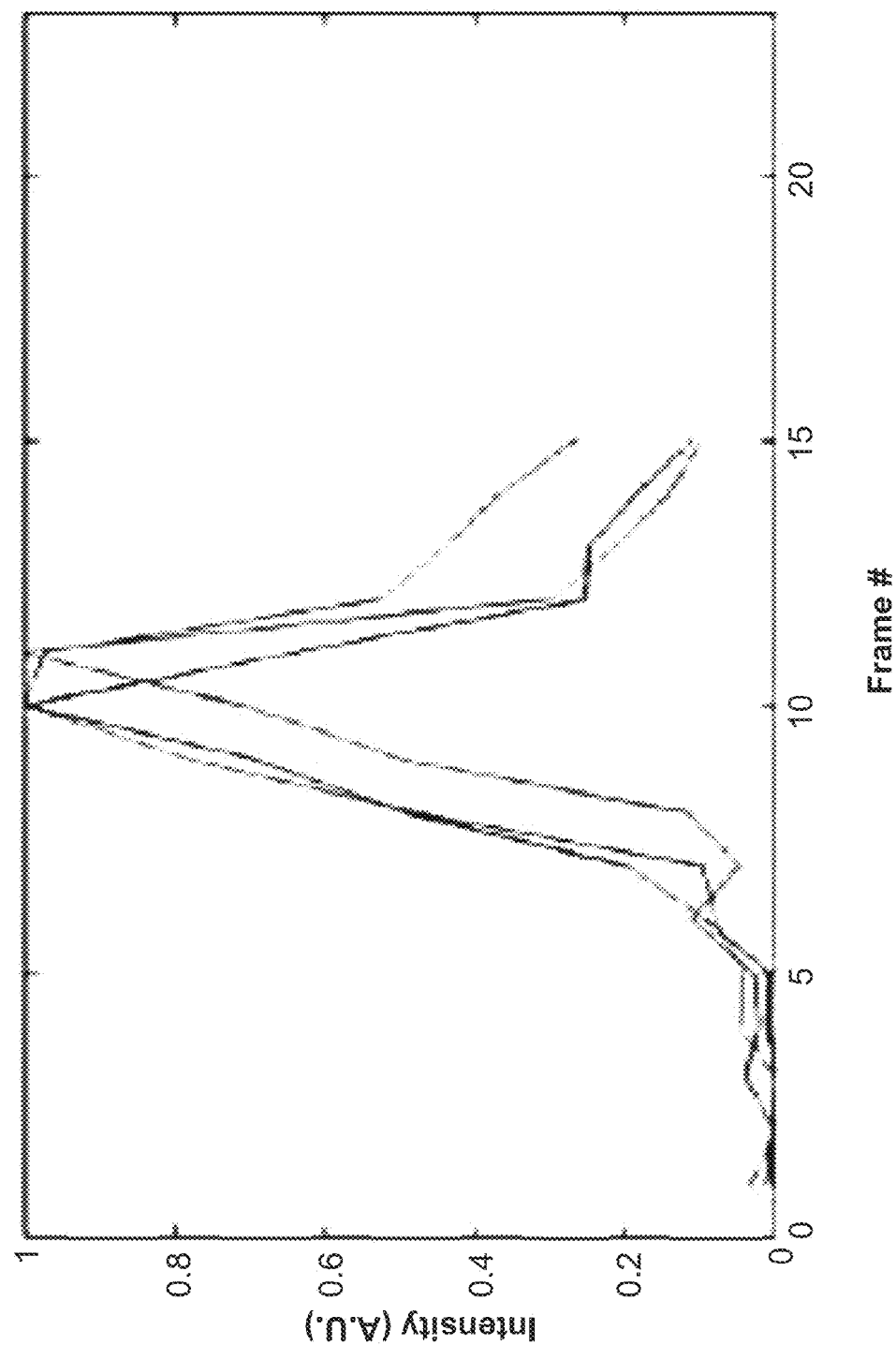
Figure 38:
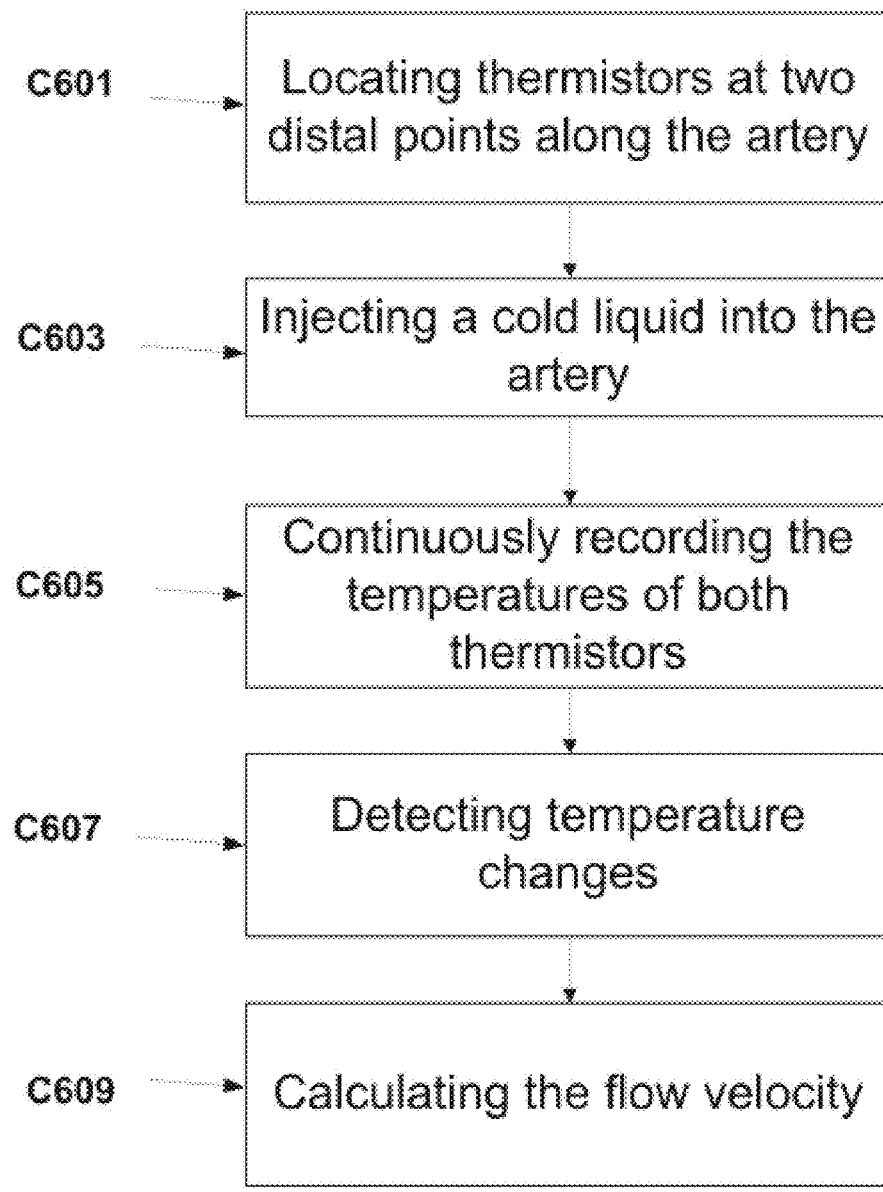
Figure 39:
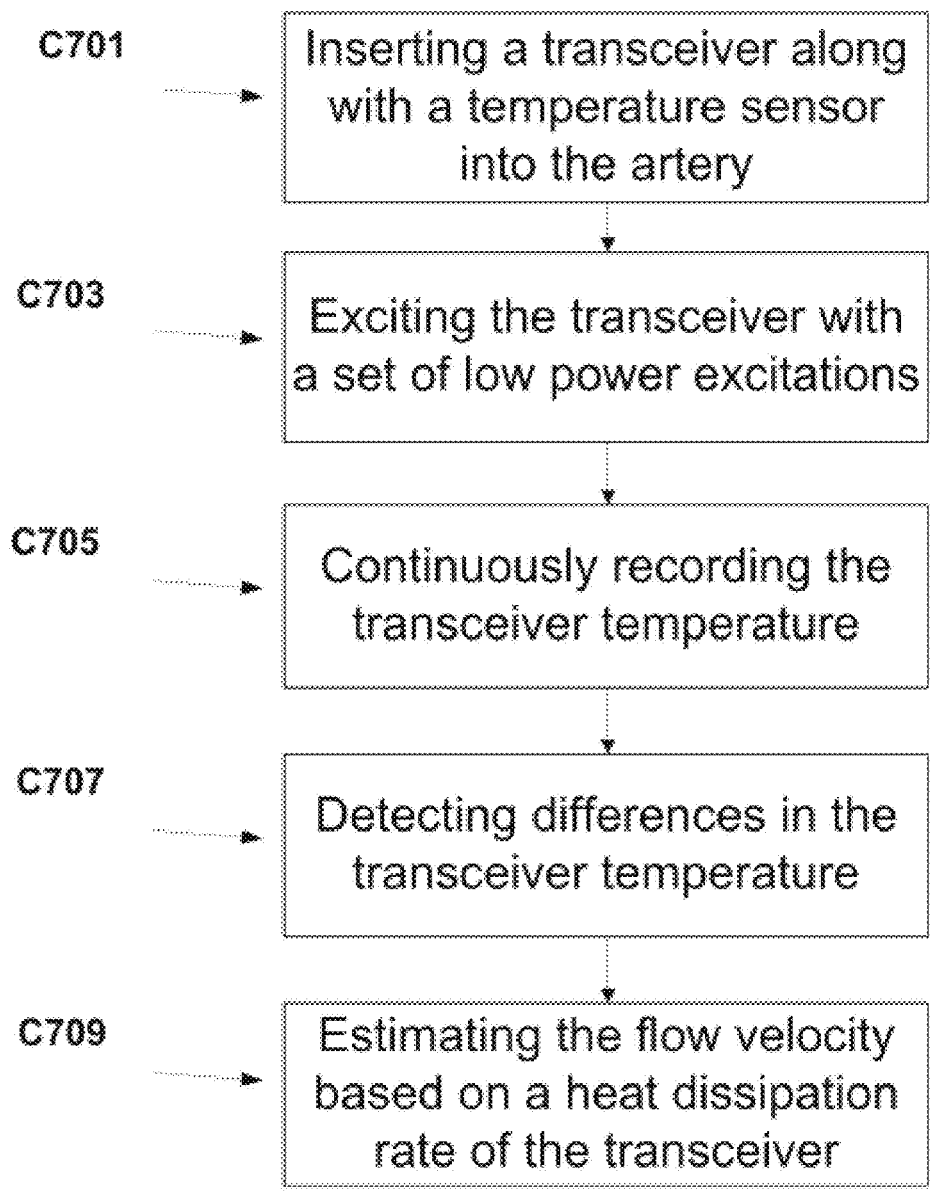
Figure 42:
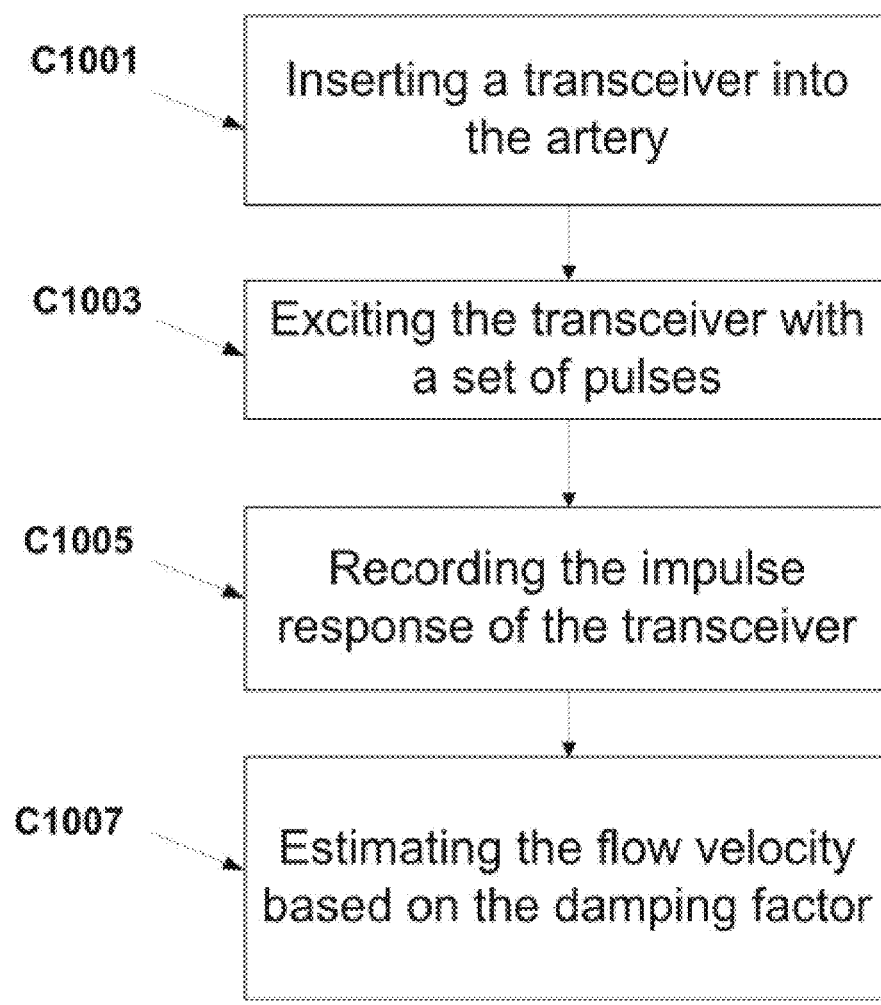
Figure 43B:
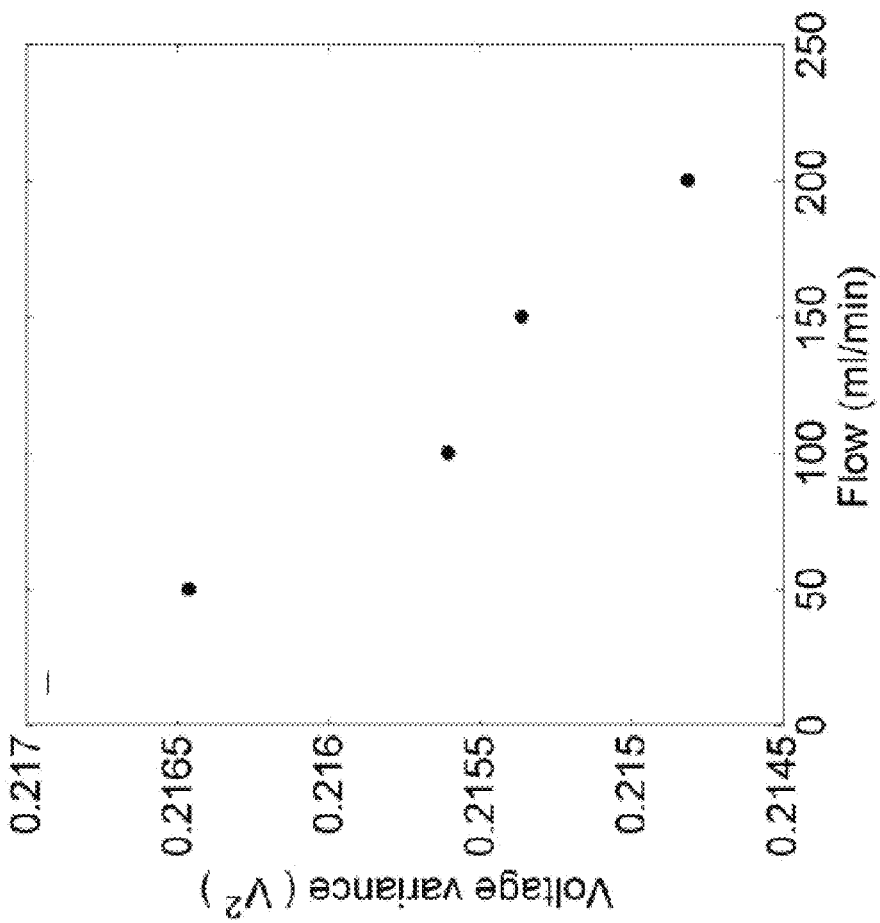
Figure 43A:
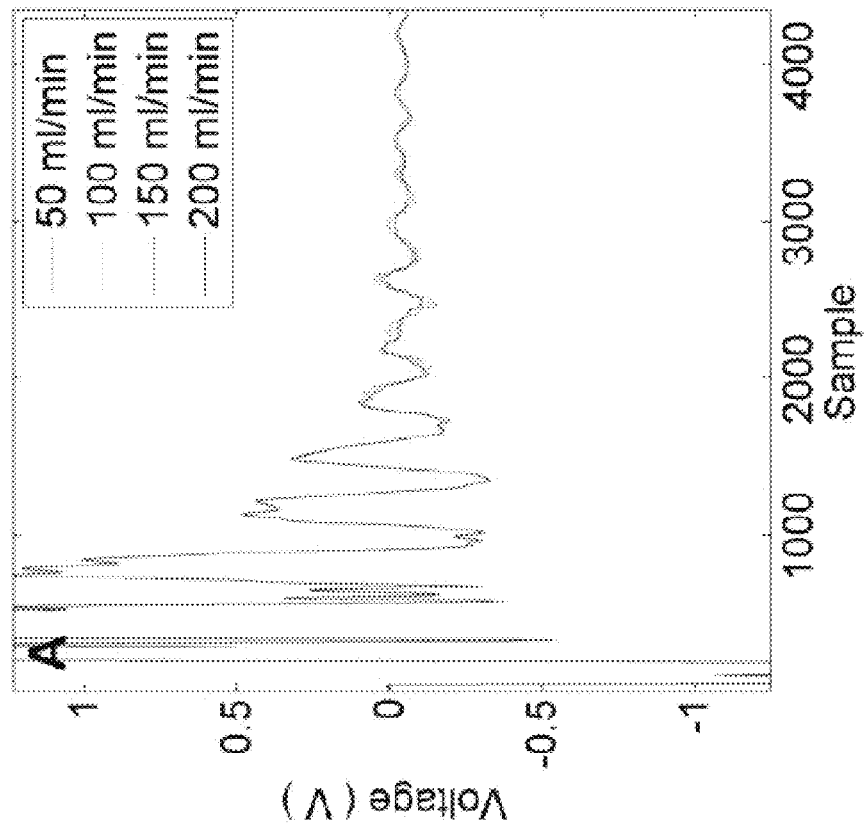
Figure 44B:
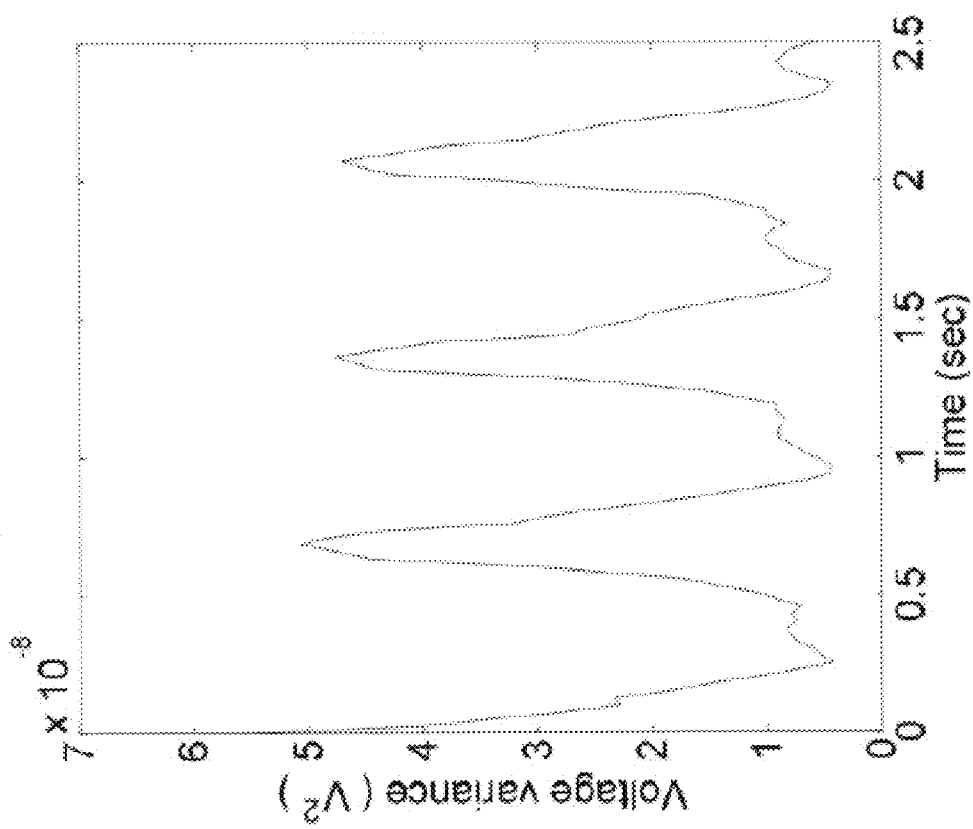
Figure 44A:
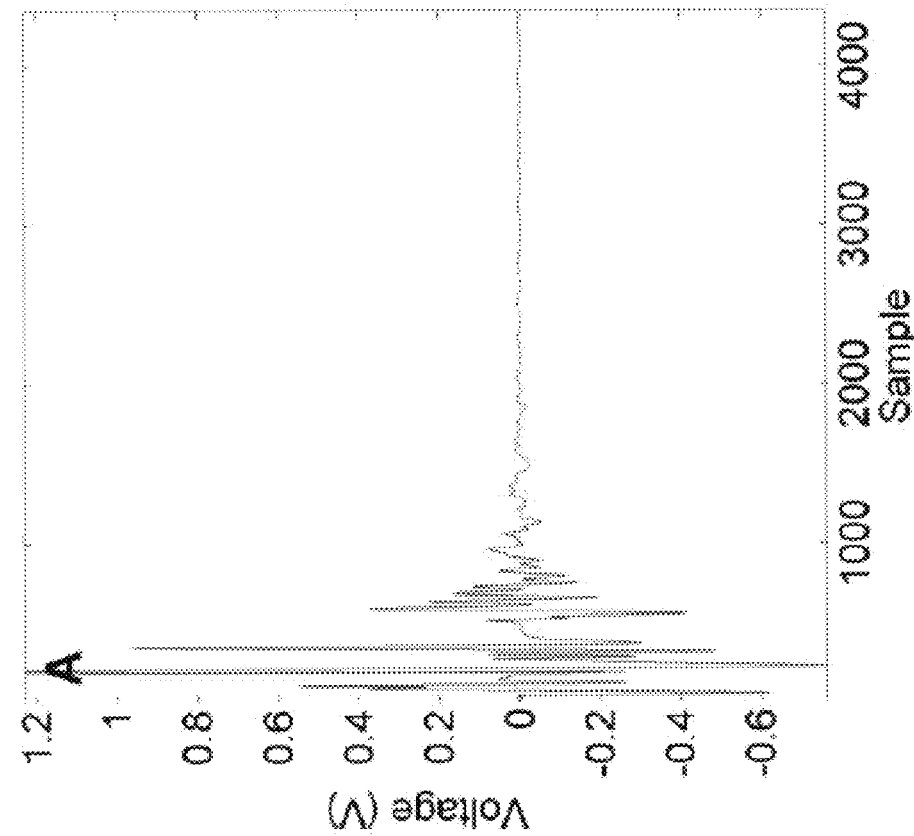
Figure 45:
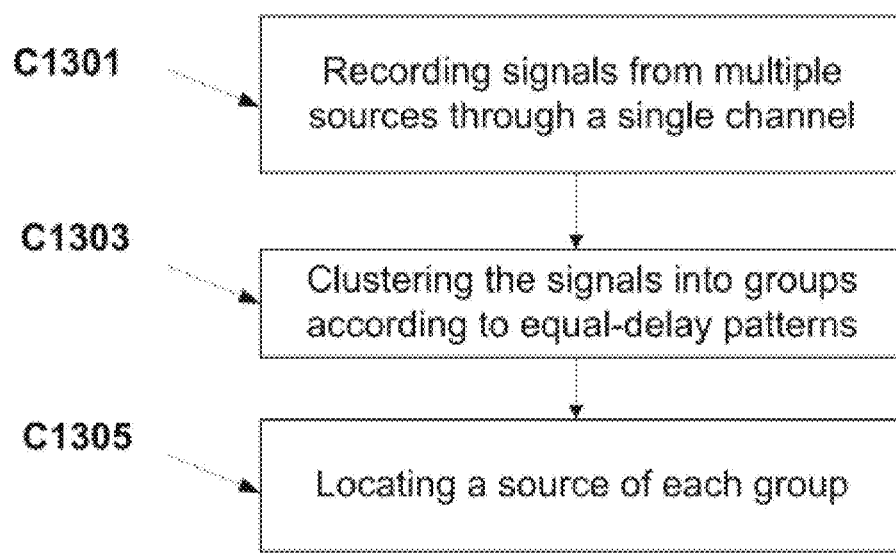
Figure 46:
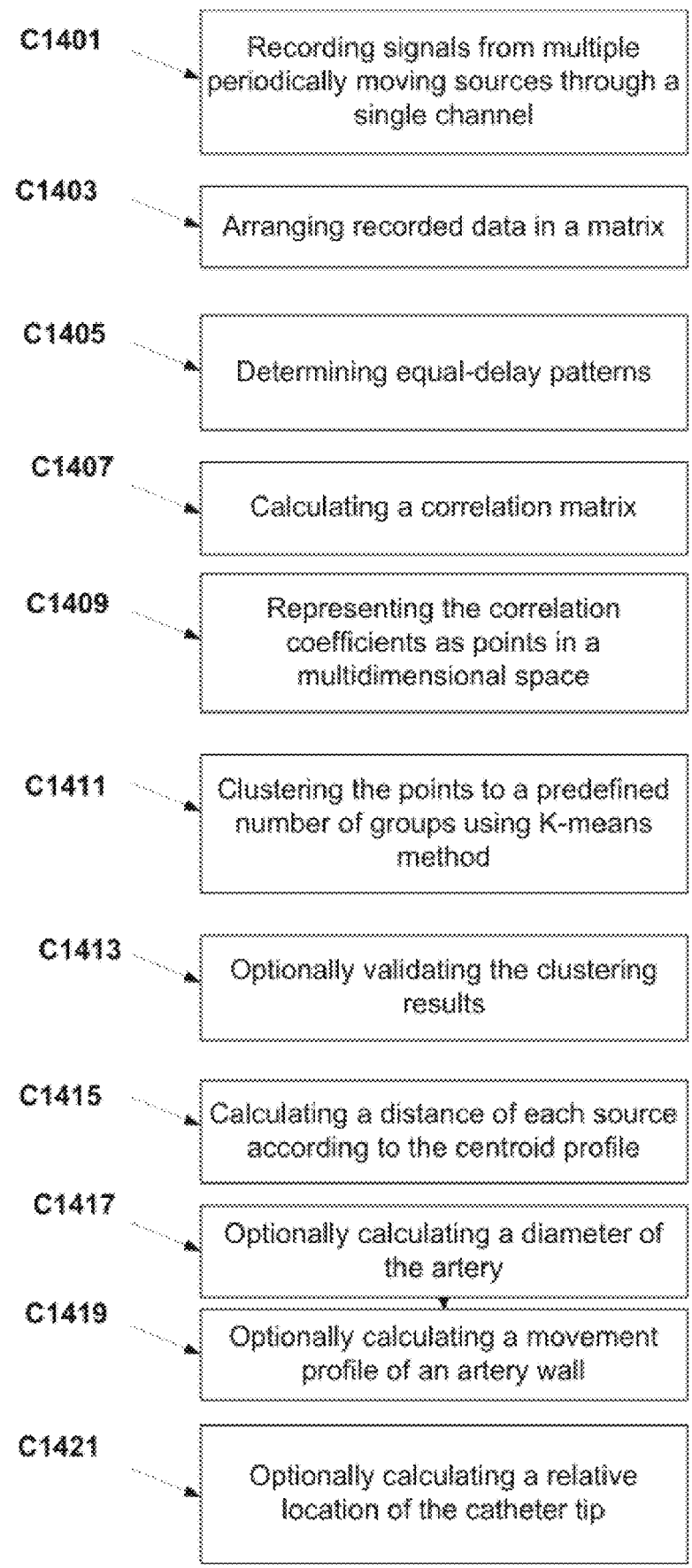
Figures 47A, 47B:
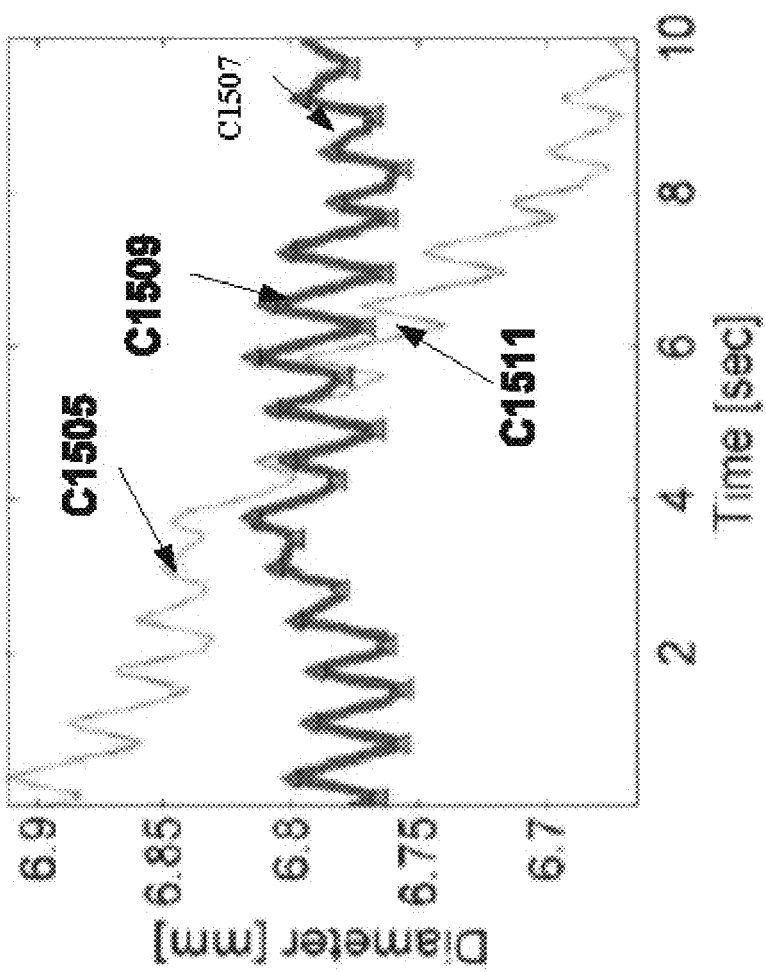
Figure 47C:
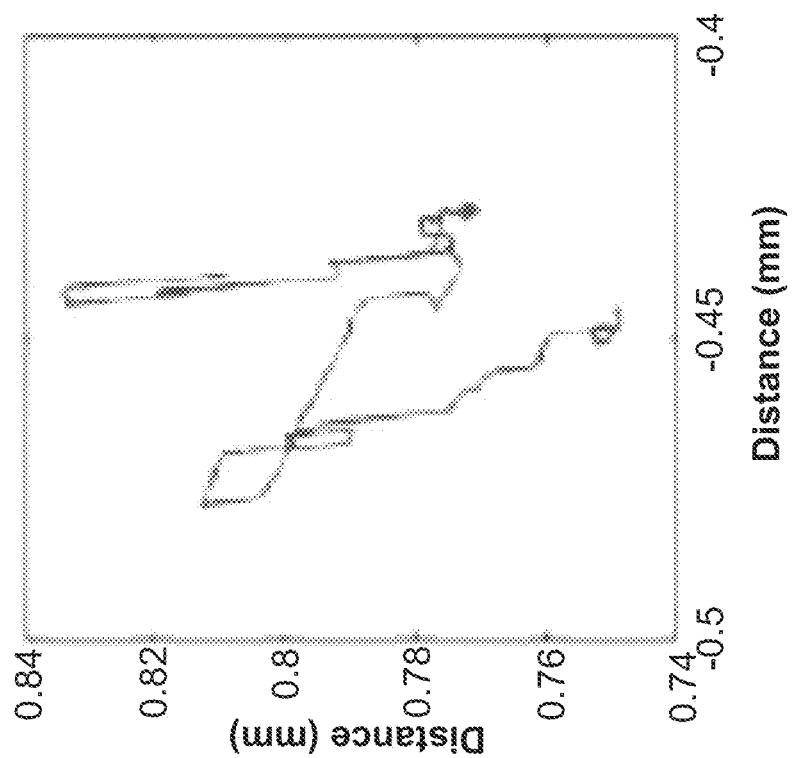
Figure 48:
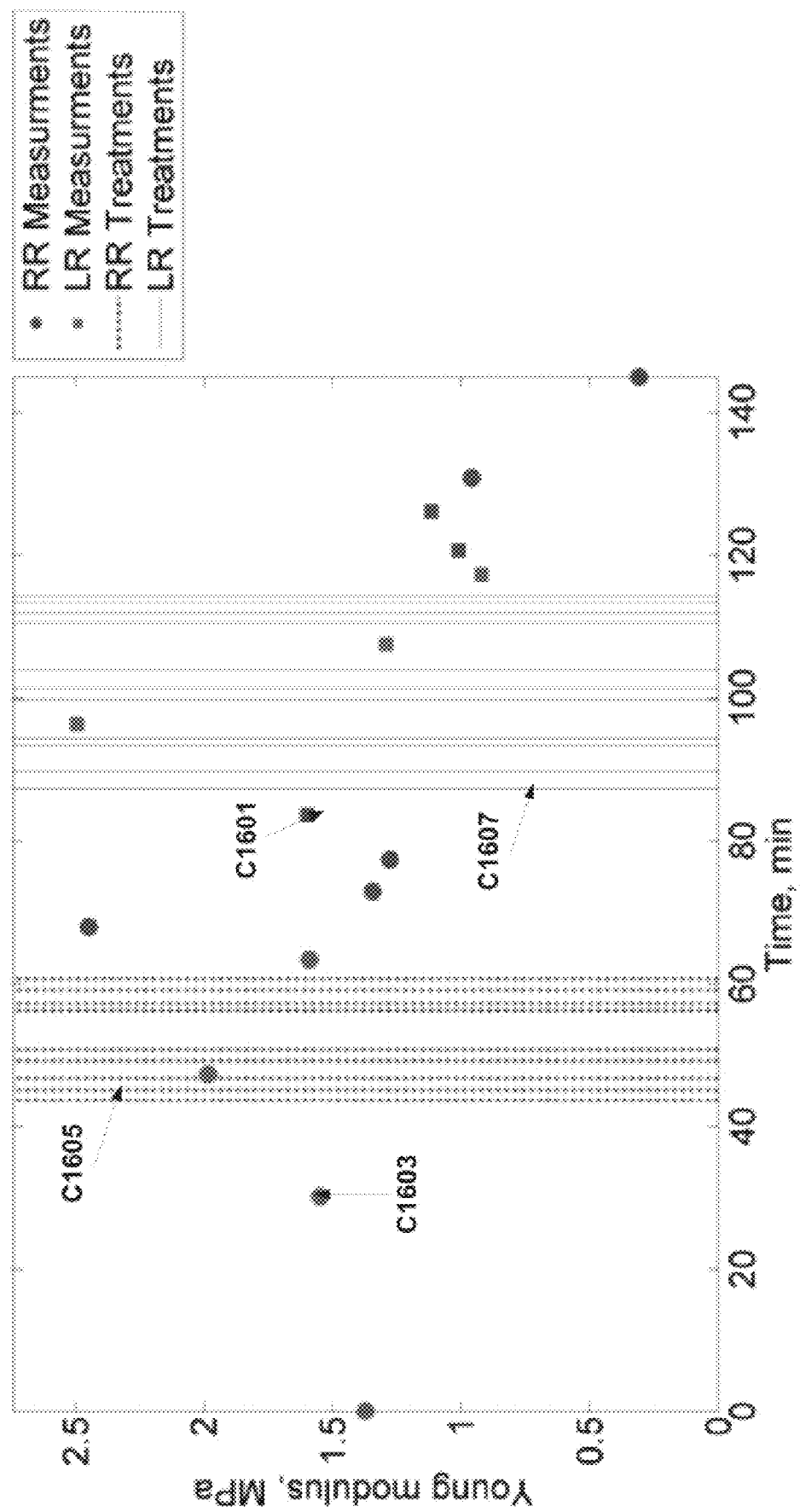
Figure 49A:
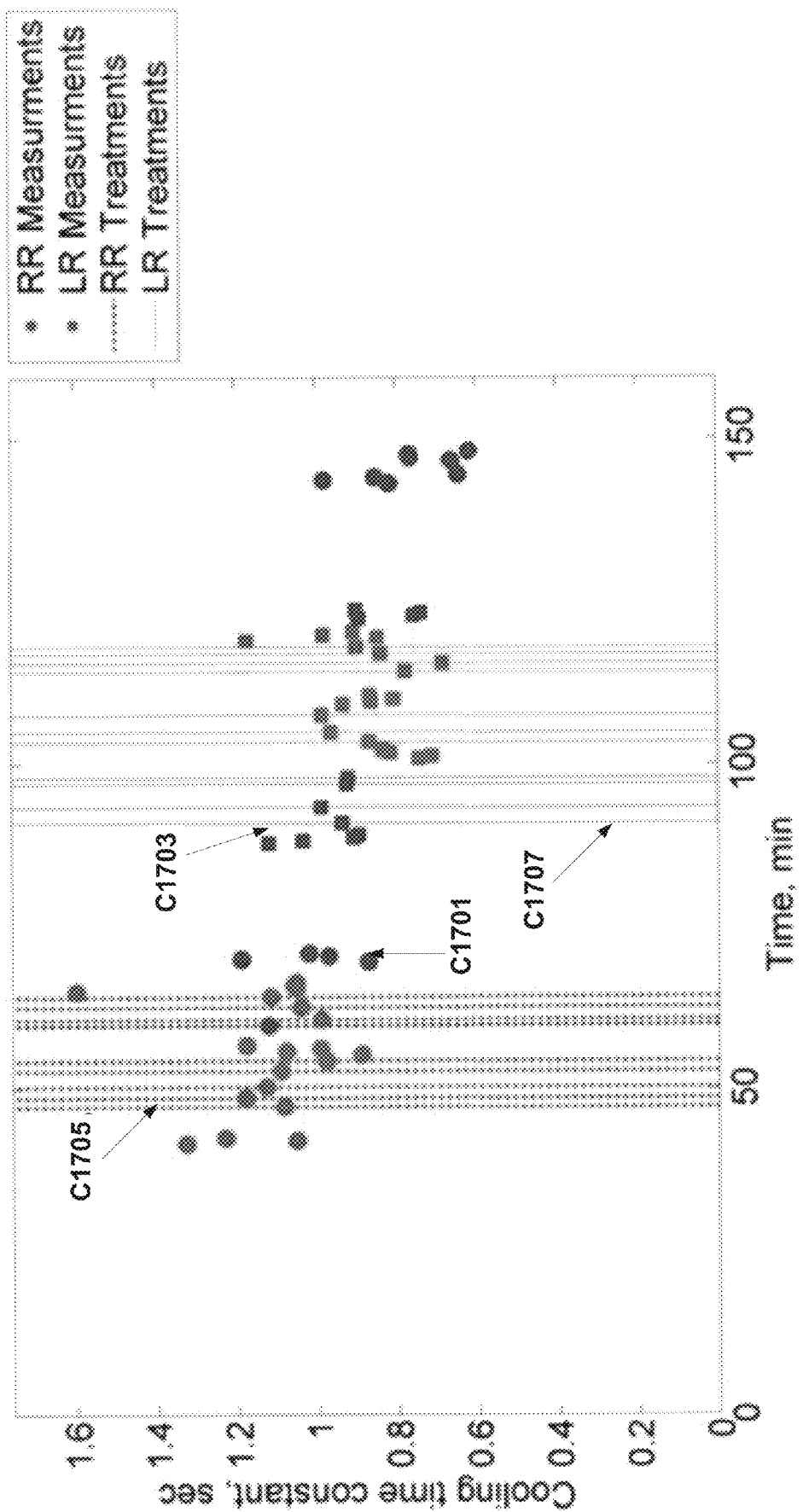
Figure 49B:
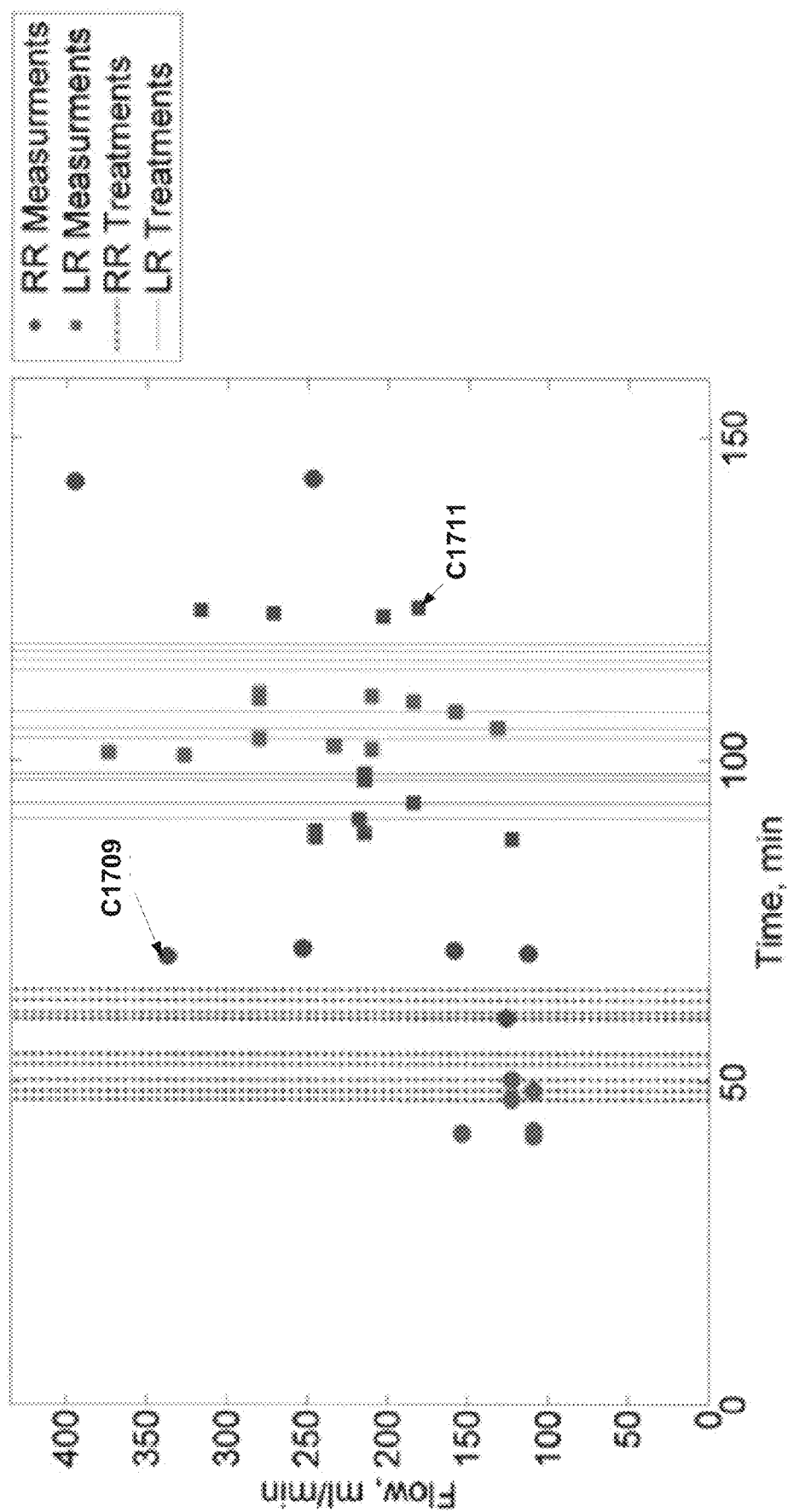
Figure 50A:
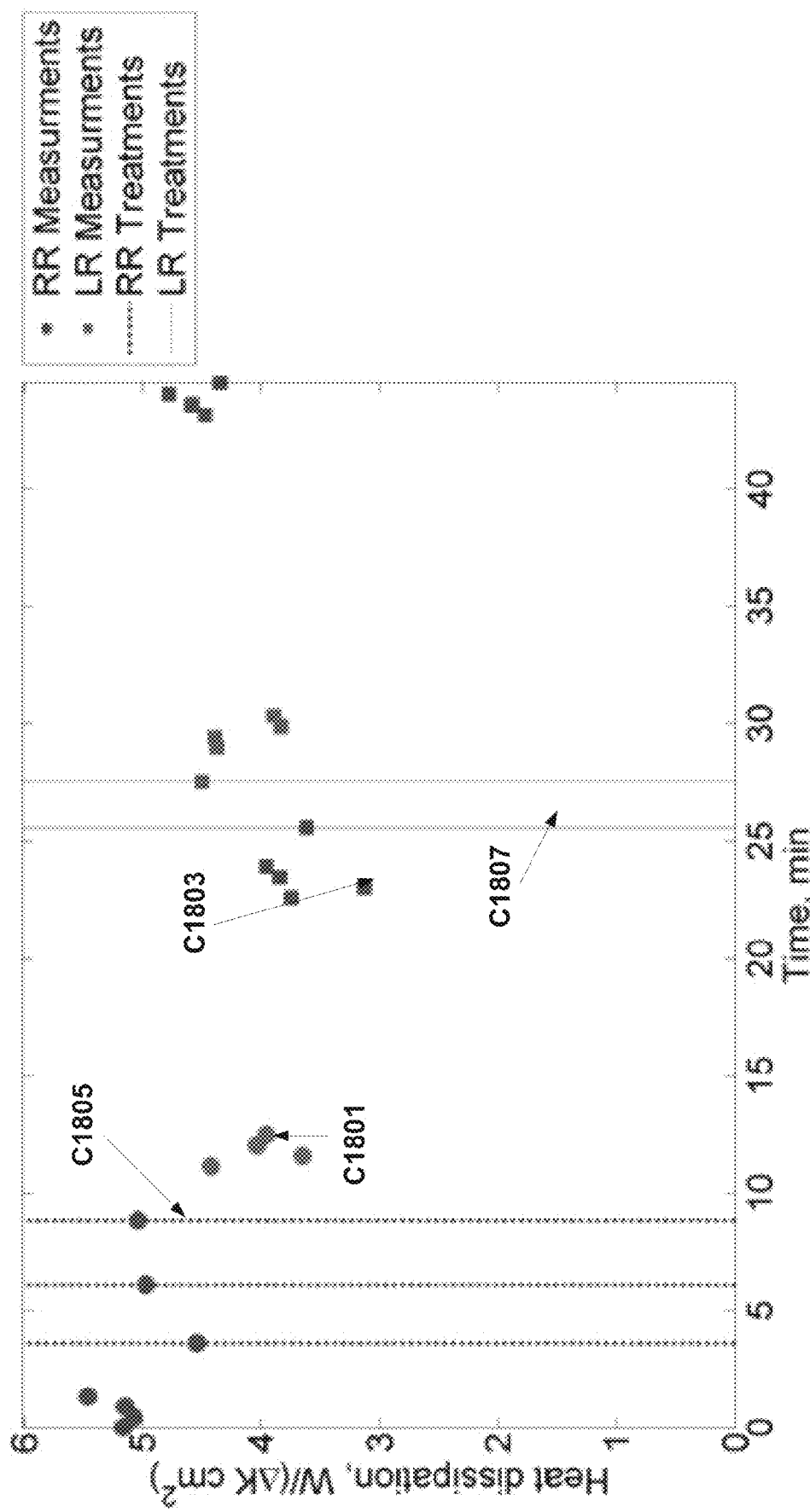
Figure 50B:
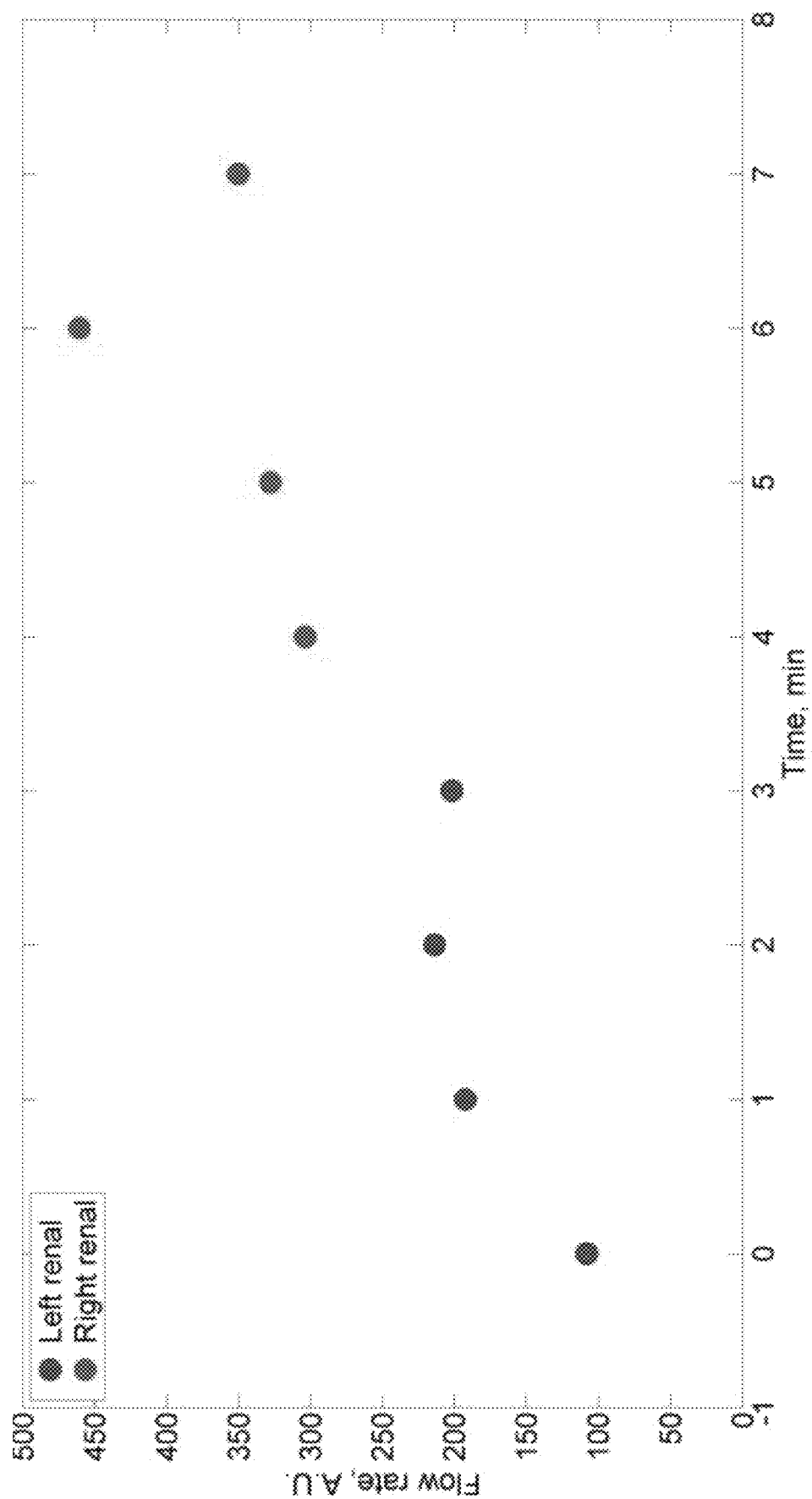
Figure 51:
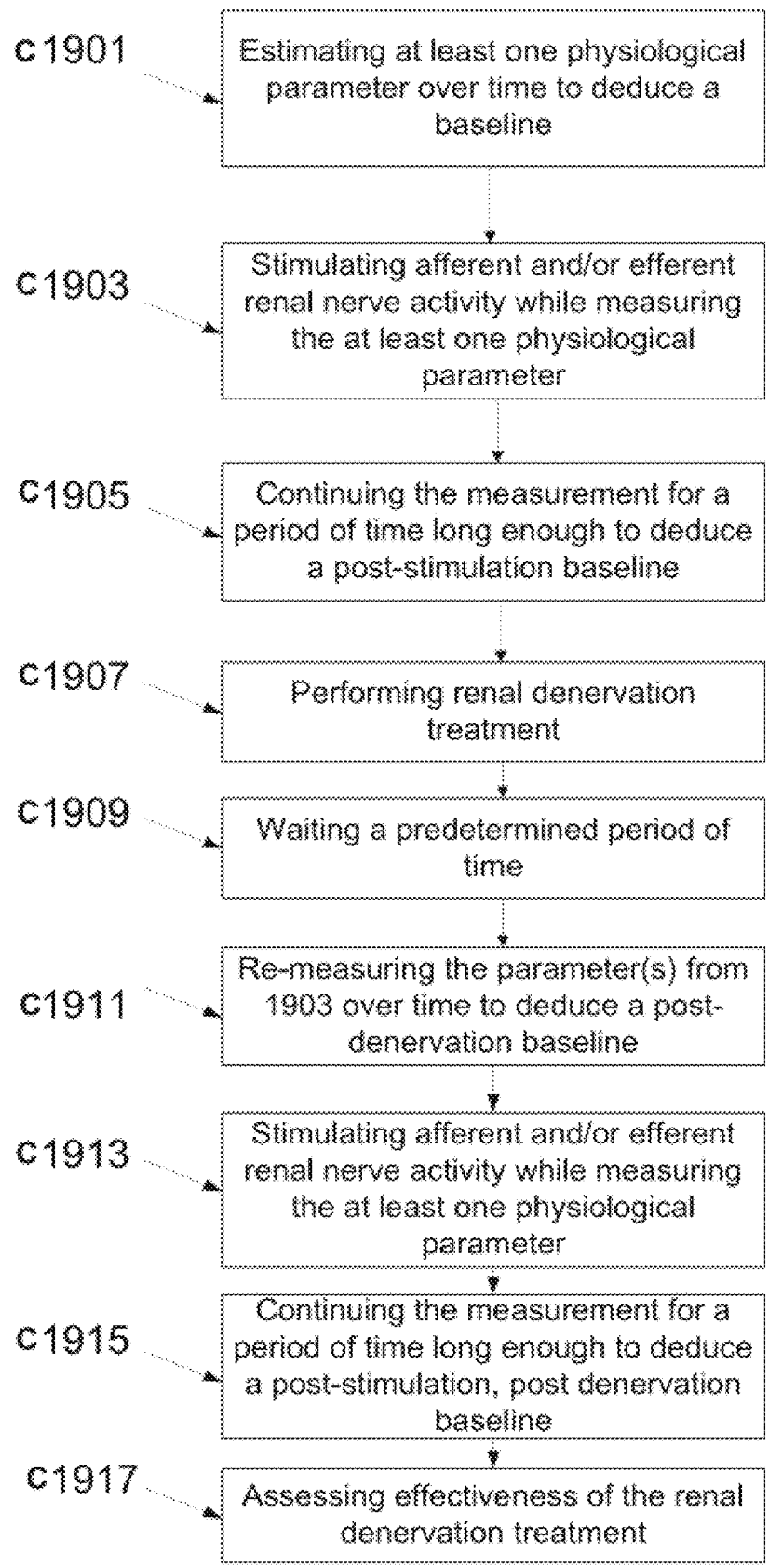
Figure 52:
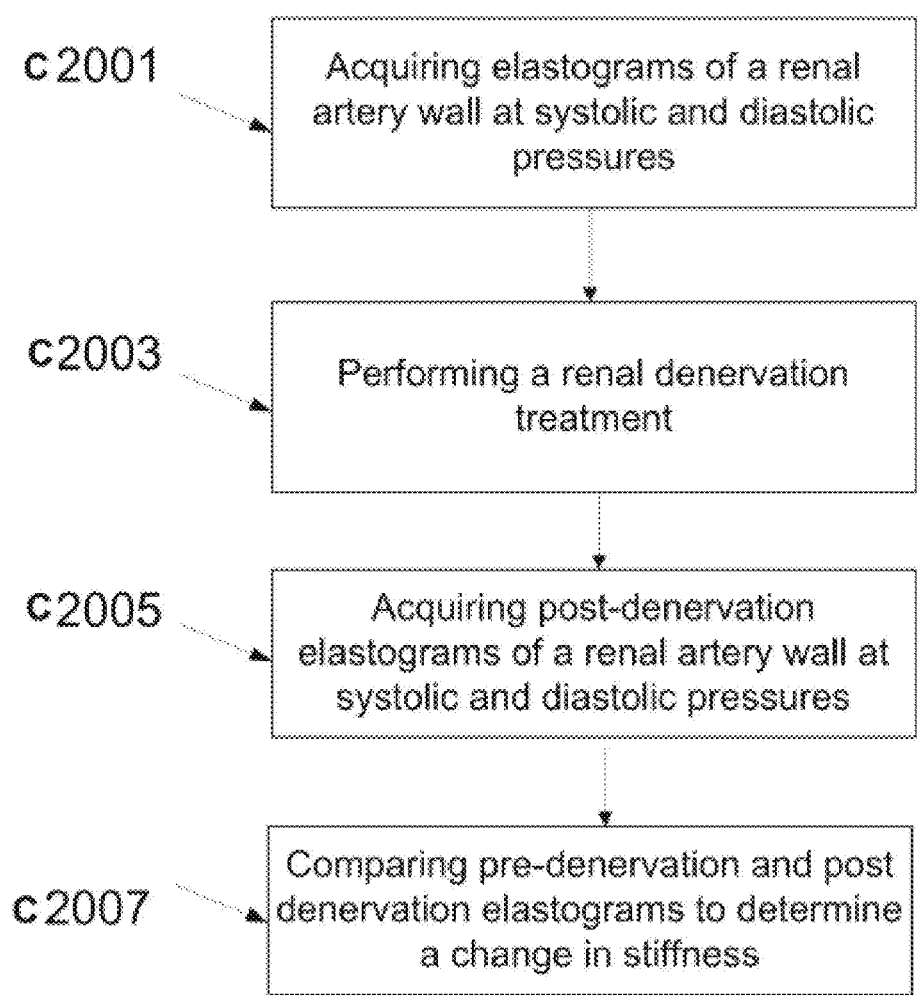
Figure 53A:
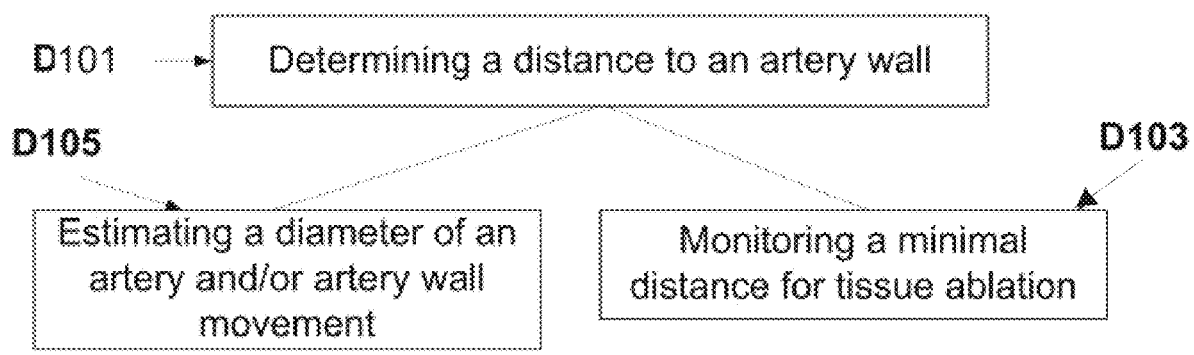
Figure 53B:
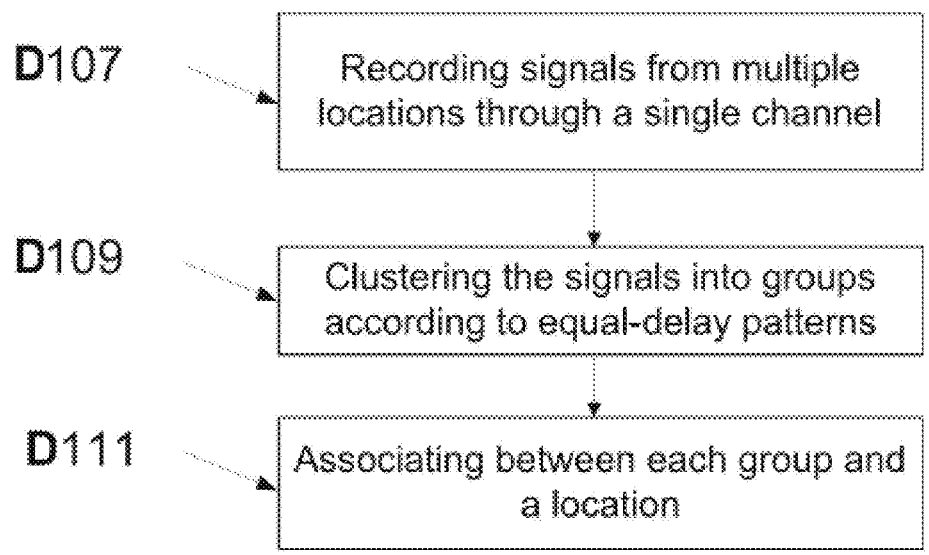
Figure 53C:
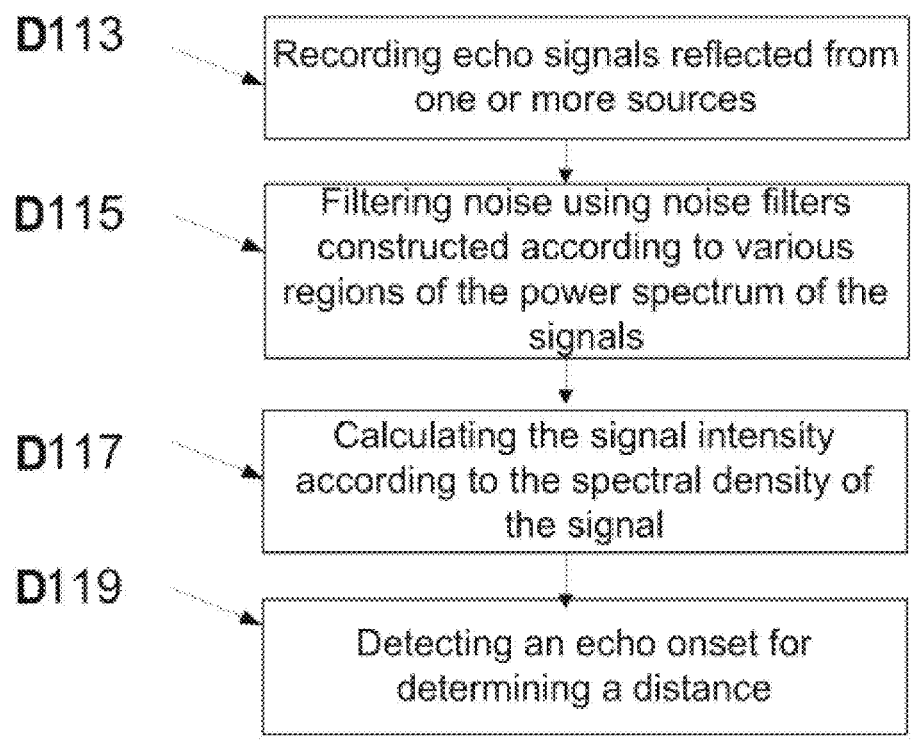
Figure 55:
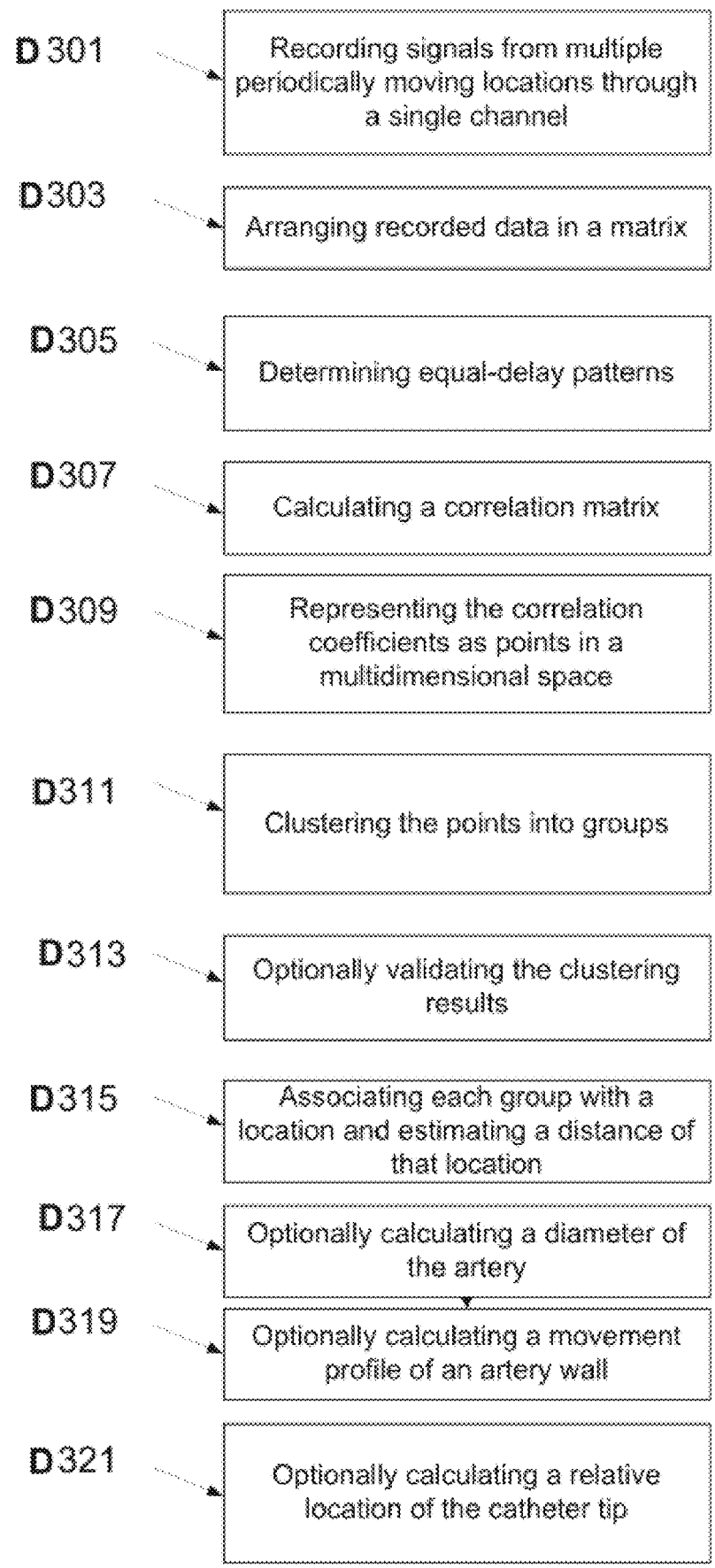
Figure 56A:
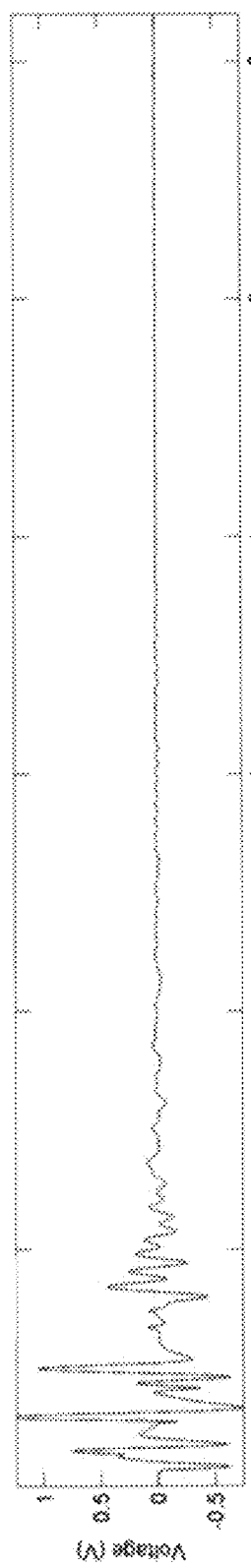
Figure 56B:
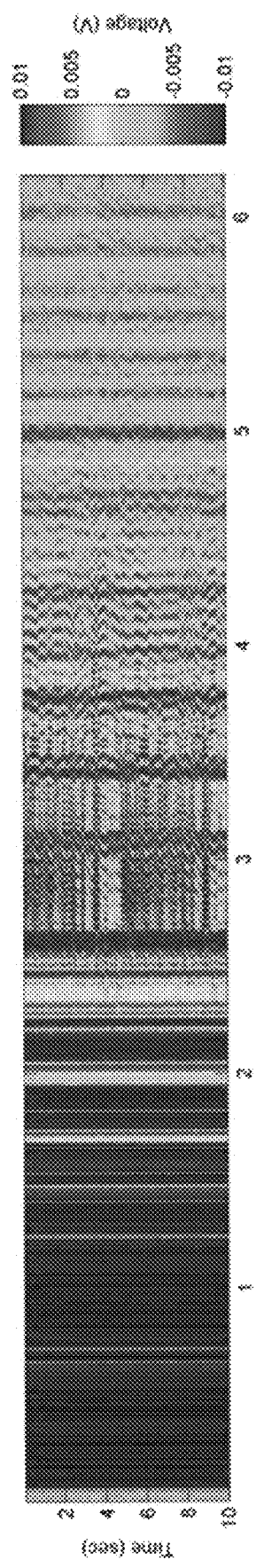
Figure 56C:
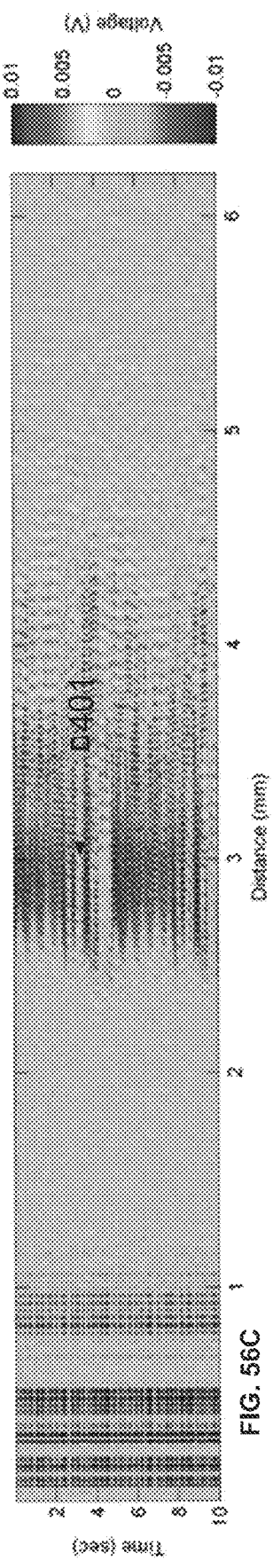
Figure 60:
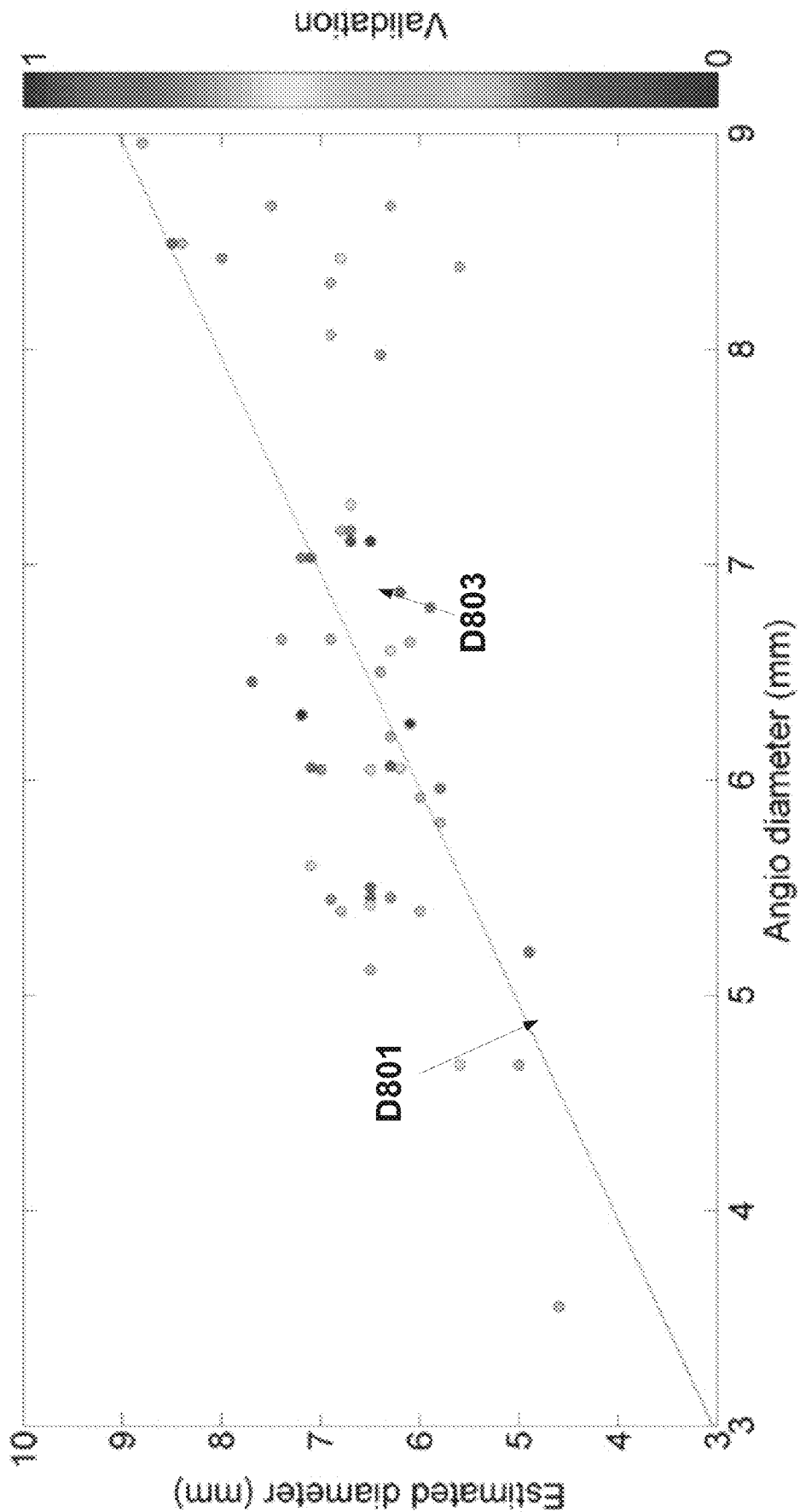
Figure 61:
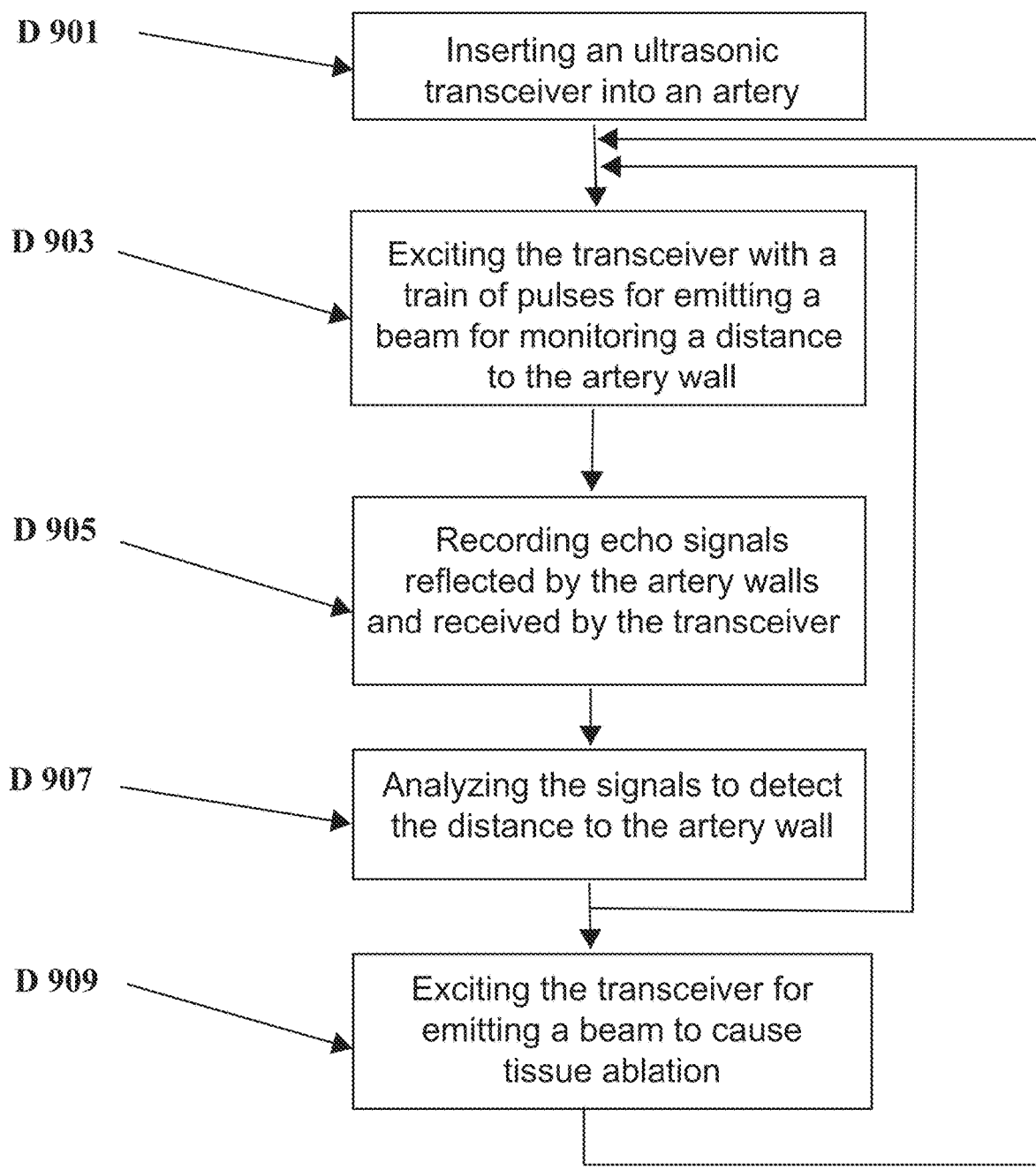
Figure 62:
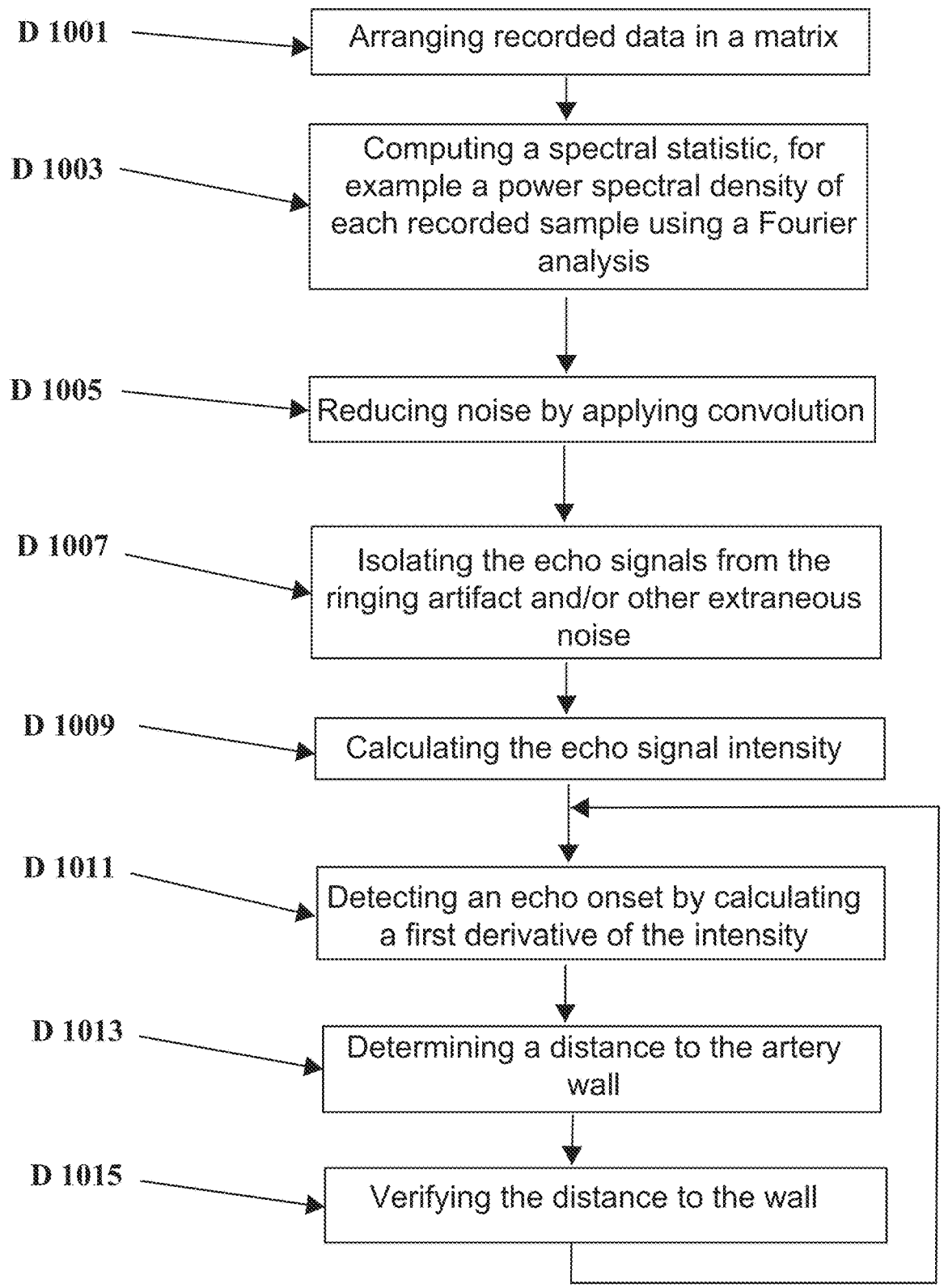
Figure 63:
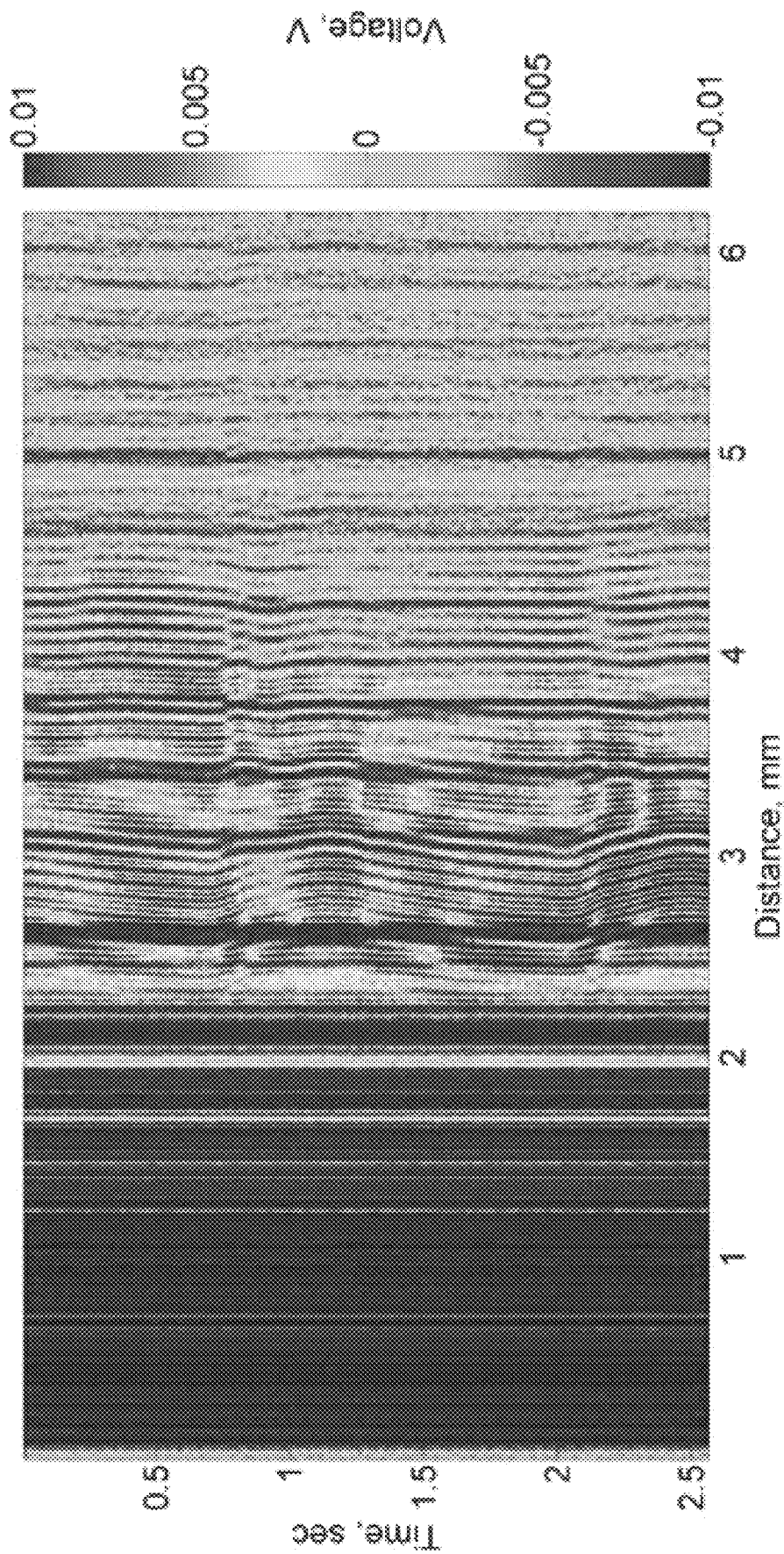
Figure 64:
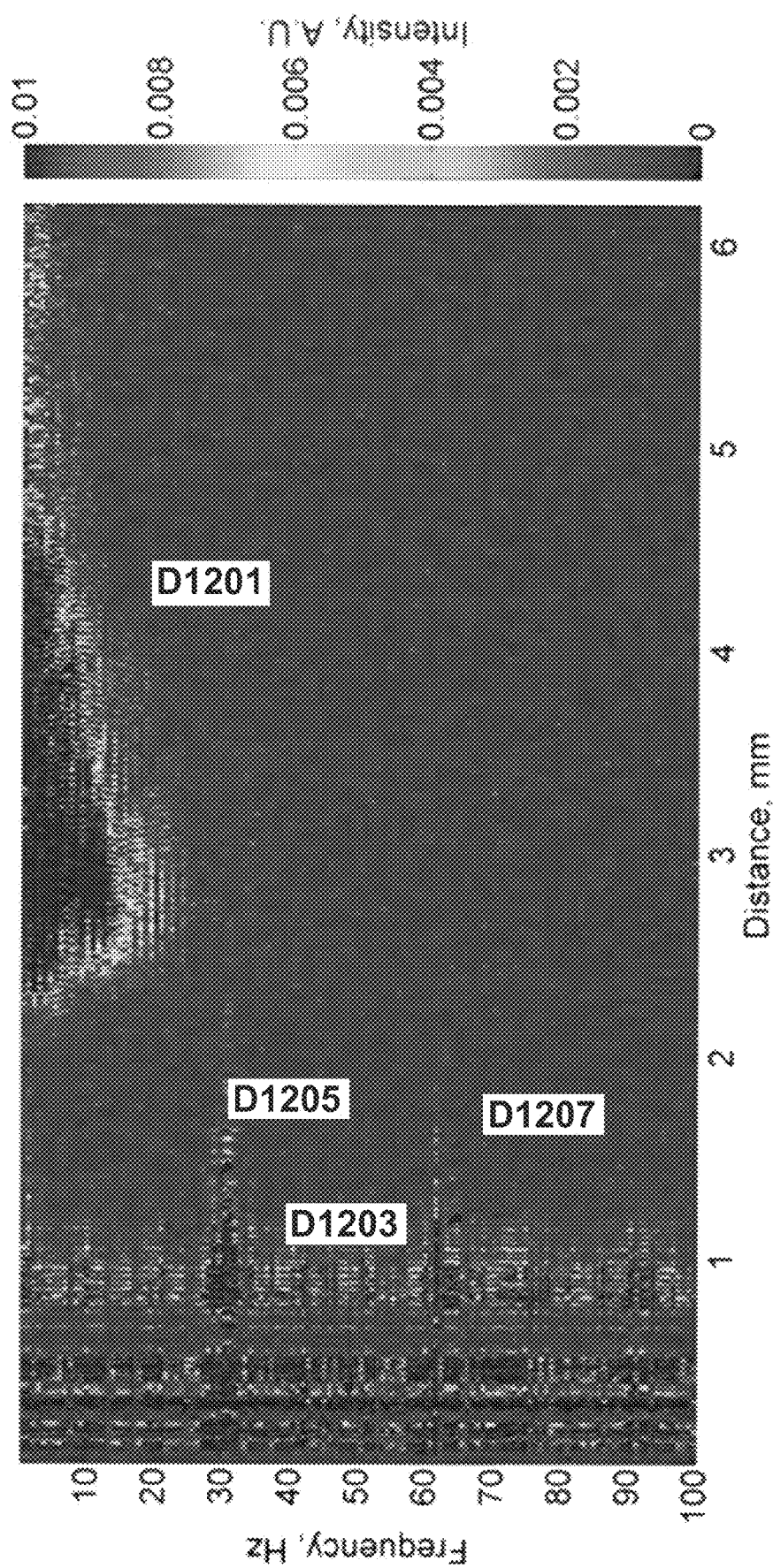
Figure 65:
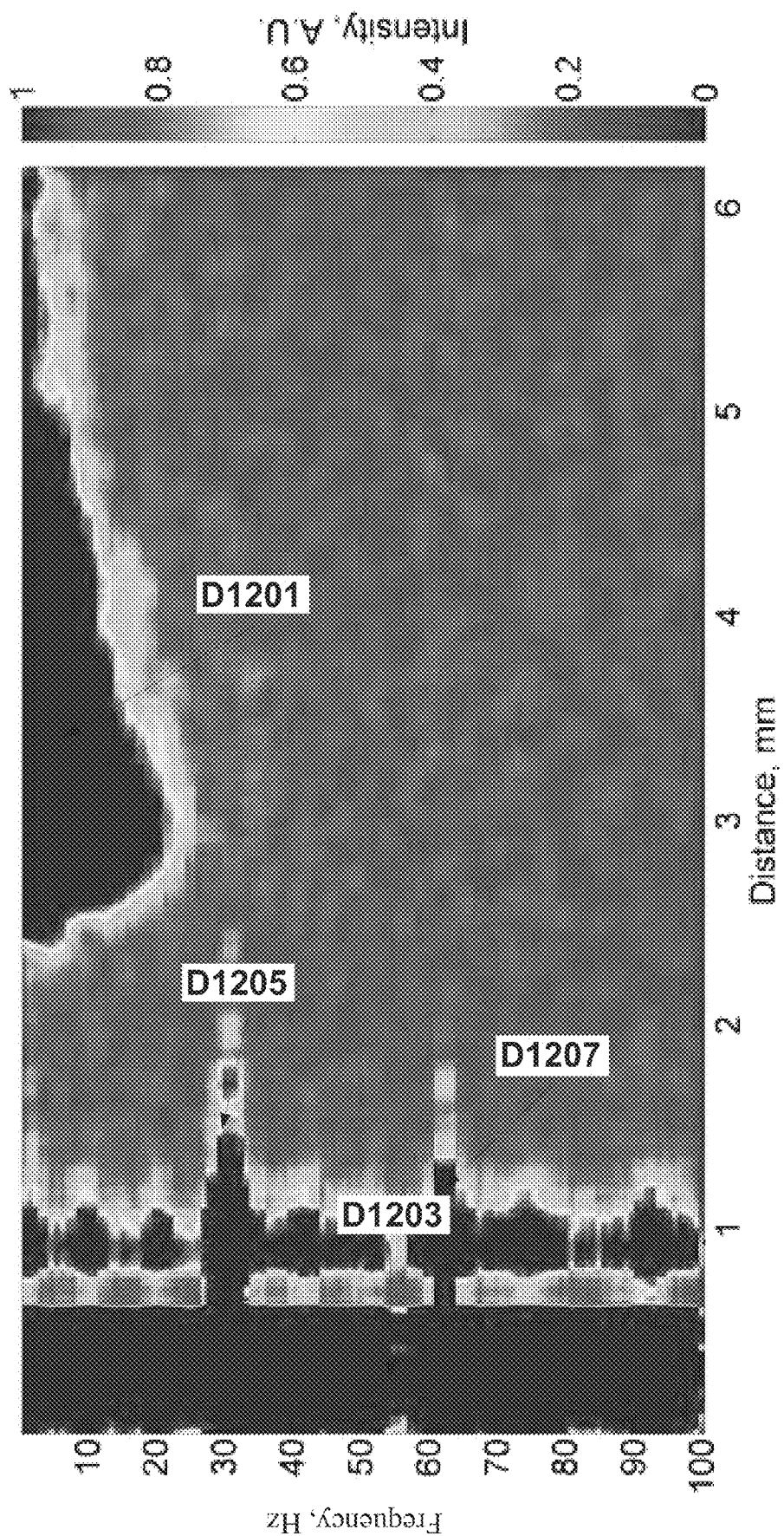
Figure 66:
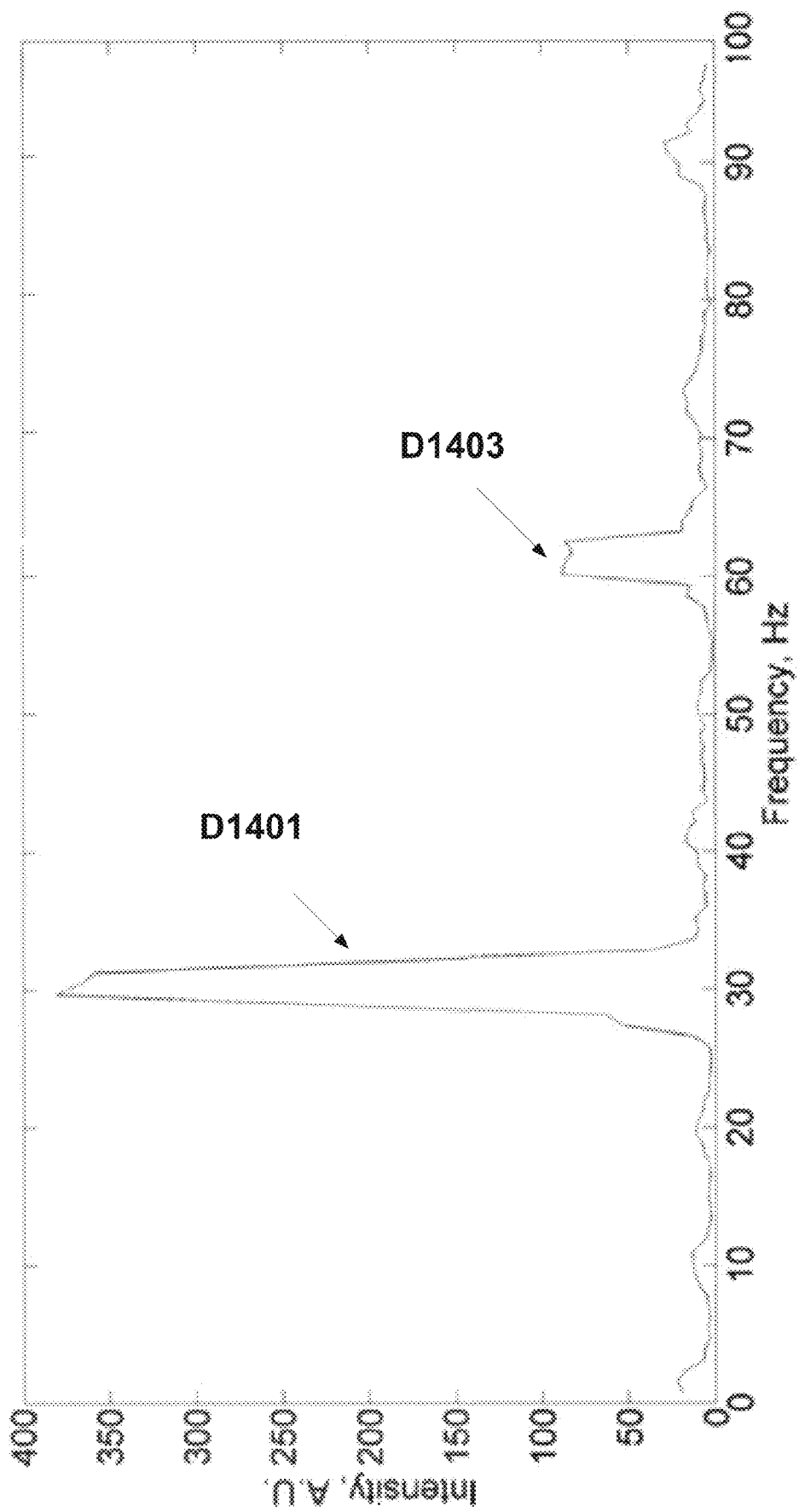
Figure 67:
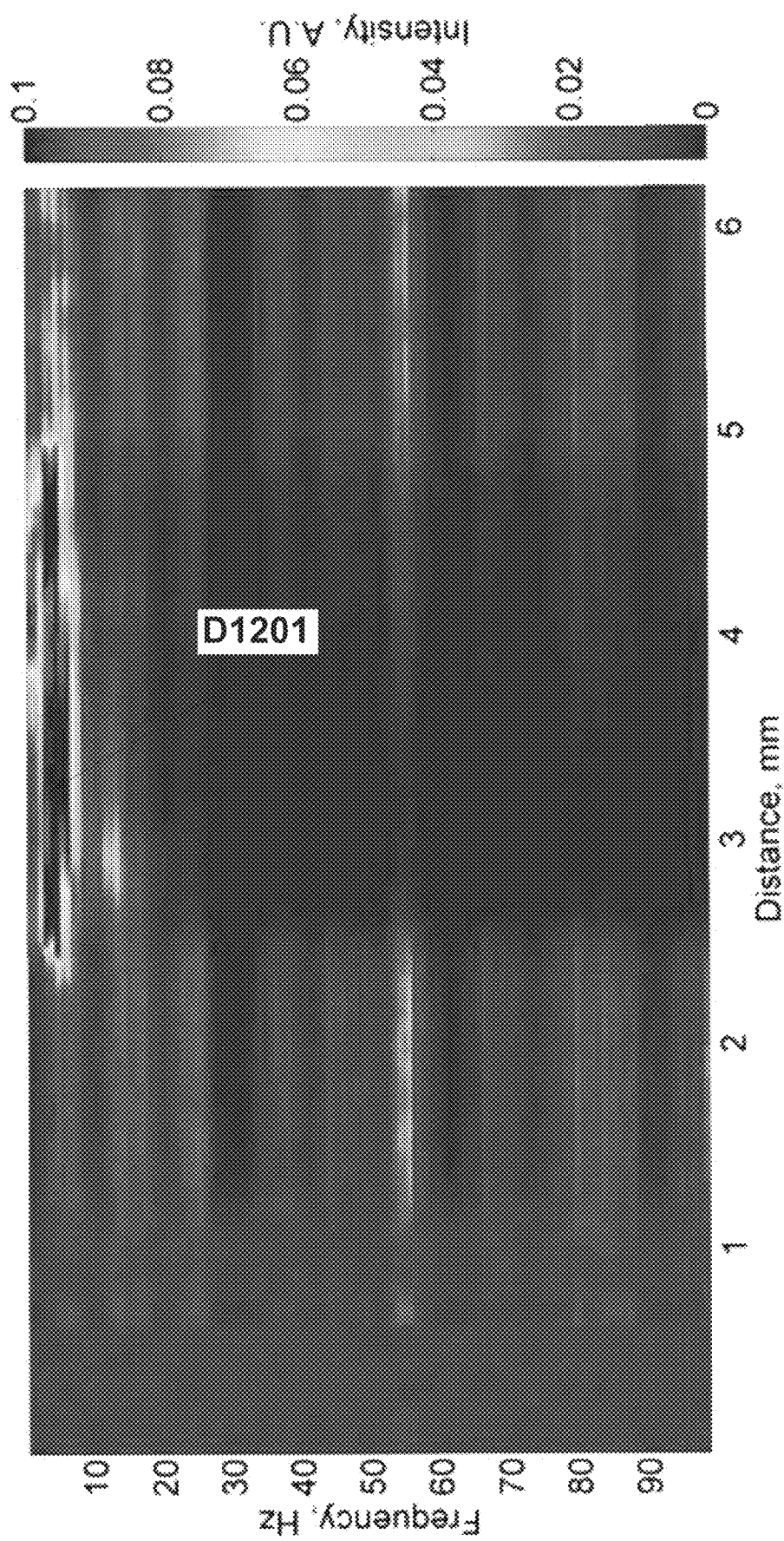
Figure 68:
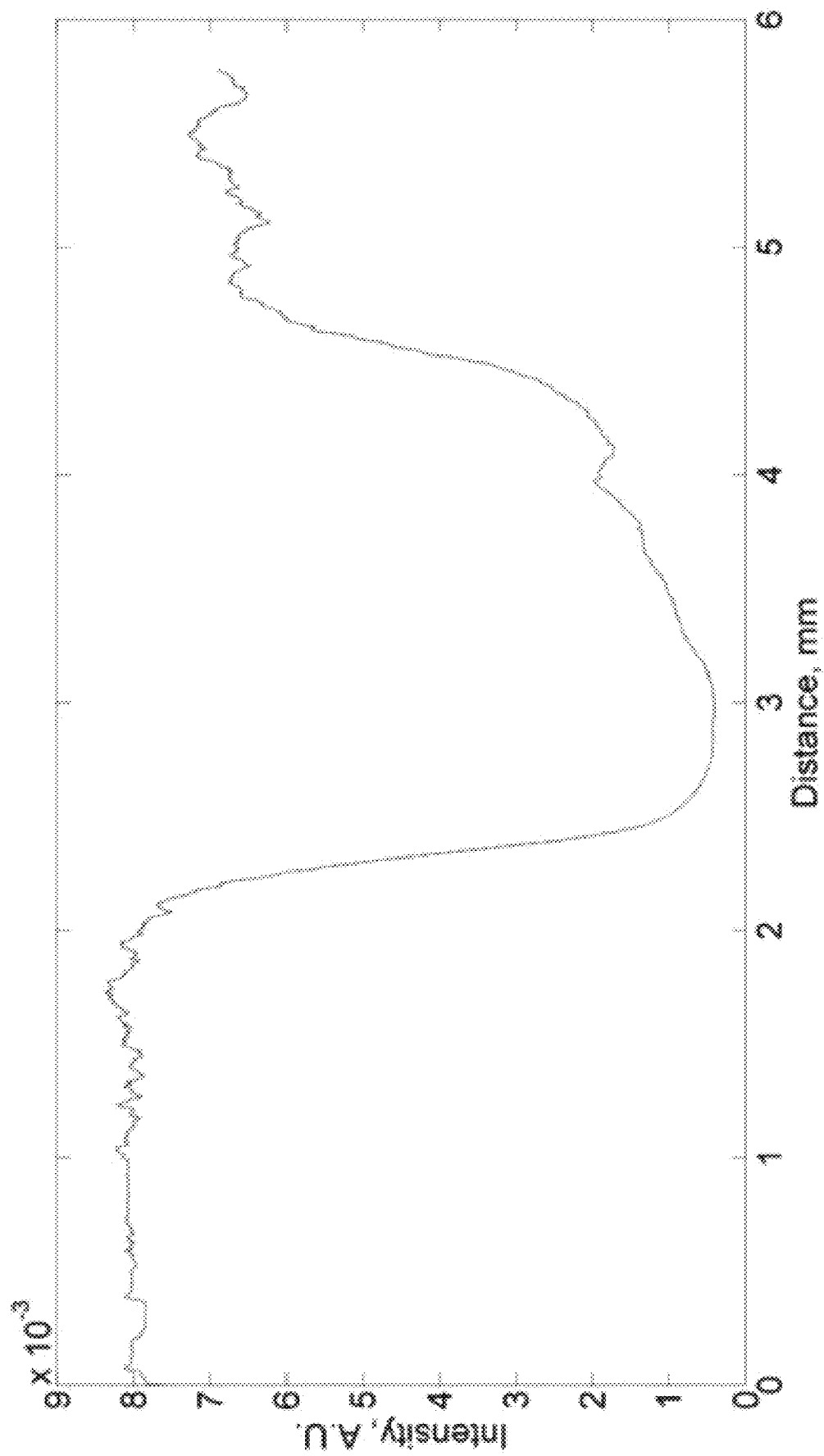
Figure 69:
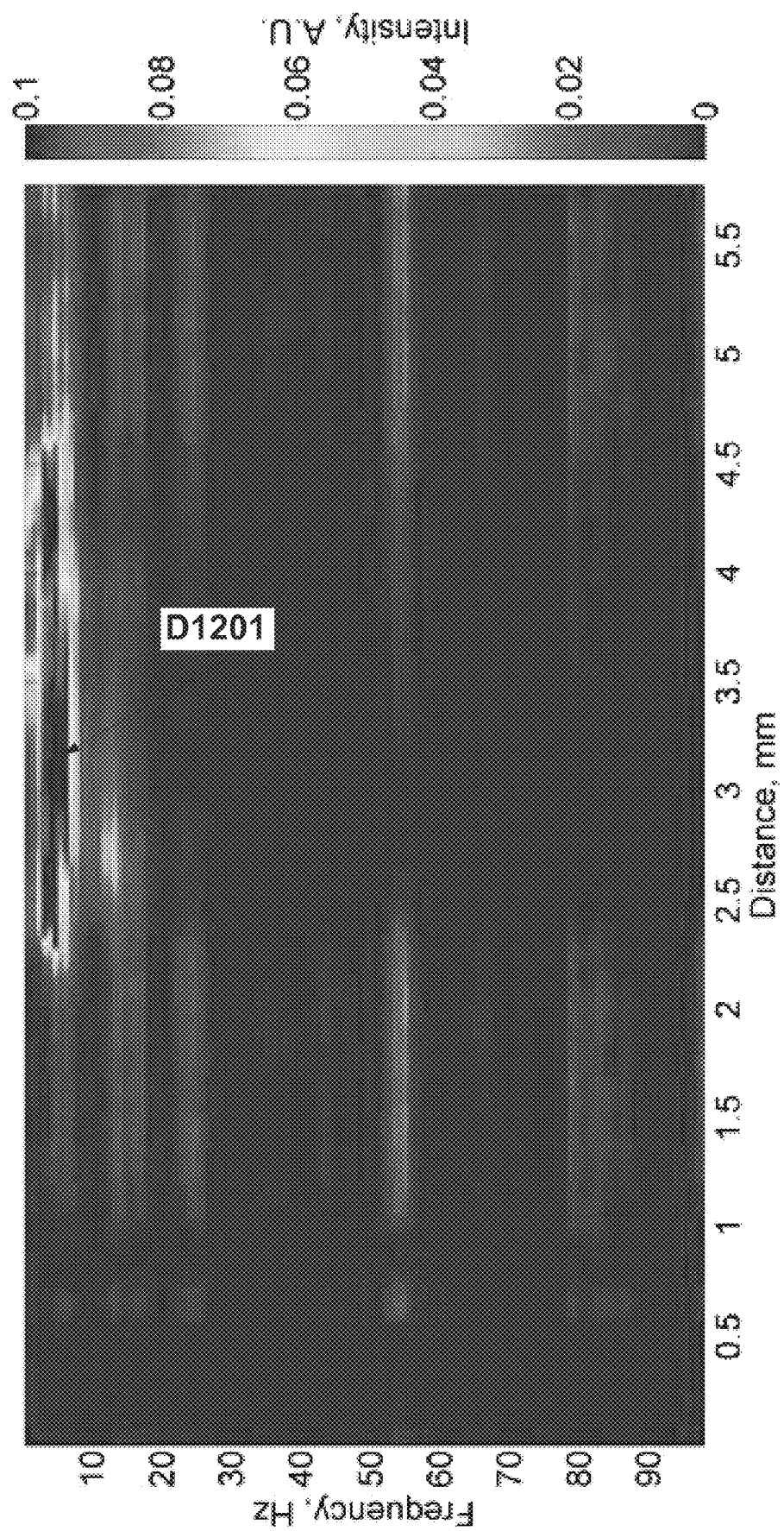
Figure 70:
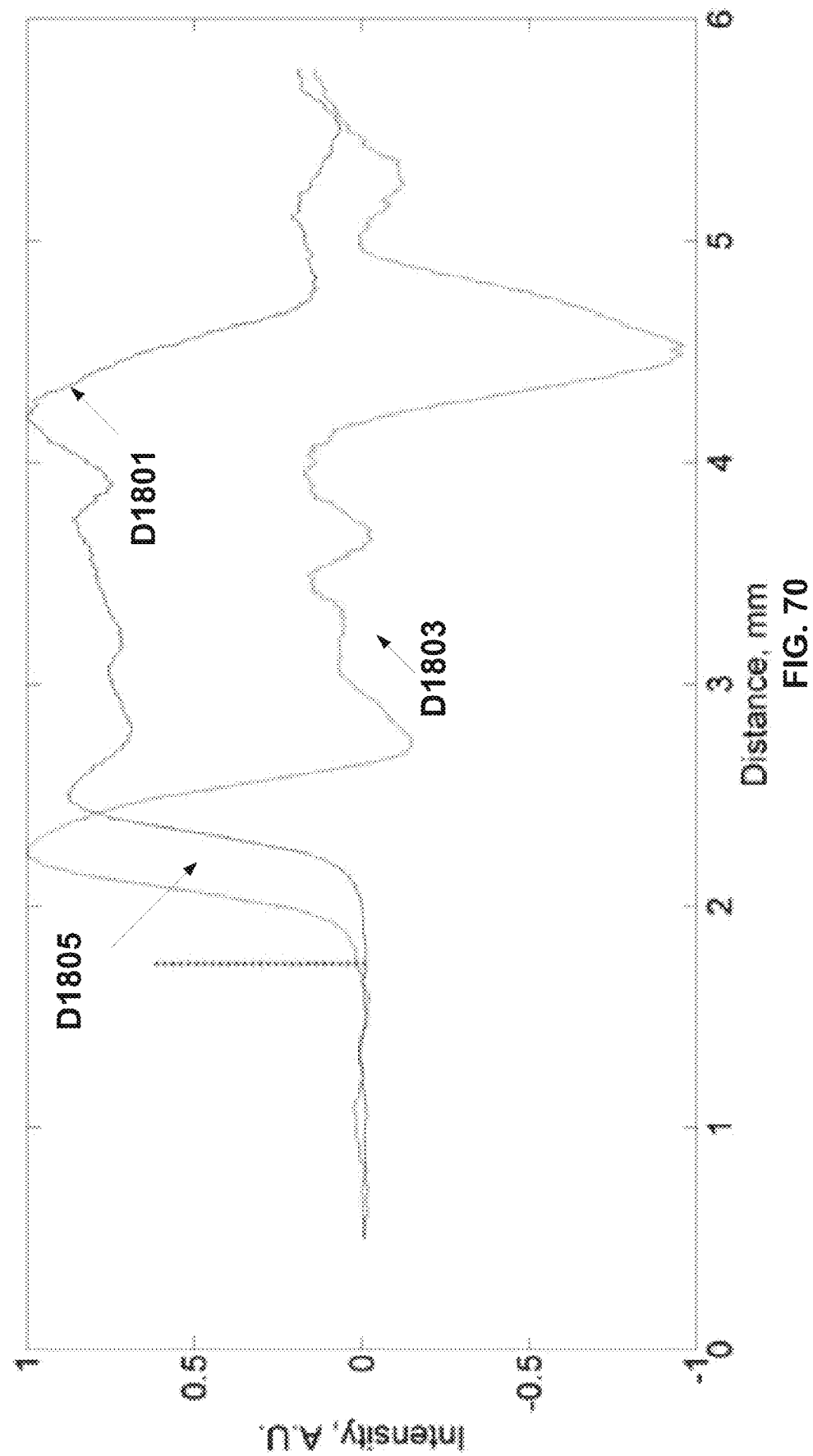
Figure 71:
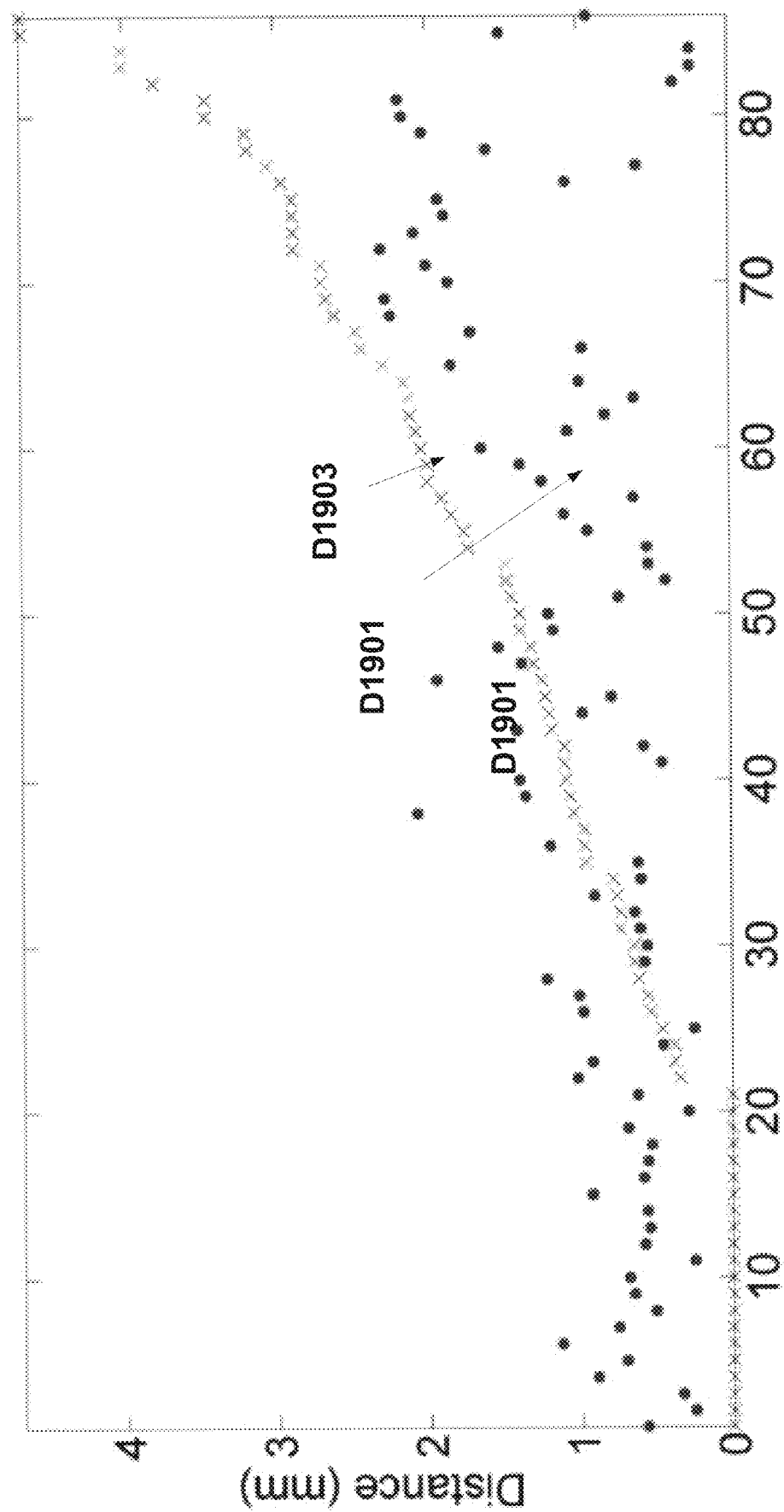
Figure 72:
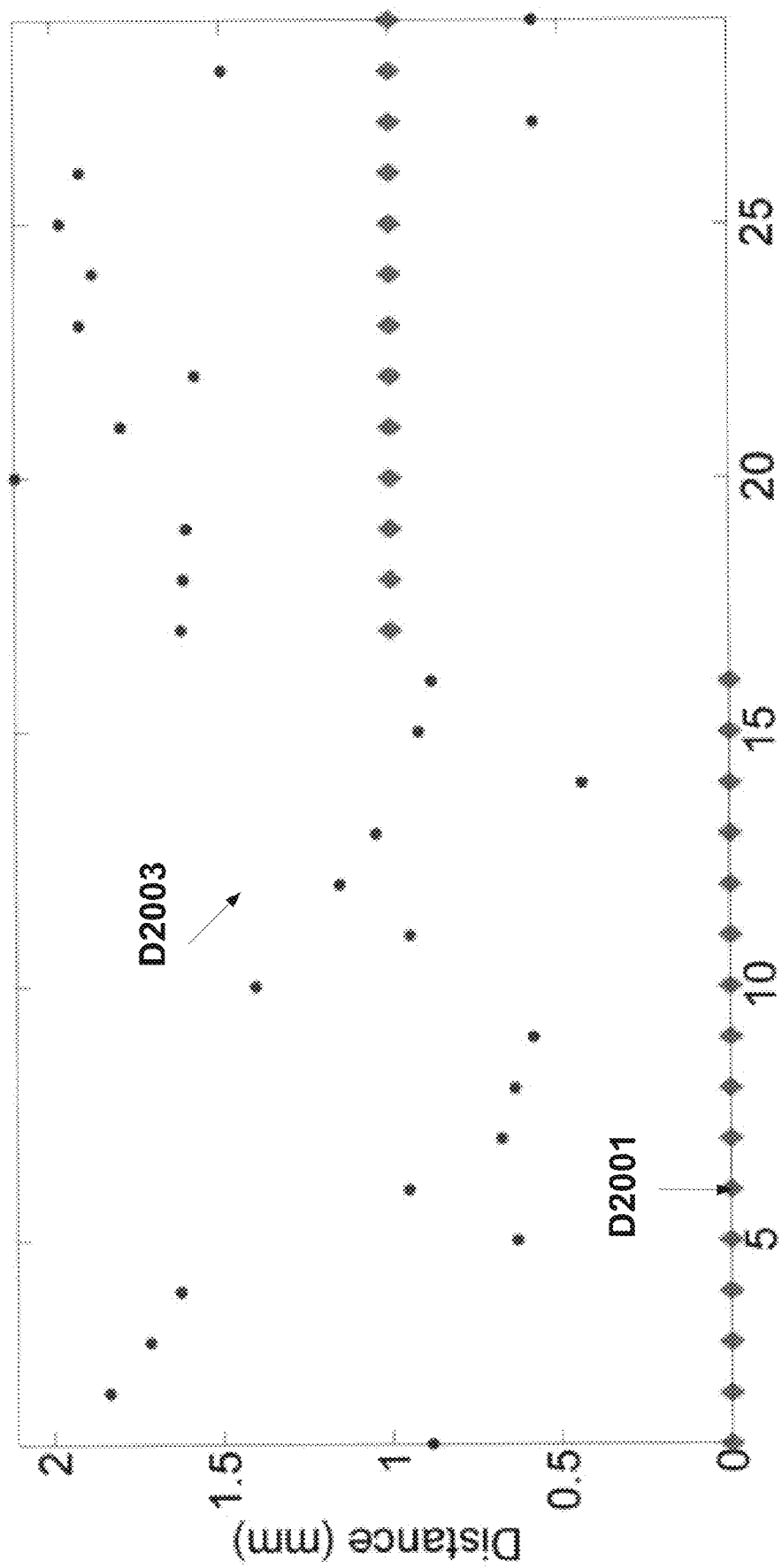
Figure 73A:
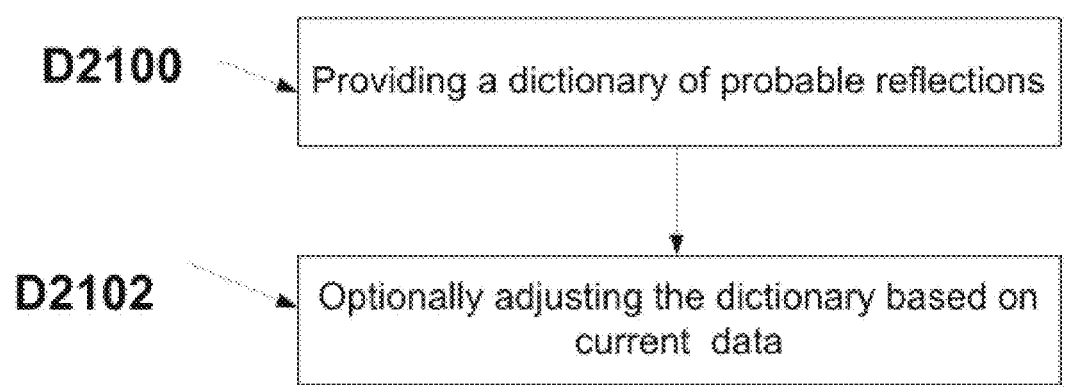
Figure 73B:
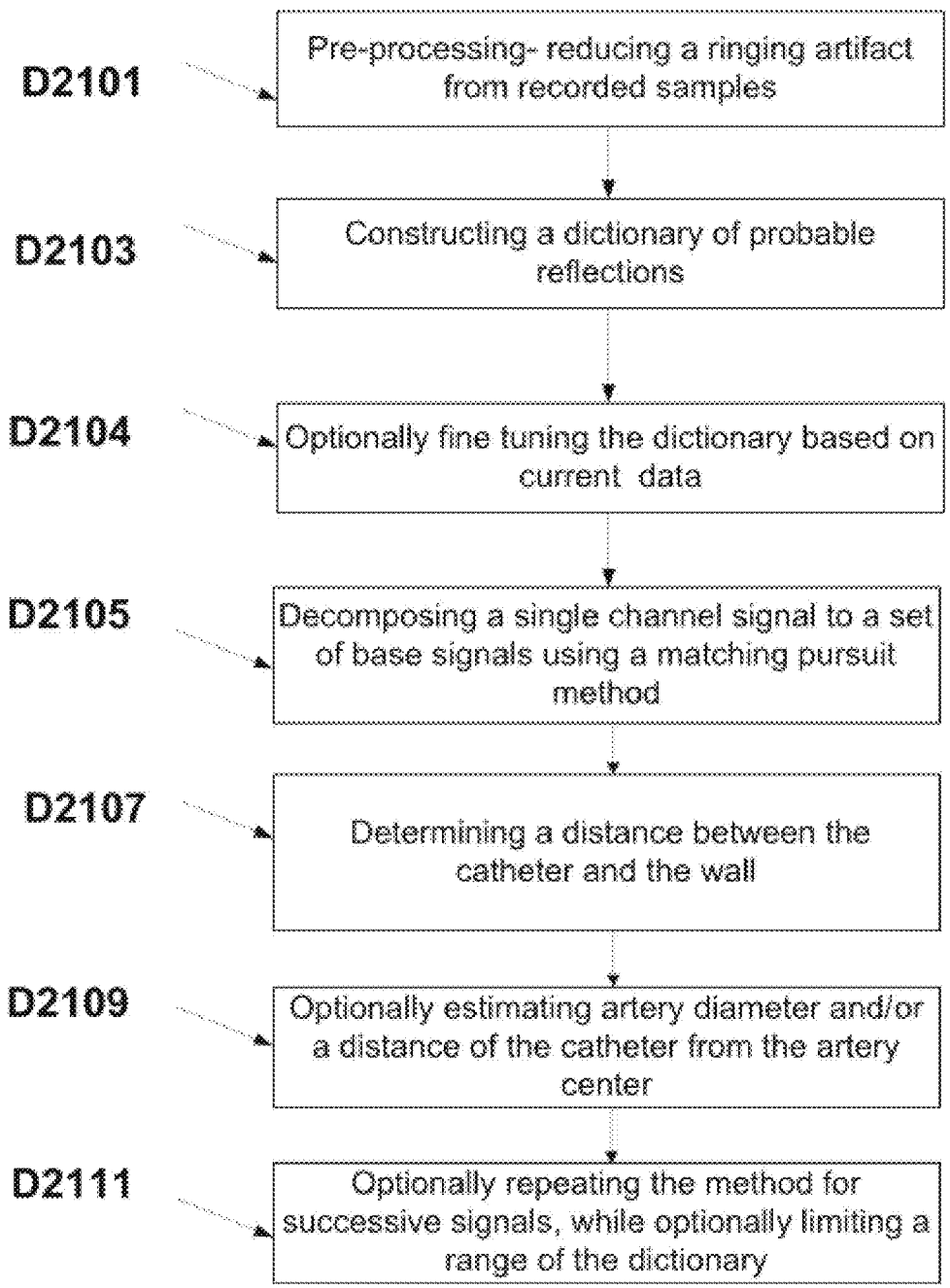
Figure 74:
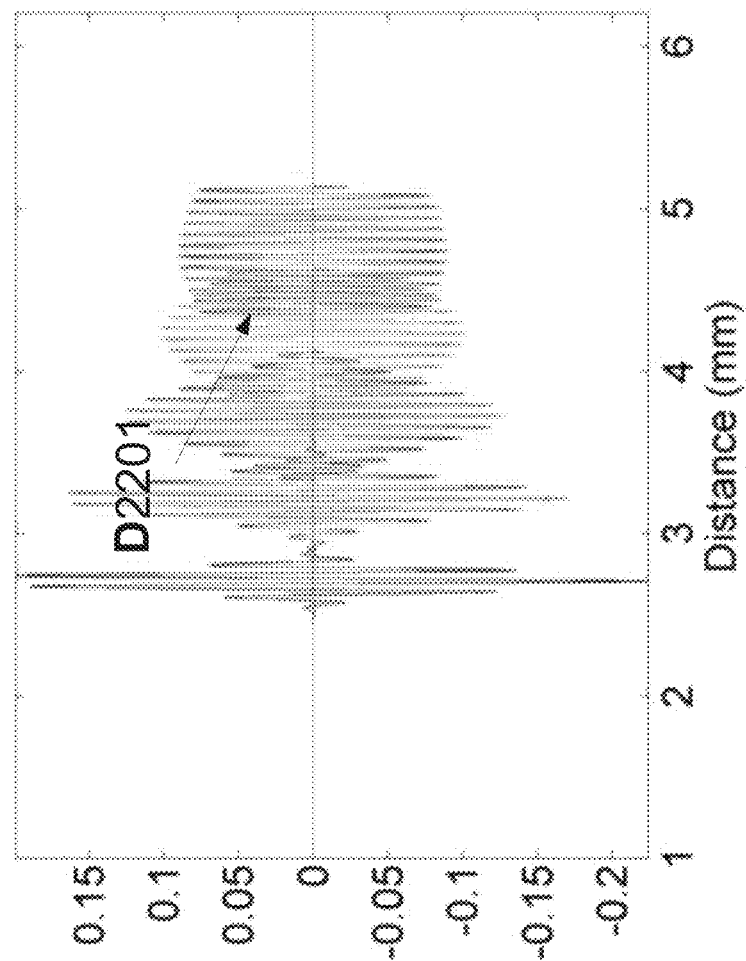
Figure 76:
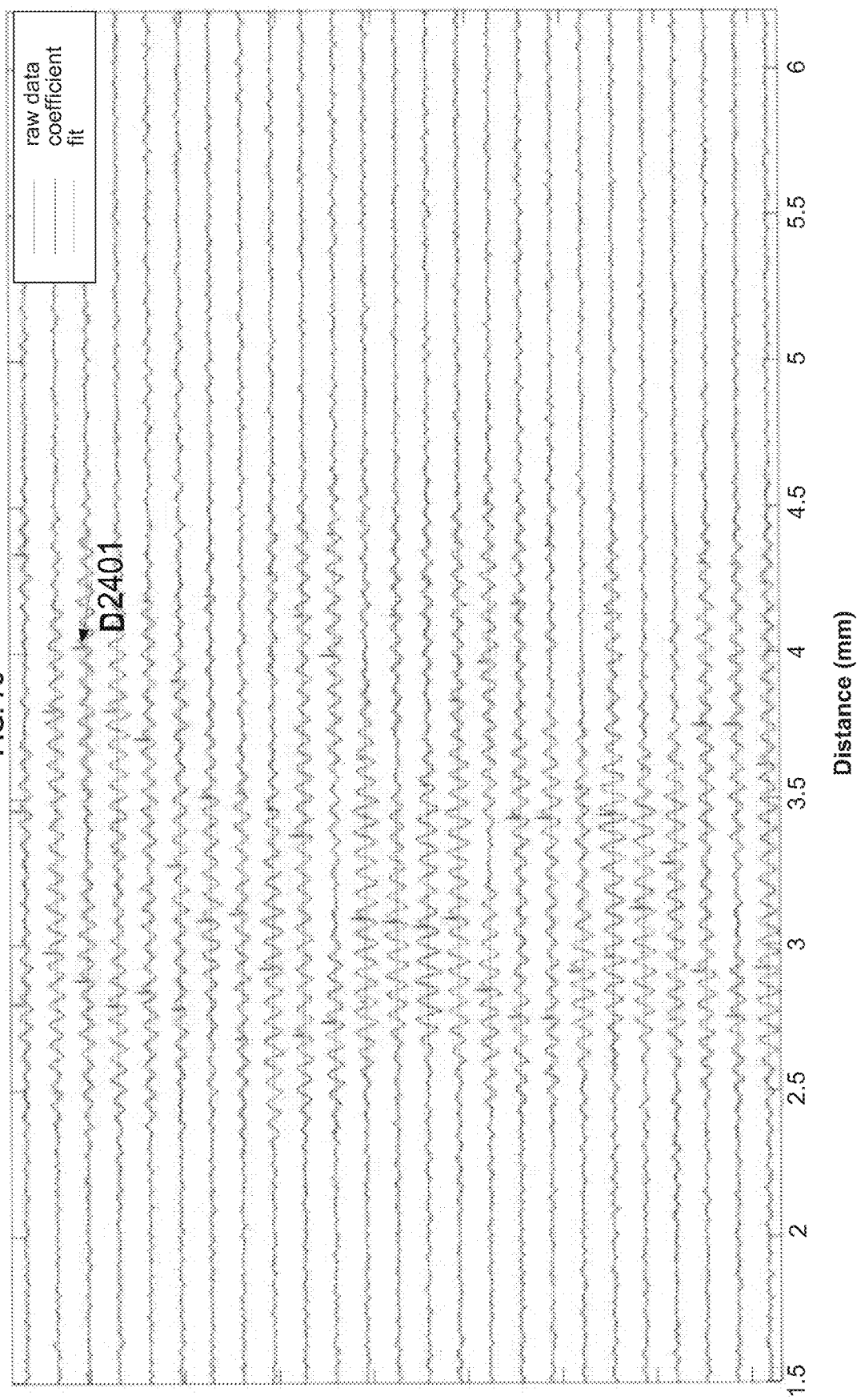
Figure 77A:
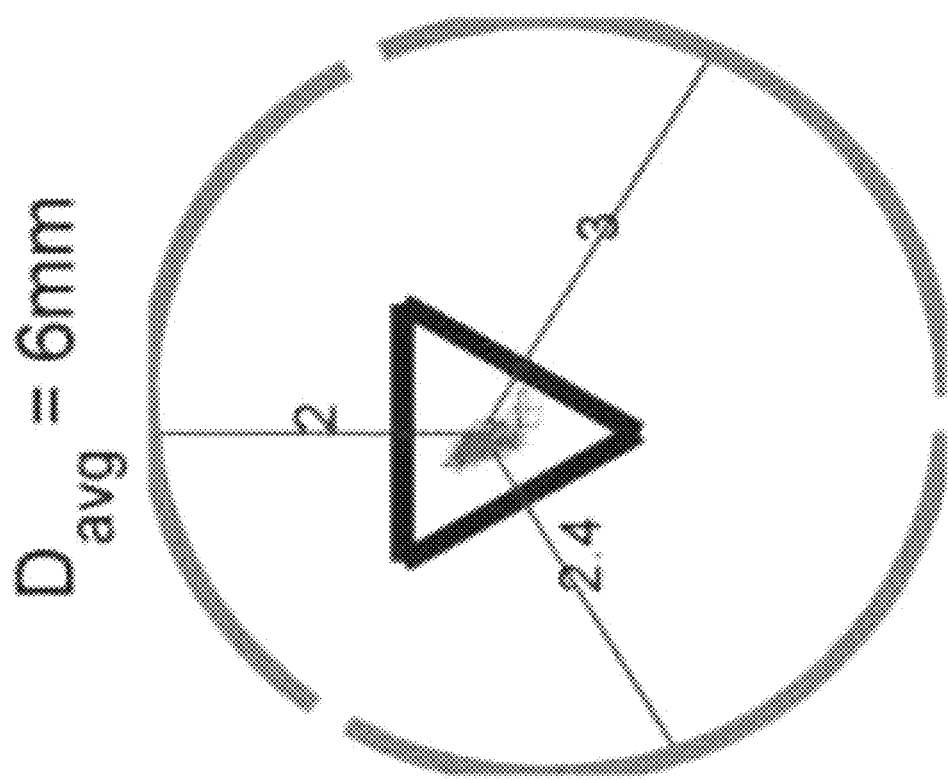
Figure 77B:
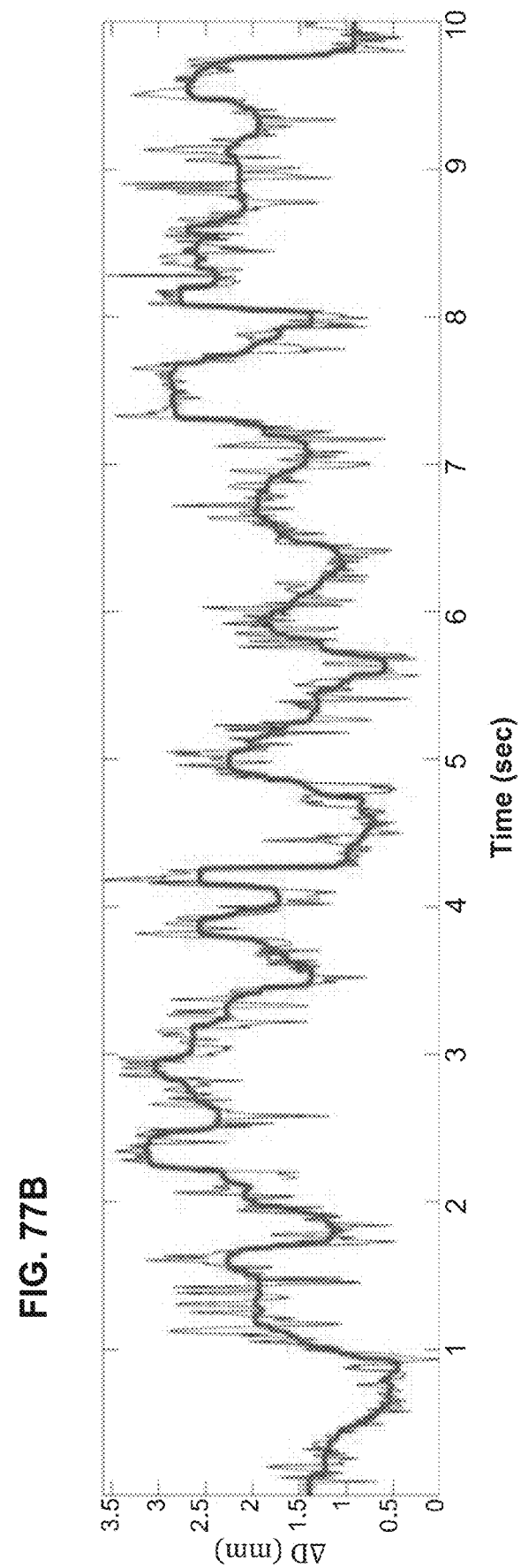

FIG. 33 is a flowchart of physiological measures that may indicate the effectiveness of a renal sympathetic denervation (RSD) treatment, according to some embodiments of the invention;

FIGS. 34A-E are schematic drawings and an angiogram relating to an endovascular ultrasonic catheter device, according to some embodiments of the invention;

FIG. 35 is a general flowchart describing exemplary methods and combinations of measurements for obtaining feedback for an RSD treatment, according to some embodiments of the invention;

FIG. 36 is a flowchart of an exemplary method for estimating blood flow rate by tracking the flow of a contrast liquid, according to some embodiments of the invention;

FIGS. 37A-B are experimental results of estimating blood flow rate by tracking contrast liquid in vivo, according to some embodiments of the invention;

FIG. 38 is a flowchart of an exemplary method for measuring blood flow velocity by tracking the flow of a cold liquid, according to some embodiments of the invention;

FIG. 39 is a flowchart of an exemplary method for estimating renal blood flow velocity based on a heat dissipation rate of a transceiver, according to some embodiments of the invention;

FIGS. 40A-B are experimental results of an in vitro experiment to show a correlation between blood flow velocity and heat dissipation rate of the transceiver, according to some embodiments of the invention;

FIGS. 41A-D are experimental results of an in vitro experiment for validating the correlation between blood flow velocity and heat dissipation rate of the transceiver, according to some embodiments of the invention;

FIG. 42 is a flowchart of an exemplary method for estimating blood flow velocity by analyzing an impulse response of a transceiver, according to some embodiments of the invention;

FIGS. 43A-B are experimental results of an in vitro experiment to show a correlation between a measured impulse response of the transceiver and the flow velocity, according to some embodiments of the invention;

FIGS. 44A-B are experimental results of an in vivo experiment including an impulse response analysis, according to some embodiments of the invention;

FIG. 45 is a flowchart of a general method for intravascular distance estimation, according to some embodiments of the invention;

FIG. 46 is a detailed flowchart of a method for analyzing a sequence of signals received from multiple sources and recorded through a single channel for estimating an artery diameter, according to some embodiments of the invention;

FIGS. 47A-C are graphical representations of a current location of a catheter tip with respect to the artery walls, according to some embodiments of the invention;

FIG. 48 shows experimental results of an in vivo experiment in swine for estimating artery stiffness according to blood pressure and arterial diameter, according to some embodiments of the invention;

FIGS. 49A-B show experimental results of an in vivo experiment in swine for estimating blood flow rate according to a cooling time constant of a transceiver and arterial diameter, according to some embodiments of the invention;

FIGS. 50A-B show experimental results of an in vivo experiment in swine for estimating blood flow rate according to heat dissipation rate of a transceiver and arterial diameter, according to some embodiments of the invention;

FIG. 51 is a flowchart of a method for assessing renal denervation effectiveness using sympathetic neural stimulation, according to some embodiments of the invention;

FIG. 52 is a flowchart of a method for estimating a change in arterial stiffness using ultrasonic elastography, according to some embodiments of the invention;

FIGS. 53A-C are flowcharts of methods which include determining a distance to an artery wall, according to some embodiments of the invention;

FIGS. 54A-E are schematic drawings and an angiogram relating to an endovascular ultrasonic catheter device, according to some embodiments of the invention;

FIG. 55 is a flowchart of a method for analyzing and separating a single channel recording to estimate one or more distances between reflection locations and one or more receivers of the reflections, according to some embodiments of the invention;

FIGS. 56A-C are exemplary graphs of a typical recording of echo signals reflected from an artery wall, according to some embodiments of the invention;

FIGS. 57A-D are graphical representations of a clustering process for separating a single channel recording, according to some embodiments of the invention;

FIGS. 58A-D are graphical representations of a movement profile of an artery wall, according to some embodiments of the invention;

FIGS. 59A-C are graphical representations of a current location of a catheter tip with respect to the artery walls, according to some embodiments of the invention;

FIG. 60 is a graph of a validation of artery diameter estimations compared to angiogram based diameter estimations, according to some embodiments of the invention;

FIG. 61 is a general flowchart of a method for monitoring a distance to an artery wall, according to some embodiments of the invention;

FIG. 62 is a detailed flowchart of a method for monitoring a distance to an artery wall based on a spectral statistic of echo signals, according to some embodiments of the invention;

FIG. 63 is an exemplary graph of raw recorded data received by a transceiver during a series of excitations, according to some embodiment of the invention;

FIG. 64 is an exemplary power spectral density graph of equal-delay patterns, according to some embodiment of the inventions;

FIG. 65 is an exemplary power spectral density graph after applying convolution, according to some embodiments of the invention;

FIG. 66 is an exemplary graph of a noise filter constructed by summing intensity values over a segment of a power spectral density graph, according to some embodiments of the invention;

FIG. 67 is an exemplary power spectral density graph after noise deconvolution, according to some embodiments of the invention;

FIG. 68 is a graph of a noise filter constructed by summing intensity values over a high frequency segment, according to some embodiments of the invention;

FIG. 69 is an exemplary power spectral density graph after noise filtering, according to some embodiments of the invention;

FIG. 70 is an exemplary graph of reflected echo intensity and a first derivative of the intensity, according to some embodiments of the invention;

FIG. 71 is a graph of a validation of a minimal artery wall distance estimations compared to angiogram based distance estimations, according to some embodiments of the invention;

FIG. 72 is a graph of a validation of the minimal distance estimations obtained using the distance monitoring method described herein and a distancing device, according to some embodiments of the invention;

FIGS. 73A-B are flowcharts of a method for decomposing a signal to a set of base echo signals and assigning the signals to a location (e.g. artery wall) using a dictionary of probable reflections, according to some embodiments of the invention;

FIG. 74 is an exemplary graph of a dictionary of probable reflections, according to some embodiments of the invention;

FIGS. 75A-C are exemplary graphs of a typical recording of echo signals reflected from an artery wall, according to some embodiments of the invention;

FIG. 76 is an exemplary graph of a matching pursuit method implementation, according to some embodiments of the invention;

FIGS. 77A-B are graphical representations of an estimation of average artery diameter and a change in diameter during a 10-second recording, according to some embodiments of the invention;

FIGS. 78A-D are simulated reflections from an artery wall, according to some embodiments of the invention;

FIGS. 79A-C are simulation results of decomposing a signal to a set of base echo signals and assigning the signals to a location (e.g. artery wall) using a dictionary of probable reflections, according to some embodiments of the invention; and FIGS. 80A-C are simulation results of obtaining an artery radius using a dictionary of probable reflections, according to some embodiments of the invention.

Figure 81:
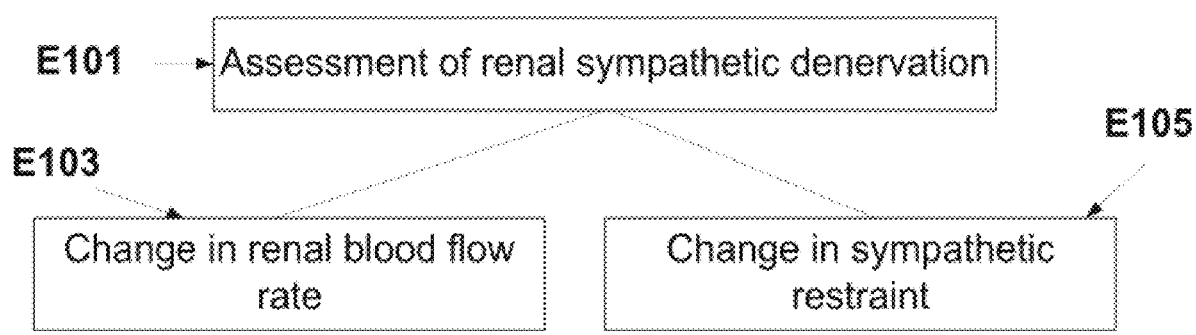
Figure 83:
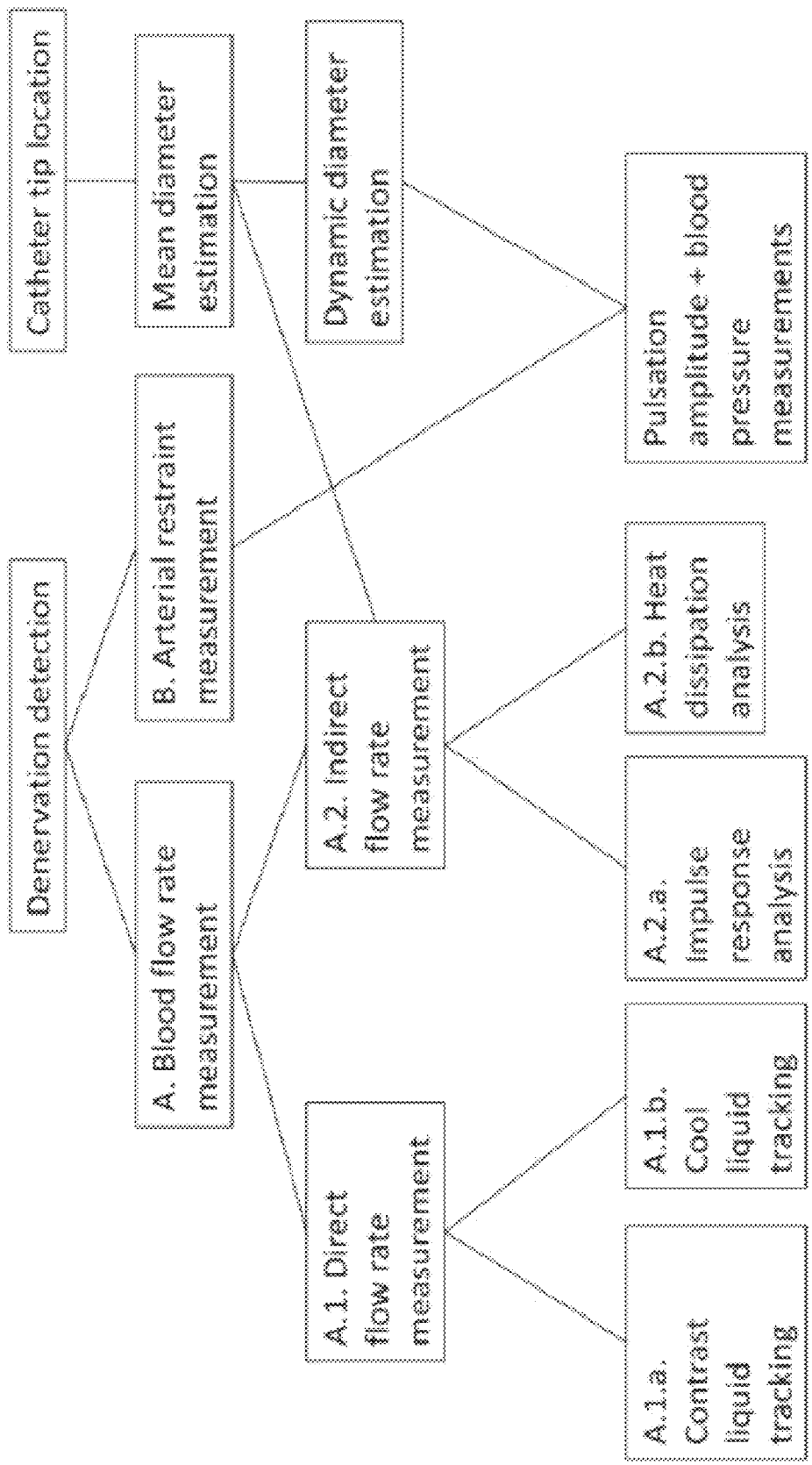
Figure 84:
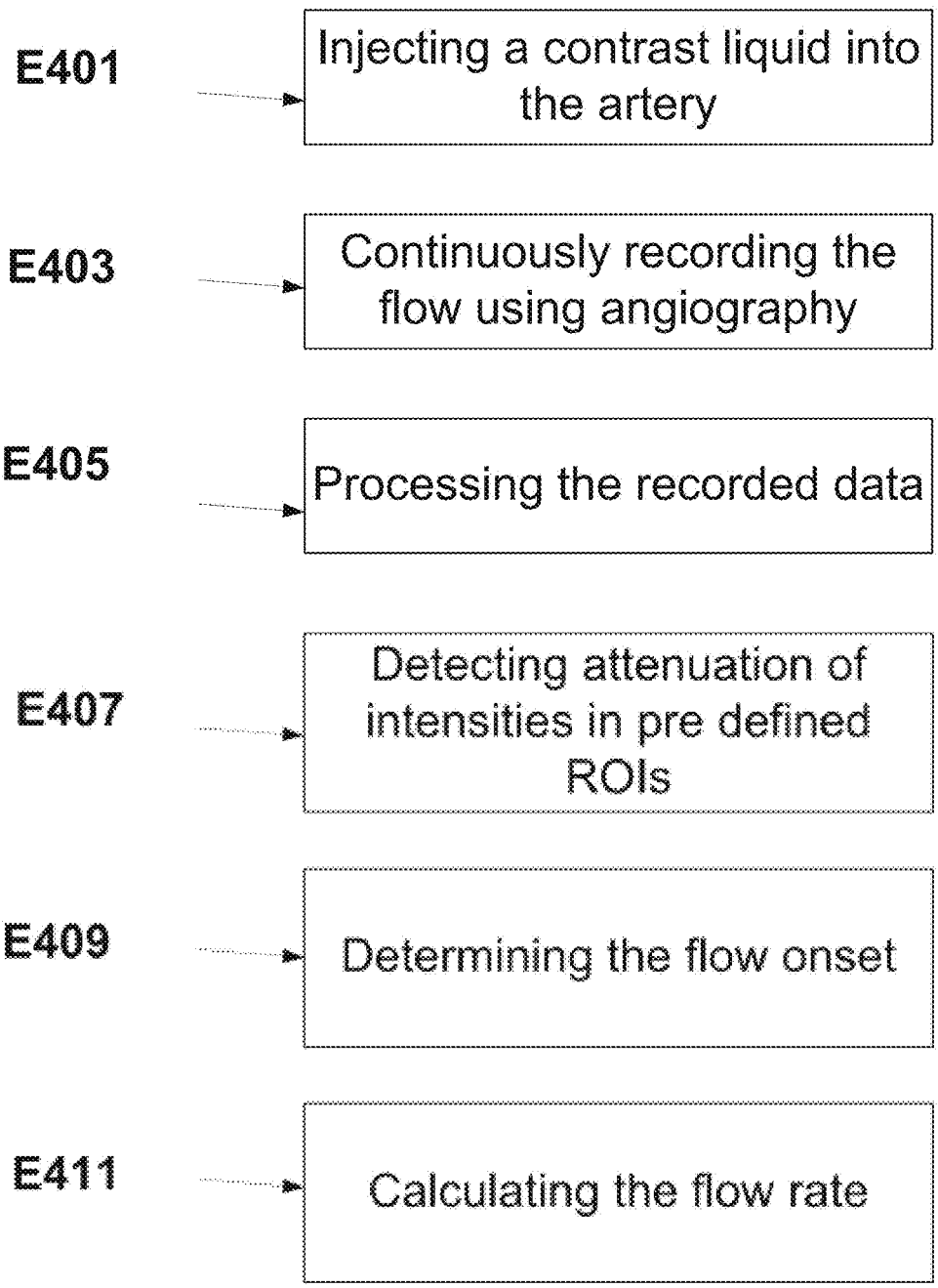
Figure 87:
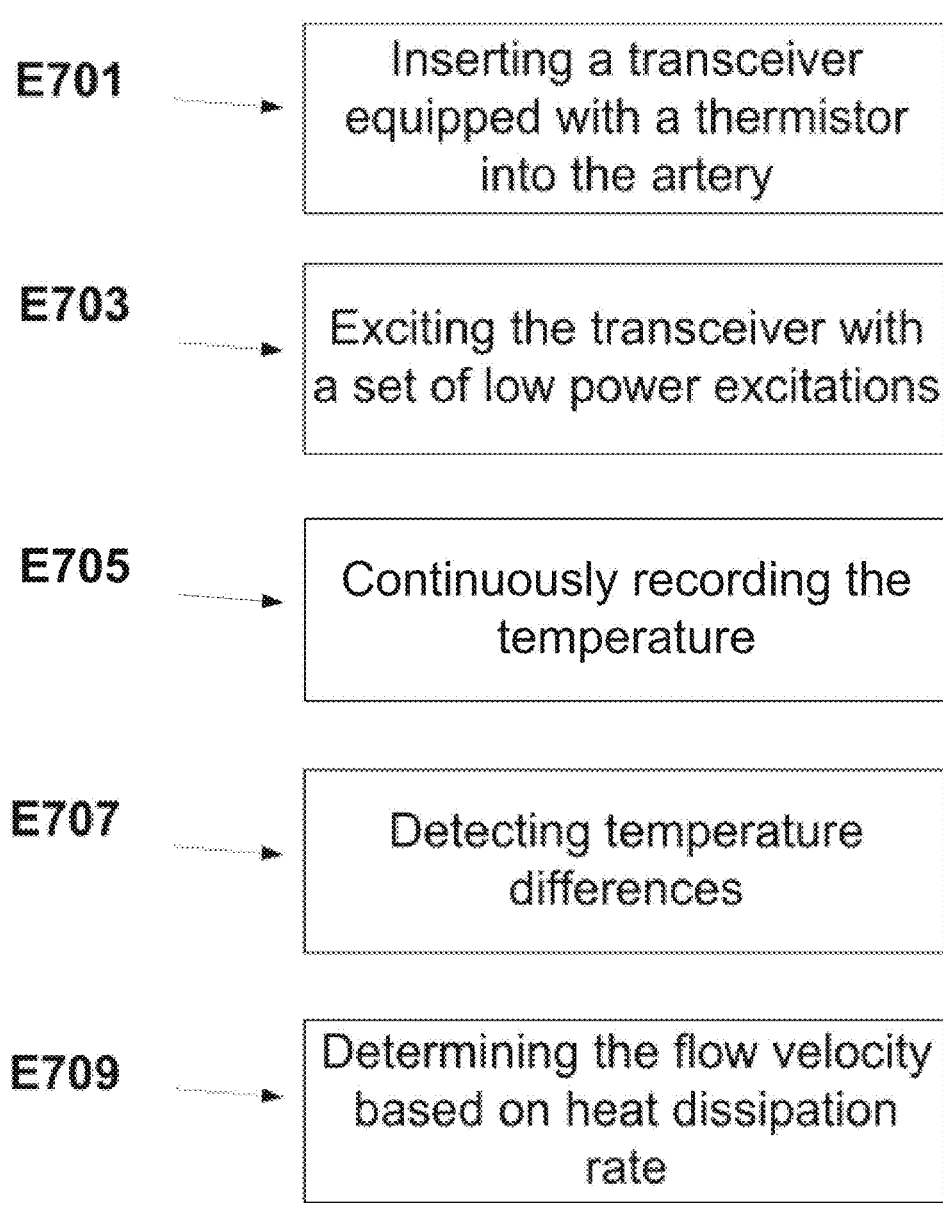
Figure 90:
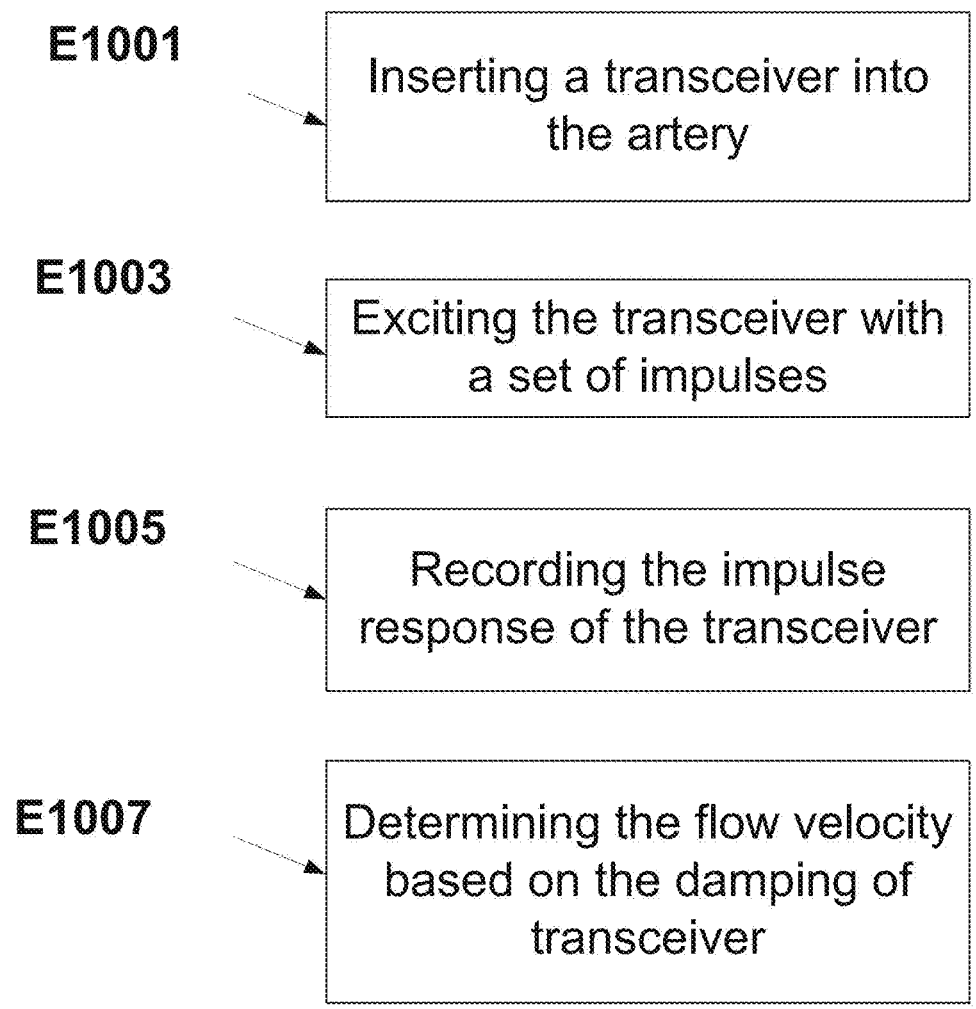
Figure 92B:
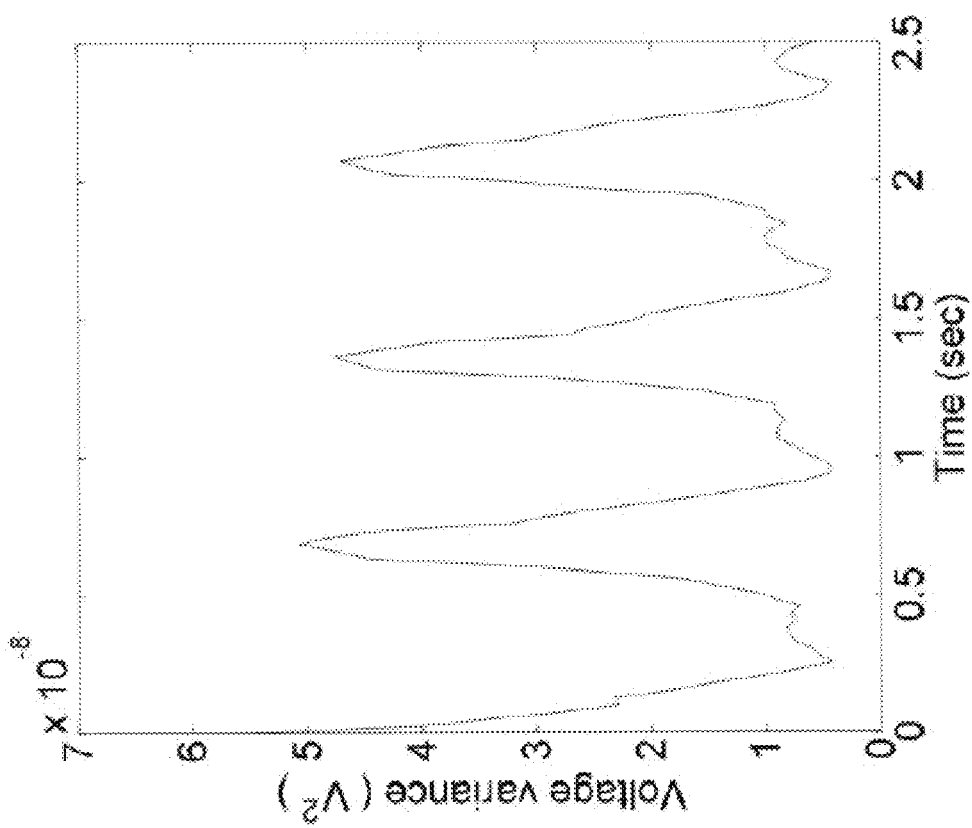
Figure 92A:
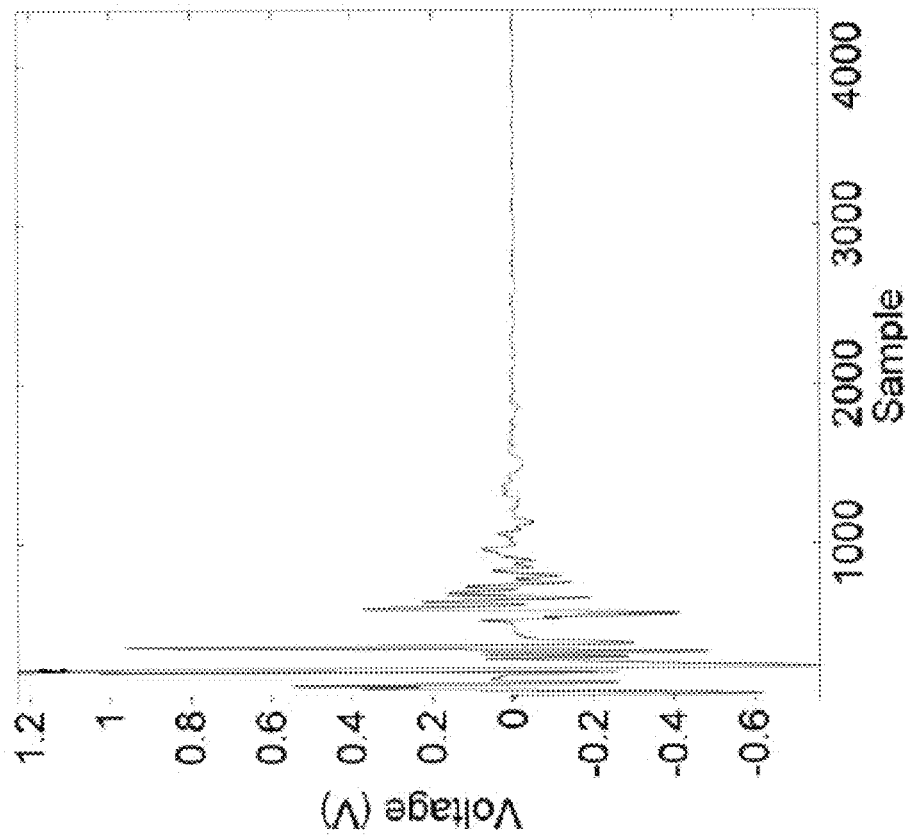
Figure 94:
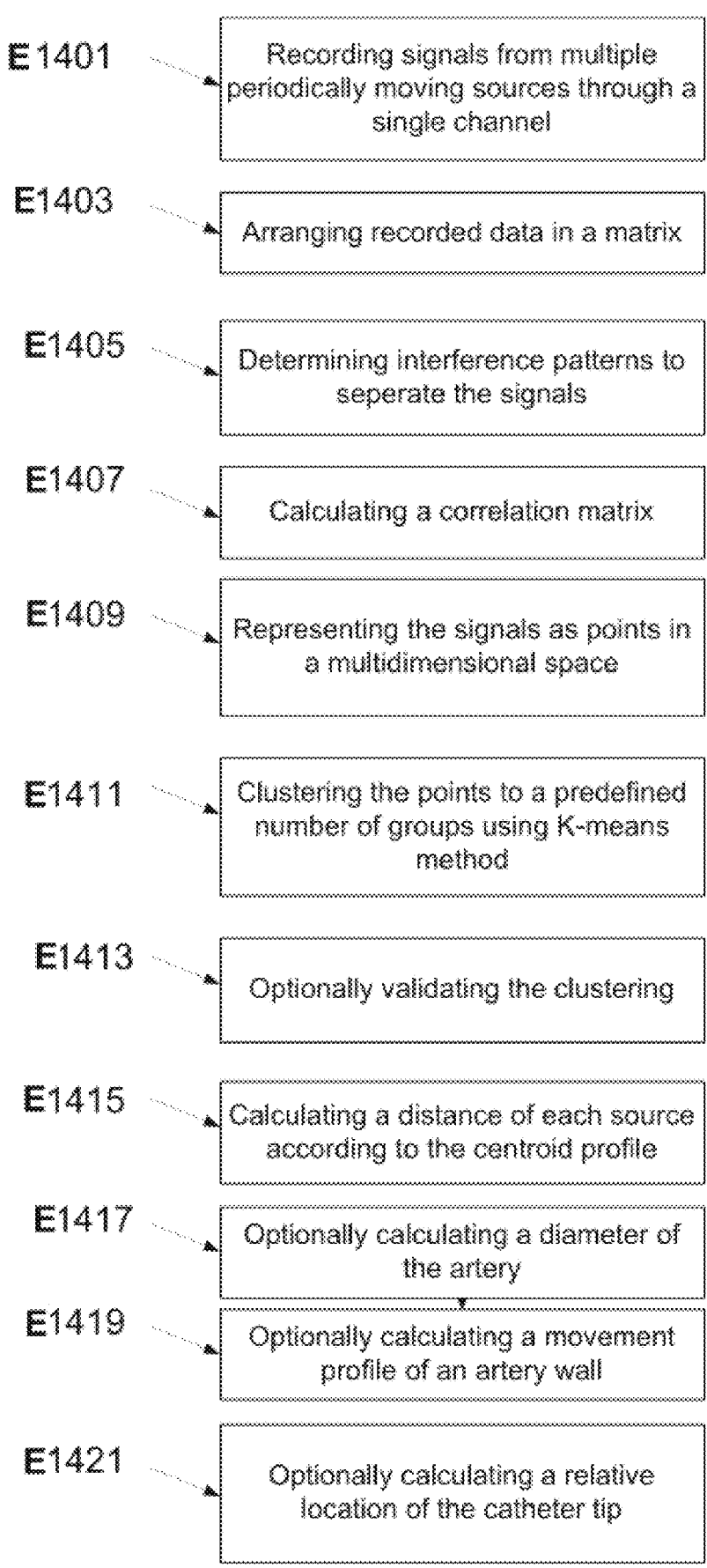
Figure 95A:
Figure 95B:
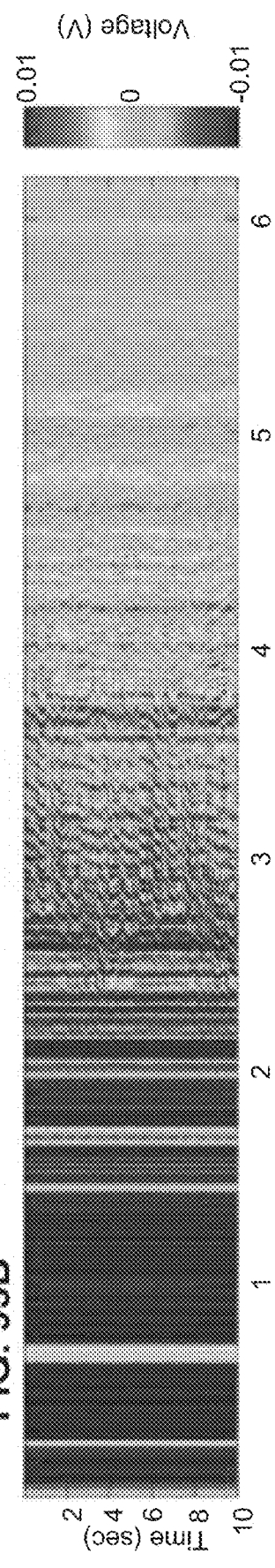
Figure 95C:
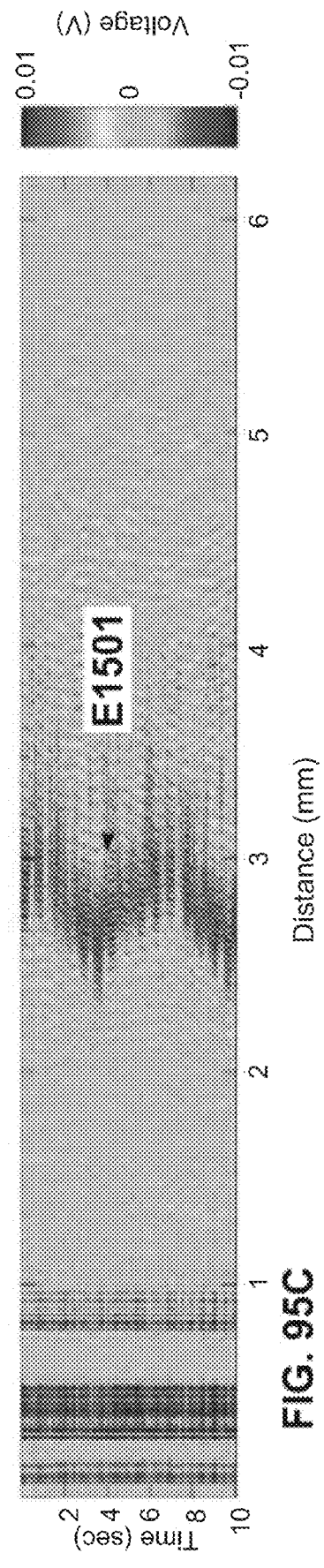
Figure 96A:
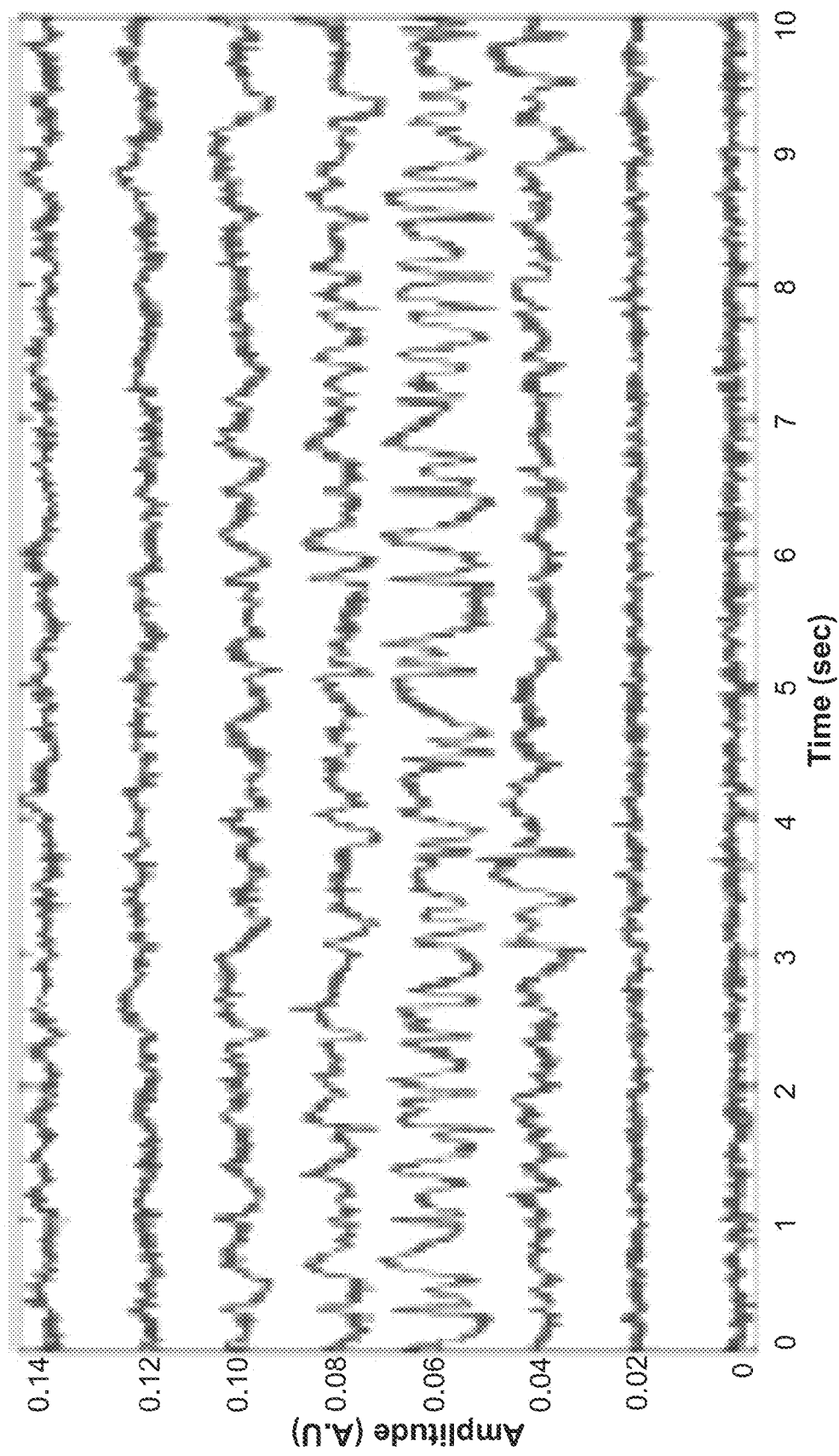
Figure 96B:
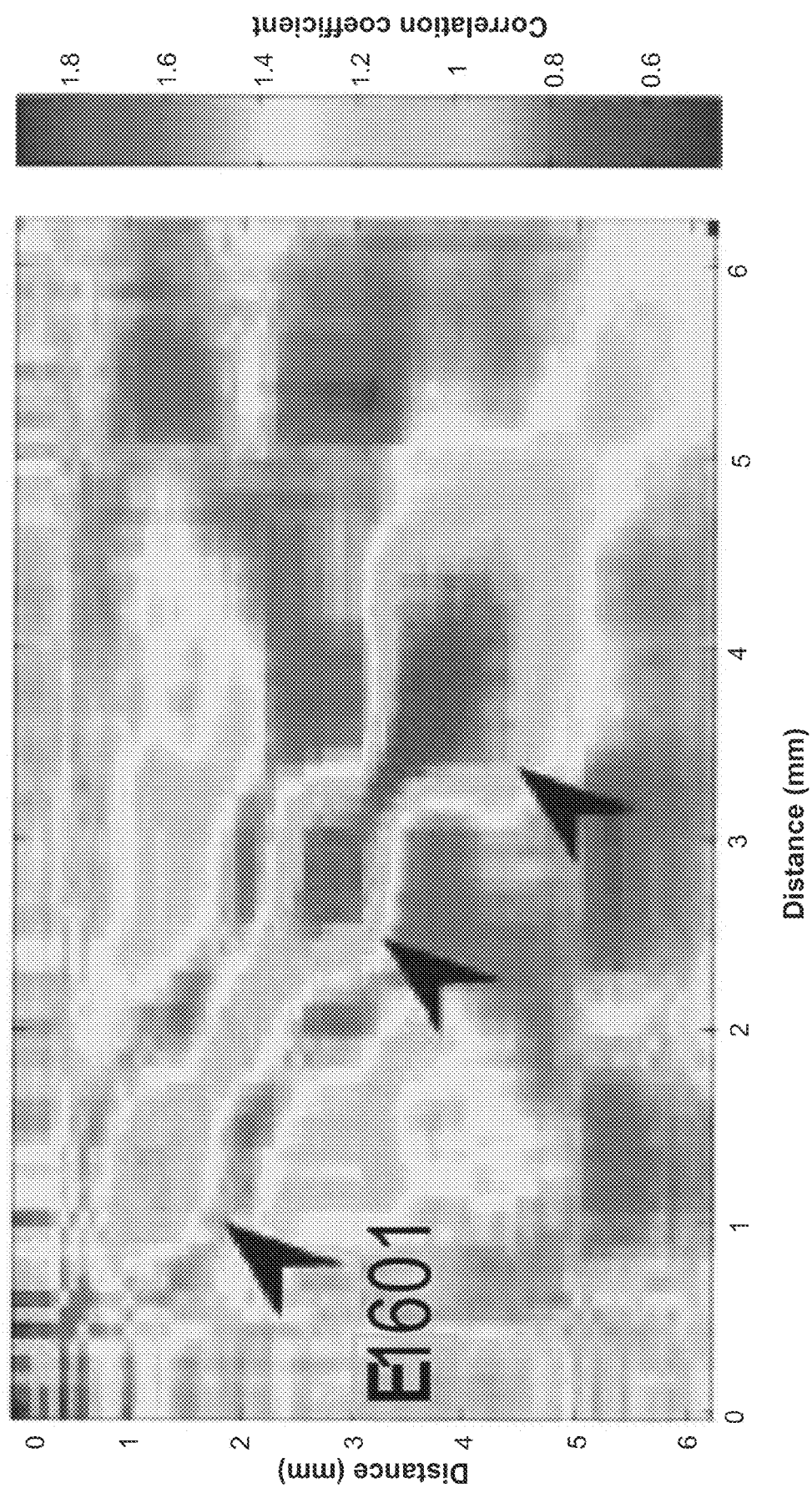
Figure 96C:
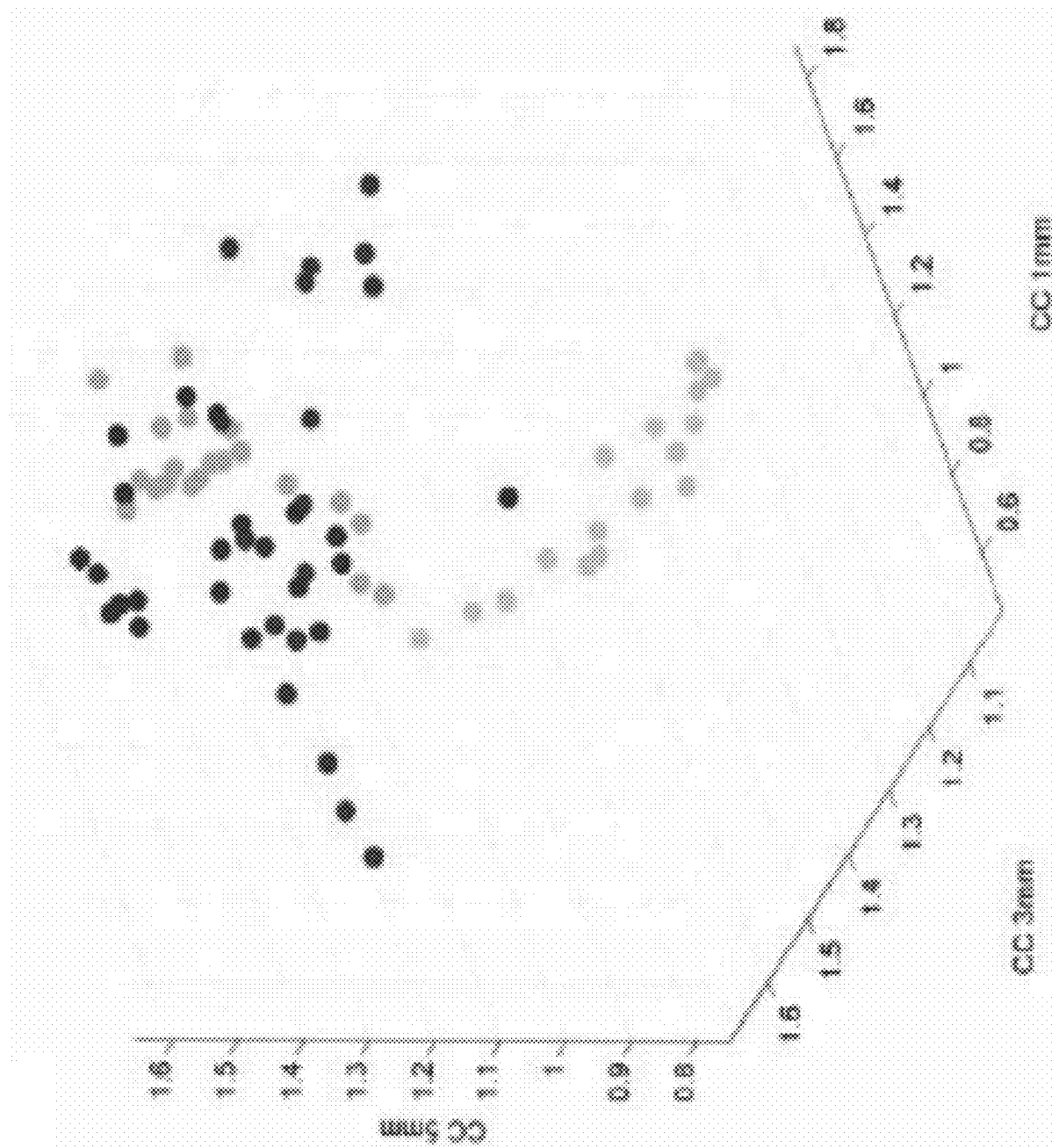
Figure 98C:
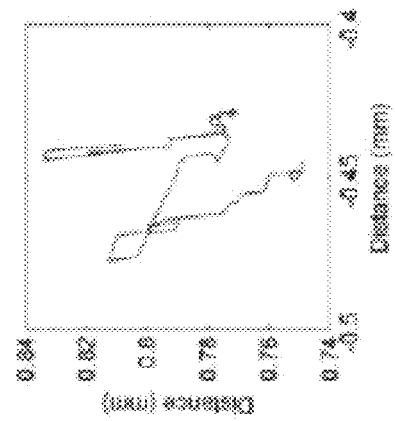
Figure 98B:
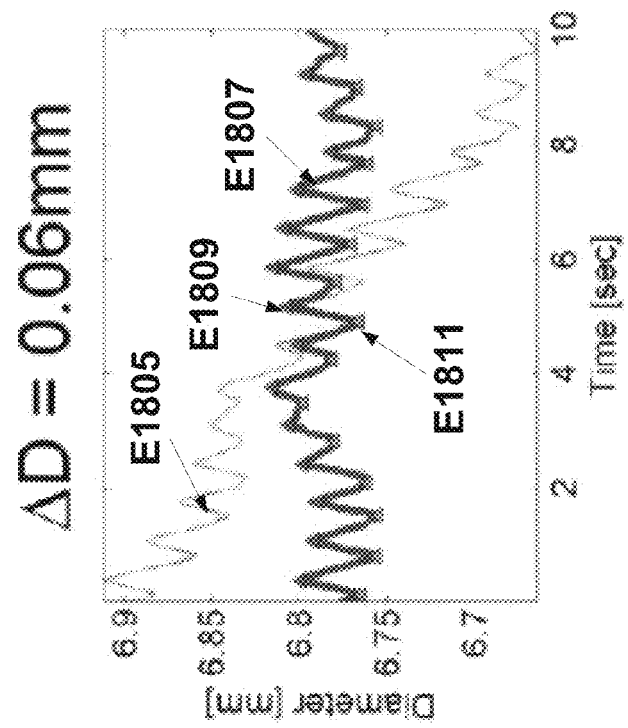
Figure 98A:
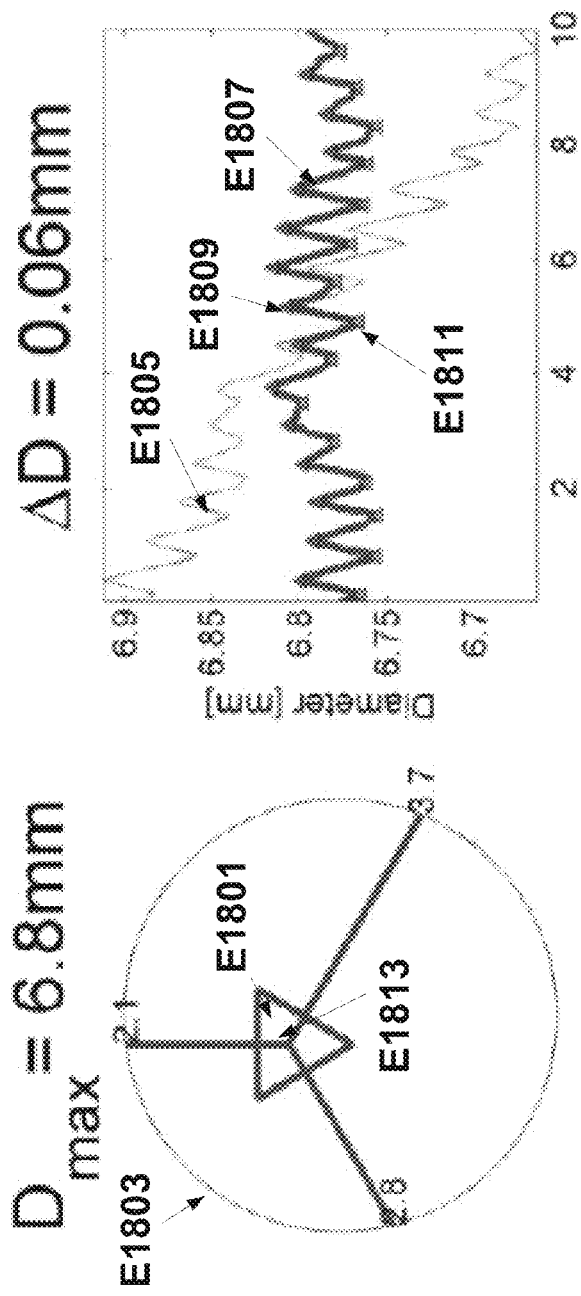
Figure 99C:
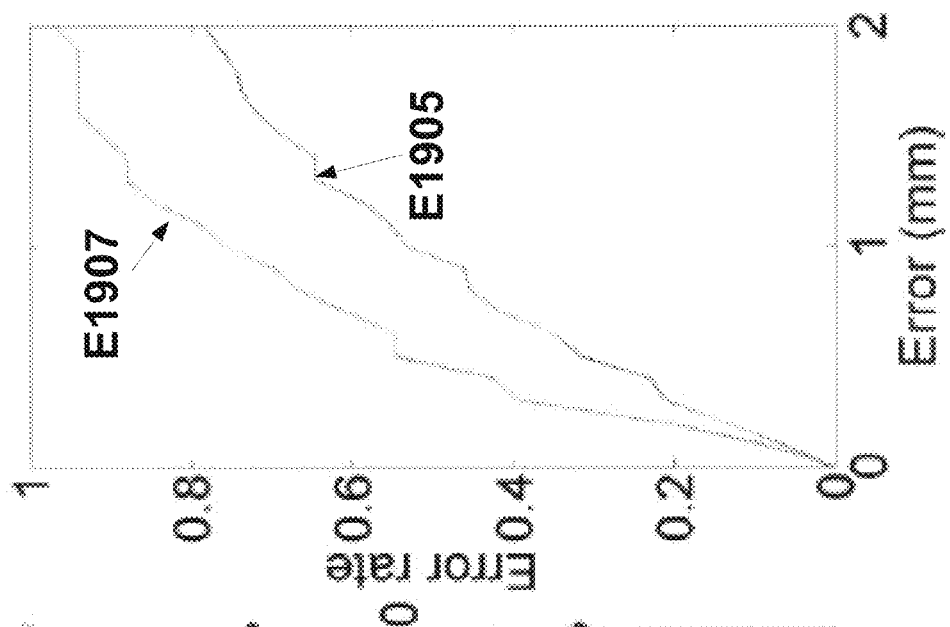
Figure 99A:
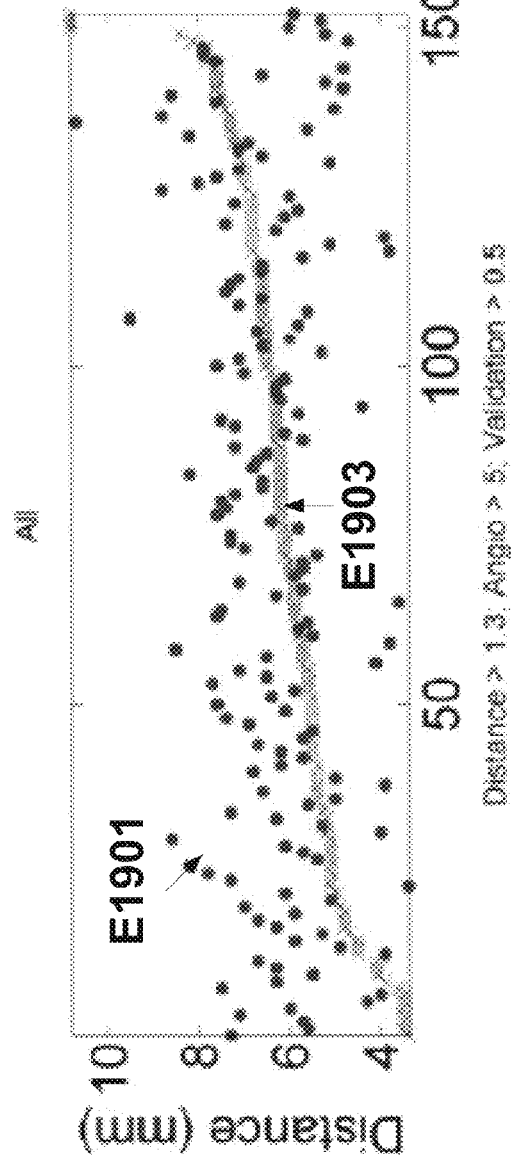
Figure 99B:
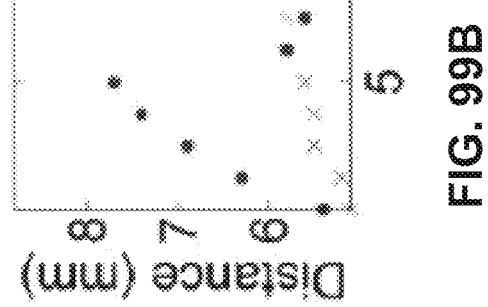

FIG. 81 is a flowchart of physiological changes that may indicate the effectiveness of an RSD treatment, according to some embodiments of the invention;

FIGS. 82A-F are schematic drawings and an angiogram relating to an endovascular catheter device, according to some embodiments of the invention;

FIG. 83 is a flowchart describing some exemplary methods for obtaining real time feedback for an RSD treatment, according to some embodiments of the invention;

FIG. 84 is a flowchart of an exemplary method for measuring blood flow rate by tracking the flow of a contrast liquid, according to some embodiments of the invention;

FIGS. 85A-D are experimental results of measuring blood flow rate by tracking contrast liquid in vivo, according to some embodiments of the invention;

FIG. 86 is a flowchart of an exemplary method for measuring blood flow rate by tracking the flow of a cold liquid, according to some embodiments of the invention;

FIG. 87 is a flowchart of an exemplary method for determining renal blood flow velocity based on a heat dissipation rate of a transceiver, according to some embodiments of the invention;

FIGS. 88A-B are experimental results of an in vitro experiment to prove a linear relation between blood flow velocity and heat dissipation rate of the transceiver, according to some embodiments of the invention;

FIGS. 89A-D are experimental results of an in vitro experiment for validating the linear relation between blood flow velocity and heat dissipation rate of the transceiver, according to some embodiments of the invention;

FIG. 90 is a flowchart of an exemplary method for determining blood flow velocity by analyzing an impulse response of a transceiver, according to some embodiments of the invention;

FIGS. 91A-B are experimental results of an in vitro experiment to prove a correlation between a measured impulse response of the transceiver and the flow velocity, according to some embodiments of the invention;

FIGS. 92A-B are experimental results of an in vivo experiment including an impulse response analysis, according to some embodiments of the invention;

FIG. 93 is a flowchart of an exemplary method for measuring arterial blood flow, according to some embodiments of the invention;

FIG. 94 is a flowchart of a method for analyzing a sequence of signals received from multiple sources and recorded through a single channel, according to some embodiments of the invention;

FIGS. 95A-C are images of a typical recording of reflected echo signals from the artery wall, according to some embodiments of the invention;

FIGS. 96A-C are graphical representations of a clustering process for separating signals according to interference patterns, according to some embodiments of the invention;

FIGS. 97A-D are graphical representations of a movement profile of an artery wall, according to some embodiments of the invention;

FIGS. 98A-C are graphical representations of estimating a current location of the catheter tip with respect to the artery walls, according to some embodiments of the invention; and FIGS. 99A-C are graphical representations of a validation of the artery diameter estimation, according to some embodiments of the invention;

DESCRIPTION OF SPECIFIC EMBODIMENTS OF THE INVENTION

The present invention, in some embodiments thereof, relates to a devices and methods for intravascular denervation and assessment thereof and, more particularly, but not exclusively, to devices and methods for renal denervation.

Some embodiments of the invention relate to an intravascular catheter configured for ultrasonic ablation of the tissue, comprising a plurality of piezoelectric transceivers. Some examples of a catheter device are found, for example, in FIGS. 1A-5, 8, 10-13B, 17-19B, and others. In some embodiments, an intravascular distancing device is provided, the device adapted for obtaining at least a minimal distance between an ultrasound emitting element and a tissue, such as the blood vessel wall. Optionally, the distancing device is coupled to the catheter. Some examples of a distancing device are found, for example, in FIGS. 20A-23B, 25A-32B, and others.

Some embodiments of the invention relate to assessment of renal sympathetic denervation (RSD) treatment effectiveness. Optionally, the assessment includes immediate assessment of the treatment in real time. Some exemplary methods of assessment are found, for example, in FIGS. 35-44B, 51-52, and others.

Some embodiments of the invention relate to processing echo of signals, such as processing of signals received by the intravascular catheter, for example following emission of the signals by the catheter. In some embodiments, processing of echo signals is performed to characterize physical and/or mechanical properties of the blood vessel. Some exemplary methods for processing of echo signals and/or results obtained by these methods are found, for example, in FIGS. 53A-80C, and others.

It should be noted some technical features are described in various contexts throughout the application, for example as a stand-alone feature or as a part of a complete system. In an example, a method for processing of echo signals acquired within a blood vessel for providing distance related measurements is referred to herein both as a stand-alone method and as a part of a general method for assessing denervation effectiveness, in which a method for estimating an intravascular distance is applied, for example, to identify a change in arterial stiffness.

The present invention, in some embodiments thereof, relates to an intravascular catheter, and, more particularly, but not exclusively, to an intravascular catheter comprising a plurality of peripherally arranged piezoelectric transceivers.

Some embodiments of the invention relate to a catheter head comprising a plurality of ultrasonic transceivers, such as 3, 4, 2, 5, 6, 8 transceivers. In some embodiments, the transceivers are configured for emitting ultrasound energy towards the vessel walls, for example to ablate tissue, such as nerve tissue surrounding the vessel. Additionally or alternatively, the transceivers are configured for sensing by receiving echo signals, such as echo signals reflected by the vessel walls. Optionally, by comprising transceivers configured for receiving echo signals, monitoring of an ablation process can be provided by analyzing the received signals.

An aspect of some embodiments of the invention relates to an intravascular catheter head comprising a cannulated chassis and a plurality of ultrasonic transceivers peripherally arranged around the chassis. In some embodiments, the transceivers are mounted onto a plurality of facets of the chassis. In some embodiments, a mounting of the transceivers and/or electrical wiring of the transceivers is configured mostly, or, in some embodiments, only, on the internally facing surfaces of the transceivers (i.e. the surfaces facing the chassis), for example to maximize an available surface area of the transceivers which faces radially outwards, and is configured for emitting and/or receiving ultrasound energy.

Optionally, a summed area of radially outward facing surfaces of the transceivers covers at least 70%, 80%, 90%, or intermediate, larger or smaller percentages of the radially outward facing facets of the chassis. Additionally or alternatively, the summed area of the transceiver surfaces covers less than 95% of the radially outward facing facets of the chassis. In some embodiments, the chassis, at least in some portions, is electrically conductive, for example for conducting current to activate the transceivers. In some embodiments, the chassis, at least in some portions, is heat conductive, for example to conduct heat away from the transceivers.

In some embodiments, a chassis comprises a polygonal cross section profile, such as a triangular profile. In some embodiments, a spatial arrangement of the transceivers matches the profile of the chassis, for example, 3 transceivers are mounted onto a triangular shaped chassis, each transceiver configured on a different facet of the chassis. In some embodiments, a chassis is shaped to align the transceivers with respect to a longitudinal axis of the chassis and/or with respect to each other, for example, the facets of the chassis are configured at an equal radial distance from the longitudinal axis of the chassis, so that the transceivers will be equally spaced from the axis. In some embodiments, a chassis is rigid, for example to reduce deformation of the transceivers that are coupled to it.

In some embodiments, the catheter head is dimensioned to reduce obstruction of blood flow when positioned within the vessel. In some embodiments, the catheter head comprises a plurality of assembled components occupying a relatively small volume. In some embodiments, a circumscribing circle of the catheter head comprises a diameter that is 2.2 mm or smaller. In some embodiments, the transceivers are spatially arranged so that a cross sectional area of the catheter head takes up a relatively small cross sectional area of the vessel, for example occupying less than 30% of the cross sectional area of the vessel. Optionally, the catheter is configured for treating vessels of various diameters.

An aspect of some embodiments relates to a PCB configured to electrically and/or mechanically couple between a chassis and an ultrasonic transceiver. In some embodiments, the PCB comprises one or more bendable extensions to fit closely around the chassis. Optionally, the extensions connect the PCB to one or more transceivers that are different from the transceiver mounted onto it. In some embodiments, a coupling between a transceiver and the PCB is suitable for transferring energy having power and intensity properties sufficient for treating tissue, such as thermally damaging the tissue. For example, in some embodiments, a transceiver is coupled to a PCB via a preselected number and/or preselected shape of contact nodes affective to reduce a damping of the transceiver. In some embodiments, the contact nodes comprise conductive glue for electrically connecting between the transceiver and the PCB.

An aspect of some embodiments relates to an arrangement of ultrasonic transceivers configured for emitting ultrasound energy such that the effective field of energy extends to a radial distance of at least 2 mm from a center of the catheter head, e.g. a center point of the chassis. In some embodiments, the emitted energy is unfocused. In some embodiments, the energy travels through the blood medium of the vessel. In some embodiments, the field of the energy spreads over more than 40%, more than 50%, more than 60% more than 75%, more than 80% of a cross sectional area of the vessel. In some embodiments, an extent of thermal damage caused by a beam may be associated with one or more of an angle between adjacent beams, an opening angle of the beam, a surface area of the transceiver. In some embodiments, an effective field produced by a triangular configuration of transceivers is better suited for treating the vessel, for example as compared to a configuration of 4 or more transceivers. Optionally, an amount of 3 transceivers has been shown by the inventors to be sufficient for effectively denervating a blood vessel such as the renal artery. Optionally, by having 3 transceivers, for example compared to a higher number of transceivers, variations in a total impedance of the transceivers are reduced. Optionally, by having 3 transceivers as opposed to a higher number, a risk of failure of one or more transceivers is reduced. Optionally, in the triangular configuration, scattering of each of the beams is relatively small, for example as compared to beams produced by a higher number of transceivers, contributing to a higher energy of the beam.

In some embodiments, a thermal effect of the ultrasound field produced by a transceiver is stronger at the outermost layers of the vessel wall, such as the adventitia layer and/or tissue surrounding it, than it is at the inner layers such as the intima or perivascular tissue, for example due to cooling of the inner layers by blood flow.

An aspect of some embodiments relates to a method for exciting a plurality of ultrasonic transceivers at an operating frequency that does not necessarily match the resonant frequencies of the transceivers, but is in the range of ±10%, ±5%, ±15%, ±20%, from an average resonant frequency of the transceivers. In some embodiments, the operating frequency is different from any of the resonant frequencies of the plurality of transceivers. In some embodiments, the transceivers of a single catheter are selected using a sorting method which groups transceivers having similar or nearby values (for example in the range of ±5%, ±10%, ±15%) of resonant frequencies and/or impedance values. A potential advantage of a catheter comprising a plurality of transceivers having similar or like characteristics may include operating the catheter at an optimal efficiency frequency range. In some embodiments, an operating frequency range for the plurality of transceivers of a single catheter is determined, for example during manufacturing, according to the resonance and/or impedance characteristics of the transceivers. Optionally, operating frequency and/or other characterizing data is programmed onto a memory unit, for example assembled on the catheter handle and/or on a connector coupling between the catheter and the console, and is identified by an operating console in communication with the catheter, for example during use. In some embodiments, the console is configured for scanning an impedance of the transceivers and comparing the scanning results to calibrated values, to determine if the catheter is qualified for use.

In some embodiments, one or more components of the catheter are manufactured and/or assembled together using common techniques, such as soldering.

The present invention, in some embodiments thereof, relates to an intravascular distancing device for a catheter and, more particularly, but not exclusively, to a device for obtaining at least a minimal distance between an ultrasound emission element and a tissue, such as a blood vessel wall. Some embodiments of the invention relate to an intravascular distancing device for positioning a catheter in a body lumen, relative to the walls of the lumen. In some embodiments, the device is configured for providing a distance between one or more ultrasound emission elements configured on an intravascular catheter, and tissue such as a blood vessel wall. In some embodiments, the device comprises an open configuration, in which the ultrasound emission element is pushed away from the tissue. In some embodiments, the device is collapsible into a closed configuration. Optionally, in the closed configuration, the device conforms to boundaries defined by the catheter. Optionally, the closed configuration provides for insertion and/or removal and/or for positioning the device within the vessel. Optionally, the closed configuration permits contact between the transceiver and the wall. In some embodiments, the distancing device conforms to a space between a catheter and a guiding sheath.

In some embodiments, a distance between the ultrasound transceiver and the vessel wall is controllable and/or adjustable. Optionally, the distance is constant. Alternatively, the distance is variable. In an exemplary embodiment of the invention, the distancing device provides for at least some volume of blood flow over the transceiver, for example, between a surface of the transceiver and the wall. In some embodiments, the device is configured for centering the catheter with respect to the vessel wall.

An aspect of some embodiments relates to a distancing device in the form of a slotted cylinder. Optionally, the slots extend longitudinally such that they are parallel to the cylinder axis. Optionally, the slots are distributed circumferentially around the cylinder walls. In some embodiments, remaining cylinder wall portions extending longitudinally between the slots form elongated leaflets. Optionally, in the open configuration, the leaflets bend into a rounded 'elbow' like configuration, pushing the ultrasound emission element away from the vessel wall. Optionally, an amount of blood flowing between a leaflet and a transceiver is sufficient to cool the vessel wall, for example a treated portion of the wall, and/or to cool the ultrasonic transceiver. Optionally, the amount of cooling provided is sufficient for reducing or preventing thermal damage to an inner wall of the vessel.

It is noted that many of the described embodiments refer to a distancing element described as a leaflet, but other elements suitable for pushing a catheter or a portion of a catheter such as an ultrasonic transceiver away from a lumen wall may also be used.

In some embodiments, the distancing device is threaded onto a catheter head and positioned such that the one or more transceivers of the head face the void of formed slots. Optionally, the elongated leaflets fit within recesses between the elements, for example in the closed configuration. In some embodiments, the leaflets are positioned such that they do not interfere with the beam ultrasound emitted by the transceiver. Optionally, the open leaflets are positioned such that they do not come across an emitting surface of the transceiver, and/or across a beam emitted by the surface. Alternatively, the device interferes relatively with the ultrasound beam, for example, relatively little interference such as by interfering with the edges of the beam. Alternatively, the leaflets intentionally interfere with the beam. Optionally, the beam is directed towards the leaflets. Optionally, thermal damage to tissue such as vessel wall tissue is obtained by heating the leaflets.

In some embodiments, the distancing device is positioned on a non-cylindrical catheter head, for example on a catheter head comprising a triangular or squared cross section profile. In some embodiments, the catheter head comprises a plurality of peripherally arranged ultrasonic transceivers, for example 3 or 4 transceivers, and the distancing device is configured such that it does not interfere with the plurality of beams emitted from the transceivers. In some embodiments, the distancing device does not interfere with the receipt of echo signals reflected from the vessel walls by the one or more transceivers.

In some embodiments, in the closed configuration, the leaflets cover at least a portion of the one or more ultrasonic elements, for example protecting a surface of the transceivers.

In some embodiments, a width of a leaflet is determined such as to reduce a thermal effect on the vessel wall. Additionally and/or alternatively, a width of a leaflet is determined such as to prevent mechanically induced damage to the vessel wall, for example scratches to the vessel wall tissue.

In some embodiments, the distancing device funnels blood flow towards the vessel wall, for example by the leaflets, in their open position, forming a slanted surface which diverts the blood flow.

In some embodiments, a shape and/or position of a bend of a leaflet with respect to a transceiver, in the open configuration, is determined according to a shape and/or size of the emitted beam. For example, the bend can be centered with respect to a longitudinal axis of the transceiver, or, alternatively, be positioned in proximity to one of the ends of the transceiver.

Optionally, a positioning of the bend affects movement of the vessel wall with respect to the one or more transceivers of the catheter. In some embodiments, the leaflet bends into a triangular, elbow like configuration. Alternatively, the leaflet bends into a rectangular or trapezoidal configuration, which may increase the contact area between the leaflet and the wall.

An aspect of some embodiments relates to an intravascular distancing device comprising a layered structure that is stiff enough to maintain at least a minimal distance between the vessel wall and the one or more ultrasonic transceivers, yet soft enough reduce or prevent mechanical damage to tissue such as the endothelium. In some embodiments, the combination of a rigid structure yet one that softly engages the tissue is obtained by layering at least two materials having different stiffness properties, which form, for example, a bendable leaflet of the distancing device.

The present invention, in some embodiments thereof, relates to methods for assessing a renal denervation treatment. Some embodiments of the invention relate to assessment of renal sympathetic denervation (RSD) treatment effectiveness. Some embodiments comprise immediate assessment of the treatment. Detection of changes in physiological parameters, optionally in real time, provides feedback for evaluation of the treatment. In some embodiments, the changes indicate an effect of neural modulation, optionally accomplished by the denervation treatment, on tissue behavior, for example artery wall tissue. Some of the physiological changes described herein are related to a physical change to the artery wall. Some of the physiological changes described herein are related to changes in hemodynamic properties of the renal artery. Some of the physiological changes described herein relate to mechanical properties of the tissue, such as a stiffness of the artery wall. Some embodiments of the invention relate to a method for measuring arterial restraint. Optionally, a change in arterial restraint of the renal artery indicates a change in the number of neural signals sent to the restraining muscles, possibly affecting the stiffness of the artery, and may indicate the efficacy of the RSD treatment.

At least some of the methods described herein comprise the insertion of one or more ultrasonic transceivers, configured for emitting and/or receiving ultrasonic energy, into a lumen of the renal artery. In some embodiments, a measurement device such as a temperature sensor is inserted into the artery. In some embodiments, the one or more transceivers and/or one or more measurement devices are mounted on an intravascular catheter.

In some embodiments, the device is adapted for emitting energy to ablate nerves, and/or perform measurements for assessing a change in artery stiffness, and/or perform measurements for assessing a change in hemodynamic properties of the artery. Optionally, two or more of these functions are performed simultaneously, for example to provide feedback during a denervation treatment. Optionally, the ablation treatment and/or measurements are performed locally, for example at various sites along the artery. In some embodiments, a transceiver is adapted for emitting energy with various profiles of parameters, such as intensity and frequency, to provide at least one of nerve ablation and emitting of energy for detection of physiological parameters related to the artery wall. In some embodiments, the transceiver is adapted for receiving echo signals reflected by the artery wall. In some embodiments, ablation and/or physiological parameter detection and/or measurements are performed from within the artery lumen, optionally without contacting the artery wall.

In some embodiments, a plurality of transceivers are activated simultaneously. Optionally, the transceivers are excited at a similar frequency, to emit energy towards the artery walls. Optionally, ultrasound energy that is reflected by the artery walls is received by the transceivers. Optionally, the returning signals are received within a time limit of 0.2 msec, 0.5 msec, 1 msec, 3 msec, 5 msec, 100 msec, 1 second or intermediate, longer or shorter time periods from the emission. A potential advantage of acquiring signals returning from various wall directions, optionally within a relatively short time period may include dynamically monitoring changes in the artery, for example a change in diameter. As denervation may induce changes to the artery during the treatment and/or over time, simultaneous activation of the transceivers followed by receipt of returning signals reflected by the walls may provide for acquiring a momentary status of the artery, which may be advantageous for monitoring changes in the artery such as a change in diameter. Optionally, the changes indicate a change in stiffness, an occurrence of a local spasm, a widening of the artery and the like.

A potential advantage of measuring from within the artery, as opposed to, for example, using external imaging, includes obtaining an assessment of higher accuracy. A potential advantage of having a dual functioning device, which is capable of measuring physiological parameters such as blood flow rate as well as provide nerve modulation by emitting ablating energy includes reducing the need for insertion of a flow wire in parallel to a denervation catheter, which is often not possible due to the limited volume of the artery lumen.

An aspect of some embodiments of the invention relates to a method for estimating blood flow rate and/or velocity. Optionally, a change in renal artery flow provides an indication related to the nerve modulation induced by a denervation treatment.

In some embodiments, blood flow rate and/or velocity are estimated by measuring the flow of a liquid agent injected into the artery. In some embodiments, the liquid agent is contrast liquid, which can be detected using an imaging technique, such as x-ray angiography. In some embodiments, the liquid agent is cold liquid, and its flow is assessed based on detection of temperature changes, for example by positioning at least two temperature sensors along a certain path in the artery, and estimating the velocity based on parameters such as the measured temperature, time, and/or distance between the temperature sensors. In some embodiments, blood flow rate is estimated by combining parameters such as the cross section area of the artery, and the blood flow velocity.

In some embodiments, blood flow velocity is estimated by analyzing an impulse response of an ultrasonic transceiver to excitation. In some embodiments, analysis of the impulse response to estimate blood flow velocity is based on a correlation between the velocity and the damping of the transceiver.

In some embodiments, blood flow velocity is estimated by analyzing the temperature change of at least one transceiver during and/or following excitation, for example by positioning a temperature sensor in proximity to the transceiver. In some embodiments, the blood flow velocity is estimated according to a heat dissipation rate of the transceiver. In some embodiments, the blood flow velocity is estimated according to a relation between a temperature of the transceiver and the excitation power. In some embodiments, the blood flow velocity is estimated according to a cooling time constant of the transceiver. Optionally, the blood flow velocity estimation is based on a calibration between cooling time constants and known flow velocities.

An aspect of some embodiments of the invention comprises estimating a change in hemodynamic properties, a change in artery wall stiffness, and/or a change in viscoelastic properties of the artery, by combining estimations of physiological parameters. For example, a method for estimating blood flow velocity is combined with the measurement of artery diameter to determine blood flow rate. In another example, a measure of arterial blood pressure and a measure of the artery diameter are combined to estimate a change resulting from, for example, damage caused to sympathetic innervations of the smooth muscle cells of the artery, changing the viscoelastic properties of the artery. In another example, a measure of the artery diameter and a measure of arterial blood pressure over time are combined to estimate a Young's modulus of the artery wall, indicating a stiffness level.

An aspect of some embodiments of the invention relates to a method for assessing renal denervation effectiveness using neural stimulation. In some embodiments, the method comprises one or more of the following: estimating one or more physiological parameters such as artery diameter, arterial blood pressure, blood flow velocity, catecholamine levels, and/or heart rate long enough to deduce a baseline, providing a stimulation to afferent and/or efferent nerves, re-measuring the one or more physiological parameters, performing a denervation treatment to damage the nerves, repeating the measuring and stimulating, and comparing the pre-denervation results to the post-denervation results to deduce effectiveness of the denervation treatment.

An aspect of some embodiments of the invention relates to a method for assessing renal denervation by acquiring elastograms of the artery, for example before and after denervation. Optionally, the elastograms are acquired at systolic and/or diastolic blood pressures. Optionally, systolic and/or diastolic blood pressure induce stress on the wall tissue, and a strain map formed before and after denervation using elastography is compared to deduce effectiveness.

Some embodiments of the invention relates to an ultrasonic device for endovascular use. In some embodiments, the device comprises a plurality of transceivers, such as 2, 3, 4, 6 transceivers. In some embodiments, the transceivers are positioned on a catheter tip. In some embodiments, the transceivers are configured to emit an ultrasonic beam. Optionally, the beam is reflected by one or more moving sources, such as the artery's walls. In some embodiments, the transceivers are configured to receive a returning echo signal from the reflectors.

In some embodiments, the device is equipped with one or more measurement devices, such as temperature and/or pressure sensor. A temperature sensor, for example, may be used for measuring a temperature of a transceiver and/or for measuring a temperature of the blood. In some embodiments, data collected by the one or more measurement devices is analyzed to assess physiological changes such a change in blood flow rate, a change in blood pressure, a change in the artery diameter, a change in blood flow velocity, and/or combination thereof.

In some embodiments, the device comprises and/or connected to a signal processor. In some embodiments, the signal processor is configured for implementing one or more algorithms relating to distance measurements within the artery, for example estimating a distance between a transceiver and an artery wall, estimating a diameter of the artery, estimating a current location of the catheter tip with respect to the artery wall, monitoring a minimal distance to the artery wall, and/or any other algorithms. In some embodiments, the signal processor is configured for implementing calculations required by the methods described herein, for example calculating a Young's modulus, calculating a cooling time constant of a transceiver, calculating a cross section area according to an estimated artery diameter, and/or any other calculation or combination thereof.

In some embodiments, immediate assessment of physiological changes, for example using the methods and/or device described herein, enables real time feedback during treatment and/or measurement.

In some embodiments, any of the methods and/or device described herein may be used for assessing physiological changes, for example changes relating to characteristics of an artery wall such as stiffness of the wall, in treatments and/or diagnostic procedures other than a renal denervation procedure, for example arterial sympathetic denervation, procedures for diagnosing and/or treating aortic aneurysms, endothelial dysfunction assessment and/or treatment.

The present invention, in some embodiments thereof, relates to methods of processing echo signals, and, more particularly, but not exclusively, to methods for intravascular distance measurement using ultrasonic echoscopy.

An aspect of some embodiments of the invention relates to a method for analyzing a sequence of signals reflected from multiple locations and recorded through a single channel. In some embodiments, a single channel recording is separated based on correlative behavior between reflections or reflection portions. Optionally, the reflections or reflections portions are clustered into groups based on their correlative behavior, and each group is associated with a location.

In some embodiments, ultrasound energy is emitted, for example in multiple directions towards multiple locations. In some embodiments, energy is emitted over time towards the locations, for example in a set of pulses, and samples of ultrasonic reflections of the energy that was emitted are acquired. Optionally, the reflections are recorded in between pulses. Optionally, the reflections arrive from multiple locations. Optionally, the reflections are recorded through a single channel. In some embodiments, due to the single channel recording, reflections from multiple locations are mixed together. For example, reflections arriving from 2, 3, 4, 5, or a higher number of locations which are received by 2, 3, 4, 5, or a larger number of receivers compose the single channel recording. In some embodiments, the single channel recording is separated. In some embodiments, segments of the single channel recording are arranged in a matrix, for example by arranging segments that were recorded over time one after the other. A structure of a matrix, for example, may include a first dimension including reflections in response to the set of pulses, and a second dimension including portions of the reflections having a similar time delay from emission of a pulse. The portions having similar time delay are referred to herein as "patterns". In some embodiments, separation is performed according to patterns.

One of the assumptions on which the method may be based on is that the single channel recording, which was performed over time, includes a plurality of reflections, from which at least some portions of the reflections have arrived from a specific location (or direction). It is assumed that a reflection portion arriving from a specific location in response, for example, to a first pulse, will have a similar time delay to a second reflection portion received from that specific location in response to a second pulse, emitted, for example, 1 msec from the first pulse. These patterns will be hereinafter referred to as "equal-delay patterns". Due to the time-distance relation of ultrasound waves, where the distance is a product of the speed of the wave prorogating through the medium (e.g. blood and/or tissue) and the time, the time delay between the energy emission and reception corresponds to a certain distance, therefore the equal-delay patterns can also be referred to as equal-distance patterns. In some embodiments, separation includes determining similarity between the patterns to cluster them into groups, and associating each group with a location. Optionally, highly correlated patterns are assumed to arrive from the same location.

In some embodiments, the reflections are received in some distance from their locations. In some embodiments, the locations are periodically moving. In some embodiments, the energy is reflected simultaneously from multiple locations. Optionally, a reflection is received by a transceiver facing a direction of the reflection location. Alternatively, a reflection is received by a transceiver which does not face a direction of the location. Optionally, reflections of various locations are received by a plurality of transceivers. Optionally, a reflection is received by a transceiver which is closer to the reflection location. Alternatively, a reflection is received by one or more transceivers which are not closest to the reflection location. Optionally, reflections of various locations and/or reflections received by the plurality of transceivers overlap.

In some embodiments, the method is used for acoustic location of walls of an artery. In some embodiments, the locations are multiple artery wall locations, from which ultrasound energy is reflected. Optionally, the number of wall locations from which ultrasound is reflected corresponds to a number of directions in which the ultrasound was originally emitted. For example, a wall location faces a transceiver from which the ultrasound was emitted and/or by which the reflected energy is received. In some embodiments, propagation velocity of one or more signals through one or more mediums is used to compute a distance, for example a distance between an artery wall location and an ultrasonic transceiver. In some embodiments, the method comprises separating a returning summed echo signal reflected from the walls of the artery, and determining a distance of each of the wall locations from the one or more transceivers receiving the reflection. In some embodiments, a diameter of the artery is estimated according to at least three distances between the ultrasonic transceivers and the artery wall locations.

In some embodiments, the method comprises determining a diameter of a blood vessel, and/or estimating a change in diameter, for example during a cardiac cycle. In some embodiments, the method comprises determining a positioning of a signal emitting source such as a transceiver, with respect to the vessel's walls and/or a center of the vessel lumen. Optionally, the signal emitting source is an ultrasonic transceiver, for example configured on an intravascular catheter. In some embodiments, signals are emitted from a plurality of transceivers, for example three transceivers arranged in a triangular configuration. Optionally, the transceivers are directed such as to receive echo signals reflected from circumferentially-distributed locations along the vessel walls.

An aspect of some embodiments of the invention relates to a method for monitoring a distance to a tissue such as an artery wall. In some embodiments, the method is applied for detecting a minimal distance to the tissue, for example during a denervation treatment. In some embodiments, the method is applied for preventing thermal ablation from a distance that is too close to the tissue, which may result in damaging the tissue. In some embodiments, the method comprises emitting monitoring signals towards the tissue, and recording echo signals reflected by the tissue. Optionally, monitoring signals are emitted in between ablation signals, and the reflected echo signals are analyzed to deduce a distance between the emitting transceiver and the tissue, to assure that ablation treatment is carried out effectively.

In some embodiments, the method includes analyzing the signals by transforming between a time domain and a frequency domain. In some embodiments, an intensity of a reflected echo signal is estimated according to a spectral statistic of the signal. Optionally, the spectral statistic includes a power spectral density of the signal. In some embodiments, analyzing includes detecting an echo onset, for example being a time sample in which the signal intensity rises, for determining a distance to an artery wall.

In some embodiments, processing the signals includes band-pass filtering of noise such as a ringing artifact. The ringing artifact may be formed, for example, as a result of exciting an undamped or partially damped transceiver. In some embodiments, additional noise filters are constructed according to at least a portion of the power spectrum of signals recorded following excitation. Optionally, by applying a noise filter, the echo signal is more easily distinguished.

An aspect of some embodiments relates to a method for decomposing a signal to a base set of echo signals, and assigning the echo signals to a location (e.g. artery wall) by matching the signals to a set of probable reflections, referred to as a "dictionary". In some embodiments, a probable reflection is characterized by a distance between a transceiver and the artery wall, and/or a shape of the excitation pulse which caused the reflection, for example a characteristic width of the pulse. In some embodiments, each probable reflection is represented by a sinusoidal Gabor function. In some embodiments, the base set of signals are matched with the set of probable reflections. In some embodiments, a matching pursuit method is applied, for iteratively generating for a sparse signal and a dictionary of probable reflections a list of coefficients which comprise a solution to the sparse signal representation. As each of the probable reflections is characterized by a different distance to the artery wall, by assigning the echo signals to a probable reflection or a combination of probable reflections, a distance to an artery wall can be determined.

In some embodiments, the dictionary is defined for a selected catheter, for example comprising one or more ultrasonic transceivers. Optionally, the dictionary varies between catheters, for example due to different resonant frequencies of the transceivers(s), which may produce a different set of probable functions. In some embodiments, the dictionary is modified to better match the data. In some embodiments, modification includes reducing a size of the dictionary. Optionally, modification is performed by analyzing a current signal using, for example, a LASSO algorithm, for obtaining a minimal number of base signals. A potential advantage of using current data to adjust the dictionary includes better fitting the dictionary to the data intended for analysis, which may lead to more accurate results, for example results of the one or more estimated distances to the artery wall.

In some embodiments, a range of probable reflections is reduced, for example by repeating the method for one or more successive signals. Optionally, an amount of probable reflections is reduced to represent a limited range of distances, for example according to the distances estimated by analyzing a preceding signal. Optionally, as a result of reducing a size of the dictionary, computation time is reduced. The reduction may be based on the assumption that a successive signal differs from its preceding signal only to a certain extent, and therefore would presumably match a corresponding range of probable reflections.

The present invention, in some embodiments thereof, relates to a device and/or methods for immediate assessment of renal sympathetic denervation (RSD). Some embodiments of the invention relate to methods for immediate assessment of renal sympathetic denervation (RSD). Detection of the physiological changes in real time may provide feedback for immediate evaluation of a renal sympathetic denervation treatment. Some of the physiological changes described herein are related to a physical change to the artery wall.

Some embodiments of the invention relate to a method for measuring arterial restraint. Optionally, a change in arterial restraint of the renal artery indicates a change in the number of afferent neural signals sent to the restraining muscles, possibly affecting the stiffness of the artery, and may indicate the efficacy of the RSD treatment. In some embodiments, the method comprises estimating a diameter of the artery. In some embodiments, the method comprises a measurement of arterial blood pressure. Optionally, arterial restraint is estimated according to a calculation using both parameters.

An aspect of some embodiments of the invention relates to a method for analyzing a sequence of signals received from multiple sources and recorded through a single channel. In some embodiments, the method comprises separating the signals to locate their source, for example by clustering the signals into one or more groups according to their interference patterns. Optionally, signals of different sources comprise different interference patterns. In some embodiments, separation is based on identifying these interference patterns, for example by calculating correlation coefficients to determine similarity between the interference patterns. Optionally, signals having a similar interference pattern originate from the same source. In some embodiments, the signals are received in some distance from their sources. In some embodiments, the sources are periodically moving sources. In some embodiments, the sources are reflectors of a signal which was originally emitted from one or more other sources, such as one or more transceivers. In some embodiments, the signals are reflected continuously. In some embodiments, the signals are reflected simultaneously from multiple sources.

In some embodiments, the method is used for acoustic location of walls of an artery. In some embodiments, propagation velocity of one or more signals through one or more mediums is used to compute a distance, for example a distance between an artery wall and a transceiver. In some embodiments, the method comprises separating a returning summed echo signal reflected from the walls of the artery, and determining a distance of each of the walls.

In some embodiments, the method comprises determining a diameter of an artery. In some embodiments, the method comprises determining a relative location of a signal emitting source such as a transceiver, with respect to the location of the artery's walls and/or center. Optionally, the signal emitting source is an ultrasonic transceiver, for example configured on a catheter. In some embodiments, signals are emitted from a plurality of transceivers, for example three transceivers arranged in a triangular configuration.

An aspect of some embodiments of the invention relates to a method for measuring blood flow rate. Optionally, a change such as an increase in renal artery flow rate indicates the efficacy of the RSD treatment.

In some embodiments, the blood flow rate is measured directly, for example by measuring the flow rate of a liquid agent injected to the artery. In some embodiments, the flow of a contrast agent is traced using imaging techniques, such as x-ray angiography. Optionally, the acquired images are analyzed using a signal processing algorithm. Additionally and/or alternatively, the flow of a liquid agent is traced based on detection of temperature changes, for example by positioning at least two temperature sensors along a certain path in the artery, injecting a cold liquid agent, and determining the flow rate based on parameters such as the measured temperature, time, and/or distance between the temperature sensors.

In some embodiments, the BFR is measured indirectly, for example calculated using parameters such as the cross section area of the artery, and the blood flow velocity.

In some embodiments, the blood flow velocity is determined by analyzing an impulse response of one or more transceivers to excitations. Optionally, the transceivers are located on a catheter tip, which is inserted into an artery. In some embodiments, the analysis is based on a correlation between the blood flow velocity and the damping of the transceiver.

In some embodiments, the blood flow velocity is determined by analyzing temperature change of at least one transceiver following excitation. In some embodiments, a temperature sensor is attached in proximity to the transceiver. Optionally, the blood flow velocity is determined according to a heat dissipation rate of the transceiver.

Some embodiments of the invention relates to an ultrasonic device for endovascular use. In some embodiments, the device comprises a plurality of transceivers. In some embodiments, the transceivers are located on a catheter. In some embodiments, the transceivers are configured to emit an ultrasonic beam. Optionally, the beam is directed at one or more moving reflectors, such as the artery's walls. In some embodiments, the transceivers are configured to receive a returning echo signal from the reflectors.

In some embodiments, the device is equipped with measurement devices, such as temperature and/or pressure sensors. Optionally, data collected using the measurement devices is analyzed to assess physiological changes such a change in blood flow rate, a change in blood pressure, and/or a change in the artery diameter.

In some embodiments, the device comprises a signal processor. In some embodiments, the signal processor is configured for implementing an algorithm for separating the reflected echo signals. In some embodiments, the signal processor determines a distance between one or more reflectors and the one or more transceivers.

In some embodiments, immediate assessment of physiological changes, for example using the methods and/or device described herein, enables real time feedback during treatment and/or measurement.

In some embodiments, any of the methods and/or device described herein may be used for assessing physiological changes, for example changes relating to characteristics of an artery wall such as stiffness of the wall, in other treatments and/or diagnostic procedures.

For clarification, the term "vessel wall/s" as referred to in this application may include at least a portion of the circumferential tissue surrounding the vessel lumen, for example comprising the perivascular, intima, media and/or adventitia layers. In some cases, the term "vessel walls" may refer to a portion of the circumferential tissue which the one or more transceivers are directed at. In some embodiments, the term "vessel walls" may refer to any boundary tissue. In some embodiments, the term "vessel walls" may refer to walls of an artery. In some embodiments, the term "vessel walls" may refer to walls of a vein. In some embodiments, the term "vessel walls" refers to tissue which ends at a lumen of the vessel. In some embodiments, the term "vessel walls" refers to tissue which is treated. Optionally, the treatment is aimed at tissue which is anatomically a part of the vessel. Additionally or alternatively, the treatment is aimed at tissue which surrounds the vessel. The term "vessel walls" is meant to include one or both.

Throughout the application, it is to be understood that where the term "vessel" is used, the method and/or device and/or any other embodiment of the invention for example as described herein refer to any type of blood vessel, such as an artery or vein. It is noted that in some embodiments, treating is limited to and/or includes tissue that is outside of the anatomical boundaries of the vessel, for example nerve tissue. At least some of the methods and/or devices described herein may be used at any type of body cavity or lumen, and are not limited to blood vessels.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

An Intravascular Catheter Device

FIGS. 1A-C are a photo (FIG. 1A) and isometric drawings (FIGS. 1B and 1C) of a catheter head comprising a chassis and a plurality of transceivers, according to some embodiments of the invention.

In some embodiments, head A101 comprises one or more piezoelectric transceivers such as transceiver A103, configured for emitting and/or receiving ultrasound by comprising a body vibratable at ultrasonic frequencies. In some embodiments, the transceivers are coupled, for example mounted onto, a chassis A109.

In some embodiments, catheter head A101 is sized to fit within a blood vessel, for example the renal artery. Optionally, head A101 is sized such that it occupies less than 50%, less than 40%, less than 30% or other percentage of the cross section of the vessel, optionally reducing the obstruction of blood flow. In some embodiments, a maximal distance defined between two furthest apart points along the periphery of head A101 ranges between 1-2 mm, such as 1.1 mm, 1.5 mm, 1.9 mm. Optionally, the maximal distance is measured between outward facing surfaces of transceivers facing different directions. Optionally, the maximal distance is a diameter of chassis A109.

A Plurality of Piezoelectric Transceivers

In some embodiments, the plurality of transceivers comprise three transceivers, for example arranged in a triangular configuration. Alternatively, the head comprises a different number of transceivers, such as 4, 5, 6, 8 or intermediate, larger or smaller number. The transceivers may be arranged in various configurations, such as a squared configuration, a hexagonal configuration, an octagonal configuration, or other polygonal configurations. Optionally, the spatial arrangement of the transceivers is configured such that a periphery of head A101 is reduced to a minimum.

In some embodiments, adjacent transceivers are positioned such that a spacing A111 is formed between them. Optionally, spacing A111 provides an electrical and/or thermal isolation between the adjacent transceivers.

In some embodiments, one or more of the transceivers is adapted for emitting ultrasound. In some embodiments, one or more of the transceivers is adapted for receiving ultrasound. In some embodiments, a single transceiver is adapted for both emitting and receiving ultrasound. Optionally, a portion of the transceiver is adapted for emitting ultrasound, and another portion is adapted for receiving ultrasound.

In some embodiments, ultrasound energy irradiated by the one or more transceivers is suitable for ablating tissue, such as nerve tissue. Optionally, the ultrasound is unfocused.

In some embodiments, the one or more transceivers are adapted for receiving echo signals, such as echo signals reflected by walls of a blood vessel.

In some embodiments, the transceivers are arranged circumferentially. Optionally, the irritated energy is suitable for treating a circumferential region of tissue, such as for ablating nerve tissue surrounding a blood vessel.

Optionally, each of the transceivers faces a different direction than the other transceivers. Optionally, each of the transceivers is configured for emitting and/or receiving ultrasound from a different portion of the vessel wall. Additionally or alternatively, two or more of the transceivers face the same portion of the vessel wall. Optionally, the transceivers are arranged so that each of the transceivers covers a sector of the cross section of the vessel, such as a semicircle, a quadrant, a sextant, or a sector having other central angle such as 20 degrees, 40 degrees, 70 degrees.

In some embodiments, for example as shown in FIG. 1A, a transceiver is shaped as a rectangle. Exemplary dimensions of a rectangular transceiver include a length L ranging between 1-8 mm, and a width W ranging between 0.5-1.5 mm. Optionally, all transceivers are uniformly shaped, for example all transceivers are shaped as rectangles.

A potential advantage of uniformly shaped transceivers may include producing a symmetric effective field. Optionally, by having a symmetric field, additional safety is provided, for example in cases where an uncontrolled axial rotation of the catheter head occurs within the vessel.

Another potential advantage may include simplifying the manufacturing process.

Alternatively, in some embodiments, each of the transceivers comprises a different shape, for example one transceiver shaped as a rectangle, a second transceiver shaped as a trapezoid, etc. Additionally or alternatively, in some embodiments, all transceivers are uniformly shaped with a shape other than a rectangle, such as a trapezoid, a circle, a triangle, or any other shape.

In some embodiments, the transceivers are selected during the assembling of the catheter. Optionally, the transceivers are sorted according to characteristics such as a resonant frequency and/or impedance properties, for example as further described herein. Optionally, a catheter assembled with pre-sorted transceivers can be operated at a frequency range that is determined according to the resonant frequencies of its transceivers, thereby optionally increasing the efficiency of the catheter.

In some embodiments, the transceivers of a single catheter comprise different resonant frequencies. Optionally, the transceivers are operated independently of one another. Alternatively, two or more of the transceivers are operated together.

In some embodiments, the catheter can be used as a unidirectional catheter, a bidirectional catheter, a triple directional catheter or any multidirectional catheter. Optionally, this is obtained by selectively operating one or more transceivers at an efficiency higher than one or more other transceivers.

In some embodiments, the operating frequency is selected and/or modified so that two opposing transceivers of a catheter (for example transceivers that are furthest apart from each other on a squared shaped catheter) are operated together. The operating frequency may then be modified to sweep between the transceivers and operate a second set of transceivers. A potential advantage of alternating between the transceivers may include reducing overheating of the transceivers, which may occur when a transceiver is activated over time.

In some embodiments, the transceivers are operated (e.g. by a controller, for example comprised within a console of the catheter) according to a lookup table. Optionally, the lookup table correlates between an efficiency of each of the transceivers and a certain operating frequency. By operating the transceivers according to the lookup table, various combinations and alternations between the transceivers can be obtained.

In some embodiments, a radially outward facing surface of the one or more transceivers is flat. Additionally or alternatively, one or more transceiver surfaces are concave. Additionally or alternatively, one or more surfaces are convex.

A Chassis of a Catheter Head

In some embodiments, chassis A109 is formed as an elongated shaft, in this example having a triangular cross section profile. Alternatively, in other embodiments, the chassis may comprise a square profile, a rectangular profile, a circular profile, a hexagonal profile, or an arbitrary profile. Optionally, a cross sectional profile of the chassis corresponds with the transceiver configuration, for example, a triangular configuration of transceivers is mounted (directly or indirectly) onto a triangular chassis.

In some embodiments, chassis A109 is cannulated. Optionally, a lumen A117 (as clearly shown, for example, in FIG. 1C) within the chassis is dimensioned to receive a guide wire. Optionally, when positioned within the vessel, blood flow is allowed to pass through the lumen. In some embodiments, substances such as saline, cooling fluid, contrast liquid, medication and/or other fluids are delivered through the lumen of chassis A109. In some embodiments, a collapsed balloon is delivered through the lumen of chassis A109, and delivered through the distal tip of the catheter to be inflated within the vessel. Optionally, an inflating substance such as air or saline is passed through the lumen to fill the balloon.

In some embodiments, a radially outward facing surface of chassis A109 such as facet A115 serves as a platform onto which a PCB and/or one or more transceivers can be mounted. Various aspects relating to the mounting will be further discussed.

In some embodiments, chassis A109 is formed of an electrically conductive material. Additionally or alternatively, chassis A109 is formed of a thermally conductive material, for transferring heat away from the transceivers. Optionally, chassis A109 is coated by a thermally and/or electrically conductive material. Exemplary materials include metal such as gold or copper. Optionally, various components of the catheter such as electrical wiring are soldered onto a surface of the chassis, and may thereby reduce the need for soldering pads. Optionally, chassis A109 is rigid enough to prevent deformation of the piezoelectric transceivers that are mounted onto it.

In some embodiments, the facets of chassis A109 are evenly distributed with respect to a longitudinal axis AA' of the chassis. For example, each facet of a triangular chassis is positioned at an equal radial distance from longitudinal axis AA'. Optionally, by mounting the transceivers onto facets such as facet A115 of the chassis, the transceivers are aligned with respect to longitudinal axis AA' and/or with respect to each other. Optionally, a radial distance between each transceiver and axis AA' is equal for all peripherally arranged transceivers. Alternatively, the distance varies for different transceivers. A potential advantage of utilizing a periphery of the catheter head for mounting of components such as the transceivers may include a simpler, more reliable manufacturing and assembly process.

FIGS. 2A-C are photos of a catheter head (FIG. 2A) and various features of a catheter head (FIGS. 2B and 2C), according to some embodiments of the invention.

In some embodiments, head A201 comprises one or more piezoelectric transceivers, such as transceivers A203 and A205, configured for emitting and/or receiving ultrasound.

In some embodiments, one or more of the transceivers is electrically coupled to a circuit board, such as PCB A209 (positioned underneath transceiver A203 and optionally extending a certain distance passed transceiver A203 in the proximal direction). Optionally, a surface of PCB A209 opposite the transceiver is mounted onto a chassis A211. Additionally or alternatively, one or more of the transceivers is mounted directly onto chassis A211.

PCB Structure and Electrical Connectivity of Transceivers

In some embodiments, PCB A209 comprises a main board, and one or more extensions of the board, such as extension A219. Optionally, extensions A219 connect one or more transceivers to PCB A209. Optionally, one or more temperature sensors are coupled onto the extensions, for example as further described herein. In some embodiments, the extensions are positioned proximal to the transceivers. Additionally or alternatively, the extensions are positioned distally to the transceivers.

Optionally, extension A219 comprises a curved portion A221, for fitting closely around chassis A211. In some embodiments, curved portion A221 comprises a hinge or other element adapted for providing a rotation of extension A219 relative to the main board of PCB A209, to fold around chassis A211. A potential advantage of foldable PCB A209 may include distributing stress circumferentially around head A201. Another potential advantage of a foldable PCB may include coupling between the plurality of transceivers, while each transceiver is positioned on a different plane.

In some embodiments, a facet of chassis A211 on which PCB A209 is mounted is adapted to receive the PCB. Optionally, the facet which receives the PCB is reduced in thickness relative to the other facets, for example so that a total thickness of the facet and the PCB will be close to or similar to the other facets. Optionally, such a configuration may cause a slight offset, forming an asymmetric triangle.

In some embodiments, a proximal end of PCB A209 extends beyond the proximal end of chassis A211 in the proximal direction, for example 3 mm, 6 mm, 10 mm or intermediate, longer or shorter distances. In some embodiments, the PCB's proximal end comprises a Y-configuration (not shown in figure), through which wires or cables may be passed. Optionally, the arms of the Y-configuration are separated, for example enabling conduction of opposite charges. Optionally, the Y-configuration allows for a certain flexibility of the arms enabling them to move closer to each other, so that the arms substantially do not extend beyond the periphery defined by head A201 in the radial direction.

In some embodiments, the transceivers are electrically connected in a parallel connection. Alternatively, the transceivers are connected in a serial connection.

Alternatively, the transceivers are connected in a combination of parallel and serial connections.

In some embodiments, voltage is applied across a volume of the transceiver through electrodes. In some embodiments, PCB A209, by comprising an electrically conductive material, serves as a first electrode, and a strip A225, made of an electrically conductive material such as metal, is wrapped around the contour of head A201 while contacting the radially outward facing surfaces of the transceivers for serving as a second electrode.

In some embodiments, at least a portion of chassis A211 is electrically conductive, for example for conducting current to PCB A209.

Additionally or alternatively, wiring is passed through chassis A211, for example through one or more holes in chassis A211 (not shown in this figure), for electrically connecting the transceivers. In an embodiment, head A201 does not comprise a PCB.

In some embodiments, a cylindrical shaft portion A223 is located distally to the transceivers. Optionally, disc shaped shaft portion A223 serves as a basis onto which a distancing device, as will be further shown, is assembled. Optionally, shaft portion A223 is positioned to protect a distal end of the transceivers. In some embodiments, shaft portion A223 is formed of a heat conductive material, for example to be used as a heat sink conducting heat away from the transceivers.

Protection of Components from Environmental Conditions

In some embodiments, one or more of the components for example as described herein are coated by a material suitable for protecting against moisture, effects of blood flow, or other conditions which may exist within the blood vessel, such as parylene material, polyurethane, epoxy material.

Optionally, the coating electrically isolates the one or more components of the catheter. Optionally, the coating comprises a biocompatible material. Optionally, a thickness of the coating, such as a parylene coating, ranges between 5-20 µm, such as 10 µm, 15 µm, 17 µm. Optionally, the applied coating is thick enough so that it provides protection for the device within the vessel For example, when the catheter is used for a renal denervation treatment, a thickness of 10 µm parylene is applied so that the device components are protected by the coating during treatment of both renal arteries, for example during a time period ranging between 15-120 minutes, such as 20 minutes, 70 minutes, 110 minutes or intermediate, longer or shorter time periods. In some cases, the thickness of the protective coating decreases with time when the device is positioned within a vessel, for example due to friction forces (for example if the catheter head contacts a vessel wall), and/or due to blood flow which may wear off the coating. In some embodiments, the console is configured to detect cracking or wearing off of the coating, for example by detecting changes in the measured impedance of the one or more transceivers. Optionally, if cracking or wearing off of the coating is detected, the catheter is removed from the vessel.

Exemplary Mounting Configuration of a Transceiver

FIG. 3 shows an exemplary mounting configuration of a transceiver onto a chassis, according to some embodiments of the invention. In some embodiments, a transceiver (not shown in this figure) is coupled to chassis A303 through one or more contact nodes A305. Alternatively, the transceiver is mounted onto a solder pad (e.g. a copper pad) of a PCB.

In some embodiments, the number of contact nodes A305 used for coupling the transceiver ranges between 1-20, such as 2, 5, 8, 10, 16 or intermediate, larger or smaller number of contact nodes. Optionally, the number of contact nodes is selected to be high enough for preventing the transceiver from disengaging the chassis or PCB, yet low enough for providing the transceiver with a relatively low level of damping. Optionally, by maintaining a relatively small total contact area between the transceiver and the chassis or PCB, such as a total contact area ranging between 0.4-3 mm$^2$, such as 1 mm$^2$, 1.7 mm$^2$, or intermediate, larger or smaller areas, relatively low damping is provided. Optionally, the total surface area is determined according to a contact area of the smaller and/or largest contact node, multiplied by the number of nodes. Optionally, the total contact area is no more than 30%, such as 10%, 5%, 20% of a surface area of the transceiver, which may range between 2-6 mm$^2$, such as 2.2 mm$^2$, 4 mm$^2$, 5.5 mm$^2$ or intermediate, larger or smaller areas. By providing the transceiver with relatively low damping, the power transmission efficiency of the transceiver may increase.

In some embodiments, the contact nodes are distributed on the chassis or PCB surface onto which the transceiver is mounted. In some embodiments, the contact nodes are arranged in a symmetrically (e.g. having equal distances between them). Alternatively, the contact nodes are arranged in an asymmetrical configuration. Optionally, as shown in this example, 8 contact nodes are used for coupling the transceiver onto the chassis. In an exemplary configuration, for a transceiver having a length of 6 mm and a width of 1 mm, the contact nodes are arranged in pairs with a fixed distance A309 of about 1.8 mm longitudinally between adjacent pairs, and a transverse distance A311 of about 0.7 mm between the nodes of each pair. Alternatively, the contact nodes are arranged in a different configuration, for example aligned along a central longitudinal axis of the transceiver, positioned at one or more corners of the transceiver, positioned along an edge of the transceiver, or other configuration. Alternatively, the contact nodes are arbitrarily arranged.

In some embodiments, the contact nodes comprise glue. Optionally, the drops of glue are equally sized. Alternatively, the drops of glue are applied with different sizes. By coupling the transceiver using equally sized glue drops, the surface of the transceiver is formed may be provided with an equal level of damping. Optionally, a symmetric effective field is produced by such a configuration when ultrasound is irradiated from the surface.

In some embodiments, a glue drop comprises a volume which ranges, for example, between 0.0001-0.002 mm^3. In some embodiments, a size of a glue drop is selected to be small enough so that it does not affect the ultrasound emission efficiency. In some embodiments, a diameter of a glue drop ranges between 1 A100-250 µm, for example 170 µm, 190 µm, or intermediate, larger or smaller sizes. Optionally, a glue drop of a predetermined volume is obtained by applying the glue drop to the chassis surface with a needle, during manufacturing of the device.

Optionally, the mounting holds the transceiver a distance above a surface of the chassis, for example ranging between 5-100 µm above the chassis, such as 7 µm, 30 µm, 70 µm or intermediate, longer or shorter distances. Optionally, the volume of the glue drops spaces between the transceiver and the chassis. In some embodiments, air and/or fluid may enter the recesses formed between the transceiver and the chassis. Optionally, an air bubble is encapsulated between the transceiver and the PCB.

In some embodiments, the glue is electrically conductive, connecting between the chassis and the transceiver. In some embodiments, the glue is formed of a matrix filled with silver needles, for example conductive silver EPO-TEK®H20E and/or any glue that is electrically conductive. Optionally, the glue points are thermally conductive, and may transfer heat away from the transceiver and/or from the chassis.

In some embodiments, the contact nodes comprise wire connections, soldering, or other electrically conductive connections.

In some embodiments, chassis A303 comprises preformed recesses for receiving the glue drops. In some embodiments, chassis A303 comprises one or more markings for indicating the location of the contact nodes, for example to be used during manufacturing. It is noted that similar configurations may apply for a PCB onto which a transceiver is mounted.

Optionally, a geometry of the chassis defines an alignment of the transceivers with respect to the chassis and/or with respect to each other, for example by having facets that are shaped and/or sized according to the shape and/or size of a transceiver. A potential advantage may include reducing assembly errors, such as an overlapping between the transceivers.

Exemplary Electrical Connectivity

FIGS. 4A-C show an electrical connection provided in the form of a strip encircling the catheter head, according to some embodiments of the invention. FIG. 4A shows a catheter head A401. A strip A403, formed of an electrically conductive material, such as silver, is wrapped around the external facing surfaces of the one or more transceivers, such that it contacts a surface of each of the transceivers and interconnects the surfaces.

In some embodiments, one end A405 of the strip is connected to PCB A407, for example by soldering, and a second end of the strip, not shown in this figure, is connected to a surface of one of the transceivers. Alternatively, the strip can be connected to a cable such as a coaxial cable, for example extending from a Y-configuration of the PCB, for example as described herein.

In some embodiments, strip A403 serves as an electrode for conducting current to the transceivers, for example providing for a parallel connection of the transceivers. Optionally, strip A403 does not contact the chassis, to prevent short circuiting in embodiments in which the chassis is used as a second electrode.

Optionally, strip A403 is fitted around the contour of head A401 so that it does not exceed the periphery of the head in the radial direction. Optionally, strip A403 mechanically bonds the transceivers to the chassis, and may prevent disengagement and/or movement of the transceivers with respect to the chassis. Optionally, a close fit is obtained by one or more folds of the strip, such as fold A409. Optionally, fold A409 defines a 90 degree angle, which maintains strip A403 within the periphery of head A401. Alternatively, the fold may define a different angle such as 30, 60, 70 degree or any intermediate, larger or smaller angles.

In some embodiments, strip A403 is positioned in proximity to a proximal edge A411 of the transceivers such as transceiver A413. Optionally, this reduces or prevents the strip from interfering with the ultrasonic beam irradiated from the external surface of transceiver A413. Optionally, the strip is positioned such that interference of the strip with echo signals received by transceiver A413 is minimized.

Additionally or alternatively, in some embodiments, an electrical connection between the one or more transceivers and the PCB and/or chassis and/or between the transceivers is provided by one or more wire bondings. Additionally or alternatively, an electrical connection between the one or more transceivers and the PCB and/or chassis and/or between the transceivers is provided by a ring, such as a metal ring. A potential advantage of the strip includes providing electrical power transmission without increasing the dimensions of the catheter head.

A PCB Including One or More Vias

FIG. 5 is a photo of a PCB A501 comprising one or more vias A503, according to some embodiments of the invention. PCB A501 is shown in this figure in a flat configuration, where the foldable extensions A505 and A507 are spread out adjacent a main board A509 of the PCB.

In some embodiments, PCB A501 comprises one or more vias A503, such as 2, A5, 8, 11 (as shown in this figure), 9, 15, 20 or any intermediate, larger or smaller number of vias. In some embodiments, PCB A501 is mechanically attached to a chassis (not shown in this figure) through vias A503, for example by soldering. In some embodiments, PCB A501 is electrically connected to the chassis through vias A503. Optionally, current is conducted by a soldering material within vias A503. Optionally, the current is further conducted by an electrically conductive glue coupling, for example as described herein.

In some embodiments, vias A503 are sized and/or arranged according to a distribution of mounting nodes which couple PCB A501 to the piezoelectric transceiver. In some embodiments, vias A503 are small enough so that they do not interfere with, for example, glue points attaching the transceiver to the PCB, for example so that the vias do not 'take in' the glue. In some embodiments, vias A503 are large enough to provide sufficient current transition. Optionally, vias A503 comprise a circular profile, having a diameter A511 ranging between 10-50 µm, such as 20 µm, 35 µm, 45 µm, or intermediate, shorter or longer diameters.

An Exemplary Acoustic Field Produced by a Catheter

FIGS. 6A-B are schematic representations of an acoustic field (FIG. 6A) and a heat distribution map (FIG. 6B) obtained by using a triangular configuration of ultrasound transceivers, according to some embodiments of the invention.

In some embodiments, by arranging a plurality of equally sized transceivers on a catheter head shaped as an equilateral polygon, for example on an equilateral triangular head A605, a symmetric field of ultrasound is obtained.

In some embodiments, as shown in FIG. 6A, 3 beams A601, corresponding with, for example, 3 transceivers, each facing a different circumferential region of vessel A603 (shown here at a cross section), are produced. Optionally, the ultrasound energy is emitted from within lumen A607 of vessel A603.

In some embodiments, a divergence of beam A601, for example as indicated by angle β defined between an edge of beam A601 and an axis A619 parallel to the beam axis (h), ranges between 5-30 degrees, for example, 5°, 15°, 20° or intermediate, larger or smaller angles. For example, when ultrasound is applied at a frequency of 11 MHz, from a transceiver having a width (a) of 1 mm, angle β (on both right and left edges of the beam) will be approximately 7.5 degrees. In another example, for a similar frequency of 11 MHz, and a width (a) of 0.7 mm, angle β will be 15 degrees.

Optionally, absorption of the ultrasound energy of beam A601 in the tissue varies between portions of the beam. Optionally, a depth of the beam, measured along axis (h), depends on the frequency. Optionally, depth (h) ranges between 1-15 mm.

In some embodiments, a beam A601 comprises a trapezoidal shape. Optionally, one base of the trapezoidal beam, marked (a), is configured along a triangular facet of head A605, where a transceiver is mounted.

Alternatively, beam A601 may be otherwise shaped and/or sized, for example having a rectangular profile, a circular profile, a triangular profile, an elliptical profile, or other shapes. Optionally, the shape and/or size of the beam are determined by the shape and/or size and/or resonant frequency and/or impedance properties of the ultrasonic transceiver, and/or by a spatial arrangement thereof.

In some embodiments, beam A601 is affective to thermally damage, (i.e. ablate) tissue, for example nerve tissue, without causing apparent damage to intima A609, for example to the endothelium or the elastic lamina. Optionally, the irradiated energy thermally damages tissue such as nerve tissue in the adventitia.

In some embodiments, as shown for example in FIG. 6B, a stronger thermal effect A615 is obtained at a tissue region configured a radial distance from head A605, for example a distance (d) from the emitting transceiver. Optionally, distance (d) ranges between 2-15 mm. In some embodiments, tissue is heated to a temperature ranging between 50-80 degrees Celsius, such as 50.5, 55, A60, A65, 70 degrees Celsius or intermediate, higher or lower temperatures. Optionally, nerve damage is caused at a temperature above 47 degrees Celsius, 49 degrees Celsius, 50 degrees Celsius, 53 degrees Celsius, 55 degrees Celsius, A60 degrees Celsius, or intermediate temperatures. In some embodiments, a clinical effect on the treated tissue is a result of the temperature to which the tissue is heated.

For example, in some embodiments, a high temperature range may cause damage sufficient to prevent a nerve from reconnecting or regenerating. Additionally or alternatively, a high temperature range may cause damage sufficient to prevent or reduce the nerve ability to produce norepinephrine or other neurotransmitters.

In some embodiments, thermal damage is caused to tissue of the adventitia A613 and/or media A611 layers of the vessel. Additionally or alternatively, thermal damage is caused to soft tissue located externally to the periphery of the vessel, perivascular tissue A617. In some embodiments, blood flowing within lumen A607, for example along the walls of intima A609 cools down the tissue. Additionally or alternatively, blood flowing along a surface of the transceiver cools down the transceiver. In some embodiments, unfocused energy is irradiated. Optionally, the unfocused energy is irradiated at an intensity ranging between 10-70 W/cm^2. Optionally, damage to the inner wall of the vessel which may be caused by the emitted ultrasound is minimized, for example by blood flow of flow of other fluid such as saline along the inner wall, which cools the wall.

In some embodiments, a thermal effect of beam A601 is stronger in radially outward layers of the vessel wall, for example relative to inner layers of the wall. Such an effect is assumed to be obtained, possibly among other reasons, due to cooling of inner layers of the vessel wall by blood flowing within the vessel, which carries heat away from the wall.

In some embodiments, the emitted energy is characterized by a frequency ranging between 8 MHz-25 MHz, an intensity ranging between 1 A10-70 W/cm^2, and an emission duration ranging between 5 seconds to 5 minutes, optionally intermittently.

In some embodiments, the shape and/or size of the beams, and/or the number of beams, vary according to the transceiver configuration.

When selecting a configuration and/or number of a plurality of transceivers, a trade off may exist between fitting the transceivers within a circumscribing shape of the head, so that they do not extend beyond the periphery of the head, while on the other hand, obtaining the largest effective field may be desirable.

A potential advantage of a triangular configuration of 3 transceivers includes fitting the transceivers within a circumscribing circle of the triangular head, for example having a diameter equal to or smaller than 2 mm, 3 mm, 4 mm, or intermediate, larger or smaller diameters, while obtaining a relatively larger acoustic field. For example, when comparing a triangular configuration of 3 transceivers to a square configuration of 4 transceivers: a total length of bases (a) of 3 rectangular transceivers each having a width of 1 mm, is, for example 3 mm, while a total length of bases of 4 rectangular transceivers, each having a width of 0.7 (such as to fit within the same circumscribing circle as the triangular head), is 2.8 mm, thereby providing, in total, a beam of smaller size.

Optionally, if a plurality of transceivers such as 5, 6, 8 transceivers are narrowed in width such as to fit circumferentially adjacent each other without extending beyond a periphery of the catheter head, the beams produced by this arrangement would widely spread, and the intensity of a beam, referred to herein as the ultrasonic energy per unit area, may be lower than, for example, an intensity of a beam produced by a transceiver of larger width, for example as used in a triangular configuration of transceivers.

Optionally, the number and/or arrangement of transceivers is selected such as to occupy the largest area from which energy can be irradiated, for example within a notional circumscribing circle of the catheter.

In some embodiments, beams A601 spread over one or more sectors of the cross sectional area of the vessel, for example covering 60%, 70%, 90%, 40%, 30%, 50% or intermediate, larger, or smaller portions of the cross sectional area.

In some embodiments, an angle α between adjacent beams A601, for example between a central longitudinal axis of the beam (along height h) is 120 degrees.

Alternatively, for example if head A605 is not formed as an equilateral triangle, angle α may range between, for example, 115-130 degrees. Such as 117 degrees, 125 degrees, A129 degrees or intermediate, larger or smaller angles.

Optionally, an angular distribution of the beams affects the extent of thermal damage, for example, a larger angle (α) between beams is associated with narrower beams that may affect an area further away from the catheter head in the radial direction, as compared to beams having a relatively small angle (α) between them.

FIGS. 7A-B are measurements of an acoustic field irradiated by a single ultrasonic transceiver, according to some embodiments of the invention. The measurements were obtained by a hydrophone scanning system having a resolution of 0.1 mm, to plot the intensity of the field. An ultrasonic transceiver was positioned within a tank filled with distilled water. In FIG. 7A, a rectangular piezoelectric transceiver having a length of 3 mm, a width of 0.7 mm was tested. In FIG. 7B, a rectangular piezoelectric transceiver having length of 6 mm, a width of 1 mm and a similar thickness was tested. Both transceivers were activated at their resonance frequency, in this example 11 MHz. Alternatively, other frequencies are used to create different sizes and/or shapes of acoustic fields. The measuring distance was 8 mm from a surface of the transceiver.

As can be observed from the measurements, in FIG. 7A an acoustic field comprising two regions A701 of relatively high intensity, such as higher than 95% of the maximal intensity, for example ranging between 20 W/cm^2 to 80 W/cm^2. (indicated by the red color) were obtained. In FIG. 7B, where a transceiver having larger dimensions was tested, the regions of relatively high intensity A701 were observed with a larger distance (d2), measured along the Y-axis, between the regions, as compared to distance (d1) of FIG. 7A. This observation suggests that the length of the piezoelectric transceiver may determine the location of high intensity regions, and the acoustic field spread in general. It is assumed by the inventors of this invention that activation of a plurality of transceivers, such as three transceivers in a triangular configuration, produces an acoustic field having similar characteristics (e.g. dimensions, intensity, or other) to an acoustic field obtained by combining the fields produced by three independently and separately operated transceivers. The inventors have shown that an intensity range and/or a shape and/or size of the effective field can be predetermined based on the number, shape, size, spatial arrangement, resonance and/or impedance characteristics of the transceivers.

A Square Configuration of Transceivers

FIG. 8 is an isometric view of a catheter head A801 comprising a square configuration of transceivers A803, mounted onto a square shaped chassis A805, according to some embodiments of the invention.

FIGS. 9A-B are schematic representations of an acoustic field (FIG. 9A) and a heat distribution map (FIG. 9B) obtained by using a square configuration of ultrasound transceivers, according to some embodiments of the invention. In some embodiments, 4 rectangular transceivers form 4 trapezoidal beams A901, spatially arranged at a cross configuration having a 90 degree angle between them. Alternatively, for example if head A903 is formed in a quadrilateral configuration other than a square, such as a rhomboid, trapezoid, rectangle or other quadrilateral configuration, an angle between adjacent beams may range between 80-115 degrees, such as 85 degrees, 90 degrees, 110 degrees or intermediate, larger or smaller angles.

An Exemplary Catheter Shaft

FIG. 10 is a schematic cross section of a shaft A1001 of an intravascular catheter, according to some embodiments of the invention. In some embodiments, portions of shaft A1001 are formed with a varying rigidity. For example, a proximal portion A1003 is rigid relative to, for example, a distal portion A1005 of the catheter, such as to transmit maneuvering forces. In some embodiments, a length of a rigid portion A1003 ranges between, for example, 500-800 mm, such as 550, 700, 770 mm, and a length of the flexible portion A1005 ranges between, for example, 60-100 mm, such as 70 mm, 85 mm, 90 mm. In some embodiments, portion A1005 is flexible enough for being pushed away from the vessel wall by a distancing device, as referred to hereinbelow. In some embodiments, materials comprising a flexural rigidity value ranging between, for example, 30-70 D such as 40 D, 63 D, or intermediate, larger or smaller flexural rigidity values are used. For example, polyamide, polyurethane, pebax.

In some embodiments, shaft A1001 is formed as a cylinder. Optionally, shaft A1001 is sized to fit within common delivery systems, for example within an 8 F guiding catheter, a 6 F guiding sheath or others, to be delivered to an anatomical location. Optionally, shaft A1001 is sized as a 3 F catheter, 4 F catheter, a 6 F catheter, or intermediate, larger or smaller sizes. In some embodiments, a diameter of shaft A1001 is selected to leave at least some radial distance between the shaft A1001 and the guiding sheath or catheter, for example to enable injection of substances into the vessel through the guiding sheath, such as contrast liquid, saline, a cooling fluid.

In some embodiments, shaft A1001 comprises one or more lumens A1007. Optionally, lumen A1007 is sized to receive a guide wire, for insertion of the catheter over a guide wire. In some embodiments, a diameter of guide wire lumen A1007 ranges between 0.01-0.1 inch, for example, 0.014 inch, 0.05 inch, 0.08 inch, or intermediate, larger or smaller diameters. Optionally, the guide wire extends through the lumen from a proximal end to a distal end of the catheter. Alternatively, the guide wire extends through a portion of the lumen, for example extending 7 cm, 12.5 cm, 20 cm or intermediate, larger or smaller distances from a distal end of the catheter. The catheter may include a "rapid exchange" mechanism for facilitating insertion, removal or replacement of a guide wire.

In some embodiments, shaft A1001 is formed as a telescopic cylinder, which can be inserted into the vessel in a compact, retracted configuration, and then extended to travel a longer distance within the vessel. Optionally, the telescopic mechanism is manipulated externally to the body, for example by a control in the catheter handle.

In an exemplary embodiment of the invention, an ultrasonic catheter for example as described herein is inserted into a location of the renal artery ostium, such as to ablate renal nerves, using the following procedure: a guide wire is inserted through the femoral artery. An introducing sheath is then threaded over the wire, and the ultrasonic catheter is passed through the sheath to be delivered to the renal artery location.

In some embodiments, a distance of the catheter shaft, for example measured between a distal end of the handle (externally to the body) and a proximal end of a transceiver ranges between 600-900 mm, such as 645 mm, 847 mm, 750 mm, or intermediate, larger or smaller lengths.

An Exemplary Catheter Handle

FIG. 11 shows an exemplary configuration of a handle of a catheter, according to some embodiments of the invention. In some embodiments, handle A1101, comprises a lever and/or pulley assembly. In some embodiments, the lever and/or pulley assembly is configured for remotely advancing and/or retracing the catheter shaft, or portions of it, in the proximal and/or distal directions. In some embodiments, the lever and/or pulley assembly is configured for remotely expanding and/or collapsing a distancing device capable of pushing the catheter head away from the vessel wall, as will be further described. For example, a user may expand the distancing device by advancing lever A1105, which protrudes externally from handle A1101, in the distal direction, or vice versa. Optionally, one or more cables connect components of handle A1101 such as lever A1105 to distal components of the catheter, such as to a distal tip of the catheter head which is retractable, and optionally causes expansion of a distancing device.

In some embodiments, handle A1101 comprises a luer A1107, protruding externally from a proximal end of the handle. In some embodiments, luer A1107 is cannulated. Optionally, a lumen of luer A1107 leads to a guide wire lumen A1109, which extends longitudinally within the handle in the distal direction, continues throughout the catheter shaft.

In some embodiments, handle A1101 is suitable for gripping by a user, such as a physician.

A Catheter Comprising One or More Temperature Sensors

FIG. 12 is a drawing of a catheter head portion comprising one or more temperature sensors, according to some embodiments of the invention. In some embodiments, temperature sensor A1201 is positioned adjacent a transceiver A1203. Optionally, the sensor is connected to PCB A1205, for example mounted (e.g. soldered) onto one of the PCB's extensions. Alternatively, the sensor is mounted onto chassis A1211. Optionally, the sensor is electrically connected through wiring, for example using jump wires. In some embodiments, the sensor is positioned, for example, 0.1 mm, 0.5 mm, 2 mm, 3 mm or intermediate, larger or smaller distances from transceiver. Optionally, by being positioned adjacent transceiver A1203, a temperature of the transceiver (such as a surface temperature of the transceiver) can be estimated according to temperatures measured by sensor A1201. Optionally, according to temperatures estimated using the data from sensors (e.g. resistance values), overheating of the transceiver (e.g. of a surface of the transceiver) is detected. Optionally, overheating of the transceiver is determined according to a change in its electrical properties, for example detected by the console.

In some embodiments, a temperature of blood within the vessel is estimated according to temperatures measured by sensor A1201. Optionally, a temperature of blood that flows over a surface of the transceiver is estimated. Optionally, according to temperatures estimated using the data from sensors (e.g. resistance values), overheating of the blood is detected, for example if blood is heated to a temperature above 43 degrees, 45 degrees, 48 degrees, 50 degrees or intermediate, higher or lower temperatures. A relatively high blood temperature may be measured during periods of excitation of the one or more transceivers. Optionally, the blood temperature is monitored to prevent damage to tissue, such as the endothelium. Optionally, excitation is modified or ceased according to the measured temperature.

In some embodiments, the number of sensors is determined according to the number of transceivers and/or the shape of the catheter head. For example, a catheter head with a triangular configuration of transceivers may include three sensors. Optionally, each sensor A1201 is positioned distally to a transceiver, for example at a distance D between approximately the center of the sensor and the distal edge of the rectangular transceiver A1203. Optionally, distance D ranges between 0.1-1.5 mm, such as 0.5 mm, 1 mm, 1.3 mm or intermediate, longer or shorter distances. Alternatively, sensor A1201 is positioned proximally to transceiver A1203. Additionally or alternatively, sensor A1201 is positioned in a different location on the catheter head, for example on any portion of tip A1209, on a proximal end of chassis A1211, or other locations.

In some embodiments, sensor A1201 includes an NTC or PTC thermistor. Other examples include a thermocouple, a fiber optic temperature sensor and a temperature sensing diode.

In some embodiments, the temperature sensors are connected in a parallel connection. Alternatively, the temperature sensors are connected in a serial connection. A potential advantage of parallel connected sensors may include reducing the number of wiring connections, for example, in a catheter head comprising 3 sensors, only 2 wires are needed to connect between 3 temperature sensors located at three different measurement locations.

In some embodiments, the catheter head comprises other measurement devices, for example a flow detector, a pressure detector.

An Intravascular Distancing Device of a Catheter

FIGS. 13A-B are photos a distancing device A1301 of a catheter in a closed configuration (FIG. 13A) and an expanded configuration (FIG. 13B), according to some embodiments of the invention. In some embodiments, distancing device A1301 is configured for pushing catheter head A1303 away from the vessel wall A1305. In some embodiments, one or more of the transceivers A1309 configured for emitting ultrasound is pushed away from the wall. In some embodiments, distancing device A1301 is configured for centering head A1303 with respect to the vessel wall.

In some embodiments, when device A1301 is in the closed configuration, a total diameter of the catheter head A1303 with distancing device threaded onto the head is small enough to provide for insertion and/or removal and/or positioning of the catheter within the vessel. For example, the total diameter ranges between 1.5-2.2 mm, such as 1.7 mm, 2 mm, 2.1 mm or intermediate, longer or shorter diameters. In some embodiments, a total diameter of head A1303 is small enough to fit within a guiding catheter or sheath.

In some embodiments, distancing device A1301 is formed in the shape of a slotted cylinder. Optionally, cylinder portions A1307 in between the slots form bendable leaflets. Optionally, in an expanded configuration, as shown for example in FIG. 13B, the leaflets are forced into a rounded 'elbow' shaped configuration, pushing the one or more transceivers A1309 away from wall A1305. Optionally, the transceiver is pushed at least 1 mm, at least 0.5 mm, at least 2 mm or intermediate, large or smaller distances away from the vessel wall.

In some embodiments, leaflets A1307 are positioned such that in the open position, they do not interfere with the field of emitted ultrasound, and in the closed position, the leaflets conform into recesses between the transceivers for maintaining a minimal diameter of the catheter.

In some embodiments, in the closed configuration, leaflets A1307 cover at least a portion of the transceiver surface and protect it. In some embodiments, a width of a leaflet is small enough to reduce an unwanted thermal effect on the vessel wall. Additionally or alternatively, a width of a leaflet A1307 is determined such as to prevent mechanically induced damage such as scratches to the vessel wall tissue.

In some embodiments, even when distancing device A1301 is expanded, blood is allowed to flow between the vessel wall and the one or more transceivers 1309. For example, blood may flow through aperture A1311 formed by bending leaflet A1307 to the elbow configuration. Optionally, the blood cools down the vessel wall.

In some embodiments, distancing device A1301 is expanded in multiple stages, for example 2, 3, 4, 5 stages. In an exemplary embodiments, distancing device A1301 is first bended such that an angle α ranging between 110-175 is formed by leaflet A1307, and in the second stage angle α is reduced to, for example, 90-110 degrees.

In some embodiments, distancing device A1301 is transferred into an open configuration by retracting distal tip A1313 of catheter head A1303 in the proximal direction. Optionally, retraction is performed by pulling an internal shaft of the catheter which is connected to tip A1313, such as a guide wire shaft, in the proximal direction. Optionally, retraction is performed by pulling on an inner cable coupled to tip A1313. Optionally, the guide wire shaft and/or the cable are coupled on one end to tip A1313, and on an opposite end to a handle configured externally to the body. Optionally, the handle comprises a lever for operating the distancing device, for example by remotely pulling on tip A1313 in the proximal direction. Optionally, a diameter of the proximal end of tip portion A1313 is equal to a diameter of the cylinder of distancing device A1301, and by retraction of tip A1313 force is applied on the cylinder of distancing device A1301 in the proximal direction, causing leaflets A1307 to bend.

In some embodiments, distancing device A1301 comprises a combination of rigid and soft materials, for example layered on top of each other. Optionally, by using a rigid material, the distance between catheter head A1303 and wall A1305 is maintained. Optionally, by using a soft material, damage to the tissue of wall A1305 is reduced or prevented. In some embodiments, distancing device A1301 comprises a soft plastic material embedded with fibers such as Nitinol fibers.

An Exemplary Distal Tip Configuration

In some embodiments, distal tip A1313 is suitable for absorbing mechanical shocks, for example for reducing the risk of deformation of the catheter head, for example during insertion to the body. Optionally, distal tip A1313 comprises a soft, flexible material for providing shock absorbance, for example pebax.

Optionally, distal tip A1313 is positioned to protect a cylindrical shaft portion such as portion 223 shown in FIGS. 2A-C. In some embodiments, a geometry of tip A1313, for example a conical profile of the tip, is selected to encourage blood to flow alongside the catheter and/or between the leaflets of the distancing device, as opposed to flowing, for example, internally towards a distal portion of the catheter.

In some embodiments, tip A1313 comprises radiopaque material, such as Barium Sulfate for being detected under imaging, for example under fluoroscopy. Additionally or alternatively, other catheter portions comprise radiopaque markings, for example a proximal end of a PCB onto which a transceiver is mounted may comprise markings for indicating a proximal end of the catheter head. In another example, a radiopaque marking for example in the form of a ring is positioned between tip A1313 and the catheter shaft. In another example, radiopaque markings are positioned on the distancing device, for example on a point of bending of a leaflet and/or on a distal end of the distancing device's cylinder.

In some embodiments, distal tip A1313 is shaped as a cone, a tapered tip, a square shaped tip, or a disc.

A System for Operating an Intravascular Catheter

FIG. 14 is a diagram of an intravascular catheter system, according to some embodiments of the invention. In some embodiments, system A1401 comprises a console A1403 in communication with a computer A1405 and with the intravascular catheter A1407.

In some embodiments, console A1403 comprises various modules for controlling the operation of catheter A1407 such as control of energy settings (e.g. power, intensity, frequency and/or duration), location settings, calibration settings, distance monitoring settings, time settings, settings of measuring devices such as a temperature sensor, or others. In some embodiments, catheter A1407 is connected to console A1403 by an electrical connection, for example through a cable and/or connector. In some embodiments, the console is configured to detect whether the catheter is connected or not. Optionally, the console is configured to detect whether the catheter has been inserted into the body, for example based on temperature indication, provided for example by one or more temperature sensors on the catheter.

In some embodiments, console A1403 is connected, for example by a cable, by a wireless connection, by a USB connection, by a LAN connection to computer A1405.

In some embodiments, a designated software for operating the system is installed onto computer A1405, for example a MATLAB based TIVUS™ software. In some embodiments, the software is configured for implementing signal processing algorithms. Various examples of algorithms include an algorithm for monitoring a distance between the vessel wall and the one or more transceivers, an algorithm for determining flow parameters such as the flow rate, velocity, and pressure, an algorithm for determining a vessel diameter and/or a respective location of the catheter head with respect to the vessel walls, an algorithm for assessing a temperature of the treated tissue, or others. In some embodiments, the analysis is based on data acquired by the transceivers, such as by echo signals reflected from the vessel walls and received by the transceivers. In some embodiments, the analysis is based on data acquired by one or measurement devices of the catheter, for example a temperature sensor, a flow sensor, or other measuring devices. In some embodiments the analysis is based on a combination of the reflected signals and data acquired by the measurement devices. In some embodiments, feedback such as denervation effectiveness feedback is provided based on the analysis of the signals. Optionally, the feedback is automatically provided to a user.

In some embodiments, console A1403 is configured for acquiring and/or saving parameters of the catheter being used, such as an operating frequency range, an impedance, or other data. Optionally, the catheter package and/or handle of the catheter are labeled with a barcode that can be read, for example scanned, by the console. Optionally, the data was obtained during manufacturing of the catheter.

In some embodiments, the console is configured for performing an impedance scan of the transceivers of the catheter being used. Optionally, scanning is performed by immersing the catheter in liquid, such as saline. In some embodiments, scanning is performed when the catheter is positioned within the vessel, where blood and/or an injected substance such as saline serve as the immersing liquid. Optionally, the results are displayed to the user as an impedance vs. frequency graph. In some embodiments, the scanning results are compared to the impedance data acquired at the end of the manufacturing process, for example to confirm that the values have not changed, or have changed within a permitted range, for example no more than ±5%, ±2%, ±10% different than the impedance measured during manufacturing. Optionally, if the scanning results exceed the permitted range, the catheter is disqualified from use.

In some embodiments, console A1403 comprises, among other components, a microcontroller (used for example for activation), a signal generator (for exciting the transceivers), a gain controller, an EEPROM reader (which for example receives the characterizing data of the transceivers). Optionally, various components of the console are programmable.

In some embodiments, a foot pedal A1409 is connected to console A1403 and/or to computer A1405. Optionally, a user such as a physician steps on the pedal for activating and/or de-activating excitation of the transceivers.

In an exemplary embodiment, console A1403 is configured for providing the following settings of operation: a sinusoidal excitation waveform, an excitation frequency ranging between 5-20 MHz, 8 MHz-12 MHz, 7-14 MHz, such as 8.5 MHz, 10 MHz, 11 MHz, 11.5 MHz, or intermediate, larger or smaller frequencies, and an excitation power smaller than 15 W, such as 2 W, 8 W, 13 W or intermediate, larger or smaller.

Alternatively, the excitation wave can be provided as a square waveform, a triangle waveform, a sawtooth waveform. Alternatively, the excitation frequency can be provided at a lower range, for example ranging between 3-7 MHz, or at a higher range, for example ranging between 13-16 MHz. Alternatively, a higher excitation power is provided, such as 16 W, 17 W, or higher. Optionally, the excitation is provided in a burst mode, for example with a pulse repetition frequency of 10-70%.

In some embodiments, console A1403 is configured for receiving temperature data, for example resistance values of the temperature sensors. Optionally, the temperature reading range of the console ranges between 5-100 degrees Celsius. Optionally, data acquired by the temperature sensors and/or other measurement devices, such as a flow detector, is analyzed and processed by the software.

FIGS. 15A-G are exemplary print screens of a user interface of the catheter system, according to some embodiments of the invention.

In some embodiments, a software program is installed on a computer, the computer connected to a console. Optionally, the software is a MATLAB based software.

In some embodiments, the user interface includes various indications such as one or more of:
  An indication of temperature, such as of the blood flowing in the vessel, the transceiver surface, the chassis or other components. Optionally, the temperature indication is estimated according to measurements obtained by the temperature sensors.
  An indication of the treatment duration, an indication of a duration of pulses and of time intervals between pulses (in cases in which treatment is provided in pulses), an indication of time left until the end of the excitation, or other time and duration indications.
  An indication of a distance between the one or more transceivers and the vessel wall, estimated, for example, by analyzing echo signals reflected by the vessel walls following sensing (i.e. monitoring) excitations of the transceiver(s). Optionally, a color coded window changes according to changes in the distance.
  Results of an impedance scan of the transceivers.
  A relation between parameters, for example, a rate of blood temperature change as a function of gain, or other parameters thereof.
  An indication of the operation mode, for example an indication of excitation of the one or more transceivers.
  An indication of system functioning and performance problems.

In some embodiments, various treatment parameters such as one or more of: the excitation power, intensity and/or frequency, the treatment duration, the size of catheter head used, the expansion and reduction of a distancing device, the estimated level of thermal damage are selected according to patient data, such as age, weight, height, medical condition or others. Optionally, the parameters are automatically selected by the program, for example according to a calibration table. In one example, a setting may include treatment of a vessel in which a stent is positioned.

Figure 15A:
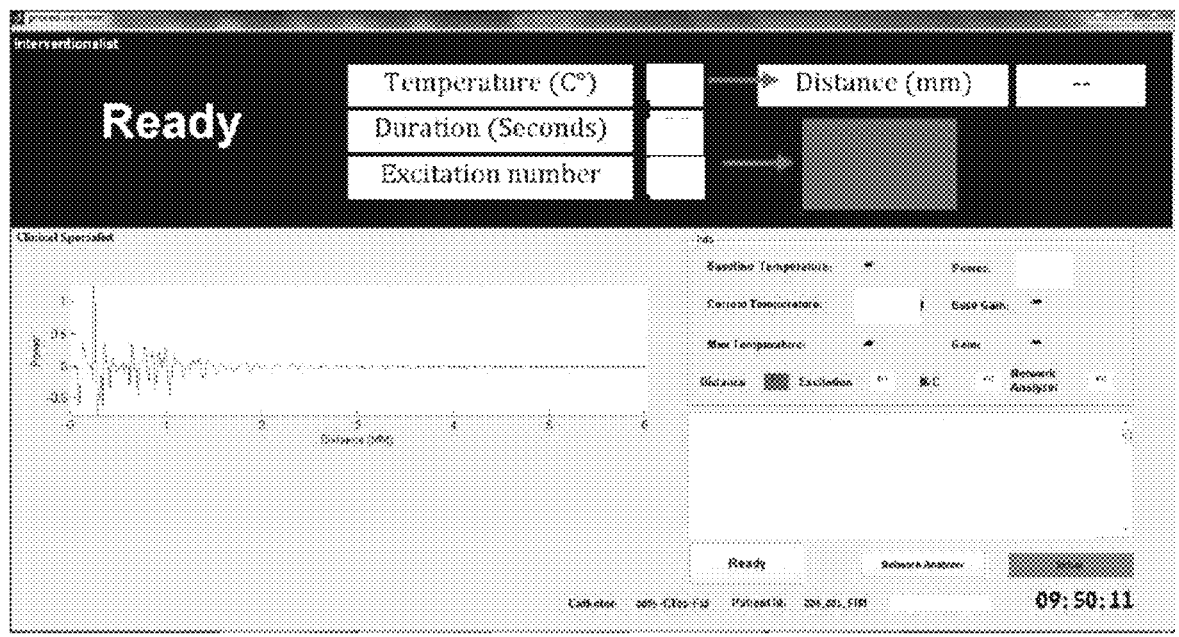
Figure 15B:
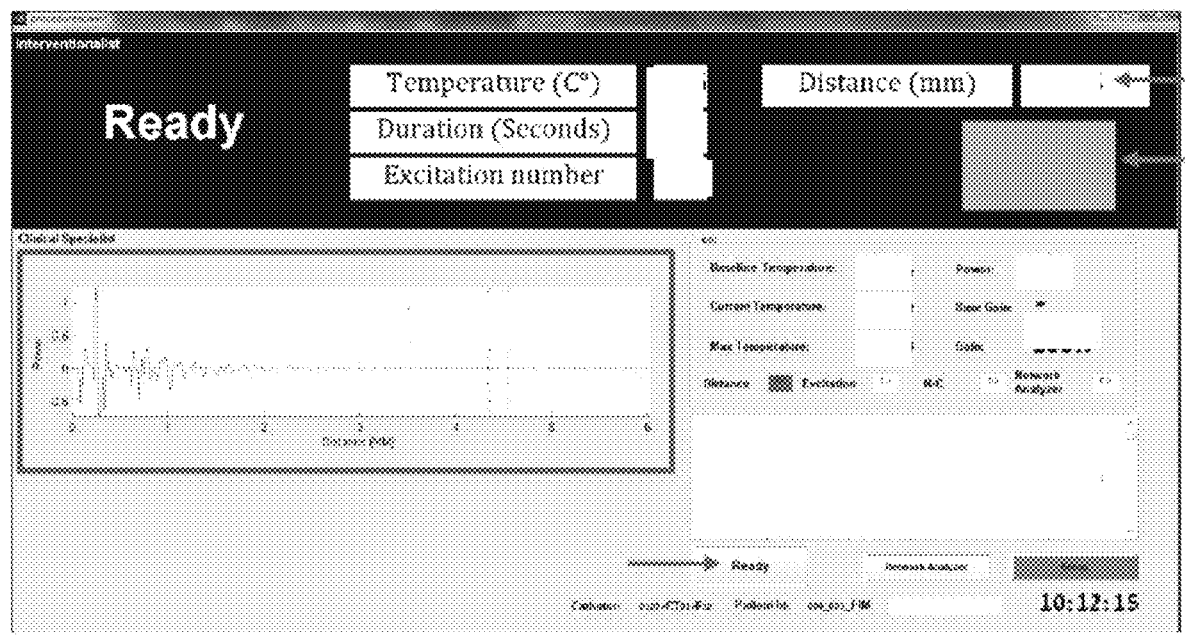
Figures 15C, 15D:
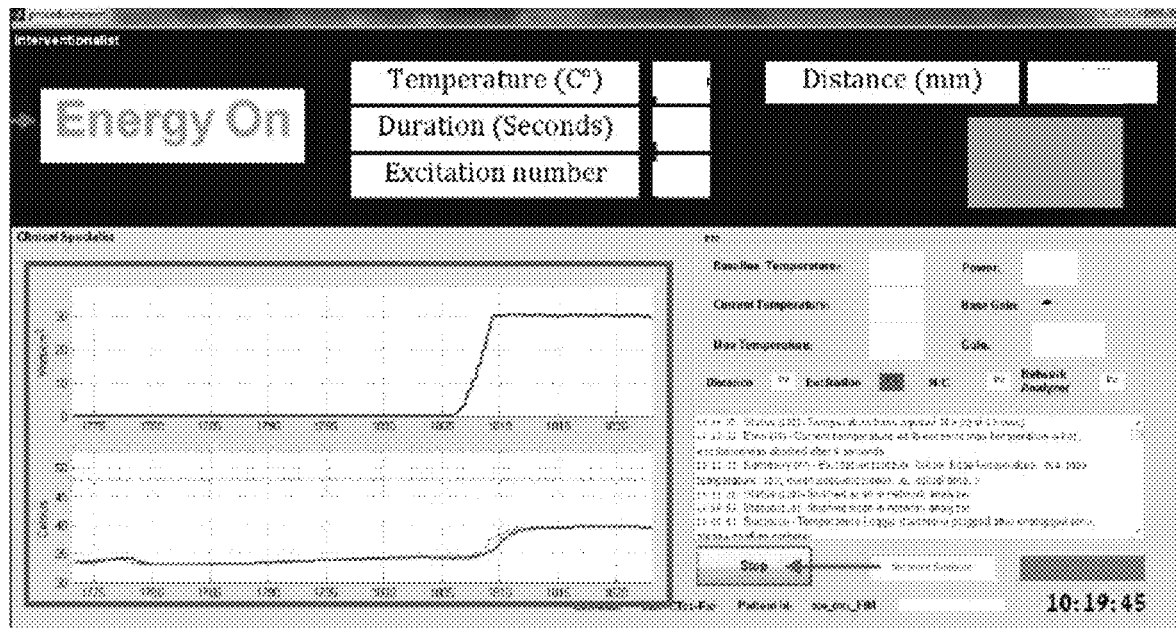
Figure 15E:
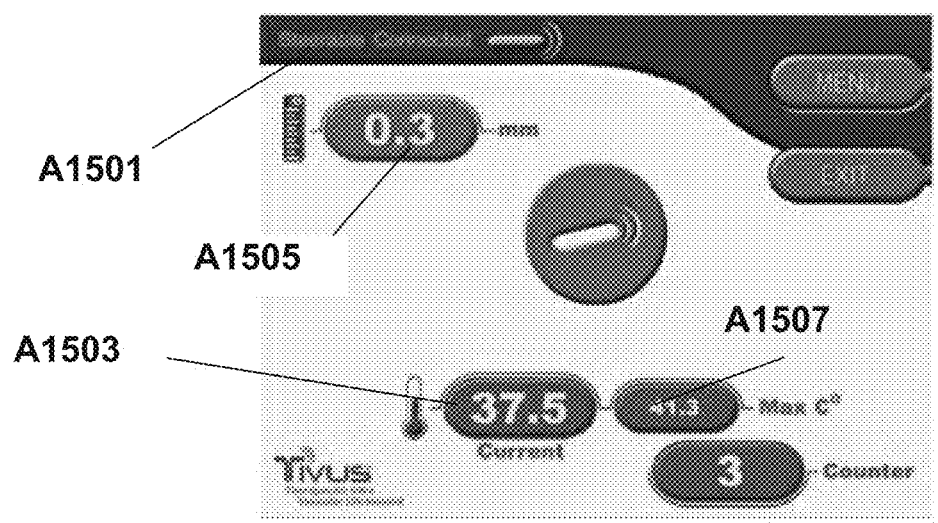
Figure 15F:
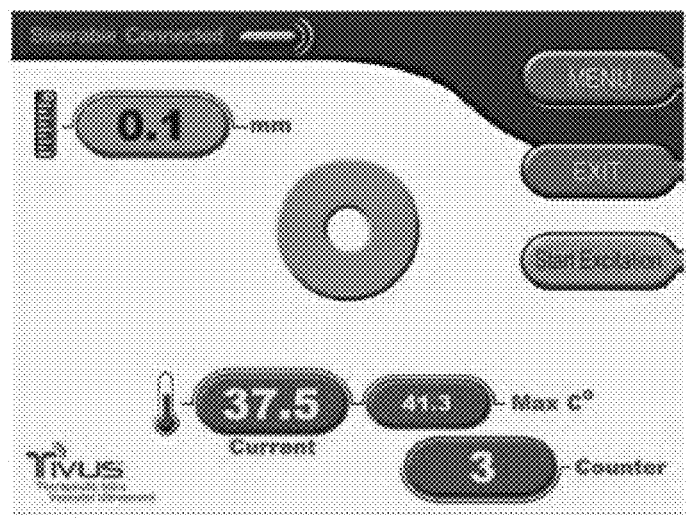
Figure 15G:
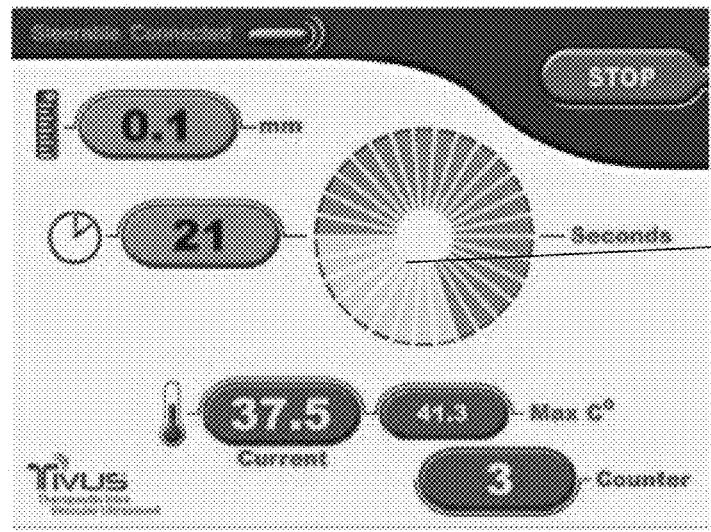

In some embodiments, the system comprises a user interface. Optionally, the user interface is configured for receiving input such as operational parameters from a user, such as a physician. Additionally or alternatively, the user interface is configured for displaying data to a user. FIGS. 15E-G are print screens of the user interface showing indications such as one or more of:
  An indication that the catheter is connected A1501.
  An indication of the current temperature A1503, measured for example by a temperature sensor configured on the catheter device. Optionally, the controller deduces from the measured temperature a current location of the catheter, for example, if the temperature is higher than a threshold (for example higher than 36 degrees) the controller deduces that the catheter has been inserted to the vessel.
  A maximal temperature indication A1507. The maximal temperature may increase during excitation periods.
  An indication of a distance A1505 of the catheter head from the vessel wall, for example a minimal distance between a transceiver and the wall. Optionally, there is a visual change on the screen when the distance changes from a distance that is too close or too far from the vessel wall to a distance that is suitable for irradiating. The visual change may include, for example, a color changing button. Optionally, when the distance is not within the range suitable for irradiating, activation of excitation is disabled. For example, a foot pedal cannot be activated when the distance from the vessel wall in not within the irradiation range.
  A countdown clock A1509 indicating a time period (e.g. 21 seconds, 50 seconds, 10 seconds or intermediate, longer or shorter time periods) that has passed from initiating an excitation of the one or more transceivers, and/or a time period remaining until the end of excitation.

A Method for Controlling a Catheter Comprising a Plurality of Ultrasonic Transceivers FIG. 16 is a flowchart of a method for controlling a catheter comprising a plurality of ultrasonic transceivers, according to some embodiments of the invention. In some embodiments, providing a catheter with a plurality of ultrasonic transceivers (A1601) for example as described herein, the method includes exciting the transceivers at a frequency that is in the range of ±10%, ±5%, ±15%, from a detected (e.g. by scanning) resonant frequency of the multi-transceiver (A1603) assembly. In some embodiments, the transceivers are excited at frequency that is in the range of ±10%, ±5%, ±15%, ±25% from an average of the individual resonant frequencies of the transceivers.

In some embodiments, the operating frequency is different from a resonant frequency of any of the plurality of transceivers.

In some embodiments, the operating frequency is selected according to an anti-resonance frequency of the individual transceivers or an average thereof.

In some embodiments, the transceivers arranged on a head of a single catheter are characterized by resonant frequencies and/or impedance properties that are similar or close to one another, for example no more than 10%, 20%, 30% different (i.e. having higher or lower values) from one another. In some embodiments, an operating frequency range of the catheter is selected according to an average of the resonant frequencies and/or impedance values of the transceivers. A potential advantage of selecting an operating frequency range according to averaged properties of the plurality of transceivers may include increasing the efficiency. Optionally, the amount of unwanted heat which is a byproduct of the energy emission is reduced.

In some embodiments, operating comprises exciting all transceivers as a single unit with a similar frequency. Optionally, the frequency is similar to the resonant frequency of the one or more transceivers. Energy can be selectively irradiated towards one or more portions of the vessel by selecting an operating frequency which matches a resonant frequency of one or more individual transceivers, and may not match a resonant frequency of other one or more transceivers.

In some embodiments, a transceiver is excited by a frequency different than the other transceiver(s). In some embodiments, a transceiver is excited independently of the other transceivers. For example, only one transceiver can be excited, such as to treat and/or monitor a selected portion of the vessel. In some embodiments, the transceivers are excited simultaneously. Alternatively, the transceivers are excited one after the other, for example with time intervals such as 1 second, 3 seconds, 15 seconds or intermediate, longer or shorter time intervals between excitations of different transceivers.

In some embodiments, a transceiver sorting method is used, for example during manufacturing of the catheter, to select a set of transceivers having similar characteristics. In some embodiments, a batch of transceivers is sorted into groups, for example into threesomes of transceivers, where each threesome is to be assembled on, for example, a triangular catheter head. Optionally, sorting is performed according to the resonant frequency and/or impedance of the transceivers. In some embodiments, the assembled catheter is scanned for determining a combined resonance frequency of the transceivers. Optionally, an efficiency of the selected resonance frequency is tested.

In some embodiments, data such as the combined resonant frequency, the efficiency, or other data is programmed onto, for example, an EEPROM (for example configured on the catheter handle) and/or on a USB device or other connector coupling between the catheter and console. Optionally, for example upon connection to a console, such as by a physician or technical personnel, this data is identified by the console. Optionally, the console is configured for re-scanning the impedance, and determining if there was a change in parameters between the end of the manufacturing process and the time of use. Such a change may disqualify the catheter from being used. In some embodiments, a user can select operation parameters based on the data identified by the console.

In some embodiments, the transceivers are sorted into groups, for example during manufacturing. Optionally, a method for sorting includes scanning a batch of transceivers, for example to detect an impedance of each of the transceivers. Optionally, an absolute impedance is determined. Optionally, sorting comprises calculating a sum of differences between a tested transceiver and an impedance vector of the other transceivers in the batch.

A Steerable Catheter Structure

The following FIGS. 17, 18A-C and 19A-B, describe a steerable catheter, according to some embodiments of the invention.

In some embodiments, as shown for example in FIG. 17, a steerable catheter A1701 comprises one or more transceivers 1703. In some embodiments, a distal portion A1705 of the catheter, comprising transceiver A1703, is bendable. In some embodiments, portion A1705 is deflected such that transceiver A1703 faces a desired direction of treatment. In some embodiments, portion A1705 is movable on a plane which includes a longitudinal axis A1707 of the catheter, for example portion A1705 may bend at an angle β ranging between A1-90 degrees with respect to a longitudinal axis of the catheter, on both sides of the axis. In some embodiments, the catheter is movable on a plane which is perpendicular to axis A1707. Optionally, two or more cables extend between distal portion A1705 of the catheter and a proximal end of the catheter, for example to a handle of the catheter (not shown in figure), for maneuvering the catheter within the vessel, for example along the planes described herein.

FIGS. 18A-C show an exemplary mechanism for deflecting a distal portion of a steerable catheter, according to some embodiments of the invention. In some embodiments, distal portion A1801 is coupled to a ring A1803. Optionally, ring A1803 is retractable in the proximal direction. Retraction of the ring may be enabled by, for example, by having a distal portion A1801 that is flexible relative to a proximal portion, providing for the distal portion to bend at an angle relative to the proximal portion of the shaft, as described herein. Optionally, pulling back on ring A1803 pulls on a wire that is passed within lumen A1805, causing the wire to bend. Optionally, the wire is coupled to ring A1803, for example by laser welding. As the wire is threaded within lumen A1805 of distal portion A1801, bending of the wire causes portion A1801 is caused to bend. Optionally, a transceiver configured on portion A1801 (not shown in this figure) is re-directed to face a different portion of the vessel wall.

Additionally or alternatively, in some embodiments, the wire is coupled to a chassis of the catheter head.

In some embodiments, a shown for example in FIG. 18C, a lumen A1809 of distal tip portion A1807, configured for delivering the wire, is located such that its entrance is slightly elevated and/or lowered with respect to an exit of lumen A1805 which leads to the tip, to receive the wire in its deflected configuration.

In some embodiments, the wire is passed through the catheter, for example by being threaded into a handle configured externally to the body for maneuvering the catheter, as shown by FIGS. 19A-B.

FIGS. 19A-B are a side view (FIG. 19A) and a longitudinal cross section (FIG. 19B) of a handle A1901 of a steerable catheter, according to some embodiments of the invention.

In some embodiments, a wire (not shown in the figure) is inserted into handle A1901 for example through an opening at a proximal end of the handle (not shown in this figure). Optionally, to direct wire A1903 into catheter shaft A1905 through the handle, handle A1901 comprises a shaft A1903 which is connected at its distal end to catheter shaft A1905. Optionally, shaft A1903 is sized to receive one or more guiding wire wires. In some embodiments, by passing the wire through shaft A1903, the wire is straightened and bending or folding of the wire is prevented.

In some embodiments, handle A1901 comprises one or more flanges A1907 and/or nuts A1909 and/or other structural elements suitable for coupling portions of the housing of handle A1901 together.

In some embodiments, lever A1911 projecting externally to handle A1901 is movable in the proximal and/or distal directions, for example to control movement of a ring which causes deflection of the steerable catheter, for example as described herein.

In some embodiments, lever A1911 is gradually movable for manipulating the distal portion of the steerable catheter at predefined distances and/or directions. Optionally, a "clicking" mechanism is utilized for indicating to a user the extent of movement.

In some embodiments, catheter shaft A1905 comprises a diameter of 5 F, 5.5 F, 6 F, 8 F. Optionally, shaft A1905 comprises two or more portions having various degrees of stiffness.

Alternatively, shaft A1905 serves as an external tube (for example a hypo-tube) which surrounds the catheter shaft. Optionally, shaft A1905 mechanically protects the catheter shaft.

An Intravascular Distancing Device

FIGS. 20A-B are photos of a distancing device B101 configured for providing a distance between an ultrasonic transceiver B103 and a wall B105 of a blood vessel (represented by the dashed lines), according to some embodiments of the invention. In some embodiments, distancing device B101 is configured on a catheter B107 comprising a plurality of transceivers such as transceiver B103. Optionally, the transceivers are peripherally arranged around the catheter head.

FIG. 20A shows device B101 in a closed configuration, and FIG. 20B shows device B101 in an open configuration.

In some embodiments, device B101 is formed as a hollow cylinder. Optionally, the cylinder comprises two or more elongated slots B109, extending in parallel to a longitudinal axis of the cylinder. In some embodiments, remaining portions of the cylinder wall that are configured in between the slots form one or more leaflets B111, configured for bending in a radially outward direction to push the one or more transceivers B103 away from wall B105. Optionally, distancing device B101 comprises a plurality of leaflets, such as 2, 3, 4, 5, 6 leaflets. Optionally, the number of leaflets is determined according to the number of transceivers. In one example, the number of leaflets is equal to the number of transceivers, for example 3 leaflets positioned in between 3 transceivers. Optionally, the transceivers are arranged in a triangular configuration.

In some embodiments, in the closed configuration, leaflets B111 lay flat in between the transceivers, for example in spaces between the transceivers. Optionally, the leaflets are in contact with a chassis onto which the transceivers are mounted.

In some embodiments, a leaflet B111 is deformable, for example bendable, into a rounded elbow shaped configuration, as shown for example in FIG. 20B. Optionally, an angle (α) is formed by the bent leaflet, for example ranging between 10-170 degrees, such as 60, 90, 120 degrees, or intermediate, larger or smaller. In some embodiments, leaflet B111 is bent gradually, for example first bent to form a 120, 130, 150 degree angle (α), and then further bent to form a 90, 100, 80 degree angle (α).

In some embodiments, a distance (d) is obtained between transceiver B103 and vessel wall B105, for example ranging between 0.1-10 mm, such as 0.5 mm, 1 mm, 3 mm, or intermediate, larger or smaller distances. Optionally, the smaller angle (α) is, the larger distance (d) is. Optionally, distance (d) is smaller than a radius of the vessel. Alternatively, distance (d) is equal to a radius of the vessel. Alternatively, distance d is larger than a radius of the vessel. In some embodiments, a distancing device is selected to provide a certain distance (d) or range of distances according to a size of the vessel to be treated, e.g. according to a diameter of the vessel.

In some embodiments, distancing device B101 centers the catheter with respect to the vessel wall, for example by engaging the vessel wall two or more circumferential locations, for example two locations positioned opposite each other along a diameter of the vessel, three locations spaced, for example, by a central angle of B120 degrees between them, or a larger number of locations. Additionally or alternatively, for example as illustrated in FIG. 20B, distancing device B101 pushes the catheter away from a single wall location. Optionally, a direction in which the device pushes the transceiver away from the wall is a direction in which treatment is applied. Optionally, treatment is applied in multiple directions, for example to multiple spaced apart regions distributed circumferentially around the artery.

In some embodiments, in the closed configuration, device B101 conforms to a profile of catheter B107, for example, it only slightly extends, or does not extend at all, beyond a periphery defined by catheter shaft B113. For example, a diameter of the cylinder of device B101 is smaller than, equal to, or only slightly larger (for example no more than 0.5 mm, no more than 0.2 mm, no more than 0.7 mm or intermediate, larger or smaller distances) than a diameter of catheter shaft B113. Optionally, a diameter of cylinder of device B101 is smaller than 2.5 mm, for example 2.2 mm, 2 mm, 1.9 mm. In some embodiments, catheter head B115 does not comprise a cylindrical profile, for example comprising a triangular, squared, or other polygonal cross section profile, and distancing device B101 conforms to or only slightly extends beyond a notional circumscribing circle of the head. In some embodiments, the closed configuration provides for passing the catheter through a guiding sheath.

In some embodiments, catheter shaft B113 is sized to fit within common delivery systems, for example within an 8 Fr guiding catheter, a 6 Fr guiding sheath or others, to be delivered to an anatomical location. Optionally, shaft B113 is sized as a 3 Fr catheter, 4 Fr catheter, a 6 Fr catheter, or intermediate, larger or smaller sizes.

In some embodiments, leaflet B111 of the distancing device or a portion of it is positioned to cover at least portion of transceiver B103, for example covering a portion of the transceiver surface, when in the closed configuration. In some embodiments, leaflet B111 is sized and/or positioned and/or shaped to form a channel or "pocket" above transceiver B103, for example in which blood is caused to accumulate and/or circulate. In some embodiments, leaflet B111 is positioned proximal to and/or distal to transceiver B103.

In some embodiments, in the open configuration, the bent leaflets B111 do not interfere with an ultrasound beam irradiated by the one or more transceivers B103. Alternatively, leaflet B111 slightly interferes with the beam, for example at the beam edges. Optionally, leaflet B111 is positioned such as to define a shape of the beam, for example by bordering between adjacent beams emitted by adjacent transceivers.

In some embodiments, a width (w) of a leaflet B111 is small enough to reduce an unwanted thermal effect on the vessel wall, which may occur, for example, if leaflet B111 absorbs at least some of the emitted ultrasound energy and heats up. In some embodiments, a width (w) of a leaflet B111 is small enough so that it does not induce mechanical damage to the tissue. Additionally or alternatively, a width (w) is large enough to keep transceiver B103 away from wall B105 without collapsing. In some embodiments, width (w) is determined such that the leaflet substantially does not interrupt the blood flow through the vessel. Width (w) may range between, for example, 0.2 mm-2 mm.

Optionally, the transceivers are excited at a power level ranging between 1-15 W, such as 5 W, B11 W, 7 W, or intermediate, higher or lower power levels.

In some embodiments, in the open configuration, an aperture B117 formed between bent leaflet B111 and transceiver B103 is large enough to allow blood to flow between vessel wall B105 and transceiver B103. Optionally, the flow of blood cools down the vessel wall. A potential advantage of allowing blood to flow between the transceiver and the wall may include reducing or preventing thermal damage to wall B105, such as to the inner intima layer. Another potential advantage may include dissipating heat from the transceiver by permitting blood to flow across a surface of the transceiver, thereby reducing or preventing overheating of the transceiver.

In some embodiments, distancing device B101 is used to control the flow rate of a liquid (e.g., blood) between the transceiver and the vessel wall, for example, by relatively increasing and/or decreasing the distance between the transceiver and the wall. Optionally, increasing and/or decreasing the flow rate between the transceiver and the wall is performed in order to relatively increase and/or decrease the cooling rate of the transceiver and/or vessel tissue.

In some embodiments, in the open configuration, the arc shaped configuration of the leaflet B111 forms slanted surfaces. Optionally, the slanted surfaces redirect a portion of the blood flowing through the vessel towards the vessel wall. The redirected flow of blood may assist in cooling the wall, for example cooling the intima, and may reduce thermal damage to the wall.

In an exemplary embodiment of the invention, distancing device B101 prevents rotation of the catheter, for example, by contacting the walls at a plurality of points arranged circumferentially. Alternatively or additionally, the amount of rotation of the catheter is controllable by using the distancing device. Alternatively or additionally, the distancing device can be used to angle the transceiver relative to the vessel wall.

In some embodiments, distancing device B101 is shaped to provide repositioning of the catheter in both the open configuration and the closed configuration. Alternatively, repositioning of the catheter is permitted only in the closed configuration.

Various mechanisms may be used for transforming distancing device B101 to the open and/or to the close configuration. In an exemplary embodiments, a tip B119 configured at a distal end of the catheter is positioned and sized so that retraction of tip B119 in the proximal direction pushes the cylinder of device B101 so that is slides in the proximal direction, causing the bending of leaflets B111. Optionally, a proximal end B121 of device B101 is fixedly connected to catheter shaft B113, so that it does not slide in the proximal direction when the distal end of device B101 is being pushed by tip B119. Optionally, tip B119 is movable independently of other components of the catheter, for example movement of the tip does not cause the one or more transceivers B103 to shift, or the catheter shaft B113 to be pushed backwards in the proximal direction. In some embodiments, as will be further described, movement of tip B119 is controlled by movement of a lever configured externally to the body, for example on a handle of the catheter. Optionally, the movement is performed manually by a physician.

In some embodiments, the catheter is coupled to a controller, configured, for example, for activating the transceivers, setting treatment parameters such as intensity frequency, duration and/or other parameters, selecting a treatment plan, or other operations. Optionally, the controller is configured for opening and/or partially opening and/or closing the distancing device, for example through wiring. Optionally, the operating of the distancing device is performed according to data received by the transceivers, for example according to an analysis of the distance from the vessel wall obtained from the received echo signals. Optionally, the controller monitors the distance from the wall. For example, an echo signals analysis may indicate that the transceiver is too close to the wall, for example only 0.1 mm away from the wall, and based on this indication the controller automatically sends a signal for opening the distancing device. Optionally, electrical wiring for activating (e.g. closing or opening) the distancing device is passed within a lumen of the chassis.

In some embodiments, leaflets B111 are positioned to cover at least a portion of a surface of the one or more transceivers. Optionally, the distance monitored by the controller provides an indication of a current state of the leaflets, to determine whether the leaflets are in a closed, open, or partially open configuration. For example, due to covering of the transceiver's surface by the leaflet in a closed configuration, the returning echo signals received by the transceiver may differ from the signals received in an open configuration of the leaflet, thereby providing an indication to a current state of the leaflet.

Optionally, by assessing a positioning of the leaflets, a diameter of the vessel can be determined. Optionally, changes in a diameter of the leaflets in an open configuration, for example due to pulsation, are monitored. Optionally, a change in the diameter of the vessel is determined according the changes in positioning and/or in diameter of the leaflets.

FIGS. 21A-C are a photo of an intravascular distancing device shown separately from a catheter (FIG. 21A); a photo of a distancing device configured on a catheter head and shown in an open configuration (FIG. 21B); and a front view photo of the distal end of the catheter, with the distancing device in an open configuration (FIG. 21C).

In some embodiments, for example as shown in FIG. 21A, distancing device 201 comprises one or more elongated slots B207, such as 2, 3, 4, 6, slots. The slots define one or more leaflets B211, extending longitudinally along at least a portion of the length of transceiver B203, as shown for example in 21B. In some embodiments, slot B207 is shaped and/or sized to expose a surface of transceiver B203, for example exposing at least 70%, 80%, 98% of the transceiver surface.

Optionally, a slot B207 is formed as a rectangle comprising rounded corners, for example comprising a U-shape B209. A potential advantage of rounded corners may include reducing a risk of scratching or damaging the vessel. In some embodiments, a length B217 of slot B207 is equal to a length of transceiver B203. Alternatively, length B217 is smaller than or larger than a length of transceiver B203. Optionally, length B217 of slot B207 is longer than the transceiver so that it does not affect the emitted beam. For example, length B217 of the slot ranges between 1-2 times a length of transceiver B203, for example, for a transceiver having a length of 6 mm, a slot may have a length B217 ranging between, for example, 6 mm to 12 mm. In some embodiments, a width B219 of slot B207 is equal to a width of transceiver B203. Alternatively, width B219 is smaller than or larger than a width of transceiver B203. For example, width B219 of the slot ranges between, for example, 0.1 mm to B2.1 mm.

In some embodiments, manufacturing of the distancing device includes forming the slots using laser-cutting techniques.

In some embodiments, in the closed configuration as shown in FIG. 21A, a diameter B213 measured between opposite leaflets B211 ranges between, for example, 1 mm to 3 mm. Optionally, in the open configuration as shown in FIG. 21B, a diameter B215 measured between two points along bent leaflets B211 that are furthest apart from each other ranges between, for example, 3 mm to 12 mm, for example 5.8 mm, 3.5 mm, 5.9 mm, or intermediate, larger or smaller diameters. Different distancing devices may comprise different maximal diameters in their expanded configuration. Optionally, a distancing device with a certain expanded diameter is selected according to the type and/or shape of the vessel into which the catheter is inserted. For example, for a catheter inserted into a renal artery having an average diameter of approximately 5 mm, a distancing device configured for expanding to a maximal diameter of 6.5 mm can be used. Optionally, diameter B215 is selected to fit a contracted state of the vessel. Optionally, leaflets B211 are formed with some flexibility, so that they can be forced by the vessel walls slightly towards their closed configuration, for example in situations in which a diameter of the vessel (or some portion of the vessel) is smaller than diameter B215, and/or in situations in which the vessel contracts.

In some embodiments, leaflets B211 are positioned with respect the surfaces of transceivers B203 in a manner that minimizes the leaflets interference with the energy beam emitted by the transceivers. In some embodiments, leaflets B211 are positioned above surfaces and/or edges of chassis B205, for example above exposed chassis surfaces in between the transceivers.

In some embodiments, distancing device B201 comprises one or more holes B221, configured for example at a proximal portion of the device, but may additionally or alternatively be configured at any other portion of the device, for example a distal portion. Optionally, the holes are large enough to permit blood to flow in and out of the holes. Optionally, the blood is allowed to flow across a surface of the one or more transceivers B203. For example, blood may flow between distancing device B201 and the one more transceivers B203. Additionally or alternatively, blood may flow along the radially outward facing portions of chassis B205. A potential advantage of permitting blood to flow within spaces formed between the distancing device and the transceivers and/or chassis B205 onto which the transceivers are mounted may include cooling of transceiver B203 and/or cooling of chassis B205 and/or cooling of leaflets B211, as heat may be carried away by the flow. Optionally, the flow is sufficient for maintaining a temperature of a transceiver or at least a surface of the transceiver under a certain temperature threshold, for example, under 46 degrees Celsius, 44 degrees Celsius, 48 degrees Celsius, or intermediate, higher or lower thresholds. Optionally, the transceiver temperature is maintained in the range of 40-44 degrees Celsius, 42-48 degrees Celsius, 39-50 degrees Celsius, 44-62 degrees Celsius, or intermediate, higher or lower temperature ranges.

In some embodiments, holes B221 are configured to receive fixation devices such as screws of pins for fixating the proximal portion of device B201 to, for example, the catheter shaft.

In some embodiments, for example during assembly of the device, materials such as glue can be delivered through holes B221 to be applied at various portions of the device. The holes may provide access to various portions of device B201 and/or the catheter head. In some embodiments, at least a portion of device B201 is formed of transparent material, such as polyurethane, nylon, PVC, for example to facilitate coupling between the components of device B201 during assembly.

In some embodiments, holes B221 provide for a slight deformation of device B201, for example enabling bending of the device with respect to its longitudinal axis. Such bending ability may facilitate insertion of the catheter head, for example when passing through curves and/or narrowings of the vessel.

In some embodiments, leaflets B211 comprise one or more holes (not shown in this figure). Optionally, fluid such as blood flows through the holes. A potential advantage of holes in leaflets B211 may include reducing interference with blood flow. Another potential advantage of holes in leaflets B211 may include obtaining a more homogenous distribution of forces acting on the leaflet.

FIG. 21C shows a front view of catheter head, in which device B201 is an open configuration. In some embodiments, leaflets B211 are circumferentially distributed so that an angle β, for example ranging between 10-180 degrees is formed between adjacent leaflets, for example 90 degrees, 120 degrees, 150 degrees. Optionally, the leaflets are equally distributed, for example as shown in this figure, where the three leaflets are equally distributed so that an angle β of 120 degrees is formed between adjacent leaflets. Alternatively, angle β differs between adjacent pairs of the leaflets, for example, in an embodiment, two leaflets may be positioned at 180 degree angle from each other, and a third leaflet positioned 90 degrees from each of the two leaflets, or any other angular distribution thereof.

In some embodiments, a tip B225 of the catheter, positioned distally to distancing device B201 is configured for providing shock absorbance, for example by being formed of a flexible material such as polyurethane, PVC, Nylon or polyethylene. In some embodiments, distal tip B225 is cannulated. Optionally, opening B223 at the distal tip leads to a lumen which extends in the proximal direction through the catheter head and/or continuing catheter shaft. In some embodiments, the lumen extends to a proximal end of the catheter, positioned outside the body. Optionally, the lumen is sized to receive a guide wire, so that the catheter can be inserted into the body over a guidewire. Optionally, the guide wire extends through the lumen from a proximal end to a distal end of the catheter. Alternatively, the guide wire extends through a portion of the lumen, for example extending 7 cm, 12.5 cm, 20 cm or intermediate, larger or smaller distances from a distal end of the catheter. The catheter may include a "rapid exchange" mechanism for facilitating insertion, removal or replacement of a guide wire.

FIG. 22 is a side view photo of a leaflet B301 of a distancing device in a bent configuration, according to some embodiments of the invention. A dashed line was added to the photo to schematically illustrate layers of the leaflet. In some embodiments, leaflet B301 comprises a plurality of layers, such as 2, 3, 4, 5, 6, layers, characterized by different mechanical properties, such as stiffness. For example, as shown in this figure, leaflet B301 comprises two layers—an external layer B303 facing the vessel wall, and an internal layer B305 facing the catheter.

In some embodiments, internal layer B305 is formed of a material stiffer than the material of external layer B303. Internal layer may be formed of, for example, plastic such as polyimide, pic, nylon. Optionally, the internal layer is stiff enough to maintain the elbow shaped configuration of the leaflet when bent, yet flexible enough to deflect into the bent configuration and/or return to the flat configuration. For example, internal layer B305 may be formed of a material with a stiffness k ranging between 2500-3000 N/m. In some embodiments, internal layer B305 is stiff enough to resist elasticity of the external layer, for example preventing the external layer from pushing the leaflet in a radially inwards direction.

In some embodiments, external layer B303 is formed of a relatively soft material, such as Pebax, polyethylene, polyurethane, silicon, Teflon. Optionally, the external layer is soft enough to minimize damage, such as mechanical damage, to the vessel wall. For example, the material does not scratch the wall when engaging the tissue.

In some embodiments, the cylinder and/or leaflets of the distancing device are formed of Nitinol. Optionally, the slots are formed in the Nitinol cylinder using laser cutting techniques. In some embodiments, the Nitinol is coated with a material such as PI or Pebax.

In some embodiments, leaflet B301 and/or other portions of the distancing device such as the cylindrical shaft portions above and/or below the slots comprise one or more radiopaque markings B307, to enable visualization of the distancing device under imaging, such as fluoroscopy. The radiopaque marking may be formed in various shapes such as a dot, a ring, a line, a circle, an arrow or other. In some embodiments, the radiopaque marking is in the form of a wire, for example extending along the length of the leaflet. In some embodiments, for example as shown in this figure, the marking is positioned at a bending point of the leaflet, for example for indicating a position of the bent leaflet with respect to the catheter shaft and/or with respect to the vessel wall. In some embodiments, the radiopaque marking is formed of a material such as tungsten, barium, tantalum or other materials suitable for visualization under imaging.

Alternatively, use of the distancing device may reduce the need for imaging, as the open configuration may define a safe distance for emitting ultrasound.

In some embodiments, the leaflets are thermally conductive, for example by comprising metal or other thermally conductive material. Optionally, the leaflets actively dissipate from the transceivers.

In some embodiments, one or more of a curvature of the leaflet in an open configuration, an elasticity of a material of the leaflet facing the vessel wall, and one or more edges of the leaflets which contact the vessel wall are suitable not cause substantial mechanical damage to the vessel wall in the configuration.

FIGS. 23A-B and 24 are a schematic illustration and a corresponding flowchart of an exemplary mechanism for operating a distancing device, according to some embodiments of the invention. It is noted that the distancing device may be maneuvered (for example, transformed into an open or closed position) using mechanisms other than the described herein.

In some embodiments, a distal tip B403 of catheter B401 is coupled, for example on a proximal end, to a tube B409 extending throughout the catheter shaft, for example extending to a proximal end of the catheter B407 and optionally into a handle of the catheter B411, the handle positioned externally to the body. In some embodiments, tube B409 is hollow, for example serving as lumen for passing of a guide wire. Optionally, the coupling between tube B409 and tip B403 is obtained by gluing the external walls of tube B409 to an internal recess within tip B403.

In some embodiments, a proximal end of tube B409, extending within handle B411 is coupled to a lever B413 in a manner that movement of the lever, for example in the distal and proximal directions, causes movement of tube B409, for example advancing the tube in the distal direction or retracting the tube in the proximal direction. Optionally, movement of lever B413 is transferred over a distance longer than 30 cm, 50 cm, 60 cm or intermediate, larger or smaller distances to remotely operate the distancing device.

In some embodiments, a proximal end of distal tip B403 is sized according to a shaft of distancing device B405, for example having a diameter equal to a diameter of the device's shaft. In some embodiments, in the closed configuration of the distancing device as shown for example in FIG. 23A, distal tip B403 is spaced from a distal end of the distancing device, for example spaced at a distance B415 ranging between 0.5-5 mm.

To transform the device into an open configuration in which the leaflets are bent, as shown for example in FIG. 23B, for example when the catheter is inserted into the blood vessel (501) and positioned at a selected location, lever B413 may be moved (503), for example pulled in the proximal direction, pulling tube B409 in the proximal direction which in turn pulls distal tip B403 in the proximal direction. Optionally, distal tip B403 is retracted, for example by a distance equal to and/or larger than distance B415, engaging a distal end of the shaft of distancing device B405, and forcing it in the proximal direction. Since a proximal end of distancing device B405 is fixed to the catheter, the applied force causes the leaflets to bend radially outward. Optionally, the bent leaflets push the one or more ultrasonic transceivers B417 of catheter B401 a distance away from the vessel wall. Optionally, the transceivers are activated to emit ultrasound (505), for example for ablating tissue such as nerve tissue surrounding the blood vessel.

Alternatively, in some embodiments, various elements may be used for coupling distal tip B403 to the handle and/or coupling distancing device B405 to the handle. For example, a cable can extend between the handle and the distal tip, and/or between the handle and a distal end of the distancing device. Optionally, the cable extends within a lumen of catheter B401. Alternatively, the cable extends on the outer walls of catheter B401. Alternatively, the cable extends part within the catheter lumen and part externally to the catheter shaft B419.

Additionally or alternatively, at least a portion of catheter shaft B419 is movable, for example advancable and retractable with respect to distal tip B403. Optionally, by pulling shaft B419 in a proximal direction, the leaflets of distancing device B405 are caused to bend. Optionally, shaft B419 is telescopic, and distancing device B405 is transferred to an open configuration when a proximal end of distancing device B405 encounters a portion of catheter shaft B419 which is of larger diameter than the shaft portion on which device B405 is positioned. Optionally, device B405 is slidable on shaft B419.

Figure 25A:
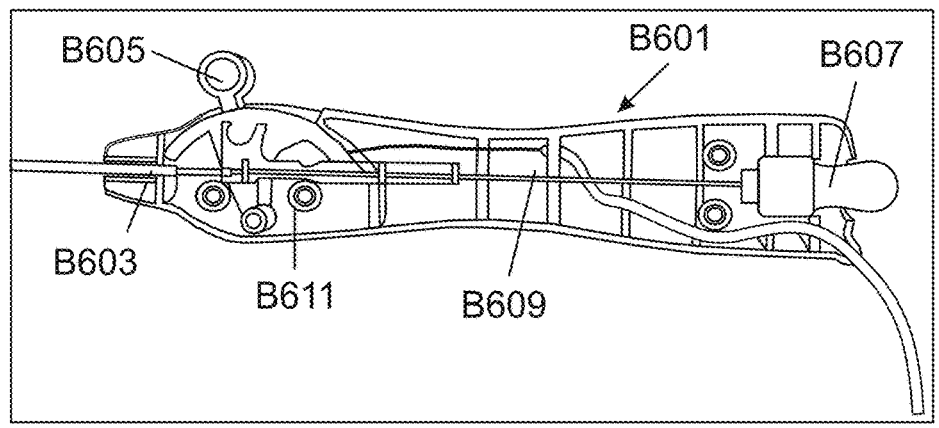
Figure 25B:
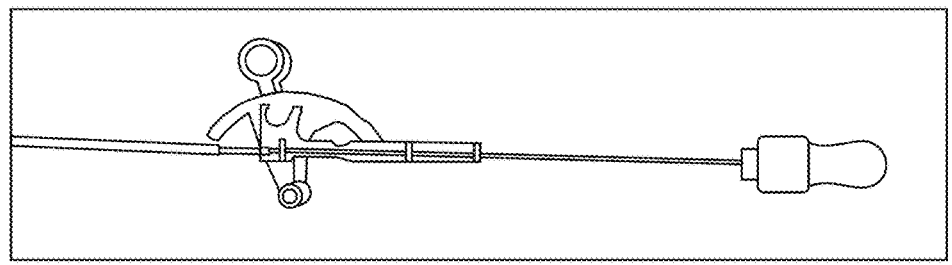
Figure 25C:
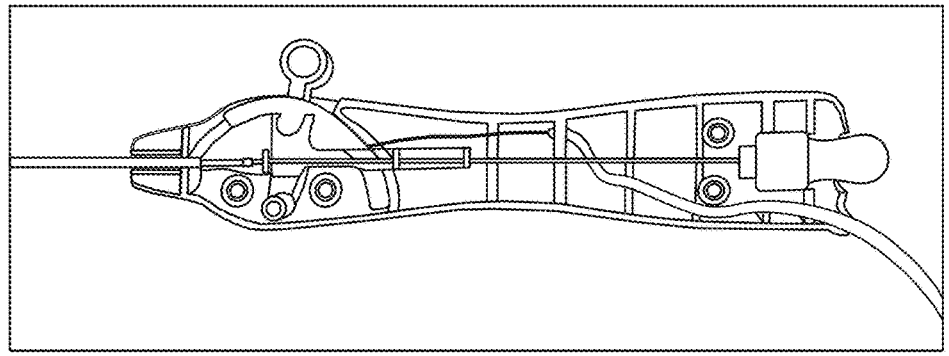
Figure 25D:
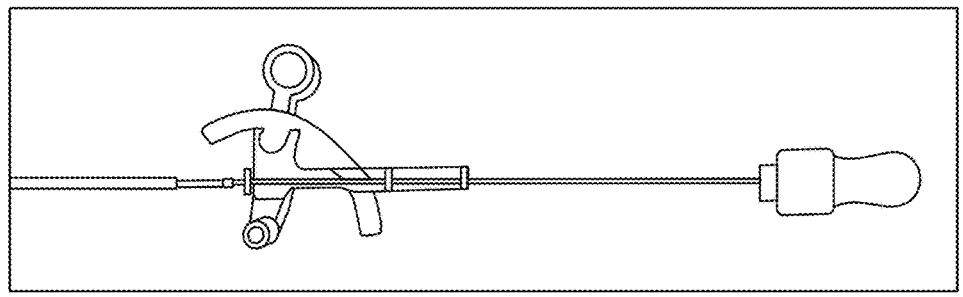

FIGS. 25A-D are photos of an exemplary handle B601 of a catheter, comprising a lever assembly for operating a distancing device, according to some embodiments of the invention. FIGS. 25A and 25B show a cross section of the handle (FIG. 25A) and an assembly comprising a guide wire tube B603 coupled to a lever B605 (FIG. 25B), for operating the distancing device for example as described herein. FIGS. 25C and 25D are corresponding photos showing the handle and operating assembly in a transformed configuration, in which, for example, a distancing device at a distal portion of the catheter is in an open configuration, pushing the one or more transceivers away from the wall.

In some embodiments, lever B605 is coupled to a pulley assembly B611. Optionally, pulley assembly B611 is arranged to provide gradual movement of lever B605. For example, lever B605 can be pulled back to open the distancing device, and can be stopped at 1, 2, 3, 4, 5, 6, stages during the movement. Optionally, at each step, the leaflets of the distancing device are bent at a different angle, for example an angle which increases as the lever is pulled further back. Optionally, sensible feedback is provided to a user (for example by a 'clicking' noise made during movement) to indicate advancing between movement stages.

In some embodiments, resistive force applied by the vessel walls onto the leaflets of the distancing device, for example force higher than a threshold, may cause the leaflets to bend towards a flat configuration. A friction based closure of the leaflets may provide additional safety, for example in situations in which a user has not mechanically transformed the device to a closed configuration, and closure of the leaflets is desired, such as for passing the device through a curve of the vessel.

In some embodiments, guide wire tube B603 is coupled to a luer connector B607. Optionally, luer connector B607 protrudes externally from a casing of handle B601, for example extending in the proximal direction. In some embodiments, luer connector B607 is cannulated, and a guide wire B609 can be threaded through the luer connector B607 to pass into guide wire tube B603. Optionally, guide wire tube B603 extends in the distal direction, for example having an opening at a distal end of the catheter.

FIG. 26 is a schematic illustration of flow B709, for example blood flow, passing through openings of a distancing device B701. In some embodiments, distancing device B701 comprises one more slots B703, for example as previously described, and/or one or more holes B705, as also described hereinabove, permitting blood to flow within a lumen of shaft B707 of the distancing device. In some embodiments, distancing device B701 is positioned over one or more transceivers, for example in a manner in which slot B703 is located above a surface of a transceiver (not shown in this figure), and blood is allowed to flow over a surface of the transceiver. Optionally, the blood then flows out of holes B705. Additionally or alternatively, blood flows only in and out holes B705, in and out of slots B703, or any combination or direction thereof.

In some embodiments, a catheter over which distancing device B709 is positioned comprises one or more temperature sensors (not shown in this figure), for example positioned in proximity to holes B705 so that flow B709 contacts the sensor when passing through distancing device B701. Optionally, a temperature of the blood is measured using the sensor. Optionally, the distancing device is positioned above the temperature sensor such that blood accumulates over the sensor before it continues to flow. For example, the distancing device may have a protrusion in shaft B707, for example located above the temperature sensor, to capture blood above the sensor. Additionally or alternatively, other measurement devices such as a flow sensor or pressure sensor may be incorporated in the catheter, and a positioning and/or structure and/or size of distancing device B701 may be selected according to the type and/or positioning of the measurement device.

FIGS. 27A-B show an exemplary configuration of a distancing device B801 comprising two sets of leaflets B803 and B805, according to some embodiments of the invention.

In some embodiments, the two sets of leaflets are arranged above two sets of transceivers B807 and B809, for example the leaflets are circumferentially arranged above and/or between circumferentially distributed transceivers of the catheter head. In some embodiments, a first set of transceivers B807 and corresponding leaflets B803 are positioned in proximity to a distal tip B811 of the catheter, and a second set of transceivers B809 and corresponding leaflets B805 are positioned proximally to the first set. In some embodiments, the sets of leaflets are angularly dispositioned with respect to each other, forming a plurality of contacting angles with the vessel walls. In one example, in a catheter head having a triangular cross section, two sets of three circumferentially arranged transceivers (e.g. two transceivers on each facet of the triangle, positioned along a longitudinal axis of the catheter head) may provide 6 treatment areas, and two corresponding sets of leaflets may be used for pushing the one or more transceivers away from the wall. Optionally, the sets leaflets are separately operated. For example, one set is closed while a second set is open. Alternatively, the sets of leaflets are similarly operated.

FIGS. 28A-D are photos of a catheter comprising a distancing device B901, which is gradually transformed into a fully open position, according to some embodiments of the invention.

Figure 28A:
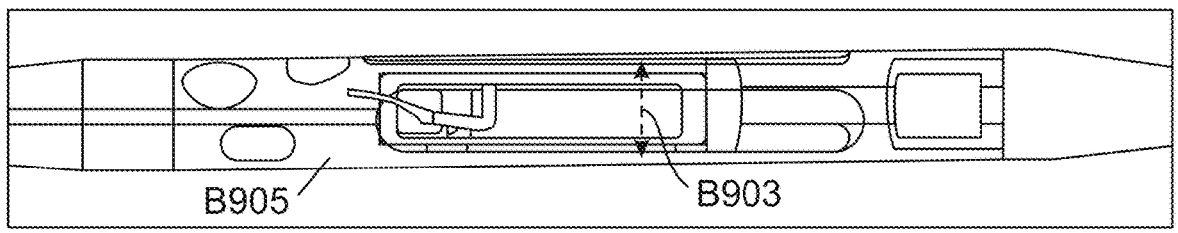
Figure 28B:
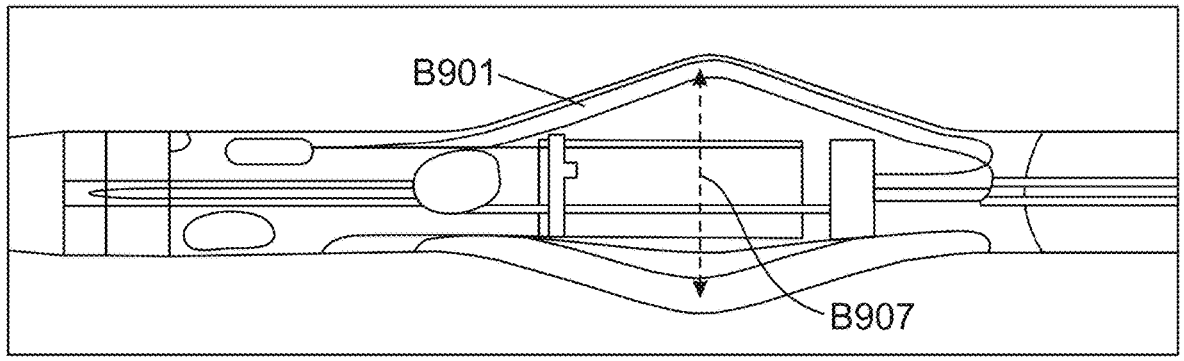
Figure 28C:
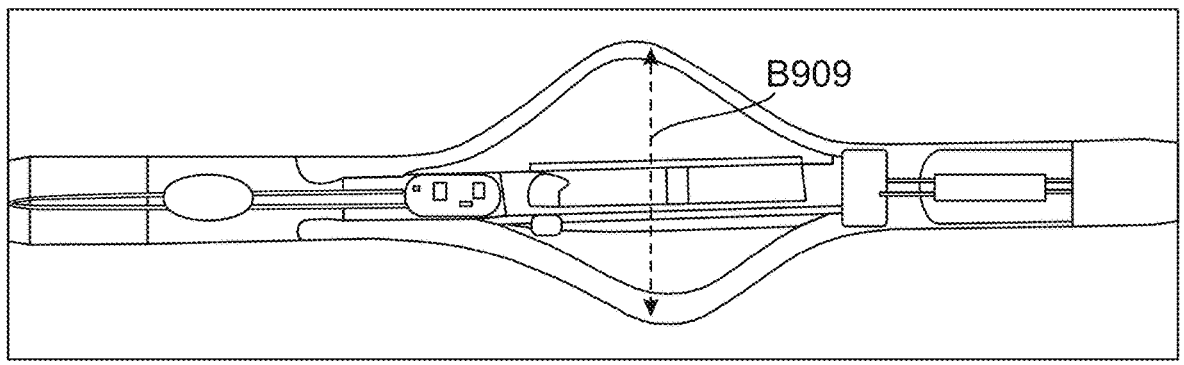
Figure 28D:
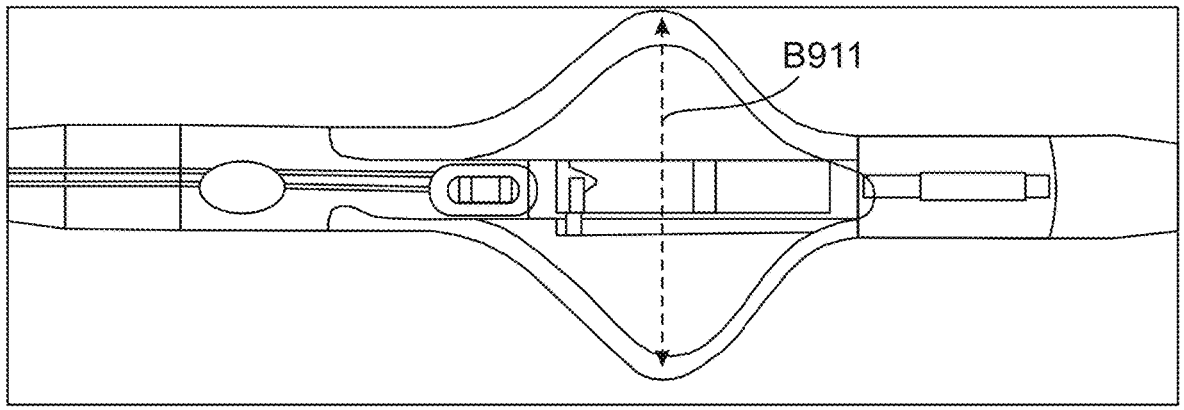

FIG. 28A shows device B901 in a closed position, in which a diameter B903 measured between the flat leaflets of the device conforms to a periphery defined by the catheter shaft, for example ranging between 1-2.5 mm, such as 1.9, 2.2, 1.5 mm or intermediate, larger or smaller diameters. Optionally, diameter B903 is equal to a diameter of the cylindrical shaft portion B905 of device B901. FIG. 28B shows device B901 at a second stage of transforming into an open position, in which a diameter B907 between the slightly bent leaflets ranges between 2.5-4.4 mm, for example 2.8, 3.5, 4.3 mm, or intermediate, larger or smaller diameters. FIG. 28C shows a third stage of transforming into an open position, in which diameter B909 ranges between, for example, 4.5-5.5 mm, such as 4.9, 5.2, 5.5 mm, or intermediate, larger or smaller diameters. FIG. 28D shows a fully open configuration of the distancing device, in which diameter B911 ranges between, for example, 5.6-6.5 mm, such as 5.7, 5.9, 6.3 mm, or intermediate, larger or smaller diameters.

Optionally, advancing between the opening stages is controlled by a user, for example through a handle on a proximal end of the catheter (e.g. using a lever system coupled to a guide wire), as previously described herein. It is noted that various embodiments may comprise various stages of opening, and that the opening diameters are not limited to the described and may vary between opening stages and/or devices.

FIGS. 29A-B are photographs taken during an experiment performed within a pipe model, simulating, for example, the structure of the renal artery. The model for example as shown herein includes a silicon pipe B1001, filled with hydrogel B1003 for imitating blood within the artery. Alternatively, a different fluid comprising properties (such as viscosity) that are similar to blood can be used.

An ultrasonic catheter comprising a distancing device B1005 was delivered through a 6 F guiding catheter B1007

(type RDC). Alternatively, a guiding catheter of a different size or type, such as 8 F, 4 F guiding catheters can be used. The catheter was threaded over a guide wire B1009, in this example a BMW Hi Torque model. Alternatively, other guide wires can be used.

Distancing device B1005 is shown in both figures in an open configuration. FIG. 29A shows the catheter being passed through a relatively straight path of the pipe. FIG. 29B shows the catheter being passed through a curve B1013 of the pipe. The curve imitates, for example, a pathway adjacent a renal artery ostium.

The leaflets B1011 of distancing device B1005 were shown to push the catheter away from the wall of the pipe to a distance ranging between 1-1.8 mm, for example 1.1 mm, 1.5 mm, 1.6 mm. Alternatively, the distancing device can push the catheter a different distance from the wall, such as 2 mm, 2.2 mm, 3 mm or intermediate, longer or shorter distances away from the wall.

Optionally, a length and/or width of distal tip portion B1015 affect a positioning of the catheter with respect to the wall. For example, a tip having a length longer than 0.5 mm may produce a diagonal positioning of the catheter with respect to the vessel wall, for example when the distancing device is open, as shown for example in FIG. 29B. Optionally, in such a positioning, tip B1015 is closer to the vessel wall than a more proximal portion of the catheter, for example marked by B1017.

FIGS. 30A-C are photos of various configuration of a distancing device B1101 formed of metal.

In some embodiments, device B1101 is made of metal such as Nitinol, stainless steel, and/or other biocompatible metals or alloys. A potential advantage of a device formed of metal may include a simpler manufacturing, for example using laser cutting techniques. Another potential advantage of a metal device may include leaflets that are reduced in width B1105, yet maintain strong enough resistance to the vessel walls to allow pushing the catheter away from the wall, due to the mechanical properties of the metal. Optionally, by reducing a width of a leaflet, a smaller contact area is formed between the leaflet and the wall, thereby optionally reducing thermal damage to the internal wall. Optionally, by reducing width of the leaflet, interference with blood flow is reduced. Optionally, by reducing width of the leaflet, interference with the acoustic field emitted by a transceiver is reduced.

In some embodiments, for example as shown in FIGS. 30B and 30C, a width B1105 of a leaflet varies, for example along a longitudinal axis of the leaflet. Optionally, a central portion of the leaflet is wider than one or both end portions B1107 and B1109 of the leaflet. Optionally, an increased width increases a contact area with the blood vessel wall. Optionally, by increasing the contact area, force is distributed so that relatively less force is applied onto smaller wall portions which comprise the contact area.

In some embodiments, for example as shown in FIG. 30C, bending of the leaflet is asymmetrical, for example a bend B1111 is formed closer to a proximal or distal end of the leaflet with respect to its longitudinal axis, as opposed to the center.

In some embodiments, the metal device is coated by a material suitable for softening contact with the vessel walls, such as pebax, polyethylene, polyurethane, silicon, Teflon.

FIGS. 31A-D are exemplary configurations of a bent leaflet, according to some embodiments of the inventions.

Some embodiments include various positioning configurations of a bend of a leaflet with respect to a transceiver. Optionally, the positioning of the bend affects the vessel wall movement with respect to the transceiver. Optionally, the positioning of the bend is determined according to a laying of the catheter within the vessel, for example counter—positioning an orientation of the catheter defined by a guiding sheath which leads the catheter into the vessel. Optionally, the positioning of the bend is determined according to a size and/or shape of an emitted ultrasound beam.

Optionally, the positioning of the bend is determined to increase the flow of blood or other fluids such as injected saline towards the vessel wall. In some embodiments, for example as shown in FIG. 31A, the bend B1205 is symmetrically positioned with respect to a longitudinal axis B1201 of the transceiver B1203. Alternatively, for example as shown in FIG. 31C, bend B1205 is positioned closer to one of the ends of the transceiver. In some embodiments, for example as shown in FIG. 31B, bend B1205 comprises a rectangular or trapezoidal configuration.

Optionally, the rectangular or trapezoidal configuration enable maintaining the proximal and distal ends and/or portions close to the ends of transceiver B1203 away from the wall. In some embodiments, for example as shown in FIG. 31D, a leaflet comprises a double bend. Alternately, a leaflet may include a triple bend, a quadruple bend, etc. A potential advantage of a having a plurality of bends, for example as opposed to a single elongated bend configuration, may include a better distribution of the force.

In some embodiments, during transformation from a close to open configuration of the distancing device and vice versa, the relative location of the bend with respect, for example, to a longitudinal axis of the transceiver may change. For example, the bend may gradually move from the center towards the proximal or distal ends of the transceiver.

In some embodiments, only a portion of a length of the leaflet is bent, for example 20%, 40%, 60%, 80% or intermediate, larger or smaller percentages of a total length of the leaflet is bent.

FIGS. 32A-B are a schematic illustration of an ultrasonic catheter comprising a distancing device positioned within a blood vessel (FIG. 32A) and a cross section of the vessel while the distancing device is an open configuration (FIG. 32B).

FIG. 32A schematically illustrates a longitudinal section of vessel B1301. Catheter B1303 is positioned within the vessel, and distancing device B1305 is open to push the transceivers B1307 away from the walls, and/or to center the catheter within the vessel. An emitting surface B1309 of transceiver B1307 is exposed between the leaflets B1309, facing radially outwards towards a wall portion. In some embodiments, a beam B1311 (schematically illustrated by the dashed lines, facing towards the reader) is emitted from surface B1309 of the transceiver. Optionally, leaflets B1319 are positioned such that they do not interfere with beam B1311. In some embodiments, a portion B1313 of vessel wall tissue which is treated by beam B1311, for example as shown in FIG. 32B, is situated in between contact areas B1315 (marked by small circles) of leaflets B1319.

In some embodiments, leaflets B1309 affect the flow of blood within vessel B1301, for example by forcing blood to flow towards the direction of treated tissue B1313, as shown for example by arrows B1317. In some embodiments, a slope formed by the bent leaflet, for example as indicated, with respect to the vessel wall, by angle β in FIG. 32A, directs blood to flow towards the wall, for example towards contact area B1315. Optionally, angle β ranges between B10-80 degrees.

In some embodiments, catheter B1303 is delivered and/or maneuvered in the blood vessel by guiding sheath (or guiding catheter) B1323. Optionally, a position of the catheter relative to the walls of the vessel is affected by a distance B1325 measured between a distal tip B1321 of the catheter, and a distal opening of guiding sheath B1323. Optionally, the guiding sheath forces the catheter into a certain position. Optionally, the size and/or shape of the leaflet are selected according to distance B1325. Optionally, one or more parameters such as a position of a bend of a leaflet relative to the catheter and/or relative to the transceiver, a curvature radius (r) of the bend, and/or the portioned length of the leaflet which is configured for bending are selected to be compatible, or alternatively, to counteract, a movement of the catheter induced by guiding sheath B1323. Optionally, a curvature radius (r) ranges between 0.1-0.5 mm, or intermediate, larger or smaller ranges.

Apparatuses and Methods for Assessing Denervation Effectiveness

General Description of Methods and an Apparatus for Assessing Renal Denervation Effectiveness Referring now to the drawings, FIG. 33 is a flowchart of physiological measures that may indicate the effectiveness of an RSD treatment, for example by detecting a change in the measures. Optionally, by estimating at least one physiological parameter before, during, and/or after a denervation treatment, a change is detected. Detection of the changes in real time may provide feedback for immediate evaluation of a renal sympathetic denervation treatment (C101).

In some embodiments, a denervation treatment comprises selectively damaging at least a portion of the renal nerve tissue, to reduce, modulate or desist the neural activity. In some embodiments, the damage to the nerves is thermal damage.

In some embodiments, changes to physiological parameters such as a change in the blood flow rate through the renal artery (C103) and/or modulation of sympathetic restraint of the renal artery (C105) are detected. In some embodiments, a change is observed by estimating a certain parameter before and after denervation. Some of the parameters are immediately affected by the treatment, for example 5 minutes, 10 minutes, 30 minutes, 1 hour, 3 hours, 5 hours after the treatment, while others may be affected in a longer term, such as 1 day, 3 days, 1 month.

In some embodiments, the one or more physiological parameters are estimated before the denervation procedure, for example 2-10 days, 3-6 weeks, or intermediate or later times before the procedure. In some embodiments, the one or more physiological parameters are estimated immediately before the denervation procedure, for example 5 minutes, 15 minutes, 45, 80 minutes and/or any intermediate and/or smaller periods of time before the procedure.

In some embodiments, the one or more physiological parameters are estimated immediately after the denervation procedure, for example 5 minutes, 15 minutes, 45, 80 minutes and/or any intermediate and/or smaller periods of time after the procedure.

In some embodiments, the one or more physiological parameters are estimated after the denervation procedure, for example 2-10 days, 3-6 weeks, or intermediate or later times after the procedure.

In some cases, reducing and/or eliminating the renal sympathetic afferent and/or efferent neural activity affects the hemodynamic properties, such as the flow rate of blood flowing through the renal artery.

In some cases, reducing and/or eliminating the afferent neural signals sent to the muscles restraining the renal artery causes a change in the artery stiffness. Optionally, modulation of the muscle sympathetic nerve activity affects vasoconstriction of the artery, for example reducing a level of vasoconstriction such that a diameter of the artery increases.

In some embodiments, the physiological changes are detected by semi-invasive measurements, for example using an endovascular catheter. In some embodiments, the physiological changes are detected by an ultrasonic catheter. Optionally, the ultrasonic catheter is capable of performing the denervation treatment by emitting ultrasound energy to ablate the nerves, as well as detecting physiological changes in real time, for example by receiving echo signals returning from the artery walls. Optionally, the treatment is adjusted in response to feedback.

In some embodiments, post-denervation measurements are compared to a table of expected results. Optionally, a decision to repeat the treatment, for example to cause further damage to the nerves, is made based on the comparison of the achieved results and the expected results.

FIGS. 34A-E illustrate some aspects of an exemplary endovascular ultrasonic catheter device, according to some embodiments of the invention. FIGS. 34A and 34B are an angiogram and a drawing of an ultrasonic catheter inserted into a renal artery. FIG. 34C is a drawing of an exemplary ultrasonic catheter. FIG. 34D is a cross section of the distal tip of the catheter of FIG. 34C, showing an exemplary configuration of three transceivers. FIG. 34E is a cross section of a distal tip of a catheter comprising four transceivers, according to some embodiments of the invention.

FIGS. 34A and 34B show an ultrasonic catheter C201 inserted into a renal artery C203. Optionally, device C201 is inserted to the renal artery through the aorta C213, for example through standard vascular access, such as from the femoral artery.

In some embodiments, device C201 is configured for emitting and/or receiving ultrasonic energy. In some embodiments, device C201 is configured for emitting ultrasonic energy for tissue ablation, to disrupt nerves C205 surrounding the artery, for example nerves lying in the adventitia tissue layer. In some embodiments, the ultrasound is unfocused ultrasound. Alternatively, the ultrasound is focused. In some embodiments, device C201 is configured for receiving ultrasonic energy, for example receiving echo signals reflected from the artery walls.

In some embodiments, a plurality of echo signals are reflected from a wall location. Optionally, the plurality of echo signals include signals that are reflected and/or received at various time points. In some embodiments, a single signal is reflected from a wall location. Optionally, the wall location includes a portion of the wall, for example a segment of the wall circumference, a local point in the wall, a line extending along the wall. Optionally, the segment of the circumference extends in an axial direction, for example extending to a distance shorter, longer or similar to a length of the one or more transceivers.

In some embodiments, device C201 comprises one or more measurement devices such as temperature sensors and/or pressure sensors and/or flow sensors C209. Optionally, using data recorded by the measurement devices, various physiological parameters such as blood flow rate, blood flow velocity, blood flow temperature, blood pressure and/or any other parameters can be estimated.

In some embodiments, device C201 is maneuvered within the artery, for example positioned in one location for performing denervation, and in a second location for performing measurements. Alternatively, measurements are performed at a location similar to the denervation location.

In some embodiments, a current location of device C201 inside the renal artery is dynamically monitored, for example by analyzing data received by the transceivers and/or measurement devices, and the location is adjusted accordingly.

In some embodiments, a duration of treatment is adjusted according to data received by the transceivers and/or measurement devices.

FIG. 34C shows an exemplary ultrasonic catheter device C201. In some embodiments, the device comprises one or more ultrasonic transceivers C207, such as C2, 3, 4, 5, 6 transceivers or a higher number. In some embodiments, one or more of the transceivers is configured for emitting and/or receiving ultrasonic energy, by comprising an acoustic element capable of vibration, such as a piezo element.

In some embodiments, transceivers C207 are spatially arranged to direct and/or receive the ultrasonic energy circumferentially, for example arranged in a triangular configuration as shown in FIG. 34D or a quadrilateral configuration as shown in FIG. 34E. In some embodiments, the transceivers are configured to emit and/or receive ultrasonic energy from multiple directions, such as, 2, 3, 4, 5, directions or a higher number. Optionally, each transceiver faces a different region of the artery wall, for example facing 60 degrees, 120 degrees, 180 degrees, 270 degrees and/or any other portion of the artery perimeter. In some embodiments, two or more transceivers face a similar artery wall region. In some embodiments, the catheter device is a uni-directional catheter, facing a single region of the artery wall. Optionally, the uni-directional catheter is axially rotated, each time facing a different wall region.

A potential advantage of circumferentially arranged transceivers may include reducing maneuvering of the device with the artery. Another potential advantage of the circumferential transceiver configuration includes emitting ultrasonic energy in multiple directions without having to rotate the catheter.

In some embodiments, a transceiver is adapted to perform one of more of the following functions: emitting energy to cause nerve ablation, emitting energy to detect a physiological parameter relating to the artery wall, emitting energy for imaging purposes such as for producing an elastograph, and receiving energy, such as echo signals reflected by the artery walls. In some embodiments, one or more of the described function are performed without having the transceiver contact the artery wall.

In some embodiments, the one or more transceivers are excited at their resonant frequencies or at a frequency within a range of 10%, 5%, 20% or intermediate, larger or smaller percentages from their resonant frequencies. Optionally, a plurality of transceivers are excited at a similar frequency, for example at a weighed resonant frequency of all transceivers. Optionally, simultaneous activation reduces a time period in which a ringing phenomena is present, for example relative to non-simultaneous activation where, for example, one transceiver is excited after the other and a time period in which ringing is present may be longer. Optionally, to reduce an amplitude and/or duration of ringing, the one or more transceivers are excited at a frequency different from their separate resonant frequencies or weighed frequency.

In some embodiments, measurement devices C209 include one or more temperature sensors, such as thermistors and/or thermocouples. Optionally, a thermistor is positioned in proximity to a transceiver, for example to measure a current temperature of the transceiver. Optionally, the thermistor measures a temperature of the blood as it flows across a surface of the device. In some embodiments, a thermistor may extend away from a catheter, for example for measuring blood temperature at a distant location along the artery. Optionally, a temperature recorded by the thermistor is affected by both the transceiver temperature and the blood temperature.

In some embodiments, data acquired by the measurement devices and/or echo signals received by the transceivers is recorded, for further analysis. In some embodiments, the data is analyzed in real time, for providing feedback during use. Optionally, parameters such as the current catheter location and/or sampling rate and/or signal intensity and/or signal frequency and/or a duration of treatment or any other parameters are adjusted according to the analyzed data.

In some embodiments, the catheter device is connected to a signal processor (not shown in this figure). Optionally, the signal processor is connected to one or more of the transceivers. In some embodiments, the signal processor is configured for implementing one or more algorithms related to distance estimation, for example an algorithm which separates echo signals reflected from multiple sources, such as the artery walls, for determining a diameter of the artery, and/or an algorithm for estimating a current location of the catheter with respect to the artery walls, and/or an algorithm for monitoring a distance between a transceiver and the artery wall, and/or any other algorithm or combination thereof.

In some embodiments, the signal processor is configured for estimating a physiological parameter by combining two or more estimations, for example blood flow velocity (estimated for example according to a transceiver cooling rate, as measured by a thermistor), and an artery diameter (estimated for example according to echo signal analysis) are combined to estimate flow rate.

In some embodiments, a distancing device C211 is configured circumferentially around device C201, for example around the tip portion comprising the transceivers, for pushing the device away from the artery walls, for example at least 1 mm away, at least 1.5 mm away, at least 2 mm away. Optionally, distancing device 211 is used for centering catheter C201 with respect to the artery walls.

In some embodiments, device C201 is connected, for example through a sheath, to a handle (not shown in this figure) which is positioned externally to the body. In some embodiments, the handle is used for activating the device, for example the handle may comprise a lever for controlling the opening and closing of distancing device C211 within the artery.

FIG. 35 is a flowchart describing some exemplary methods for obtaining online feedback for a renal denervation treatment, according to some embodiments of the invention.

In some embodiments, assessing denervation comprises estimating blood flow rate (A). Additionally or alternatively, a change in sympathetic restraint of the artery is estimated (B).

In some embodiments, the blood flow rate and/or velocity are measured directly (A.1), for example by tracking flow of a liquid agent. As referred to herein, direct measurement may include estimating blood flow based on flow of a liquid having a similar behavior to the blood, for example by injecting the liquid so that it flows along with the blood. In some embodiments, the method comprises tracking a contrast liquid. Additionally or alternatively, the method comprises tracking a cold liquid.

In some embodiments, the blood flow rate and/or velocity are measured indirectly (A.2), for example by observing a parameter which is affected by flow rate and/or affected by the flow velocity, and provides an indication of the flow. As referred to herein, indirect measurement may include assessing a physical property of a measurement device which is affected by the flow of blood, for example a temperature of a transceiver following excitation and/or an impulse response of a transceiver.

In some embodiments, indirect measurement of the blood flow rate comprises estimating a cross-sectional area of the artery (for example calculated according to an estimation of the artery diameter) and estimating the blood flow velocity. In some embodiments, blood flow velocity is determined by analyzing an impulse response of the transducers to excitation, optionally based on a correlation between arterial pulsation and the recorded impulse response. Additionally or alternatively, blood flow velocity is calculated by analyzing a heat dissipation rate of the transceivers, optionally based on a correlation between a difference in temperatures and the flow velocity.

In some embodiments, intra-arterial distances are estimated. Optionally, these distances are used for deducing, for example, a current location of the catheter with respect to the artery walls, a diameter of the artery, a minimal distance to an artery wall, and/or any other distance related parameters.

In some embodiments, the artery diameter is calculated using at least two distances measured between the catheter and the artery walls. In some embodiments, a mean diameter of the artery is obtained, for example, by continuous estimation of the diameter over time. In some embodiments, a dynamic diameter of the artery is estimated, for example a diameter changing during heartbeat pulsations. In some embodiments, a cross sectional area of the artery is calculated based on the diameter estimation.

In some embodiments, a waveform signal of the artery wall, indicating wall movement, is analyzed. Optionally, artery wall movement is correlated with pulsation. In some embodiments, a diameter is estimated during systolic and/or diastolic stages. Optionally, a difference in the diameter length between the stages provides an indication for a stiffness level of the artery wall.

In some embodiments, the arterial blood pressure is measured, for example using a pressure transducer. Optionally, the pressure transducer is configured on an ultrasonic catheter device. In some embodiments, detection of changes in sympathetic artery restraint involves estimating arterial blood pressure and/or estimating a wall movement pattern.

Methods for Estimating Hemodynamic Properties Using a Liquid Agent

A Method for Estimating Blood Flow Rate and/or Velocity Using Contrast Liquid

FIG. 36 is a flowchart of an exemplary method for estimating blood flow rate and/or velocity by tracking the flow of contrast liquid, according to some embodiments of the invention. In some embodiments, contrast liquid such as iodine or gadolinium is injected into the renal artery (C401), for example injected into a location of the ostia of the renal artery. In some embodiments, the flow of the contrast liquid is continuously imaged, for example using x-ray angiography (C403). In some embodiments, the recorded data is processed (C405), for example automatically or semi-automatically analyzed, such as by using a MATLAB software. In some embodiments, the continuous recording is divided into time frames.

In some embodiments, the analysis includes modeling the relevant artery segment, defining one or more regions of interests (ROIs) along the artery segment, and detecting the attenuation of intensities of the x-ray signals in each of the ROIs (C407). In some embodiments, the analysis includes comparing pixel intensities between the time frames. Optionally, the degree of attenuation in the pixel intensities changes as the energy travels through the contrast liquid medium, indicating a current location of the contrast liquid.

In some embodiments, the analysis includes detecting a flow onset for each of the ROIs (C409). In some embodiments, the flow onset is indicated by pixel intensities above a baseline intensity value, for example 20%, 50%, 40% and/or intermediate, smaller, or higher values above a baseline.

In some embodiments, the analysis includes estimating the flow rate (C411). In some embodiments, flow rate is estimated based on estimating the distance that the contrast liquid has passed, for example the distance between two sequential ROIs, and the time duration in which the contrast liquid passed between the two points. Optionally, detecting a flow onset of two sequential ROIs in a relatively short time period indicates a higher flow rate in comparison to the flow rate indicated by onsets occurring within a longer time period between them. For example, detecting the onsets of two ROIs within a time period of 1-4 frames, equivalent to 40-160 msec, indicates a flow rate ranging between, for example, 250-350 ml/min which is higher than, for example, a flow rate ranging between 50-100 ml/min indicated by onsets detected within a longer time period, such as 300-400 msec.

In some embodiments, a diameter and/or cross section area of the artery, for example at an ROI, is estimated according to the angiogram. Optionally, flow rate is estimated according to a velocity of the contrast liquid prorogating through the artery, and the cross section area.

In some embodiments, the ROIs are selected at a location along the artery that is similar to a location of a previously performed denervation. Alternatively, the ROIs are selected in between the treatment regions.

FIGS. 37A-B are experimental results of estimating blood flow rate and/or velocity by tracking contrast liquid in vivo, according to some embodiments of the invention. FIG. 37A is an angiography image of the aorta C501 and both renal arteries C503, after the injection of contrast liquid to the ostium of the renal artery in the aorta and before RSD treatment. FIG. 37B is a graphical analysis of the x-ray intensities measured at three ROIs C505, selected along the artery, before the RSD treatment. Each colored line indicates an intensity measured at a different ROI.

A Method for Estimating Blood Flow Rate and/or Velocity Using Cold Liquid

FIG. 38 is a flowchart of an exemplary method for estimating blood flow rate by tracking the flow of a cold liquid, according to some embodiments of the invention.

In some embodiments, the method includes positioning at least two thermistors at a distance from each other along a segment of the renal artery (C601). In some embodiments, a distance between the thermistors ranges between 0.5-8 cm, for example 0.6 cm, 2 cm, 4 cm, 5 cm, or intermediate, smaller or higher distances. In one example, a first thermistor is positioned at the renal artery ostium, and a second thermistor is positioned at a distance from the first thermistor, for example in the direction of the kidney. Optionally, the thermistors are mounted onto a single catheter, or, alternatively, each thermistor is mounted onto a different catheter.

In some embodiments, a cold liquid (such as cooled saline) is injected into the renal artery (C603), for example injected into a location of the renal artery ostium. In some embodiments, a temperature of the cold liquid ranges between 4-25° Celsius.

In some embodiments, a temperature measured by the two or more thermistors is recorded (C605). In some embodiments, the sampling rate of the thermistors is determined according to a predefined estimation of the flow velocity. In one example, the estimated flow velocity ranges between 10-100 cm/sec, and the sampling rate of the thermistors is 50 Hz.

As the cold liquid flows through the artery and passes a location of a thermistor, a temperature drop is indicated. Optionally, the temperature descends instantaneously upon the passing of the cold liquid.

In some embodiments, the recorded temperatures are analyzed to detect a temperature difference as measured by a single thermistor, and/or detect a temperature difference between two or more thermistors (C607). In some embodiments, a pre-defined threshold is applied to select specific temperature values and/or differences.

In some embodiments, the blood flow rate and/or velocity are estimated (C609). Optionally, the estimation is based on parameters such as the distance the liquid has passed within the artery lumen and/or the time period observed between the temperature drops of the thermistors. In one example, a temperature measured by a first thermistor descends, and after a certain time period a temperature measured by a second thermistor, for example located further along the artery, descends. Optionally, the estimated velocity and a diameter and/or cross section area of the artery, measured for example by the methods described herein, are combined to determine flow rate.

Methods for Estimating Hemodynamic Properties by Exciting an Intravascular Transceiver A Method for Estimating Blood Flow Velocity Based on Heat Dissipation Rate of a Transceiver FIG. 39 is a flowchart of an exemplary method for estimating renal blood flow velocity based on a heat dissipation rate of a transceiver, according to some embodiments of the invention. In some embodiments, one or more transceivers are inserted into the renal artery (C701). In some embodiments, a temperature sensor, such as a thermistor and/or a thermocouple, is configured in proximity to the transceiver so that a current temperature of the transceiver can be measured. For example, the temperature sensor can be mounted onto the catheter at a distance ranging between 0-1 mm from the transceiver, for example positioned proximally or distally to the transceiver.

In some embodiments, the transceiver is excited by one or more short duration excitations. Alternatively, the transceiver is excited by long duration excitations. In some embodiments, the transceiver is excited by low power excitations (C703). Alternatively, the transceiver is excited by high power excitations.

Optionally, the excitation power ranges between 5-30 Watt, for example 7, 15, 30 Watt or intermediate, higher or lower values. In some embodiments, the excitation is performed periodically, for example applying a series of excitation pulses over a 10 second period, and then waiting for a 10 second interval before reapplying the excitation.

In some embodiments, before and/or during the excitation and/or waiting interval between excitations and/or after the end of the last excitation, a temperature measured by the thermistor, indicating the temperature of the transceiver, is continuously recorded (C705).

In some embodiments, the recorded temperature is analyzed. Optionally, differences in measured temperature are detected (C707), for example by applying a threshold. In some embodiments, a heat dissipation rate of the transceiver is estimated according to the measured temperature differences. Flow velocity is determined based on the heat dissipation rate (C709), for example as explained below.

In some embodiments, the temperature of the transceiver during excitation is analyzed. Optionally, a temperature of the transceiver is affected by the power level of applied excitation, and/or by the velocity of the flow. In some embodiments, the analysis takes into account temperature deviations from a mean temperature of the transceiver, which may occur during excitation. In some embodiments, a steady state temperature, which may represent equilibrium between the applied heating and the cooling by the flow of blood, is taken into consideration. Optionally, the transceiver temperature is affected by the efficiency of the transceiver. In some cases, the transceiver efficiency may affect the robustness of the method, for example because the efficiency may change with time during the time period in which the transceiver is inserted into the artery, or, for example, due to the fact that various transceivers may have different efficiencies, making it more difficult to apply a general algorithm.

In some embodiments, the temperature of the transceiver following the excitation is analyzed. As suggested by experiments conducted by the inventors, a power law relation exists between the heat dissipation rate of the transceiver (following the excitation) to the flow velocity. Optionally, for example as observed in the experiments, following the excitation period, the transceiver's temperature declines exponentially. A cooling time constant of the transceiver (calculated as the temperature drop to 1/e of the maximal temperature value) has been to shown to be proportional to the flow velocity.

In some embodiments, the duration of excitation and/or waiting period is determined according to a heating time constant of the transceiver, and/or possible noise in the recorded temperature measurement.

FIGS. 40A-B show experimental results of an in vitro experiment to show a power law relation between blood flow velocity and heat dissipation rate of the transceiver.

The experiment was performed in a 6-mm diameter pipe, simulating the renal artery. Optionally, a pipe having a smaller or large diameter can be used, for example 4 mm, 5 mm, 7 mm, 9 mm or intermediate, larger or smaller diameters. The inventors note that a similar experiment was performed in pipe having a diameter of 5 mm, yielding similar results. A glycerol solution having similar viscosity to blood at normal body temperature and having a flow velocity range similar to blood was used. The glycerol solution used in this experiment comprised 45% glycerol and 55% water. Optionally, in some embodiments, a different solution having similar viscosity and velocity range properties may be used.

FIG. 40A shows the measured heat dissipation rate of the transceiver as a function of predefined flow velocity values of the glycerol solution flowing through the pipe (shown by dots C801). The flow velocities were controlled by a peristaltic pump connected to a flow meter. A power law model C803 is fitted through the results.

FIG. 40B shows the cooling time constant of the transceiver (measured in seconds, calculated as the temperature drop to 1/e of the maximal temperature value) as a function of the flow velocity. As can be observed from the graph, the cooling time constant of the transceiver is shorter as the flow velocity increases.

FIGS. 41A-D show experimental results of an in vitro experiment for validating the power law relation between blood flow velocity and heat dissipation rate of the transceiver.

A similar experimental setup to the above was used, using two pipes to simulate the renal artery instead of one: one pipe having a diameter of 6 mm (marked by the blue markings), the other having a diameter of 8 mm (marked by the red markings). FIGS. 41A and 41C show the heat dissipation rate of the transceiver as a function of flow rate (41A) and flow velocity (41C). FIGS. 41B and 41D show the cooling time constant of the transceiver as a function of the flow rate (41B) and the flow velocity (41D).

A Method for Estimating Blood Flow Velocity Based on Impulse Response Analysis

FIG. 42 is a flowchart of an exemplary method for estimating blood flow velocity by analyzing an impulse response of a transceiver. In some embodiments, a transceiver is inserted into the renal artery (C1001). In some embodiments, the transceiver is excited by a set of pulses (C1003) or by a single pulse, for example at a power ranging 10-40 Watt, for example 20 Watt, 30 Watt, 35 Watt or intermediate, higher or lower powers. Optionally, the frequency of the excitations ranges between 100-400 Hz, for example 200, 300, 350 Hz or intermediate, higher or lower frequencies. In some embodiments, a damping factor of the impulse response of the transceiver is analyzed (C1007).

In some embodiments, the flow velocity is estimated (C1009). In some embodiments, the flow velocity is estimated based on correlation between the impulse response variance and the flow velocity, as shown by the inventors in the following experiments. Optionally, a second correlation exists between arterial pulsation and variance of the recorded impulse response.

FIGS. 43A-B show experimental results of an in vitro experiment to show a correlation between a measured impulse response of the transceiver and the flow velocity.

The impulse response of a transceiver inserted into a water filled pipe was measured at predetermined flow velocities. Using a "pulser-receiver" device, the transceiver was excited with a set of impulses, and the voltage tracing of the transceiver following the impulse was recorded. FIG. 43A shows the voltage tracing of the transceiver following an impulse. FIG. 43B shows the calculated voltage variance at four different predetermined flow velocities, suggesting a linear correlation between the voltage variance (the impulse response variance) and the velocity of the flow.

FIGS. 44A-B show experimental results of an in vivo experiment including an impulse response analysis.

The experiment setup included inserting a transceiver (for example configured on a catheter tip) into a renal artery of a swine, exciting the transceiver by a set of impulses, and recording the impulse response. FIG. 44A shows the recorded voltage trace of the transceiver following the impulse. FIG. 44B shows the variance of the measured voltage as a function of the time following an impulse (2.5 seconds). As previously suggested, the graph shows a correlation between the impulse response variance and the arterial pulsation.

Methods for Estimating Physical Changes to the Artery Wall

As previously described, a change in sympathetic restraint of the artery may indicate the effectiveness of an RSD treatment. Optionally, movement of the artery walls relative to an axis of the artery, for example movement due to pulsation, provides an indication for the level of artery restraint.

FIGS. 45-47C relate to an exemplary method of intravascular distance measurement, which can provide an indication for the level of artery restraint, for example by estimating the artery diameter.

An Exemplary Method for Intravascular Distance Measurement

FIG. 45 is a flowchart of a general method for separating echo signals recorded through a single channel, which were received from multiple sources such as artery walls.

In some embodiments, the method includes recording signals from multiple sources through a single channel (C1301). Optionally, the number of sources (e.g. artery wall locations) corresponds to the number of receiving elements configured on the intravascular device, for example a device with three ultrasonic transceivers may receive signals from three corresponding artery wall directions.

In some embodiments, the recorded signals are analyzed by identifying equal-delay patterns of the signals, and determining a correlation between equal-delay patterns. In some embodiments, an equal-delay pattern comprises reflections having a similar time period passing between emission of a pulse, and receipt of a reflection resulting from that pulse. Due to the time-distance relation of ultrasound waves, where the distance is a product of the speed of the wave propagating through the tissue and the time, the time delay between the signal emission and reception corresponds to a certain distance, therefore the equal-delay patterns can also be referred to as equal-distance patterns.

Optionally, highly correlated patterns are assumed to arrive from the same source. A clustering algorithm is then applied to separate the signals into groups (C1303), based on a relative distance between the calculated correlations. Optionally, the number of groups is defined according to the number of sources (corresponding with a number of transceiver directions) and an additional group for separation of noise.

In some embodiments, a source of each group of clustered signals is identified (C1305). Optionally, identifying the source includes determining a distance between the transceiver and the source artery wall. In some embodiments, the distance is determined according to a centroid profile of each clustered group.

In some embodiments, by determining, for example, 3 or more distances between the transceivers and the artery wall, an artery diameter can be calculated using the circular coordinates defining the artery circumference. In some embodiments, by tracking distances over time, for example over one or more cardiac cycles (i.e. heartbeat periods), wall movement can be tracked. Optionally, a mean difference of the artery diameter changing during a cardiac cycle is calculated.

FIG. 46 is a flowchart of a method for analyzing a sequence of signals received from multiple sources and recorded through a single channel, according to some embodiments of the invention.

In some embodiments, the method is applied for acoustic location of walls of an artery, for example to determine a diameter of the artery. In some embodiments, the method is applied to determine a location of a catheter tip with respect to the artery walls. Generally, the method can be applied to other signal processing implementations, which require separation of signals, and more specifically to signals recorded through a single channel.

For clarification purposes, the method will be described in the context of measurement of an artery diameter using an ultrasonic catheter device comprising 3 transceivers arranged in a triangular configuration, as explained above in FIGS. 2A-C.

In some embodiments, the transceivers are excited by narrow band energy in a series of short pulses, for example 1000 pulses, 500 pulses, 1500 pulses or intermediate, higher or lower number to emit unfocused ultrasonic energy towards the artery walls. Optionally, excitations are provided during a 2.5-10 seconds time period, for example 3 seconds, 5 seconds, 15 seconds. The repetitive pulse frequency ranges, for example, between 100-400 Hz.

In some embodiments, the ultrasonic energy emitted by the transceivers is reflected by the artery walls. Optionally, the reflections are recorded in between pulses. Optionally, the artery walls which reflect the energy are moving, for example moving periodically due to pulsation.

In some embodiments, the algorithm assumes the following conditions:

A. The signals are reflected (or, in other embodiments, emitted) from a known number of sources, or, alternatively, the number of receivers directed towards different sources is known.

B. The sources move periodically, optionally in a synchronized manner

C. The width of the signals is larger than the Eigen wavelength of the transceiver.

D. The signals are reflected simultaneously during at least one cardiac cycle.

In some embodiments, the reflected echo signals, received by the one or more transceivers, are recorded through a single channel (C1401) over time. Alternatively, the signals may be received through multiple channels. Optionally, the recording duration following each excitation of the transceivers is defined according to cardiac cycles (i.e. measured between heartbeats), for example being as long as 1, 2, 5, 20, 100 or smaller, intermediate, or higher number of cardiac cycles. Optionally, the recorded signal includes overlapping signals received from various sources (e.g. wall locations).

In some embodiments, the single channel recording is arranged in a matrix (C1403). Optionally, the recording is segmented, and the segments are stacked one after the other in the matrix. In one example, each column in the matrix contains recordings acquired following one of the pulses out of the set of the emitted pulses, and each row contains samples recorded at a specific time delay between the emission and receipt of the reflections.

In some embodiments, the mixed signals are separated to determine a source of each of the signals. In some embodiments, separation includes determining a signal's energy during the recorded time course. Optionally, separation is based on a phase difference between the mixed signals, which may indicate a distance between the source and the transceiver. However, in some cases, superposition of the signals and/or measurement noise may interfere with the separation of the signals according to their phase differences. Therefore, in some embodiments, separation of the mixed signals is performed by analyzing equal-delay patterns of the signals (C1405).

In some embodiments, an equal-delay pattern is a set of voltage values received at a certain time delay from the emission. A measure of correlation is performed between two or more of these sets of voltage values, each set of values having a time delay that is different from a time delay of a second set.

In some embodiments, patterns reflected from similar sources are highly correlated. Respectively, patterns from different sources will a lower or no correlation between them.

In some embodiments, the signals are grouped by determining correlations between equal-delay patterns. In some embodiments, a Pearson correlation coefficient is calculated, ranging between −1 for patterns with a negative correlation, and 1 for highly correlated patterns. In some embodiments, the correlations are calculated between samples with an interval of at least one wavelength between them, for example to prevent negative correlation as a result of two similar signals that are in opposite phases, and/or to reduce the number of analyzed samples. Optionally, the results of the correlation computation are arranged in a symmetric matrix of correlations (C1407). In some embodiments, at this step, the correlation of each pattern to itself (which equals 1) is replaced by an average of adjacent correlation values.

In some embodiments, the correlation matrix is multiplied by −1, and normalized, so that the correlation values range between 0 and 1. Optionally, the new matrix is arranged as a "correlation distance" matrix, where uncorrelated patterns are distant from each other, and correlated patterns are close to each other.

In some embodiments, to associate each signal to its source, the calculated correlation coefficients are represented as points in a multidimensional space (C1409).

In some embodiments, a K-means algorithm is applied to cluster the points to groups (C1411). Optionally, the number of groups is predefined, for example it may be set to 4 groups: 3 groups being 3 source directions, such as the artery walls at which the three transceivers are directed, and one group being noise. In some embodiments, a threshold is applied to cluster points representing an energy level that is higher than one quarter, one third, one half, or any other fraction of the average energy level.

In some embodiments, the K-means algorithm iteratively searches for centroids, for example 4 centroids in the example described herein, one for each group. Optionally, the centroids are artificial vectors which provide a minimal distance to the clustered points of a specific group, and/or a maximal distance to points belonging to a different group. Optionally, during each iteration, the centroids are recalculated for better fitting the clustered groups.

In some embodiments, the clustering results are validated (C1413). Optionally, validating includes constructing a corresponding binary matrix, for example including a 0 to represent patterns from different groups, and 1 for representing patterns from the same group. Optionally, the normalized covariance of both matrices is a measure of their similarity, and is used to determine the quality of the clustering. For example, a normalized covariance above 0.5 indicates reliable clustering results. Additionally or alternatively, a measure of similarity between the matrices is provided by applying a k-nearest-neighbors algorithm to the binary matrix, and comparing the result to the original clustering.

In some embodiments, the noise group is identified. Optionally, a threshold is applied to the centroids to determine which of the groups represents noise. For example, a centroid with a maximal value below a threshold of 0.1 may be identified as the noise centroid.

In some embodiments, a distance of each of the sources, for example from a distance between a transceiver and the artery wall from which signals were reflected, is calculated (C1415). In some embodiments, the distance is determined according to the centroid profile. In some embodiments, a maximal value of a centroid (representing a single group) is the mean distance of the source (artery wall) from the transceiver. In some embodiments, a point (from the same group) that exceeds the median of the centroid indicates the minimal distance of the source from the catheter.

In some embodiments, the artery diameter is calculated according to the measured source distances. In some embodiments, a peak of each centroid profile is detected. The peak does not necessarily indicate an initial location of wall tissue, but may indicate an area in the tissue which caused the strongest reflection. Therefore, a threshold may be applied to detect the most proximate tissue location with respect to the transceiver. Optionally, by detecting 3 points (one corresponding to each transceiver facing the artery wall), the artery circumference is defined, and a diameter is calculated. In some embodiments, more than 3 points such as 4, 6, 8 points or intermediate or higher number of points corresponding with a number of the transceivers may be used as a coordinates for defining a circle indicating the artery circumference.

In some embodiments, a movement profile of each wall is traced (C1417). In some embodiments, the movement profile is traced by finding a delay between successive time windows of the recording. Optionally, the delay is estimated by applying a cross correlation between the windows, and identifying a shift which maximizes the correlation. Additionally or alternatively, the delay is estimated according to a difference between the local maximum of successive time windows. In some embodiments, the identified shifts are summed, for example starting from a mean distance of each signal, to yield the distances of the source during movement.

In some embodiments, a relative location of the catheter tip with respect to the artery walls is calculated. In some embodiments, to calculate the location of a center of the catheter tip (assuming a circular tip), the following equations are applied:

$$f_i = -(x_i^2 + y_i^2) \quad A = \begin{bmatrix} x_1 & y_1 & 1 \\ x_2 & y_2 & 1 \\ x_3 & y_3 & 1 \end{bmatrix}^{-1} \cdot \begin{bmatrix} f_1 \\ f_2 \\ f_3 \end{bmatrix}$$

$$R = \sqrt{\frac{A_1^2 + A_2^2}{4} - A_3} \quad (C_x, C_y) = (-0.5A_1, -0.5A_2)$$

$(x,y)_{1,2,3}$ are the Cartesian representation of the calculated distances to the artery walls, after adding an inner radius of the catheter tip, R is the calculated radius of the artery, $C_{x,y}$ are the catheter coordinates relative to the artery center, $A_{1,2,3}$ are the three dimensional coordinates of an intermediate vector.

In some embodiments, the method includes an algorithm for eliminating a ringing artifact of the recorded signal. Optionally, the ringing artifact appears mostly during the initial recording segment. The ringing artifact may be affected by factors such as the excitation intensity and the damping of the transceivers. For example, if an undamped transceiver is used, optionally for increasing the ablation efficiency, a stronger ringing artifact is observed as opposed to using a damped transceiver.

In some embodiments, elimination of the artifact is based on the assumption that the artifact is a relatively constant signal, while a reflected echo signal varies in intensity, for example due to the movement of the artery wall. In some embodiments, eliminating the artifact comprises subtracting a mean value of equal-delay samples from the matrix, for example from the matrix columns.

In some embodiments, the method includes applying a sampling algorithm for correcting sampling irregularities. Optionally, the algorithm aligns the ringing artifact before its subtraction. In some embodiments, the sampling algorithm includes increasing a sampling rate (upsampling), for example during the initial segment, cross correlating the artifact with the first received signal, determining a shift which is required to achieve a maximal correlation between the artifact and the first signal, and then decreasing the sampling rate (downsampling), for example back to the original rate.

FIGS. 47A-C are graphical representations of a current location of a catheter tip with respect to the artery walls, according to some embodiments of the invention.

FIG. 47A shows a current position of catheter tip C1501 in a cross section of the lumen of the artery, based on the calculated distances from the artery walls C1503. In some embodiments, the calculation assumes a circular shape of the artery. Assuming a triangular configuration of the transceivers, a center of the catheter tip C1513 is determined. In some embodiments, the location of catheter tip C1513 is dynamically monitored. Optionally, catheter tip C1513 is repositioned by the user according to a current indication of the location. For example, a user may reposition tip C1513 in a center of the artery, for example for evenly applying ablating energy towards the artery walls.

FIG. 47B shows fluctuations in the measured artery diameter as a function of time, in this example during a 10 second time period. Blue line C1507 shows the diameter pulsation waveform. The diameters measured during systoles are marked by the red triangles C1509. The diameters measured during diastoles are marked by the green triangles C1511. An average of the differences (deltas) between systolic artery diameters and diastolic artery diameters can be calculated, in this example an average delta of 0.06 is observed. In some embodiments, the average delta in diameter is determined before, during, and/or after a denervation treatment. Optionally, by combining the diameter delta with other measured parameters such as blood pressure, artery stiffness can be deduced, optionally indicating an effectiveness of a denervation treatment.

FIG. 47C shows an estimation of a location of catheter tip C1513 with respect to the center of the artery lumen. In some embodiments, a movement range of the catheter tip inside the artery is estimated. In some embodiments, a stability of the catheter tip is estimated, for example over time.

Exemplary Combinations of Methods for Estimating a Level of Artery Restraint and/or Hemodynamic Properties of the Artery The following is a description of some exemplary combinations of the methods described herein. Some embodiments of the invention may include applying one or more of the methods, or various components of the methods, to estimate physiological changes such as a change in blood flow rate or a change in artery restraint to deduce the effectiveness of a denervation treatment. In some embodiments, the methods are applied simultaneously, for example blood flow velocity and arterial diameter are approximated at a specific time period and/or at a specific region of interest along the artery. In some embodiments, one or more of the methods are applied periodically, such as between ablation periods of denervation procedure. In some embodiments, one method is applied continuously, and the other method applied periodically. For example, a heat dissipation rate of the transceiver is estimated at certain time points, for example every 5 seconds following excitation of a transceiver. In another example, a diameter of the artery is measured continuously over a period of time, for example to deduce a mean diameter.

FIG. 48 shows experimental results of an in vivo experiment in swine for estimating artery restraint according to blood pressure and arterial diameter, according to some embodiments of the invention. In some embodiments, to provide a measure of the artery stiffness, the Young's modulus of the tissue comprising the artery wall is estimated. In some embodiments, a diameter of the artery is estimated along with a measure of blood pressure amplitude, and a Young modulus (E) is calculated, using the following equation:

$$E = \frac{\Delta P}{\Delta D/D}$$

wherein D is a mean diameter of the artery, estimated for example by tracking a diameter at a specific location within the artery over time;
ΔD is a difference between a diameter of the artery at a specific time point, and the diameter mean; and
ΔP is a difference between blood pressure measured at the specific time point, and a blood pressure mean, estimated for example by tracking the arterial blood pressure over time.

FIG. 48 shows Young modulus estimations at various time points during the denervation treatment. Young modulus estimations at the left renal artery are indicated by square markers C1601, and Young modulus estimations at the right renal artery are indicated by circles C1603. Also presented on the graph are lines indicating the denervation treatment at different times, a dashed line C1605 indicating right renal artery treatments, and a full solid line C1607 indicating left renal artery treatments. Denervation treatments followed by blood pressure and arterial diameter estimations were performed at three locations along each of the arteries: a location proximal to the aorta (i.e. near the renal artery ostium) indicated by blue markings, a middle location indicated by red markings, and a distal location closer to the kidney indicated by purple markings.

Blood pressure measurements were performed using a pressure transducer connected externally to the denervation catheter. Optionally, blood pressure measurements can be performed using a pressure transducer mounted onto the denervation catheter, or by using any other sensor and/or device adapted for measuring arterial blood pressure.

Arterial diameter estimations were performed by analyzing a sequence of echo signals returning from the artery walls and received by ultrasonic transceivers, for example using the method for determining a diameter of an artery described herein.

As suggested by the results shown at FIG. 48, in both left and right arteries, the estimated Young modulus the artery wall tissue is generally characterized by a decreasing trend which is observed as the treatment progresses. Optionally, the lower Young modulus values measured post treatment indicate a reduced stiffness of the artery walls. Optionally, the reduced stiffness of the artery walls is related to a change in the artery restraint—as less neural signals are sent to the restraining muscles of the artery due to denervation, the restraining level decreases, and the elastic properties of the artery walls are improved. Optionally, improved elastic properties are associated with an increased volumetric flow rate. Optionally, the reduced Young modulus values indicate that the denervation treatment was effective.

FIGS. 49A-B show experimental results of an in vivo experiment in swine models for estimating blood flow rate according to a cooling time constant of a transceiver and arterial diameter, according to some embodiments of the invention. In some embodiments, an ultrasonic transceiver is excited by a series of short duration, low power excitations. In some embodiments, a temperature sensor such as a thermistor and/or thermocouple is configured in proximity to the transceiver, for example mounted on the catheter adjacent to the transceiver, so that a current temperature of the transceiver can be measured.

In some embodiments, a cooling time constant of the transceiver is estimated according to the temperatures measured following the excitation. Optionally, the cooling time constant is calculated as the temperature drop to 1/e of the maximal temperature value of the transceiver. FIG. 49A shows cooling time constants estimated at the right renal artery (indicated by circles C1701), and left renal artery (indicated by squares C1703) of the swine. Also presented on the graph are lines indicating the denervation treatment at different times, a dashed line C1705 indicating right renal artery treatments, and a full solid line C1707 indicating left renal artery treatments. Denervation treatments and measurements of cooling time and diameter were performed at three locations along each of the arteries: a location proximal to the aorta (i.e. near the renal artery ostium) indicated by blue markings, a middle location indicated by red markings, and a distal location closer to the kidney indicated by purple markings.

The cooling time constants in FIG. 49A are shown as a function of time. The inventors have concluded that the cooling time constant of a transceiver is not affected by and/or associated with the power level of the transceiver excitation.

The inventors have concluded, based on in vitro experiments, that a cooling time constant is proportional to the flow velocity. By combining estimations of the flow velocity (determined according to cooling time constants) and artery diameter estimations, for example using methods described herein, renal blood flow rate can be estimated.

FIG. 49B shows the flow rates estimated at the right renal artery (indicated by circles C1709), and left renal artery (indicated by squares C1711) of the swine, corresponding with the above described treatment times and locations. As suggested by the results shown at FIG. 49B, flow rate values measured in both arteries post treatment are, in general, higher than flow rates measured before and/or during the treatment. Optionally, the higher flow rates indicate that the denervation treatment was effective.

FIGS. 50A-B show experimental results of an in vivo experiment in swine for estimating blood flow rate according to heat dissipation rate of a transceiver and arterial diameter, according to some embodiments of the invention.

In some embodiments, for example using methods described herein, such as by using a temperature sensor in proximity to a transceiver, a heat dissipation rate of the transceiver is measured during excitation. Optionally, the heat dissipation of the transceiver depends on the power level of the excitation. FIG. 50A shows heat dissipation rates measured at the right renal artery (indicated by circles C1801), and left renal artery (indicated by squares C1803) of the swine. Also presented on the graph are lines indicating the denervation treatment at different times, a dashed line C1805 indicating right renal artery treatments, and a full solid line C1807 indicating left renal artery treatments.

Denervation treatments, followed by measurements of heat dissipation rate and artery diameter estimation, were performed at three locations along each of the arteries: a location proximal to the aorta (i.e. near the renal artery ostium) indicated by blue markings, a middle location indicated by red markings, and a distal location closer to the kidney indicated by purple markings. Optionally, the heat dissipation rate depends on the power level of the excitation.

The inventors have concluded, based on in vitro experiments, that the heat dissipation rate of the transceiver is proportional to the flow velocity by power law relation. By combining estimations of the flow velocity (determined according to a heat dissipation rate of one or more transceivers) and artery diameter estimations, for example using methods described herein, renal blood flow rate was estimated.

FIG. 50B shows flow rates measured at the right renal artery (indicated by the red circles), and left renal artery (indicated by the blue circles) of the swine, corresponding with the above described treatment times and locations. Follow up measurements of blood pressure were performed 30 days and 90 days after the treatment, and a decrease in blood pressure was observed in both.

A Method for Assessing Denervation Effectiveness Using Neural Stimulation

FIG. 51 is a flowchart of a method for assessing renal denervation effectiveness which incorporates stimulation of the afferent and/or efferent renal nerves, according to some embodiments of the invention. In some embodiments, the method comprises comparing a response to neural stimulation by estimating a physiological parameter before and after a renal denervation treatment, and indicating the effectiveness of the treatment according to changes in the response to stimulation.

In some embodiments, a physiological parameter is estimated over a period of time, for example a time period long enough to deduce a baseline (C1901). The physiological parameter may be an intra-arterial measure, such as an artery diameter and/or changes in a diameter thereof, arterial blood pressure, blood flow velocity, changes to viscoelastic properties of the artery, and/or combinations of them, for example a combination of blood flow velocity and artery diameter which can indicate blood flow rate. Additionally or alternatively, the physiological parameter may include external measures such as heart rate and/or blood pressure. Additionally or alternatively, the physiological parameter may include muscle activity level. Additionally or alternatively, the physiological parameter may include catecholamine levels (such as norepinephrine) or other hormones. Additionally or alternatively, the physiological parameter may include blood plasma concentration.

In some embodiments, physiological parameters are estimated using an ultrasonic device and/or methods as described herein, for example a diameter of the artery and/or changes in a diameter thereof are estimated by analyzing echo signals received by ultrasonic transceivers positioned within the artery, or in another example blood flow velocity is estimated according to a heat dissipation rate of a transceiver. Additionally or alternatively, other devices are used, for example, referring to measurements related to artery diameter and/or hemodynamic properties, a duplex Doppler ultrasound device can be used externally to the artery.

In some embodiments, a parameter is measured over a period time, for example ranging between 5-30 minutes. Optionally, the duration is set according to a time required for stabilization of the measured parameters. Optionally, the duration is set according to the time period required for establishing a reliable baseline of the parameter. In some embodiments, the parameter is measured continuously. Alternatively, the parameter is measured in various time intervals, for example every 1 second, every 10 seconds, every minute, every 10 minutes, or any intermediate, lower or higher time intervals.

While the measurement of the selected one or physiological parameters continues, a stimulation of the afferent and/or efferent renal nerves is provided (C1903). In some embodiments, the method comprises a systemic stimulation, for example including evoking a response of the sympathetic nervous system which may also affect renal efferent signals. Alternatively, the method comprises evoking a local response of the kidney, which may affect sensory afferent signals from the kidney. Optionally, stimulating one kidney may induce a change in the neural activity of the other kidney. Optionally, activation of sympathetic efferent nerves may cause activation of sensory afferent nerves, and vice versa.

Various methods may be applied to create such stimulation. Some of the methods may be suitable for sympathetic stimuli in human; others may be suitable for sympathetic stimuli in animals, for example while performing in vivo experiments.

In some embodiments, stimulation is applied over a period of time. Optionally, stimulation is applied continuously. Alternatively, stimulation is applied periodically, with pre set time intervals between stimulations. Optionally, a single stimulation signal is applied. A duration of the stimulating signal or series of signals may depend on the type of stimulation provided, and may range, for example, between 0.5-10 minutes, 5-20 seconds, or intermediate, shorter, or longer time periods.

Examples for sympathetic stimulation of efferent neural activity include the following methods, some of which were presented in previous art, and/or combinations of them:

a. applying a cold pressor test, for example by immersing the patient's hand in ice-cold water (between 0-3° C.) for 1-2 minutes. The cold pressor test may activate the sympathetic nervous system and cause elevated blood pressure in response (Loyke, 1995). Additionally or alternatively, the cold pressor test may cause changes to any of the physiological parameters described herein.

b. having the patient perform a static fatiguing handgrip exercise by voluntarily contracting the arm, and measuring blood pressure by inflating a blood pressure cuff around the arm. Optionally, the handgrip exercise activates the sympathetic nervous system and causes an increase in blood pressure and an increase in renal vascular resistance. The renal vascular resistance is calculated according to renal blood flow velocity, measured using a duplex Doppler ultrasound device (Momen, 2005).

c. having the patient perform a handgrip exercise at graded intensity, by voluntarily contracting the arm, and measuring blood pressure by inflating a blood pressure cuff around the arm. Optionally, the handgrip exercise activates the sympathetic nervous system and causes an increase in renal vascular resistance, The renal vascular resistance is calculated according to renal blood flow velocity, measured using a duplex Doppler ultrasound device (Momen, 2005).

d. applying a cold pressor test and tilting the patient's head up. Optionally, head tilting is related to the renin-angiotensin hormone system that regulates blood pressure and fluid balance (Mangos, 2012).

e. applying a cold pressor test and injecting sodium nitroprusside to activate the sympathetic nervous system (Vase, 2011).

f. injecting furosemide, which is a diuretic substance, causing stimulation of renal sympathetic nerve activity and affecting plasma renin activity (Peterson and DiBona, 1995).

g. applying a cold pressor test and having the patient perform a mental arithmetic stress test, for example for 5 minutes, while distracting the patient, for example by talking to the patient, ringing a bell, and/or using any other type of distraction. Optionally, elevation of blood pressure, heart rate, epinephrine and norepinephrine levels is measured in response (Maki, 1992).

h. cooling the body skin surface, for example by circulating water in 15-18° C. in a designated suit for 20 minutes, may cause renal vasoconstriction as measured using a duplex Doppler ultrasound device (Wilson 2007).

i. applying a localized cold stimulation, for example using a hand cuff filled with water at a low temperature, such as 10° C. (Bornmyr 2011).

j. applying a thermal stimulus using a water perfused thermal suit, optionally causing changes in blood pressure, heart rate, and/or sweating (Fechir et al., 2009).

k. electrically stimulating the renal nerves using low intensity RF delivered by a catheter to the ostium of the renal artery, optionally causing changes in blood pressure, heart rate, and/or catecholamine levels (which may be elevated following such stimulus) (Chinushi et al., 2013).

l. intraventricular injection of angiotensin II, which optionally stimulates the sympathetic nerves and/or elevates the mean arterial pressure (Dorward and Rudd, 1991).

Examples for sympathetic stimulation of afferent (sensory) neural activity include the following methods, some of which were presented in previous art, and/or combinations of them:

a. bradykynin and/or adenosine injection to one or both renal arteries, which affects the renin-angiotensin II system, causing dilation of the renal artery and optionally reducing blood pressure. In response, sensory (afferent) nerves are activated.

b. electrically stimulating the renal nerves using low intensity RF delivered by a catheter to the ostium of the renal artery, optionally causing changes in blood pressure, heart rate, and/or catecholamine levels (which may be elevated following such stimulus) (Chinushi et al., 2013).

c. intraventricular injection of angiotensin II, which optionally stimulates the sympathetic nerves and/or elevates the mean arterial pressure (Dorward and Rudd, 1991).

In some embodiments, a norepinepherine spillover method (Esler et al., 1988) is used. The method includes infusing radio-labeled norepinpherine (NE) to the renal artery, for example delivered by a catheter, and estimating efferent nerve activity according to the clearance level of the labeled NE. Optionally, blood and/or plasma samples are collected and the level of labeled NE in a sample is detected. In some embodiments, the NE spillover method is applied before denervation treatment, for example 1 hour, 1 day, 3 days, 1 month or any other time before the procedure, and re-applied after the procedure, for example 1 hour, 1 day, 3 days, 1 month post denervation to deduce the effectiveness of the treatment.

Following the stimulation of renal nerve activity, the measurement of the one or more selected physiological parameters continues (C1905). Optionally, the measurement is extended to a duration that is long enough to deduce a post stimulation baseline.

Once the pre-denervation response to stimulation of the one or more selected physiological parameters is acquired, a renal denervation treatment is performed (C1907). Optionally, treatment is performed using the ultrasonic device described herein, by applying ultrasonic energy from within the artery lumen to denervate nerves, for example nerves that are embedded within the soft tissue surrounding the artery. Other devices adapted for renal nerve ablation may be used for denervation treatment as well.

At C1909, before repeating the physiological parameter measurement, the method includes waiting a predefined period of time, for example ranging between 1-60 minutes, such as 2-10 minutes, 15-30 minutes, 15-60 minutes, and/or intermediate, larger or smaller ranges of time periods. Optionally, the denervation treatment affects the viability and/or functionality of the targeted nerves, thereby affecting the sympathetic activity, causing changes to one or more physiological parameters for example as described herein. Optionally, following the treatment, sympathetic stimulation has a different effect on arterial parameters such as arterial stiffness, blood flow rate, arterial diameter, and/or any other parameters compared to the effect of sympathetic stimulation before the treatment.

The following steps of the method (blocks C1911-C1915) include repeating the steps described at blocks C1901-C1905, post denervation. In some embodiments, a measurement of the selected one or more physiological parameters is repeated after the denervation treatment and the waited time period (C1911). When a post-denervation baseline is acquired, neural stimulation is provided again (C1913) while the measurement of the parameter continues. Optionally, the selected method of neural stimulation is similar to the method performed before the denervation treatment, to eliminate possible physiological changes which may be associated with a different stimulation method, and to induce a similar effect on the nerve activity as was induced before the denervation treatment. Following the stimulation, the measurement continues until a post denervation, post stimulation baseline of the one or more selected physiological parameters is acquired (C1915).

To determine the effectiveness of the treatment, the measurements acquired in response to stimulation before the denervation treatment and in response to stimulation after the denervation treatment are compared (C1917). Optionally, some physiological parameters, such as artery-related parameters (diameter, stiffness, viscoelastic properties, etc.) are directly affected by the modulation of the nerves due to denervation, while other parameters, such as heart rate or catecholamine levels may be affected indirectly. For example, a change in sympathetic artery restraint may affect the arterial blood pressure, which in turn may affect the heart rate.

In some embodiments, a change indicating that the treatment was effective includes detecting a rise in a parameter, for example detecting a higher renal blood flow rate as compared to the flow rate before denervation. Additionally or alternatively, a change indicating that the treatment was effective includes detecting a drop in a parameter, for example detecting a lower blood pressure than as compared to blood pressure before denervation. Additionally or alternatively, a combination of a rise in one parameter and a drop in a second parameter indicate an effective treatment.

In some cases that involve sympathetic stimulation, for example using an adenosine injection and/or a cold pressor test, it is expected that the stimulation will temporarily increase the stiffness of the artery wall, thereby reducing the flow temporarily, for example for 1 minute, 5 minutes, 10 minutes, or intermediate, shorter or longer time periods. Following the stimulation, the artery will recover, and the stiffness level and flow will return back to their initial state. Optionally, a time scale and durations of these changes are correlated with a temporary rise in blood pressure associated with the neural stimulation, as reported in literature.

A Method for Estimating Arterial Stiffness Using Ultrasonic Elastography

FIG. 52 is a flowchart of a method for estimating arterial stiffness, or a change in arterial stiffness, using ultrasonic elastography.

In some embodiments, ultrasonic elastography technique (Korte et al., 1998) is applied to determine the effect of a denervation treatment. Briefly described, ultrasonic elastography is an imaging modality which includes acquiring an elastogram, which is a strain image obtained from tissue when stress is applied to the tissue. The technique is based on the assumption that stiff regions in the tissue undergo less deformation than soft regions in the tissue when stress is applied to the tissue, forming contrast variations in the strain image. The strain image may represent the Young's modulus distribution, indicating a level of stiffness.

In some embodiments, elastograms of the renal artery wall are acquired (C2001). In some embodiments, elastograms are acquired at systolic and/or diastolic stages in the cardiac cycle. Optionally, the changing blood pressure induces varying stress on the artery walls, resulting in varying strain levels. An intravascular ultrasonic catheter, for example as described herein, may be used for delivering the ultrasound pulses. Echoes originating from a stiff region in the tissue, where deformation is relatively small, will be less distorted than echoes originating from a soft region in the tissue.

In some embodiments, once elastograms of one or both renal arteries are acquired, for example a set of two elastograms—one obtained during a systolic stage and a second obtained during a diastolic stage, a denervation treatment is performed (C2003). In some embodiments, during and/or following the treatment, a second set of elastograms is acquired (C2005). Optionally, the elastograms are obtained from an artery location similar to the location of the first set. In some embodiments, the pre-denervation set of elastograms is compared to the post-denervation set of elastograms, for example to estimate a change in stiffness (C2007). Optionally, a pre-denervation elastogram of a systolic stage is compared to a post-denervation elastogram of a systolic stage. Additionally or alternatively, a pre-denervation elastogram of a diastolic stage is compared to a post-denervation elastogram of a diastolic stage. Additionally or alternatively, a pre-denervation elastogram of a diastolic stage is compared to a post-denervation elastogram of a systolic stage, or any other combination thereof.

In some embodiments, changes in the artery lumen area are detected, indicating a change in distensibility of the artery, resulting from the denervation treatment. In some embodiments, an artery diameter estimation and/or an estimation of a change in artery diameter, for example between the systolic and diastolic stages, is combined with the elastography results to deduce the effectiveness of the treatment.

Methods for Echo Signal Processing

FIG. 53A is a general flowchart of methods which include determining a distance to an artery wall (D101), according to some embodiments of the invention.

In some embodiments, a distance to an artery wall includes a distance between at least a portion of an intravascular device, such as an ultrasound catheter, and a vessel wall. In one example, the distance between an ultrasonic transceiver and the renal artery wall is determined. In some embodiments, a distance measurement can be applied for assessing the effectiveness of a renal artery denervation treatment. In some embodiments, a distance measurement can be applied during a denervation treatment, for example for controlling a positioning of the device in the artery with respect to the artery walls.

In some embodiments, a distance measurement includes monitoring a minimal distance to an artery wall D103, for example during and/or in between ablation periods. Optionally, monitoring includes establishing a safe distance from an artery wall for preventing damage such as overheating of the tissue. In some embodiments, positioning of the device within the artery can be adjusted according to an estimated distance from the wall.

In some embodiments, a distance measurement includes estimating a diameter of the artery and/or estimating artery wall movement (D105). Optionally, changes in the artery wall location during a cardiac cycle are estimated, for example a difference in artery diameter between a systolic state and a diastolic state. In some embodiments, a diameter and/or wall movement measurement can be combined with a measure of a different physiological parameter, such as blood pressure, blood flow velocity, and/or blood flow rate, to deduce an effectiveness of a renal denervation treatment. Optionally, artery diameter and/or artery wall movement measurements are analyzed to deduce a level of arterial stiffness, augmentation, and/or arterial restraint.

In some embodiments, the processing methods for distance estimation make use of natural changes to the artery wall due to pulsation, for example during a cardiac cycle. Optionally, a changing pressure between the systolic and diastolic stages of the cycle causes periodical movement of the artery wall. As this movement is characterized by a repetitive increasing and decreasing amplitude, it may allow differentiating between a signal that is a result of artery wall movement or an artery wall current location, and a relatively constant noise, for example a ringing artifact.

FIG. 53B is a flowchart of a general method for separating echo signals recorded through a single channel, which were received from multiple locations such as artery walls.

In some embodiments, the method includes recording signals from multiple locations through a single channel (D107). Optionally, the number of locations is equivalent to a number of receiving elements configured on the intravascular device, for example a device with three ultrasonic transceivers may receive signals from three corresponding artery wall directions. Optionally, the signals are recorded through a single channel. Optionally, recording through a single channel reduces the number of cables and/or other electrical wiring required for transmitting the received data. A potential advantage may include minimizing a size of the intravascular device, for example a diameter of a catheter with ultrasonic transceivers may be reduced due to the limited use of cables and/or wiring.

In some embodiments, the recorded signals are analyzed by identifying equal-delay patterns of the signals, and determining a correlation between equal-delay patterns. Optionally, highly correlated patterns are assumed to arrive from the same location. A clustering algorithm is then applied to separate the correlation coefficients into groups (D109), based on a relative distance between the calculated correlations. Optionally, the number of groups is defined according to the number of locations (which optionally corresponds to a number of transceiver directions), and an additional group for separation of noise is optionally added.

In some embodiments, each group is associated with a location (D111). In some embodiments, a characterizing pattern which represents the group is determined, and a distance between a wall location and a transceiver is estimated based on the pattern and a time information associated with the group. Optionally, the characterizing pattern is a centroid profile, optionally artificial, of each clustered group. Optionally, the characterizing pattern is closest to the other members belonging to that group, and is different from the characterizing patterns of the other groups.

In some embodiments, by determining, for example, 3 or more distances between the transceivers and the artery wall, an artery diameter can be calculated using the circular coordinates defining the artery circumference. In some embodiments, by tracking distances over time, for example over one or more cardiac cycles (i.e. heartbeat periods), wall movement can be tracked. Optionally, a mean difference of the artery diameter changing during a cardiac cycle is calculated.

FIG. 53C is a general flowchart of a general method for monitoring a distance to an artery wall.

In some embodiments, the method includes recording signals reflected from the artery walls (D113), for determining a minimal distance between, for example, a transceiver and an artery wall. In some embodiments, the method is applied during a denervation treatment, for example in between energy emission for ablating nerves, to monitor a safe distance to the artery wall.

In some embodiments, the method includes transforming the signals from a time domain to a frequency domain, by applying a Fourier analysis (Fast Fourier Transform) to compute the power spectral density of the samples of the recorded data.

In some embodiments, to separate the reflected echo signal signature from noise such as a ringing artifact and/or sampling noise, band-pass noise filter and/or other noise filters are constructed (D115), for example according to various portions of the calculated power spectrum. For example, a noise filter is constructed using a relatively high frequency range segment of the power spectrum, where the signal signature is expected to be negligible.

In some embodiments, an intensity of the reflected echo signal is calculated according to the spectral density profile of the signal. Optionally, a first derivative of the intensity signal is calculated for deducing an onset of the intensity signal (D119), from which a distance to an artery wall can be calculated.

In some embodiments, a threshold is applied to determine whether the calculated distance is within a predefined safe range for providing an ablation treatment.

In some embodiments, using a therapeutic transceiver for distance monitoring purposes may introduce various constraints. For example, for the purpose of monitoring, as used in common intravascular imaging techniques, a relatively large number of damped transceivers having a wide frequency band are used. However, as the transceiver may be used for ablation of nerves as well as for distance monitoring purposes, various methods and/or algorithms may be applied to compensate, enabling a dual functioning transceiver. For example, since an undamped or partially damped transceiver provides a higher ablating efficiency, a more dominant ringing artifact may be present following excitation, masking the returning echo signals. Therefore, the signal processing procedure compensates for the use of an undamped transceiver by eliminating the ringing artifact using a compatible noise filter.

In some embodiments, the method determines a minimal distance of at least 1 mm from the artery wall. Optionally, if the minimal distance is under 1 mm, for example if the transceiver directly contacts the artery wall, an accurate distance estimation might not be provided by applying the method, since the reflected echo signal from such a short distance is masked by noise.

FIGS. 54A-E illustrate some aspects of an exemplary endovascular ultrasonic catheter device, according to some embodiments of the invention. FIGS. 54A and 54B are an angiogram and a drawing of an ultrasonic catheter inserted into a renal artery. FIG. 54C is a drawing of an exemplary ultrasonic catheter. FIG. 54D is a cross section of the distal tip of the catheter of FIG. 54C, showing an exemplary configuration of three transceivers. FIG. 54E is a cross section of a distal tip of a catheter comprising four transceivers, according to some embodiments of the invention.

FIGS. 54A and 54B show an ultrasonic catheter D201 inserted into a renal artery 203. Optionally, device 201 is inserted to the renal artery through the aorta D213, for example through standard vascular access, such as from the femoral artery.

In some embodiments, device D201 is configured for emitting and/or receiving ultrasonic energy. In some embodiments, device D201 is configured for emitting ultrasonic energy for tissue ablation, to disrupt nerves D205 surrounding the artery, for example nerves lying in the adventitia tissue layer. In some embodiments, device D201 is configured for receiving ultrasonic energy, for example receiving echo signals reflected from the artery walls, to determine a diameter of the artery and/or a distance between the device and an artery wall.

In some embodiments, device D201 comprises one or more measurement devices such as temperature sensors and/or pressure sensors and/or flow sensors D209. Optionally, using data recorded by the measurement devices, various physiological parameters such as blood flow rate, blood flow velocity, blood flow temperature, blood pressure and/or any other parameters can be calculated.

In some embodiments, device D201 is maneuvered within the artery, for example positioned in one location for performing denervation, and in another location for performing measurements. Alternatively, measurements are performed at the denervation location, for example to assess a parameter such as blood flow rate at a cross section of the artery where denervation was performed. In some embodiments, a current location of device 201 inside the renal artery is dynamically monitored, for example by analyzing data received by the transceivers and/or measurement devices, and the location is adjusted accordingly. In some embodiments, a duration of denervation treatment is adjusted according to data received by the transceivers and/or measurement devices.

FIG. 54C shows an exemplary ultrasonic catheter device D201. In some embodiments, the device comprises one or more ultrasonic transceivers D207, such as 2, 3, 4, 5, 6 transceivers or a higher number. In some embodiments, one or more of the transceivers is configured for emitting and/or receiving ultrasonic energy, by comprising an acoustic element capable of vibration, such as a piezo element.

In some embodiments, transceivers D207 are spatially arranged to direct and/or receive the ultrasonic energy circumferentially, for example arranged in a triangular configuration as shown in FIG. 54D or a quadrilateral configuration as shown in 54E. In some embodiments, the transceivers are configured to emit and/or receive ultrasonic energy from multiple directions, such as, 2, 3, 4, 5, directions or a higher number. Optionally, each transceiver is directed at a different circumferential location in the artery wall. Optionally, two or more transceivers are directed at the same circumferential location. In some embodiments, the catheter device is a uni-directional catheter, for example having one or more transceivers directed at a single location. A potential advantage of circumferentially arranged transceivers may include reducing maneuvering of the device with the artery. Another potential advantage of the circumferential transceiver configuration includes emitting ultrasonic energy in multiple directions without rotating the catheter. In some embodiments, nerves are denervated in a predetermined lesion pattern.

In some embodiments, measurement devices D209 include one or more temperature sensors such as thermistors and/or thermocouples. Optionally, a thermistor is positioned in proximity to a transceiver, for example to measure a current temperature of the transceiver. Optionally, the thermistor measures a temperature of the blood as it flows across a surface of the device. In some embodiments, a thermistor may extend away from a catheter. Optionally, a temperature recorded by the thermistor is affected by both the transceiver temperature and the blood temperature.

In some embodiments, data acquired from the measurement devices and/or from signals received at the transceivers is recorded. Optionally, the data is further analyzed. In some embodiments, the data is analyzed in real time, for providing feedback during use. Optionally, parameters such as the current catheter location and/or sampling rate and/or signal intensity and/or signal frequency and/or a duration of treatment or any other parameters are adjusted according to the analyzed data.

In some embodiments, the catheter device is connected to a signal processor (not shown in this figure). Optionally, the signal processor is connected to one or more of the transceivers. In some embodiments, the signal processor is configured for implementing an algorithm which separates echo signals reflected from multiple locations, such as the artery walls. In some embodiments, the signal processor is configured for estimating a distance to each of the locations, for example the artery walls, to monitor ablation.

In some embodiments, the signal processor is configured for estimating a physiological parameter by combining two or more measurements, for example blood flow rate can be estimated based on flow velocity that is indicated according to a transceiver cooling rate, (for example as measured by a thermistor), and a cross section area of the artery, estimated based on the detected artery diameter.

In some embodiments, a distancing device D211 is configured circumferentially around device D201, for pushing at least a portion of the device such as the one or more transceivers away from the artery walls, for example at least 1 mm away. Optionally, distancing device D211 is used for centering catheter D201 with respect to the artery walls. In some embodiments, distancing device D211 is threaded onto catheter 201.

In some embodiments, device D201 is connected, for example through a sheath, to a handle (not shown in this figure) which is positioned externally to the body. In some embodiments, the handle is used for activating the device, for example the handle may comprise a lever for opening and closing distancing device D211 within the artery.

A Method for Determining a Diameter of an Artery

FIG. 55 is a flowchart of a method for analyzing a sequence of signals received from multiple locations and recorded through a single channel, according to some embodiments of the invention.

In some embodiments, the method is applied for acoustic location of walls of an artery, for example to determine a diameter of the artery. In some embodiments, the method is applied to determine a location of a catheter tip with respect to the artery walls. Generally, the method can be applied to other signal processing implementations, which require separation of signals, and more specifically to signals recorded through a single channel.

For clarification purposes, the method will be described in the context of measurement of an artery diameter using an ultrasonic catheter device comprising 3 transceivers arranged in a triangular configuration, for example as explained above in FIGS. 2A-C.

In some embodiments, the transceivers are excited by narrow band energy in a series of short pulses, for example 1000 pulses, 500 pulses, 1500 pulses or intermediate, higher or lower number, to emit ultrasonic energy towards the artery walls. Optionally, the energy is unfocused. Optionally, excitations are provided over a time period ranging between 2.5-10 seconds, for example 3 seconds, 5 seconds, 15 seconds. The repetitive pulse frequency ranges, for example, between 100-400 Hz.

In some embodiments, the ultrasonic energy emitted by the transceivers is reflected by the artery walls. Optionally, the artery walls are moving, for example the walls may be moving periodically due to pulsation.

In some embodiments, the algorithm assumes the following conditions:

A. The signals are reflected (or, in other embodiments, emitted) from a known number of locations, or, alternatively, the number of receivers directed towards different locations is known.

B. The locations move periodically, optionally in a synchronized manner.

C. The width of the signals is larger than the Eigen wavelength of the transceiver.

D. The signals are reflected simultaneously during at least one cardiac cycle.

In some embodiments, the reflected echo signals, received by the one or more transceivers, are recorded through a single channel (D301). Alternatively, the signals may be received through multiple channels. Optionally, the recording duration following each excitation of the transceivers is defined according to cardiac cycles (i.e. measured between heartbeats), for example being as long as 1, 2, 5, 20, 100 or smaller, intermediate, or higher number of cardiac cycles.

In some embodiments, the single channel recording is arranged in a matrix, (D303), for example by segmenting the recording that was performed over time and arranging segments of the recording, for example one after the other. In one example, each column in the matrix contains recordings received following emission of a specific pulse out of the set of pulses, and each row contains samples having a similar time delay between the emission and the receipt.

In some embodiments, the single channel recording is separated. In some embodiments, separation includes determining a signal's energy during the recorded time course. Optionally, separation is based on a phase difference between the mixed signals, which may indicate a distance between the location and the transceiver. However, in some cases, superposition of the signals and/or measurement noise may interfere with the separation of the signals according to their phase differences. Therefore, in some embodiments, separation of the single channel recording is performed by analyzing equal-delay patterns of the signals (D305).

In some embodiments, an equal-delay pattern is a set of voltage values detected at a certain time delay from the emission. A measure of correlation is performed between two or more of these sets of voltage values, each set of values having a time delay that is different from a time delay of a second set.

Alternatively, in some embodiments, the patterns include reflection portions having different time delays. Optionally, for example when an intravascular ultrasound catheter is used for emitting and/or receiving the energy for acoustic location of the vessel walls, the patterns are determined in accordance to a movement profile of the catheter. Optionally, the patterns are determined in accordance to a movement profile of the vessel walls. Optionally, a sampling rate is adjusted based on one or both of the profiles.

In some embodiments, patterns reflected from the same location are highly correlated.

In some embodiments, correlations between the patterns are calculated. In some embodiments, a Pearson correlation coefficient is calculated, ranging between −1 for patterns with a negative correlation, and 1 for highly correlated patterns. In some embodiments, the correlations are calculated between samples with an interval of at least one wavelength between them, for example to prevent negative correlation as a result of two similar signals that are in opposite phases, and/or to reduce the number of analyzed samples. Optionally, the results of the correlation computation are arranged in a symmetric matrix of correlations (D307). In some embodiments, at this step, the correlation of each pattern to itself (which equals 1) is replaced by an average of adjacent correlation values.

In some embodiments, the correlation matrix is multiplied by −1, and normalized, so that the correlation values range between 0 and 1. Optionally, the new matrix is arranged as a "correlation distance" matrix, where uncorrelated patterns are distant from each other, and correlated patterns are close to each other.

In some embodiments, the calculated correlation coefficients are represented as points in a multidimensional space (D309).

In some embodiments, the points are clustered into groups. Optionally, a K-means algorithm is applied to cluster the points to groups (D311). Optionally, the number of groups is predefined, for example it may be set to 4 groups: 3 groups being 3 locations, such as the artery walls at which the three transceivers are directed, and one group being noise. In some embodiments, a threshold is applied to cluster points representing an energy level that is higher than one quarter, one third, one half, or any other fraction of the average energy level.

In some embodiments, a characterizing pattern is determined to represent each group. Optionally, the characterizing pattern is a centroid profile. In some embodiments, the K-means algorithm iteratively searches for centroids, for example 4 centroids in the example described herein, one for each group. Optionally, the centroids are artificial vectors which provide a minimal distance to the clustered points of a specific group, and/or a maximal distance to points belonging to a different group. Optionally, during each iteration, the centroids are recalculated for better fitting the clustered groups.

In some embodiments, the clustering results are validated (D313). Optionally, validating includes constructing a corresponding binary matrix, for example including a 0 to represent patterns from different groups, and 1 for representing patterns from the same group. Optionally, the normalized covariance of both matrices is a measure of their similarity, and is used to determine the quality of the clustering. For example, a normalized covariance above 0.5 indicates reliable clustering results. Additionally and/or alternatively, a measure of similarity between the matrices is provided by applying a k-nearest-neighbors algorithm to the binary matrix, and comparing the result to the original clustering.

In some embodiments, the noise group is identified. Optionally, a threshold is applied to the centroids to determine which of the groups represents noise. For example, a centroid with a maximal value below a threshold of 0.1 may be identified as the noise centroid.

In some embodiments, each of the groups is associated with a location. Optionally, a distance of each of the locations from a receiver of the signals, is estimated (D315). In some embodiments, the distance is determined according to the centroid profile. In some embodiments, a maximal value of a centroid (representing a single group) is the mean distance of the location (artery wall) from the transceiver. In some embodiments, a point (from the same group) that exceeds the median of the centroid indicates the minimal distance of the location from the catheter.

In some embodiments, the artery diameter is calculated according to the estimated distances. In some embodiments, a peak of each centroid profile is detected. The peak does not necessarily indicate an initial location of wall tissue, but may indicate an area in the tissue which caused the strongest reflection. Therefore, a threshold may be applied to detect the most proximate tissue location with respect to the transceiver. Optionally, by detecting 3 points (one corresponding to each transceiver facing the artery wall), the artery circumference is defined, and a diameter is calculated. In some embodiments, more than 3 points such as 4, 6, 8 points or intermediate or higher number of points corresponding with a number of the transceivers may be used as a coordinates for defining a circle indicating the artery circumference.

In some embodiments, a movement profile of each wall is traced (D317). In some embodiments, the movement profile is traced by finding a delay between successive time windows of the recording. Optionally, the delay is estimated by applying a cross correlation between the windows, and identifying a shift which maximizes the correlation. Additionally and/or alternatively, the delay is estimated according to a difference between the local maximum of successive time windows. In some embodiments, the identified shifts are summed, for example starting from a mean distance of each signal, to yield the distances of the location during movement.

In some embodiments, a relative location of the catheter tip with respect to the artery walls is calculated. In some embodiments, to calculate the location of a center of the catheter tip (assuming a circular tip), the following equations are applied:

$$f_i = -(x_i^2 + y_i^2) \quad A = \begin{bmatrix} x_1 & y_1 & 1 \\ x_2 & y_2 & 1 \\ x_3 & y_3 & 1 \end{bmatrix}^{-1} \cdot \begin{bmatrix} f_1 \\ f_2 \\ f_3 \end{bmatrix}$$

$$R = \sqrt{\frac{A_1^2 + A_2^2}{4} - A_3} \quad (C_x, C_y) = (-0.5A_1, -0.5A_2)$$

$(x,y)_{1,2,3}$ are the Cartesian representation of the calculated distances to the artery walls, after adding an inner radius of the catheter tip, R is the calculated radius of the artery, $C_{x,y}$ are the catheter coordinates relative to the artery center, $A_{1,2,3}$ are the three dimensional coordinates of an intermediate vector.

In some embodiments, the method includes an algorithm for eliminating a ringing artifact of the recorded signal. Optionally, the ringing artifact appears mostly during the initial recording segment. The ringing artifact may be affected by factors such as the excitation intensity and the damping of the transceivers. For example, if an undamped transceiver is used, optionally for increasing the ablation efficiency, a stronger ringing artifact is observed as opposed to using a damped transceiver. In some embodiments, elimination of the artifact is based on the assumption that the artifact is a relatively constant signal, while a reflected echo signal varies in intensity, for example due to the movement of the artery wall. In some embodiments, eliminating the artifact comprises subtracting a mean value of each equal-delay sample, from all equal delay samples, for example appearing in the matrix columns.

In some embodiments, the method includes applying a sampling algorithm for correcting sampling irregularities. Optionally, the algorithm aligns the ringing artifact before its subtraction. In some embodiments, the sampling algorithm includes increasing a sampling rate (upsampling), for example during the initial segment, cross correlating the artifact with the first received signal, determining a shift which is required to achieve a maximal correlation between the artifact and the first signal, and then decreasing the sampling rate (downsampling), for example back to the original rate.

FIGS. 56A-C are graphs of a typical recording of echo signals reflected from an artery wall, according to some embodiments of the invention.

FIG. 56A is a recording of an echo signal reflected following one excitation pulse of the transceiver, showing the voltage tracing as a function of the distance. FIG. 56B is a recording of multiple echo signals reflected following a series of excitation pulses, showing multiple voltage tracings positioned on a time vs. distance axis (can be referred to as a 90 degree rotation of the signal of FIG. 4A, accompanied by a plurality of additional recorded signals). FIG. 56C is the recording of FIG. 56B, after a ringing artifact is suppressed from the recorded signal.

In some embodiments, two types of noise are present in the recording. A ringing artifact following excitation may appear in the initial distance (time delay) segment, for example in a range up to 0.5 mm, 1 mm, 1.5 mm, indicated by the relatively high voltage levels measured across the transceiver following the excitation. A second type of noise may include sampling noise, which may be caused, for example, by a mistimed sampling.

In some embodiments, as shown in FIG. 56C, the suppression of noise, comprising a DC component of the signal, reveals a clearer echo signal pattern D401 for further analysis. Optionally, an average DC value is subtracted from the signal to filter noise.

FIGS. 57A-D are graphical representations of a clustering process for separating signals according to correlations between equal-delay patterns, according to some embodiments of the invention.

Figure 57A:
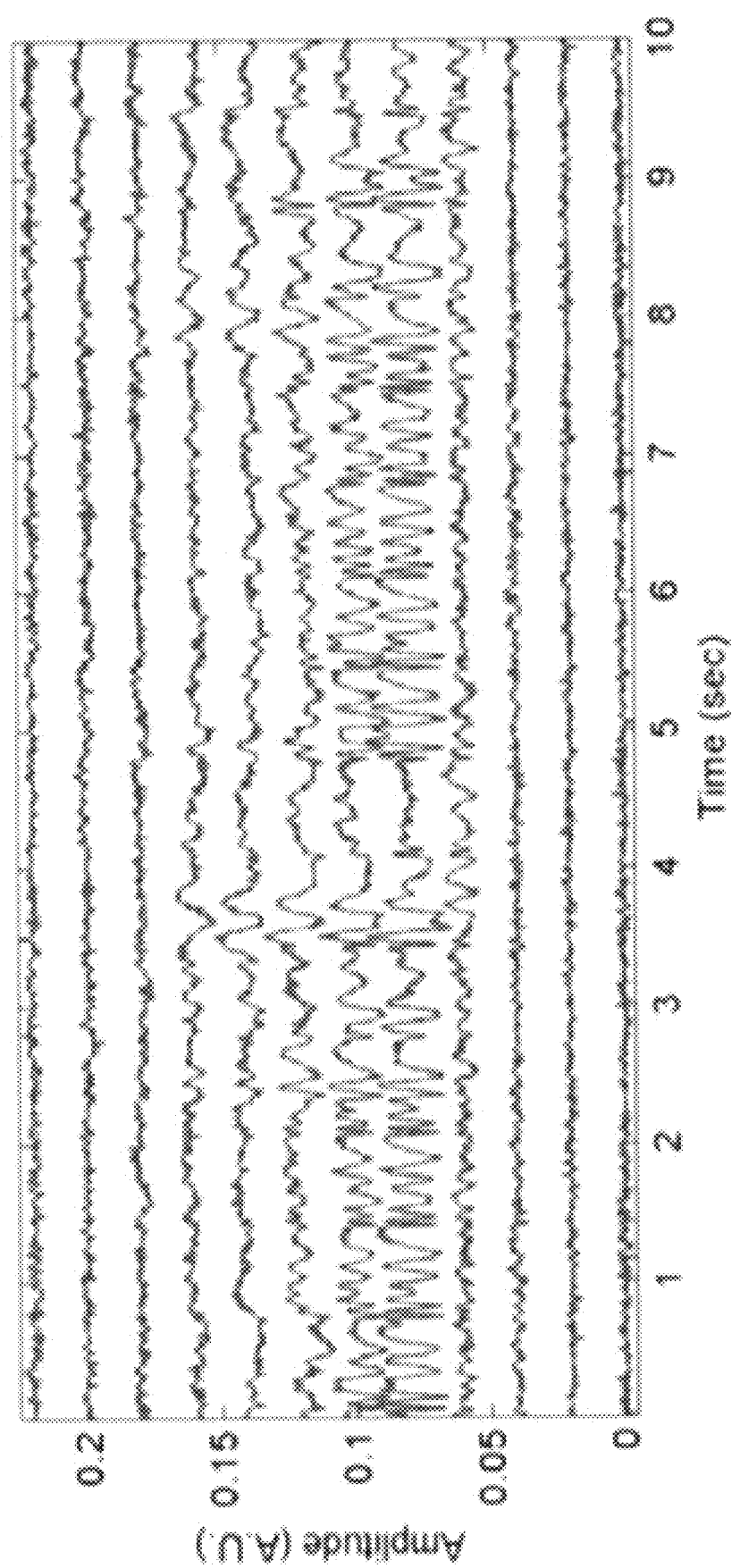

FIG. 57A shows multiple echo signals that were reflected from one or more walls of an artery, and recorded. Optionally, the signals were received by one more transceivers, for example 3 transceivers.

Figure 57B:
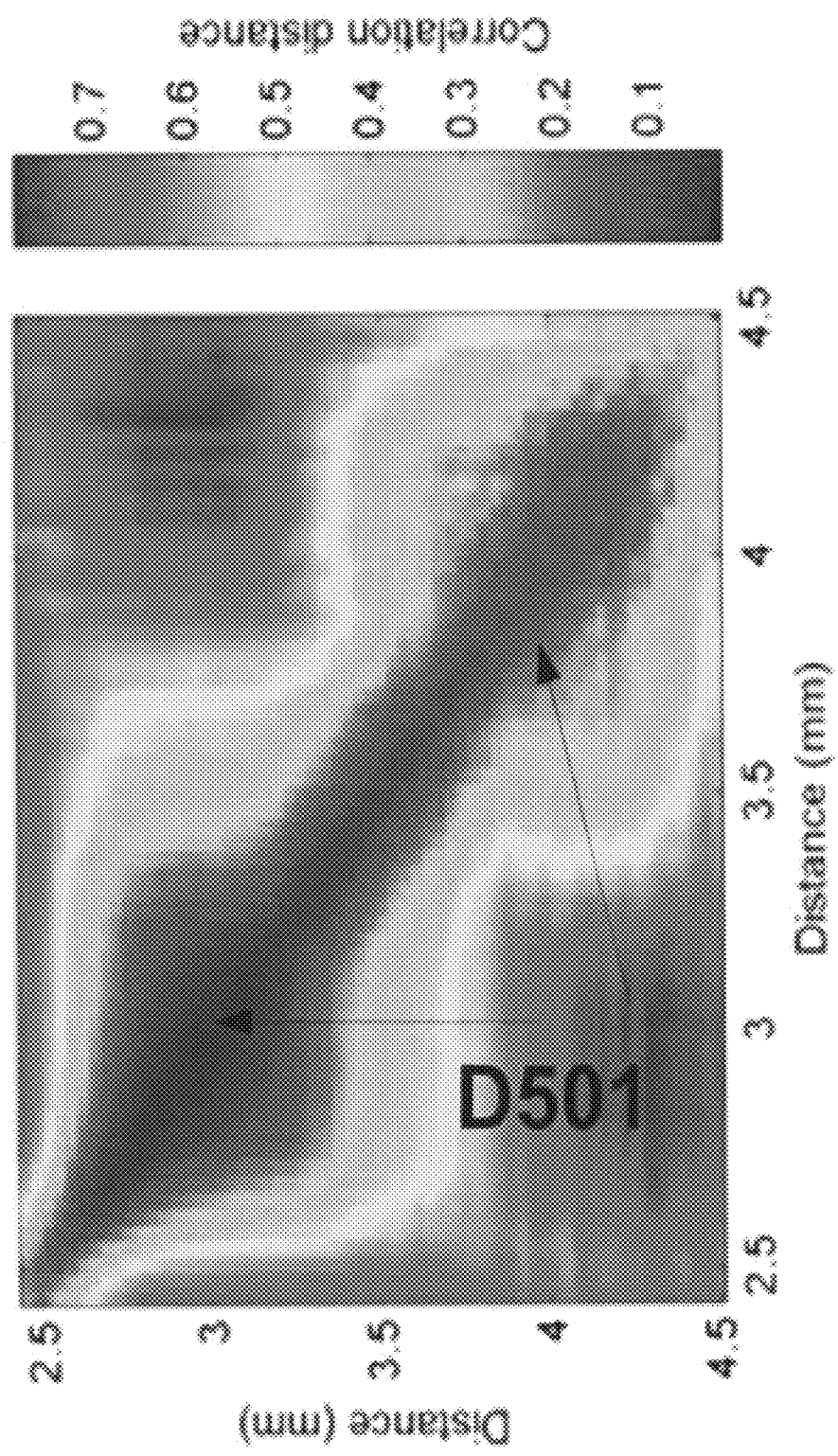

FIG. 57B shows a symmetrical correlation distance matrix, where uncorrelated equal-delay patterns are distant from each other, and correlated equal-delay patterns are close to each other. Areas having a correlation coefficient of approximately 1, marked by arrows 501, indicate samples with highly correlated patterns. Optionally, these samples were reflected from a similar location.

Figure 57C:
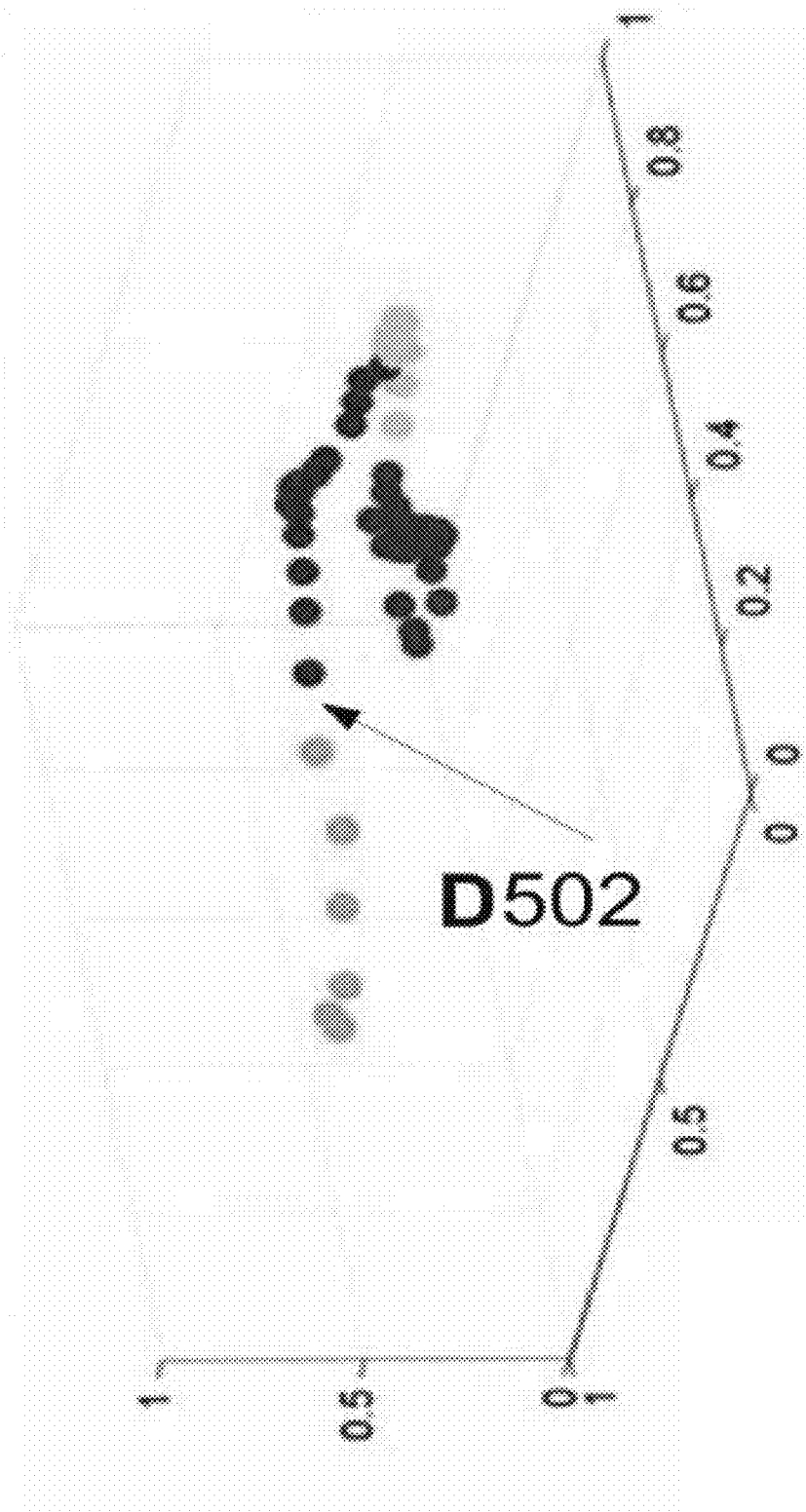

FIG. 57C is a representation of the normalized correlation coefficients as points 502 in a multi dimensional space. In this example, the points are clustered, for example using a K-means algorithm, to 4 groups, each marked by a different color: 3 groups being 3 location directions, and one group being noise.

Figure 57D:
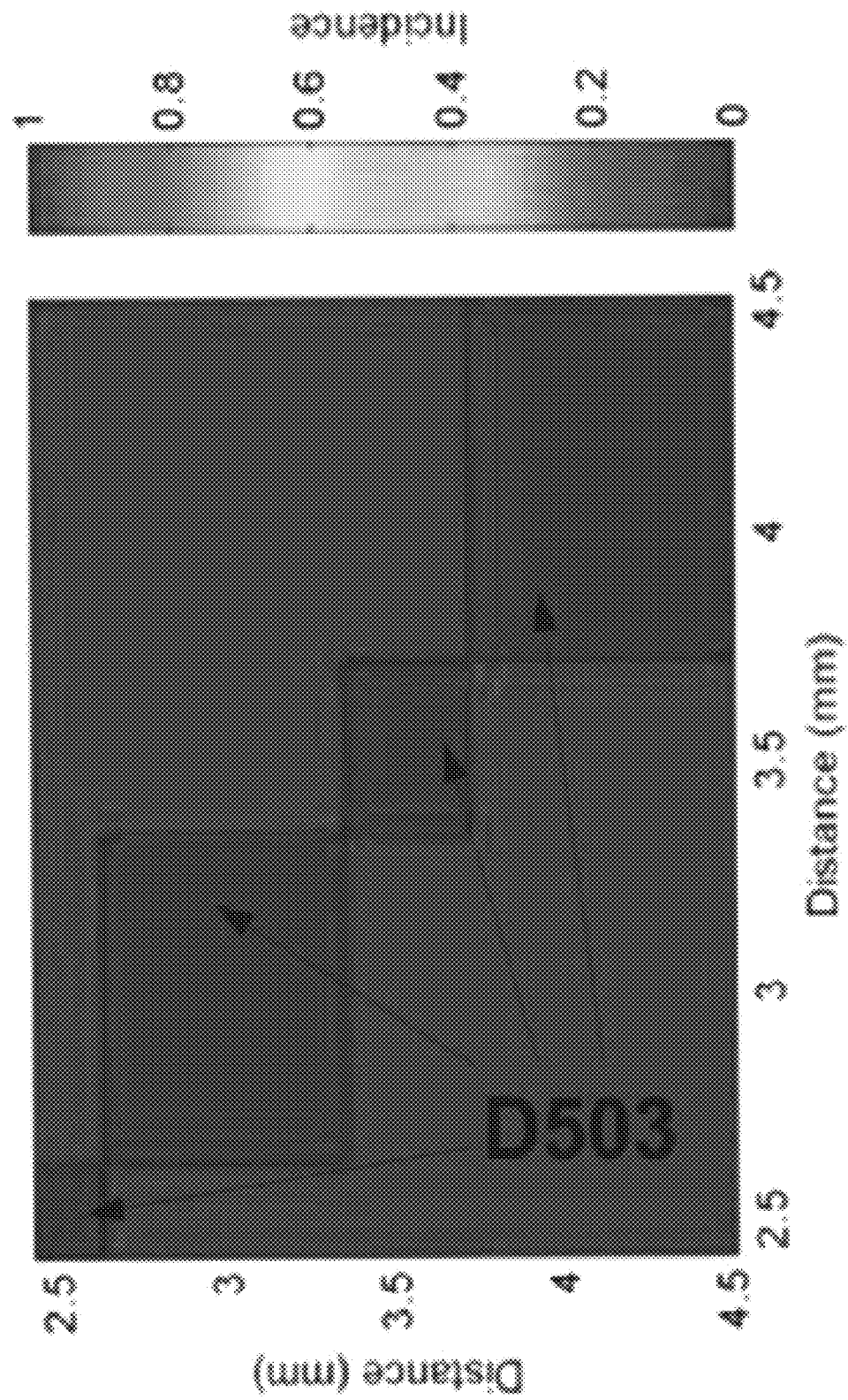

FIG. 57D shows an incidence matrix, which can be calculated for evaluating the separation into groups. Optionally, the incidence matrix is calculated by setting a value of 1 to correlations that belong to the same group and a value of 0 to correlations that do not belong to the same group. As can be observed from the graph, four rectangles 503, representing the four groups in this example (1 group for each location and another group for noise), are arranged diagonally across the incidence matrix. In some embodiments, in order to assess the accuracy of the clustering process, a matrix such as the matrix presented in FIG. 57B can be compared to an incidence matrix, for example as shown in FIG. 57D.

In some embodiments, to validate the results, an additional clustering process can be applied. Optionally, a clustering model can be trained according the incidence matrix, and the clustering results can be compared to the correlation distance matrix. This may be referred to as a "backwards" implementation of the algorithm.

FIGS. 58A-D are graphical representations of a movement profile of an artery wall, according to some embodiments of the invention.

FIG. 58A shows changes in the correlation coefficients of the 3 identified groups (for example using the methods described in FIG. 14) as a function of the distance between the artery wall and the transceiver. The mean values of the three centroid profiles, one for each of the groups, are marked by red arrowheads D601.

Optionally, the mean value of a centroid profile represents a mean distance to an artery wall. The three profiles (blue, red and green lines) indicate the extent to which each equal-distance (equal time delay) pattern of a group is close to the centroid profile of its group.

Figure 58B:
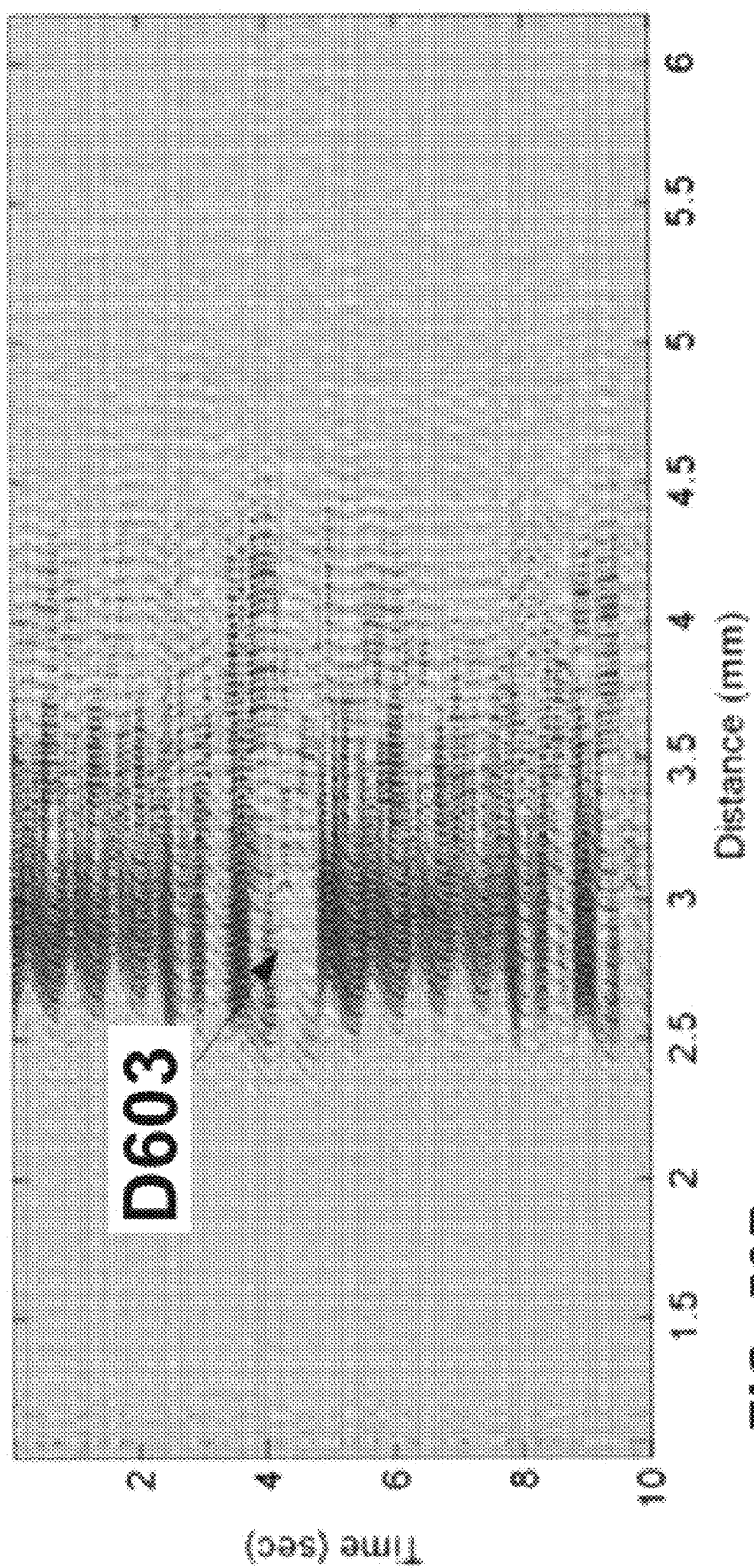

FIG. 58B shows a graph of the echo signals used for computing wall movement. Optionally, a segment D603 (indicated by the dashed lines) of the graph is selected. Optionally, the segment is selected to cover a distance range above and below the calculated mean value of a centroid profile, for example 1 mm above and 1 mm below the mean value.

Figure 58C:
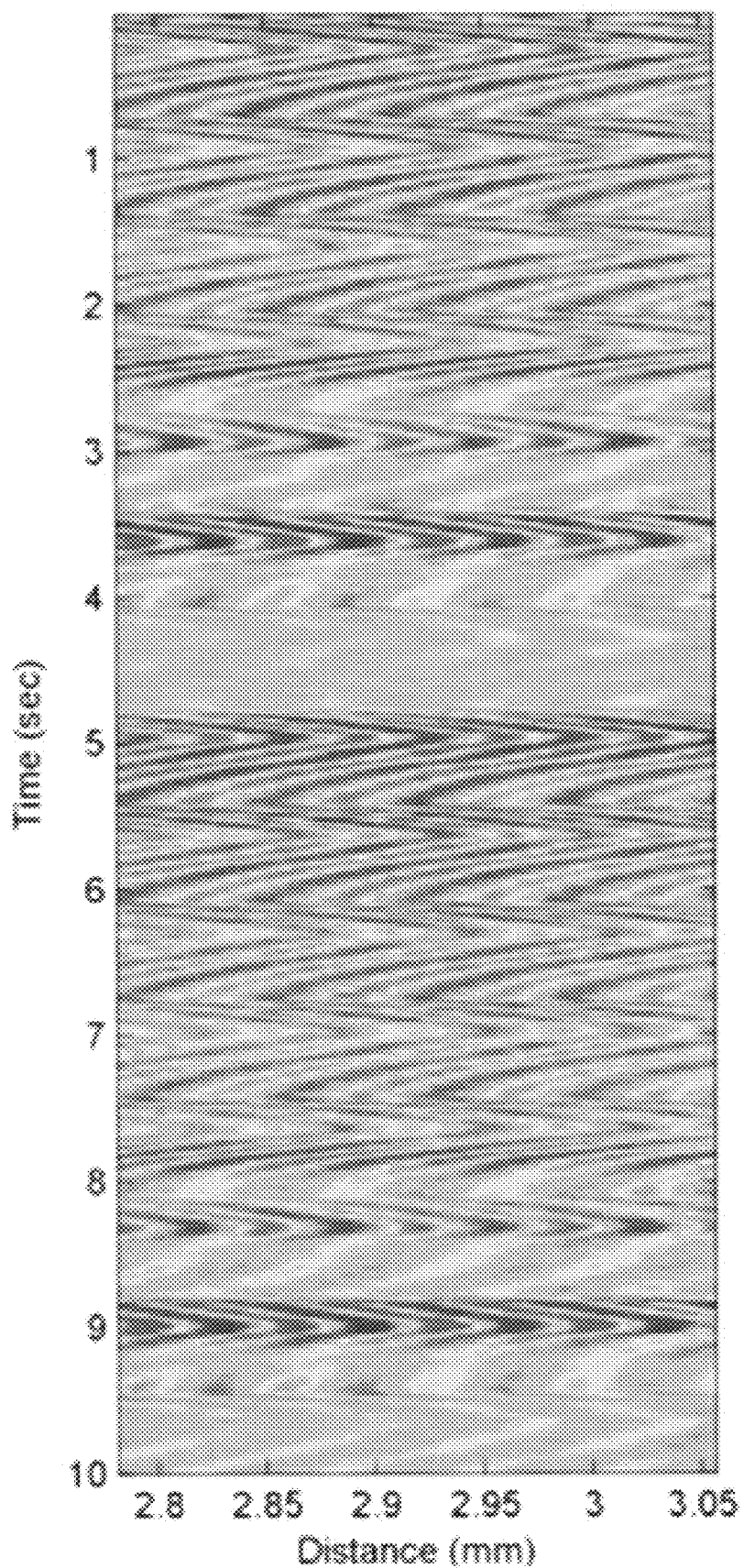

FIG. 58C is an enlarged view of a segment selected between 2.8 and 3.05 mm.

Figure 58D:
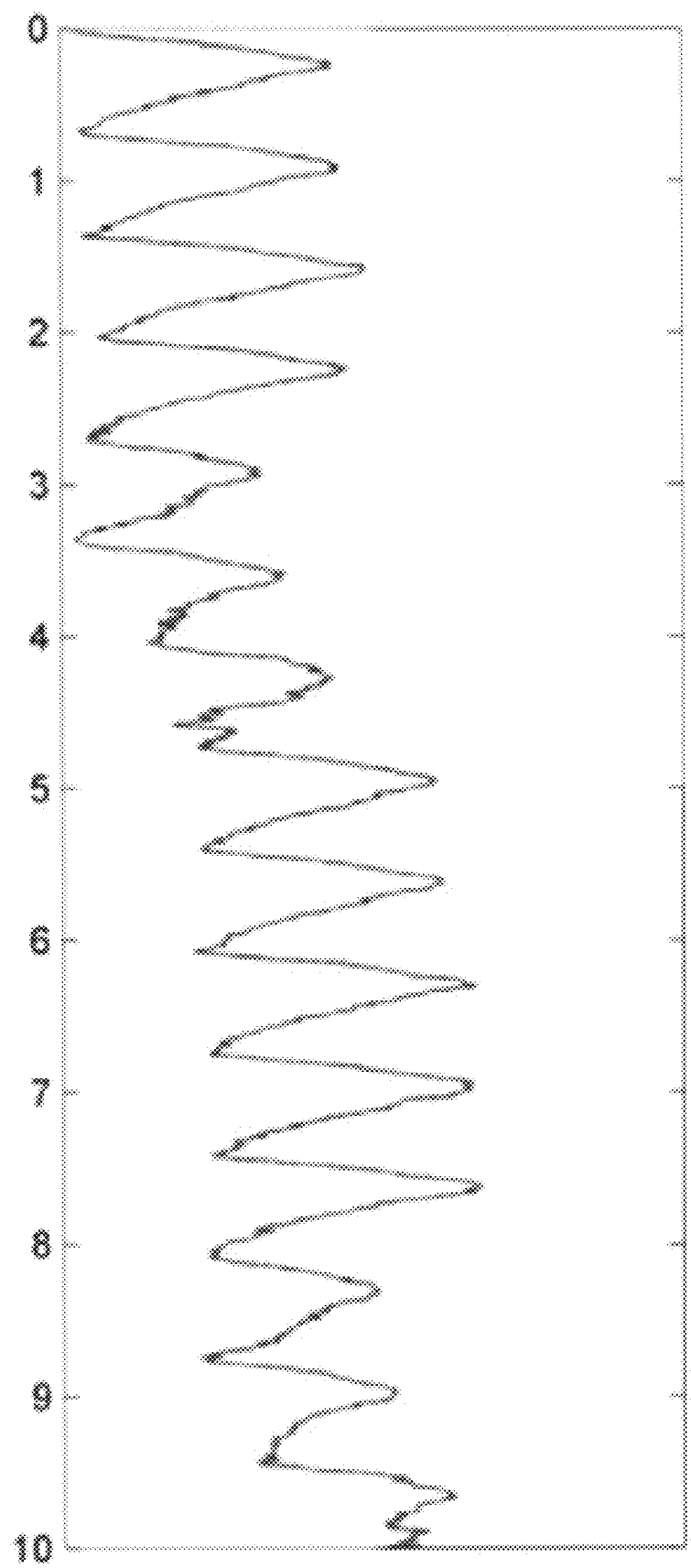

FIG. 58D shows the traced movement of the artery wall, calculated using the selected segment. Optionally, the movement was calculated by summing the shifts required to increase the correlation between two sequential time windows, for example as described in FIG. 55.

In some embodiments, synchronous artery wall movement is observed due to pulsation. The artery wall movement may change with the cardiac cycle, for example a relatively large distance difference may be observed between the diastolic and systolic stages of the cardiac cycle. Optionally, the method is applied for detecting a difference in distances (a delta) between the stages. As a consequence, the artery diameter may also change, and the method can be applied to detect a delta in artery diameter.

FIGS. 59A-C are graphical representations of a current location of a catheter tip with respect to the artery walls, according to some embodiments of the invention.

FIG. 7A shows a current position of catheter tip D701 in a cross section of the lumen of the artery, based on the calculated distances from the artery walls D703. In some embodiments, the calculation assumes a circular shape of the artery. Assuming a triangular configuration of the transceivers, a center of the catheter tip 713 is determined. In some embodiments, the location of catheter tip D713 is dynamically monitored. Optionally, catheter tip D713 is repositioned by the user according to a current indication of the location. For example, a user may reposition tip D713 in a center of the artery, for example for evenly applying ablating energy towards the artery walls.

FIG. 59B shows fluctuations in the measured artery diameter as a function of time, in this example during a 10 second time period. Blue line D707 shows the diameter pulsation waveform. The diameters measured during systoles are marked by the red triangles D709. The diameters measured during diastoles are marked by the green triangles D711. An average of the differences (deltas) between systolic artery diameters and diastolic artery diameters can be estimated, in this example an average delta of 0.06 is observed. In some embodiments, the average delta in diameter is determined before, during, and/or after a denervation treatment. Optionally, by combining the diameter delta with other measured parameters such as blood pressure, artery stiffness can be deduced, optionally indicating an effectiveness of a denervation treatment.

FIG. 59C shows a tracing of the location of catheter tip D713 with respect to the center of the artery lumen. In some embodiments, a movement range of the catheter tip inside the artery is estimated according to the tracing. In some embodiments, a stability of the catheter tip is estimated, for example over time.

FIG. 60 is a graph of a validation of artery diameter estimations compared to angiogram based diameter estimations, according to some embodiments of the invention.

To validate the diameter estimation, the inventors compared the results of the estimated diameter to a diameter measured by analyzing angiograms of the artery. The diameter estimation and angiograms were performed on a renal artery of a swine model.

Red line D801 indicates a linear fit (having a slope of 1). Colored dots D803 located along line D801 indicate measurements where the diameter estimated by applying the algorithm described herein is equal to a diameter calculated from an angiogram.

In some embodiments, a validity scale ranging between 0 to 1 (indicated by the color bar) is applied to the diameter measurements. Each measurement is given a value that indicates the reliability of the measurement. In some embodiments, the value is determined according to results of an incidence matrix, for example as shown in FIG. 57D. In some embodiments, a mean square error is calculated by thresholding the validity scale, i.e. taking into account measurements having a value lower or higher validity value than the threshold. For example, while referring to FIG. 60, a mean squared error calculated according to measurement having a validity value above 0.6 is 0.6 mm, and a mean squared error calculated according to all measurements is 0.9 mm.

A Method for Monitoring a Distance to an Artery Wall

FIG. 61 is a flowchart of a method for monitoring a distance to an artery wall, according to some embodiments of the invention. In some embodiments, the method is applied for detecting a minimal distance to tissue. In some embodiments, the method is applied for preventing thermal tissue ablation from a distance that is too close the tissue, which may result in damaging the tissue. The method may be particularly useful in confined spaces, such as a blood vessel, or any other body cavity.

In some embodiments, the method comprises directing ultrasonic energy towards tissue to cause ablation. Optionally, for example in between ablations, monitoring signals are directed towards the tissue to assure that ablation is being carried out effectively.

In some embodiments, an ultrasonic transceiver intended for intracorporeal use is inserted into a blood vessel (D901). In some embodiments, the transceiver is configured for emitting ultrasonic energy to cause tissue ablation. In some embodiments, the transceiver is a narrow band transceiver. Optionally, the transceiver's resonant frequency ranges between 10-12 MHz.

In some embodiments, the transceiver is undamped, for example to increase its ablation efficiency. Optionally, damping reduces the transceiver's efficiency, and a damped transceiver may cause excessive heating which could harm the ablated tissue and/or surrounding tissue. One of the disadvantages of using an undamped transceiver, specifically for signal detection purposes, may include a ringing artifact which adds noise to the measurement, therefore possibly making it more difficult to isolate signals from noise during processing. As the ringing artifact itself may also be reflected from the vessel wall, it may further interfere with the signals.

In some embodiments, the transceiver is connected to a signal processor. Optionally, data received by the transceiver is processed by the signal processor. Optionally, processing includes determining a distance to the artery walls, as described herein.

In some embodiments, for example before, after, and/or in between ultrasonic emission for ablation, the transceiver is excited by a series of pulse excitations for the purpose of distance monitoring (D903). Optionally, the number of pulses in a series and the corresponding sampling frequency are selected according to a duration of one cardiac cycle, for example a duration of 1 second, 1.5 seconds, 0.8 seconds and/or intermediate, higher or smaller time periods. Optionally, the sampling frequency is higher than 100 Hz, for including a range of lower frequencies such as 0-40 Hz where the reflected echo signal is dominant.

In one example, a series of 256 pulses at a frequency of 200 Hz is provided over a 1 second time period. Optionally, the monitoring signals emitted by the transceiver during the series of excitations do not cause ablation, for example since each excitation pulse is applied for a short time period. Optionally, the emitted monitoring signals are reflected by the artery walls.

In some embodiments, a plurality of transceivers are activated simultaneously. Optionally, the transceivers are excited at a similar frequency, to emit energy towards the artery walls. Optionally, ultrasound energy that is reflected by the artery walls is received by the transceivers. Optionally, the returning signals are received within a time limit of 0.2 msec, 0.5 msec, 1 msec, 3 msec, 5 msec, 100 msec, 1 second or intermediate, longer or shorter time periods from the emission. A potential advantage of acquiring signals returning from various wall directions, optionally within a relatively short time period may include dynamically monitoring changes in the artery, for example a change in diameter. Optionally, the changes indicate a change in stiffness, an occurrence of a local spasm, a widening of the artery and the like.

In some embodiments, the transceiver is configured for receiving primary echo signals reflected from surrounding tissue, such as the artery walls. In one example, for a series of monitoring pulses at a frequency of 200 Hz, a sampling frequency of 250 MHz may be used. In some embodiments, the echo signals are recorded (D905) immediately following each excitation during the series of excitations. Optionally, the transceiver is adapted to receive echo signals only during a non-emitting state.

In some embodiments, the echo signals are analyzed (D907) in order to detect a distance to the artery wall. If the estimated distance to the wall does not surpass the predetermined safe range for ablation, the transceiver is excited (D909) for emitting a beam to cause tissue ablation. In some embodiments, an acceptable distance for performing ablation ranges between 1-4 mm, as measured between an artery wall and the transceiver. Optionally, a minimal distance is determined according to the type of tissue to be ablated. Optionally, a minimal distance is determined according to a size of the blood vessel, for example according to a diameter of the blood vessel. For example, in a renal artery having a diameter of 7-10 mm, and an ultrasonic device having a diameter of 2 mm, the distance between the artery wall and the transceiver does not exceed 4 mm. Optionally, a minimal distance is determined according to a safety requirement level.

In some embodiments, a frequency of the ablation excitation ranges between 10-12 MHz. In some embodiments, the ablation excitation has an intensity ranging between 30-40 W. Optionally, the ablation excitation is provided as a continuous signal. In one example, the ablation excitation comprises a continuous sinus wave form, having a frequency of 11 MHz and an intensity of 30-35 W/cm^2. Typically, the ablation time period is 40 seconds. Optionally, other time periods such as 5, 10, 30, 50, 120 seconds or intermediate, shorter or longer time periods may be used. In some embodiments, the ablation excitations are provided at the resonant frequency of the transceiver, for example for achieving maximal vibration. Optionally, the returning primary echo signals tend to share the excitation frequency, albeit at varying phases and amplitudes.

In some embodiments, the one or more transceivers are excited at their resonant frequencies or at a frequency within a range of 10%, 5%, 20% or intermediate, larger or smaller percentages from their resonant frequencies. Optionally, a plurality of transceivers are excited at a similar frequency, for example at a weighed resonant frequency of all transceivers. Optionally, simultaneous activation reduces a time period in which a ringing phenomena is present, for example relative to non-simultaneous activation where, for example, one transceiver is excited after the other and a time period in which ringing is present may be longer. Optionally, to reduce an amplitude and/or duration of ringing, the one or more transceivers are excited at a frequency different from their separate resonant frequencies or weighed frequency.

In some embodiments, a plurality of echo signals are reflected from a wall location. Optionally, the plurality of echo signals include signals that are reflected and/or received at various time points. In some embodiments, a single signal is reflected from a wall location. Optionally, the wall location includes a portion of the wall, for example a segment of the wall circumference, a local point in the wall, a line extending along the wall. Optionally, the segment of the circumference extends in an axial direction, for example extending to a distance shorter, longer or similar to a length of the one or more transceivers.

In some embodiments, a surface of the transceiver is used for both ablation and monitoring purposes. Alternatively, separate surfaces of the transceiver may be used, for example one surface for ablation and one surface for monitoring, as long as the ablated tissue is the tissue being monitored.

In an embodiment, the monitoring and applying may be carried out using the transceiver described herein. Alternatively, a known ablation device may be used in conjunction with an ultrasonic detector.

FIG. 62 is a flowchart of a method for analyzing echo signals reflected by the artery walls for monitoring a distance to the artery wall, according to some embodiments of the invention.

In some embodiments, data received by the transceiver and recorded is arranged in a matrix (D1001). In one example, each column in the matrix contains recordings of one signal of the recorded sequence, and each row contains samples recorded at a specific time delay from the emission.

In some embodiments, a spectral statistic is computed for the recorded data. Optionally, the spectral statistic is a power spectral density. In some embodiments, a Fourier analysis (FFT) is applied to compute the power spectral density (PSD) of each sample of the recorded data (D1003). Optionally, by applying FFT, a DC component of the signal which comprises excitation artifacts can be removed. Optionally, since the artery wall moves periodically with pulsation during a cardiac cycle, removing the DC component of the signal allows deducing a current distance to the artery wall.

In some embodiments, convolution (D1005) is applied over the power spectral density window using, for example, a square kernel convolution. Optionally, convolution provides averaging which assists in marking noise (causing noise to appear as more dominant component), for further filtration of the noise. In some embodiments, a distance dimension of the convolving window is determined according to a wavelength complying with the resonant frequency of the transceiver. In some embodiments, a frequency dimension of the convolving window is determined according to a minimal frequency range interval, where variance of the signal intensity is relatively low, for example an interval of 4 Hz, 3 Hz. 6 Hz.

In some embodiments, the echo signals are isolated from noise (D1007), for further analysis of the signals. In some embodiments, various noise filters are applied to isolate the reflected echo signal signature. In some embodiments, white noise (for example a ringing artifact which may appear due the transceiver being undamped) is filtered. In some embodiments, noise originating from a mistimed sampling is filtered.

In some embodiments, a noise filter is constructed using a specific segment and/or area of the PSD matrix. In some embodiments, a noise filter is constructed by summing an initial segment of the power spectral density matrix, where an excitation artifact may be dominant. Additionally and/or alternatively, a second noise filter is constructed by summing a high frequency range of the PSD matrix, where the echo signal component is expected to be negligible.

In some embodiments, the echo signal intensity is calculated (D1009). Optionally, the echo intensity is constructed by summing a low frequency segment of each equal-distance sample, where the echo signal component is expected to be dominant.

In some embodiments, a first and/or second and/or third or a higher order derivative of the signal is calculated. Optionally, a first derivative is used for detecting an echo onset (D1011). In some embodiments, the onset indicates a specific sample at which the monitoring pulse hits an artery wall, from which it is reflected back to the transceiver. In some embodiments, an onset is detected by thresholding the first derivative of the intensity signal. Optionally, the threshold is determined according to a mean of the intensity signal. Optionally, when setting the threshold, the standard deviation of the intensity signal is taken into consideration. For example, the threshold for detecting an onset can be calculated as a sum of the mean of the intensity signal and a factor of the standard deviations, for example calculated as the intensity mean+0.3*the standard deviation, or as 0.5*the intensity mean+0.6*the standard deviation, or as 0.3*the intensity mean+0.1*the standard deviation, and/or any other combinations or factors. In some embodiments, before calculating the threshold, the derivative function is smoothed, for example by applying convolution.

Once an onset is detected, a distance between the transceiver and the artery wall is determined (D1013). Optionally, calculating a distance includes dividing by the sampling frequency, in order to transform from the frequency domain to the time domain. The result is then multiplied by the propagation speed of sound waves through blood (for example ~1.57 mm/μsec). The final result is divided by two, as it indicates the forgoing (from the transceiver to the artery wall) and returning (from the artery wall towards the transceiver) distances.

In some embodiments, the calculated distance is verified (D1015). Optionally, a possible range for the distance is defined according to a maximal diameter of the artery. For example, the maximal diameter is divided by two to calculate an artery radius. If the calculated distance is longer than the radius, the distance calculation may not comply with an actual distance between the transceiver and the artery wall. In that case, the threshold can be adjusted, for example to detect a different onset. Optionally, the threshold is automatically adjusted by the signal processor. Alternatively, the threshold is manually adjusted by a user. Optionally, the threshold is adjusted according to a current location within the artery, for example one threshold may be applied for monitoring a distance during ablation at the renal artery ostium, and a second threshold may be applied for monitoring a distance during ablation near the renal artery bifurcation.

FIG. 63 is an exemplary graph of raw recorded data which was received by the transceiver during a series of excitations. The graph indicates the voltage measured across the transceiver following each excitation. In some embodiments, monitoring excitation is provided at short pulses, for example less than 1 μsec each, at a relatively high intensity level, for example higher than 30 W, 35 W, 40 W or any intermediate or higher levels. Optionally, due to the short time duration of the pulses, the monitoring excitations do not affect the tissue.

Data shown by the exemplary graph of this figure was acquired following a series of 1000 pulses at a frequency of 400 Hz, with a time interval of 2.5 msec between excitations. In the matrix represented by this graph, each row is a recording over 7 μsec following an excitation of the transceiver. A time period of 7 μsec is equivalent to imaging of a distance of 6 mm, as shown by the horizontal axis of the graph.

When observing the graph along the distance axis, (being an actual time delay of the echo signal), higher voltages appearing at distances shorter than 2 mm may be a result of additional vibration of the transceiver following the excitation. Optionally, since the transceiver is undamped, oscillation continues passed the excitation itself (ringing artifact). Additional vibration of the transceiver is caused by returning echo signals. These may be observed, for example, at an area which is not masked by the ringing artifact, such as the area between 4-6 mm.

FIG. 64 is a power spectral density graph of equal-delay samples. The reflected echo signal signature, D1201, can be observed, in this example, at frequencies lower 10 Hz and distances (time delay) higher than 2 mm. Two types of noise masking the signal can be observed: noise due to excitation (ringing artifact) D1203, appearing mainly at a distance (corresponding to a time delay) less than 0.5 mm, and sampling noise, for example caused by a mistimed sample, which appears as spikes D1205 and D1207.

FIG. 65 shows a power spectral density graph after applying a square kernel convolution, for example the graph of FIG. 64. Optionally, convolution is performed as a preceding step to noise filtering, marking noise (and the reflected signal) more dominantly. Optionally, the echo signal signature (D1201) and the two noise factors (D1203, D1205, D1207) are detected more easily.

FIG. 66 is an exemplary graph of a noise filter constructed by summing intensity values over an initial segment of a power spectral density graph, where the noise is expected to be dominant, according to some embodiments of the invention. For example, the noise filter in this figure was constructed according to a segment up to a distance of 0.5 mm of the graph in FIG. 65. Optionally, the filter can be applied to remove the sampling noise. As can be observed from the graph, a spike D1401 at the 25-35 Hz frequency range corresponds with spike 1205 shown at FIGS. 64 and 65, and spike D1403 at the 55-65 Hz frequency range corresponds with spike D1207.

FIG. 67 shows a power spectral density graph, for example the graph of FIG. 65, after applying a noise filter, for example as shown at FIG. 66. Optionally, applying includes dividing the power spectrum by the noise filter.

FIG. 68 is a graph of a noise filter constructed by summing intensity values over a high frequency segment, where the echo signature is expected to be negligible, for example above 50 Hz, above 60 Hz, above 80 Hz, or any intermediate, higher or lower values, according to some embodiments of the invention. Optionally, summing is performed in a perpendicular direction to the summing applied during construction of the filter of FIG. 66, for example in FIG. 66 the values are summed across the rows, and in FIG. 68 the values are summed across columns.

FIG. 70 shows a power spectral density graph, for example the graph of FIG. 67, after applying a noise filter, for example the noise filter shown at FIG. 16, according to some embodiments of the invention. Optionally, applying the filter includes subtracting the intensity values of the filter form the power spectrum. As can be observed from the graph, intensity values observed at the initial segment (for example up to a distance of 0.5 mm) have been reduced in comparison the intensity values shown at the corresponding segment in FIG. 67, indicating that noise was successfully filtered.

FIG. 70 is a graph of the reflected echo intensity, for example of the echo signature indicated by D1201 in the previous figures, shown by blue line D1801. The intensity is calculated by summing a low frequency segment, for example under 10 Hz, under 20 Hz, under 40 Hz or intermediate or lower frequency range, where the echo signature is expected to be significant. Red line D1803 indicates a normalized first derivative of the intensity signal, which may assist in detecting an onset of the intensity.

Dashed line D1805 indicates an onset point of the echo signal, followed by an ascending trend of the first derivative function.

FIG. 71 is a graphical representation of a validation of the minimal distance estimations obtained using the distance monitoring method described herein. The graph includes a comparison between distances to artery walls that were estimated using the monitoring method (indicated by dots D1901) and distances to artery walls that were estimated according to angiograms of the transceiver(s) within the artery (indicated by X's D1903). Since the angiogram is only a two dimensional projection of the artery, the distance estimations according to the angiograms set an upper boundary for the results obtained using the monitoring method. For example, a distance to an artery wall as measured using the angiogram is either identical or longer than the minimal distance estimated using the method described herein. Due to a blind range caused by noise masking the reflected echo signals at distances shorter than 1 mm from the artery wall, the initial segment of the graph, where distances measured using angiograms are equal zero (i.e. the transceiver contacts the artery wall), the method may not be capable of estimating an accurate minimal distance to an artery wall. As the distance measured using the angiogram increases, distances estimated using the method indicate lower minimal distances to the artery wall, as expected.

FIG. 72 is a graphical representation of a validation of the minimal distance estimations obtained using the distance monitoring method described herein. In this validation, a distancing device was assembled on the catheter tip, which comprises the ultrasonic transceivers, to allow pushing the transceiver away from the wall. Two positions of the distancing device were selected for this validation: an open position which prevented the transceivers from contacting the artery walls, maintaining a distance of at least 1 mm from the wall, and a closed position which enabled possible contact between the transceiver and the artery walls. In measurements 1-15, the distancing device was in a closed position, as indicated by diamonds D2001 (positioned on a value of 0 mm on the distance axis). In measurements 16-30, the distancing device was in an open position, as indicated by diamonds D2001 positioned on a value of 1 mm on the distance axis. In this validation, by using the distancing device, a lower boundary was set for the distance estimations obtained by applying the monitoring method, indicated by dots D2003. Optionally, the validation described herein is applied for assessing the functioning of the distancing device.

FIGS. 73A-B are flowcharts of a method for decomposing a signal to a set of base signals and assigning the signals to a location (e.g. artery wall) based on a dictionary of probable reflections, according to some embodiments of the invention. In some embodiments, a dictionary of probable reflections is provided (D2100). Optionally, the dictionary is constructed, for example using previously known and/or current data acquired by the transceivers, for example as further described herein. Optionally, the dictionary is adjusted, for example reduced in size, based on data from a current signal intended to be analyzed (D2102).

In some embodiments, the method comprises determining the components of a sparse signal, such as a signal recorded through a single channel which comprises echo signals reflected from various artery walls. In some embodiments, the echo signals are determined and assigned to a location (e.g. artery wall) by matching them to components of a larger set of probable reflections, which is referred to hereby as a "dictionary".

In some embodiments, a ringing artifact (i.e. excitation artifact), is removed from recorded samples (D2101). In some embodiments, removing or reducing the effect of a ringing artifact for obtaining less noisy signals is performed by subtracting a mean intensity value of an equal delay sample, for example as described hereinabove, from its corresponding sample. The subtraction is performed for each of the equal delay samples of the recording. Optionally, reducing the ringing artifact is based on the assumption that the artifact is a substantially constant signal, while a reflected echo signal varies in intensity.

In some embodiments, a dictionary of probable reflections is constructed (D2103). In some embodiments, the dictionary is a set of sinusoidal Gabor functions, each function comprising a Gaussian distribution around a certain operating frequency of an ultrasonic catheter, i.e. a resonant frequency of a single transceiver, or a an operating frequency obtained by combining resonant frequencies of multiple transceivers of the catheter. In some embodiments, a probable reflection is characterized by a distance between the transceiver and the artery wall, and/or by the shape of the excitation pulse which caused the reflection. Therefore, each of the Gabor functions, representing a probable reflection, indicates a theoretical distance of the catheter from a location (e.g. artery wall), and a characteristic width of the excitation pulse, indicated by the variance of the Gabor function (distribution around the center).

In some embodiments, a dictionary is constructed per a selected catheter. Optionally, various catheters comprise different sets of probable reflections, for example because each catheter comprises transceivers of varying resonant frequencies, which may produce a different set of possible reflections.

Optionally, in some embodiments, fine tuning of the dictionary is performed (D2104). In some embodiments, fine tuning comprises adjusting the dictionary based on the current data to be analyzed. In some embodiments, a LASSO ("Least Absolute Shrinkage and Selection Operator") algorithm is implemented. Optionally, the algorithm receives the current sparse signal or a segment of the signal, and the dictionary of probable reflections, and deconstructs the signal to a minimal number of base signals. Optionally, the number of base signals is automatically assessed by the algorithm which seeks to minimize a difference between the raw sparse signal and a deconstructed signal, for example as opposed to being predefined. In some embodiments, the resulting base signals are clustered into groups, for example 3 groups. Optionally, the clustering is performed according to the vicinity and/or phase of the base signals. Optionally, the clustering process takes into account the intensities of the base signals. In some embodiments, each base signal is given a score representing its fit to the clustered group. Optionally, a new dictionary is constructed according to the clustered groups which received the highest scoring.

In some embodiments, a first recorded signal is decomposed to a set of base signals using a matching pursuit method (D2105). In some embodiments, the method comprises iteratively generating for the signal and the dictionary of probable reflections a sorted list of coefficients which comprise a solution to the sparse signal. Optionally, a solution comprises representing the echo signals (components) of the sparse signal using a probable reflection, or a combination of probable reflections, out of the dictionary. In some embodiments, the combination is a linear combination. Implementation of a matching pursuit method for analysis of ultrasonic signals has been shown by Lu et al., in a publication titled "Numerical implementation of matching pursuit for the analysis of complex ultrasonic signals", 2008.

In some embodiments, based on the solution obtained using the matching pursuit method, a distance to the location (e.g. artery wall) is determined (D2107). Optionally, by assigning an echo signal to a probable reflection or a combination of probable reflections, the distance to the wall is determined, as each of the probable reflections was characterized by a different distance between the catheter and the wall.

In some embodiments, an artery diameter and/or a distance of the catheter tip from a center of the artery are estimated according to the determined distance (D2109), for example using methods described hereinabove.

Optionally, in some embodiments, the method is repeated for successive recorded single channel signals (D2111). In some embodiments, based on the assumption that a successive signal will differ from an initial and/or preceding signal only to a certain extent, a range of probable reflections is selected out of the dictionary, thereby limiting the number of probable reflections. Optionally, the probable reflections are reduced to represent a limited range of distances, based on the distances obtained for the initial and/or preceding signal. In some embodiments, the dictionary range is dynamically changed, for example reduced, as the method is repeated for successive signals. By reducing the size of the dictionary, computation time involving iterations of the matching pursuit method may be reduced, as there are fewer options to compare to. Optionally, by reducing the size of the dictionary, the results of the distance estimations are more consistent. Consistent results may provide an advantage, for example in cases of a recording having a relatively low signal to noise ratio.

FIG. 74 is an exemplary graph of a set of probable reflections (referred to as a "dictionary"). In this example, the dictionary comprises 5425 components, or 5425 probable reflections. Generally, the number of components of a dictionary may range between 3-10000, for example 10, 200, 4000, or any other amount. Optionally, the amount of probable reflections depends on the number of excitation pulse shapes (e.g. widths) being considered and/or the number of theoretical distances being considered. A theoretical distance may range between 1-8 mm, for example 2 mm, 4 mm, 6 mm, with an exemplary resolution of half a wavelength.

Function D2201 is an exemplary sinusoidal Gabor function, out of the set of 5 functions included in this example, representing a probable reflection. The function is centered at a distance of approximately 2.75 mm. The variance of the function represents the width of the excitation pulse.

In some embodiments, energy of a probable reflection, for example as indicated by the vertical axis of FIG. 72, is normalized.

FIGS. 75A-C are exemplary graphs of a typical recording of echo signals reflected from an artery wall, according to some embodiments of the invention. FIG. 75A shows a recording of an echo signal reflected following one excitation pulse of the transceiver, showing the voltage tracing as a function of the distance. FIG. 75B is a recording of multiple echo signals reflected following a series of excitation pulses, showing multiple voltage tracings positioned on a time vs. distance axis (can be referred to as a 90 degree rotation of the signal of FIG. 75A, accompanied by a plurality of additional recorded signals). FIG. 75C is the recording of FIG. 75B, after a ringing artifact is suppressed from the recorded signal.

FIG. 76 shows exemplary results of a matching pursuit method implementation. Raw data is indicated by the blue lines. Each of the raw data signals is fitted, in this example, with a combination of 3 probable reflections comprising the dictionary. The coefficients producing the proposed combination that each of the raw data signals is fitted with are indicated by the red markings D2401.

FIGS. 77A-B are graphical representations of an estimation of average artery diameter and a change in diameter during a 10-second recording, according to some embodiments of the invention.

In some embodiments, by determining a distance between one or more transceivers and the artery walls is determined by fitting the base echo signals with the set of probable reflections, a diameter of the artery and/or a change in the artery diameter can be estimated. FIG. 77A shows diameter estimation and an average diameter calculation based on distances determined between three transceivers arranged in triangular configuration, and the artery walls. Optionally, the diameter is estimated by using the determined distances to set circular coordinates that define the artery, for example as described above. FIG. 77B shows a change in diameter, in mm, estimated over a 10-second recording. Optionally, a change in diameter is associated with arterial pulsation.

FIGS. 78A-80C are graphs obtained from a simulation of a method for decomposing a signal to a set of base signals and assigning the signals to a location (e.g artery wall) based on a dictionary of probable reflections, according to some embodiments of the invention.

Figure 78A:
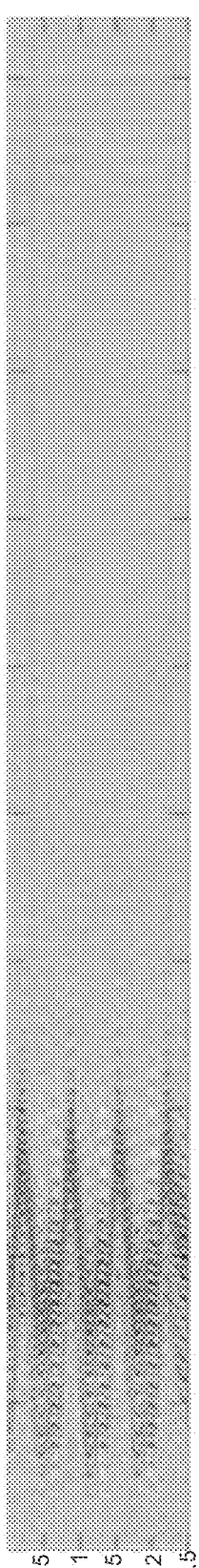
Figure 78B:
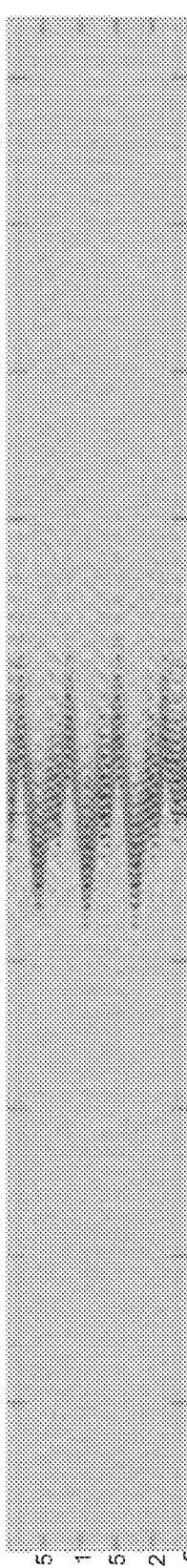
Figure 78C:
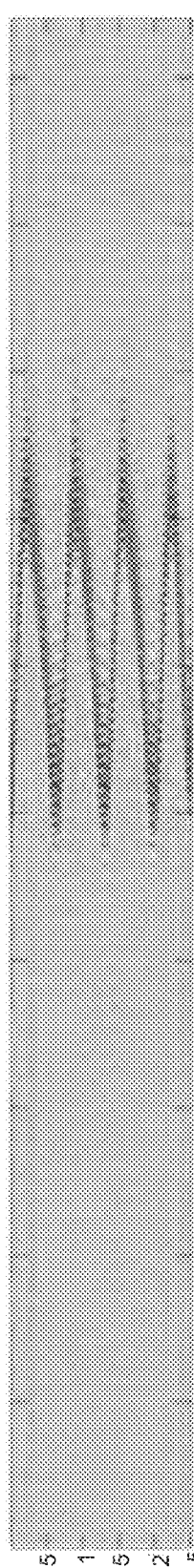
Figure 78D:
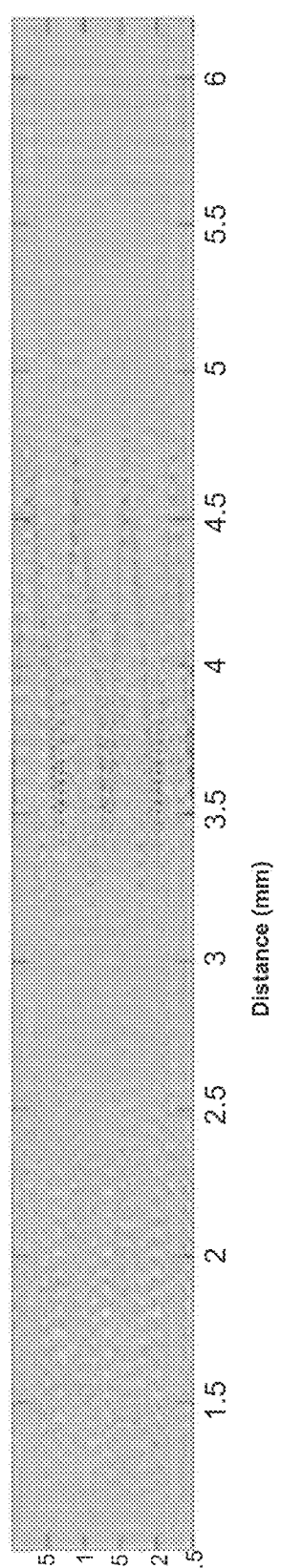

FIGS. 78A-C show simulated reflections received by three transceivers, for example reflections from 3 different portions of the vessel wall. FIG. 78D shows a sparse signal which is formed of the 3 combined reflections.

FIGS. 79A-C illustrate decomposition of three artificial signals, shown in FIG. 79A. The signals shown in FIG. 79A were combined into a single signal, which was then decomposed back into the base signals. The results of decomposing are shown by FIGS. 79B and 79C, where each color (red, blue or green) represents a signal received by one of the three transceivers. The resulting signal represents a varying distance from the transceiver to the vessel wall, for example a sinusoidal distance signal caused, for example, by pulsation. In this figure, FIG. 79B shows results of implementing steps D2101-D2017 for example as described in FIGS. 73A-B, without fine tuning the dictionary of probable reflections as described at D2104. FIG. 79C shows the results of implementing all steps described at D2101-D2017, where the dictionary is optionally better suited to the current data after "learning" the signal by identifying its minimal number of components.

FIG. 80A shows an artificial signal of an artery radius, according to some embodiments of the invention. FIG. 80B shows artery radius results after implementing steps D2101-2019 for example as described in FIGS. 21A-C (using the artificial signal of FIG. 80A), without fine tuning the dictionary of probable reflections as described at D2104. FIG. 80C shows artery radius results after implementing all steps described at D2101-D2019 (using the artificial signal of FIG. 80A), where the dictionary is optionally better suited to the current data after "learning" the signal by identifying its minimal number of components. In both methods of analysis, the mean radius was obtained with an error of ±0.2 mm (5%) as compared to the original artificial radius signal of FIG. 80A. The amplitude of the radius signal (i.e. pulsation amplitude) was obtained with an error ±0.15 mm (27%) using the method described for FIG. 80B, and an error of ±0.05 mm (9%) using the method described for FIG. 80C.

General Methods for Assessing Renal Denervation Effectiveness

General Description of Methods and an Apparatus for Measuring Renal Denervation Effectiveness Referring now to the drawings, FIG. 81 is a flowchart of some physiological changes that may indicate the effectiveness of an RSD treatment. Detection of the physiological changes in real time may provide feedback for immediate evaluation of a renal sympathetic denervation treatment (E101). In some embodiments, changes such as a change in the blood flow rate through the renal artery (E103) and/or a modulation in sympathetic restraint of the renal artery (E105) are detected. Optionally, the physiological changes are observed immediately after the denervation procedure, for example 5 minutes, 15 minutes, 45, 80 minutes and/or any intermediate and/or smaller periods of time after the procedure. In some embodiments, the changes are detected using the described methods and/or device as they occur. In some embodiments, the changes are detected at a later time post procedure, for example 2-10 days, 3-6 weeks, or intermediate or later times.

In some cases, a decrease in the renal sympathetic afferent and/or efferent neural activity may affect hemodynamic properties, for example the flow rate of blood flowing through the renal artery. Optionally, an increase in the blood flow rate through the renal artery indicates that the treatment procedure was effective.

In some cases, a decrease in the afferent neural signals sent to the muscles restraining the renal artery indicates that the treatment procedure was effective. Optionally, modulation of the muscle sympathetic nerve activity affects vasoconstriction of the artery, for example reducing it such that a diameter of the artery increases. Optionally, a stiffness of the artery is reduced.

In some embodiments, the physiological changes are detected by semi-invasive measurements, for example using an endovascular catheter. In some embodiments, an ultrasonic catheter is used for performing the RSD treatment, for example by emitting ultrasound energy for ablation of the renal nerves, and/or for real time assessment of the physiological changes. Optionally, the physiological changes are detected by the device during the treatment duration, providing real time feedback. Optionally, the treatment is adjusted in response to feedback. Optionally, the physiological changes are detected after the treatment, for example immediately after. In some embodiments, the device is equipped with measurement devices, for example a temperature sensor, for acquiring data which may be used for estimating parameters such the blood flow rate.

Figure 82F:
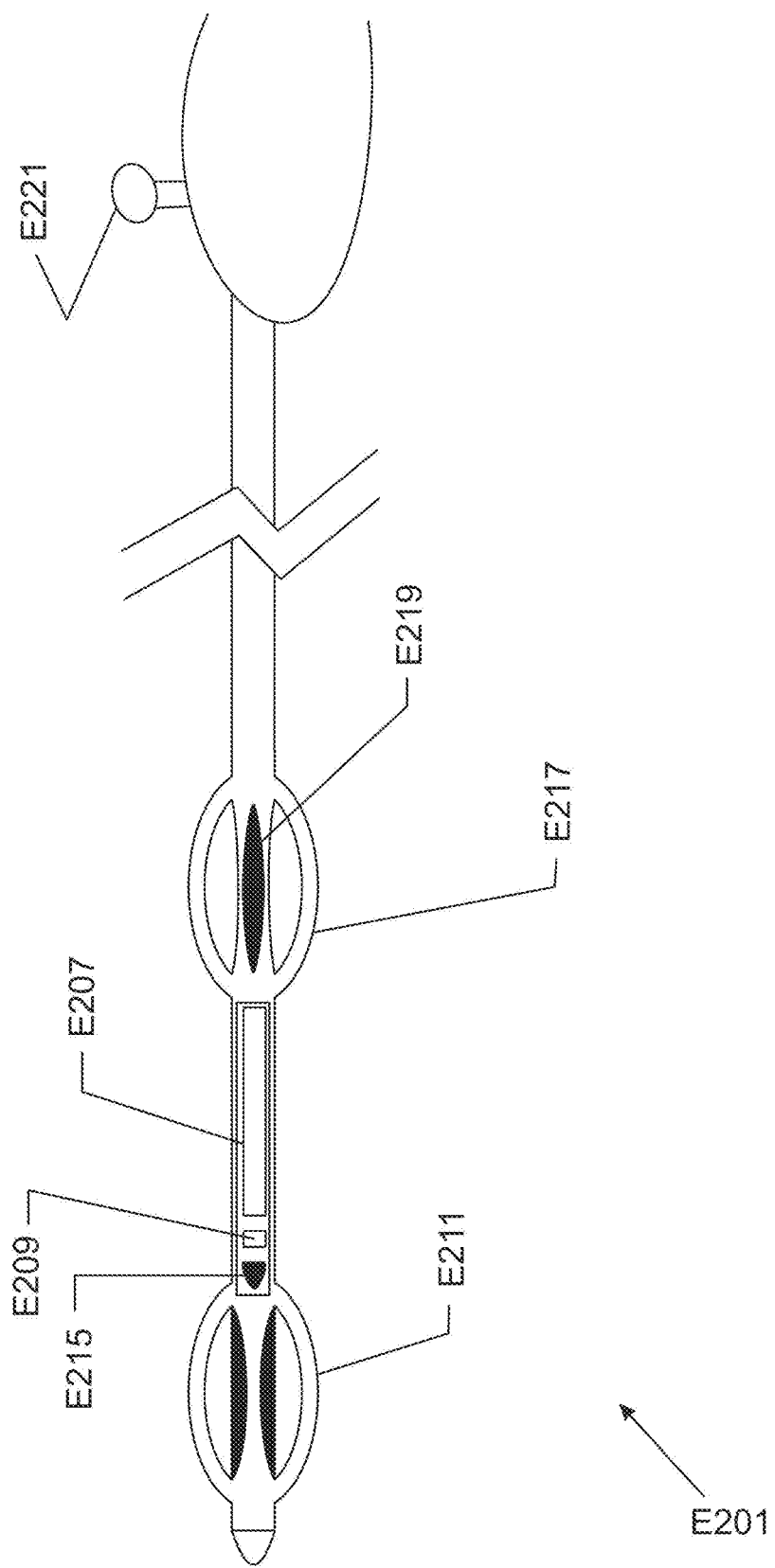

FIGS. 82A-F illustrate some aspects of an exemplary endovascular catheter device, according to some embodiments of the invention. FIGS. 82A and 82B are an angiogram and a drawing of a catheter device inserted into a renal artery. FIG. 82C is a drawing of an exemplary catheter device. FIG. 82D is a cross section of the distal tip of the catheter of FIG. 82C, showing an exemplary configuration of three transceivers. FIG. 82E is a cross section of a distal tip of a catheter comprising 4 transceivers, according to some embodiments of the invention.

FIGS. 82A and 82B show a catheter device E201 inserted into a renal artery E203. Optionally, catheter device E201 is inserted to the renal artery through the aorta E213. In some embodiments, the catheter is an ultrasonic catheter, configured for emitting and/or receiving ultrasonic energy. In some embodiments, the specific anatomical location of the catheter in the artery is decided according to various factors. For example, if the catheter is used for performing an RSD treatment, the device may be positioned such as to disrupt the surrounding nerves E205, for example nerves lying in the adventitia. In some embodiments, the device is used for physiological measurements, for example by comprising one or more measurement devices such as thermistors and/or pressure sensors. Optionally, in that case, the device is positioned such as to measure, for example, blood pressure and/or temperature in a certain section of the artery. In some embodiments, the device is maneuvered within the artery, for example positioned in one location for performing denervation, and in another location for performing measurements. In some embodiments, a current location of the catheter inside the artery is dynamically monitored, for example by analyzing data received by the catheter, and the location is adjusted accordingly.

FIG. 82C shows an exemplary catheter device E201. In some embodiments, the device comprises one or more transceivers E207, such as 2, 3, 4, 5, 6 transceivers or a higher number. In some embodiments, the transceivers are ultrasonic transceivers, for example configured for emitting and/or receiving ultrasonic energy. Optionally, the transceivers are undamped, for example to increase efficiency. Optionally, the transceivers are configured to receive a returning echo signal, for example a signal reflected from one or more of the artery walls. In some embodiments, the device comprises separate elements for emitting and receiving, for example one transducer for emitting energy and another transducer for receiving energy.

In some embodiments, transceivers E207 are spatially arranged to direct and/or receive the ultrasonic energy circumferentially, for example arranged in a triangular configuration as shown in FIG. 82D or a quadrilateral configuration as shown in 82E. In some embodiments, the transceivers are configured to emit and/or receive ultrasonic energy from multiple directions, such as, 2, 3, 4, 5, directions or a higher number. Optionally, each transceiver is directed at a different circumferential location in the artery wall. Optionally, two or more transceivers are directed at the same circumferential location. In some embodiments, the catheter device is a uni-directional catheter, for example having one or more transceivers directed at a single location.

Optionally, the circumferential transceiver configuration allows emitting ultrasound energy in multiple directions without rotating the catheter.

In some embodiments, catheter device E201 is equipped with one or more measurement devices, such as temperature sensors or pressure sensors E209. In one example, the device is equipped with one or more thermistors. Optionally, these devices are used to measure physiological changes, for example change in blood flow rate and/or a change in blood pressure. In some embodiments, a thermistor is positioned in proximity to a transceiver, for example to measure a current temperature of the transceiver. Optionally, the thermistor extends away from the catheter, for example to measure a current temperature of the blood. Optionally, the acquired data such as a current temperature of the transceiver is recorded.

In some embodiments, data acquired from the measurement devices and/or from signals received at the transceivers is recorded. Optionally, the data is further analyzed, for example to assess physiological changes such as a change in blood flow rate. Optionally, the data is analyzed in real time, and provides feedback during use. Optionally, parameters such as the current catheter location and/or sampling rate and/or an emitted signal intensity are adjusted according to the analyzed data.

In some embodiments, the catheter device is connected to a signal processor (not shown in this figure). In some embodiments, the signal processor is embedded within the catheter. Optionally, the signal processor is connected to one or more of the transceivers. In some embodiments, the signal processor is configured for implementing an algorithm which separates echo signals reflected from multiple sources, such as the artery walls. In some embodiments, the echo signals are recorded through a single channel. In some embodiments, the signal processor is configured for estimating a distance to each of the sources, for example the artery walls. In some embodiments, the artery diameter is calculated based on the distance. In some embodiments, the current location of the catheter in the artery, with respect to the artery walls, is estimated.

In some embodiments, the signal processor is configured for calculating a blood flow rate, for example using temperature data acquired by the one or more thermistors. In some embodiments, the signal processor is configured for calculating a blood flow velocity, for example based on a measured impulse response of the transceiver.

In some embodiments, the device comprises two activation modes, one for treating and one for measuring. Optionally, a user such as a physician may select a current mode. Optionally, switching between modes is performed during the RSD treatment, for example to determine if additional treatment is required. Optionally, data received by the transceivers and/or the measurement devices is analyzed, for example during treatment.

In some embodiments, a distancing device E211 is configured circumferentially around catheter E201, for maneuvering device E201 away from one or more artery walls. Optionally, distancing device E211 is used for centering catheter E201 with respect to the artery walls. In some embodiments, device E211 is threaded onto catheter 201.

FIG. 82F illustrates an embodiment of a catheter device E201. In some embodiments, a measurement device such as a temperature sensor 209 is positioned on the catheter, for example in proximity to the catheter tip. Optionally, temperature sensor E209 is positioned at any other location along catheter E201. In some embodiments, catheter E201 comprises a flow sensor E215, for example to measure blood flow rate and/or velocity during and/or pre and/or post renal denervation treatment. In some embodiments, catheter E201 comprises one or more transceivers E207, for treating and/or measuring using ultrasonic energy. In some embodiments, catheter E201 comprises a flow regulation structure E217. In some embodiments, catheter E201 comprises a sensor for measuring blood pressure E219, for example to measure blood pressure during and/or pre and/or post renal denervation treatment. In some embodiments, catheter device E201 is connected to a handle, for example positioned externally to the body, which is manipulated by a user such as a physician for operating catheter E201. For example, a user may expand distancing device 211, activate on or more transducers E207, and/or activate measurement devices such as the temperature sensor and/or blood pressure sensor and/or flow sensor.

FIG. 83 is a flowchart describing some exemplary methods for obtaining immediate, real time feedback for an RSD treatment, according to some embodiments of the invention.

In some embodiments, assessing denervation comprises measuring a flow rate of blood flowing through the renal artery (A). Additionally and/or alternatively, a change in sympathetic restraint of the artery is measured (B).

In some embodiments, the blood flow rate is measured directly (A.1). Alternatively, the blood flow rate is measured indirectly (A.2).

In some embodiments, direct measurement of the blood flow rate comprises measuring the propagation of an external liquid. In some embodiments, the method comprises tracking a contrast liquid. Optionally, the contrast liquid is injected into the renal artery. Additionally and/or alternatively, direct measurement of the blood flow rate comprises tracking a cold liquid. Optionally, the cold liquid is injected into the artery.

In some embodiments, indirect measurement of the blood flow rate comprises estimating a cross-sectional area of the artery (for example by estimating the artery diameter) and calculating the blood flow velocity. In some embodiments, blood flow velocity is calculated by analyzing an impulse response of the transducers to excitation, optionally based on a correlation between arterial pulsation and the recorded impulse response. Additionally and/or alternatively, blood flow velocity is calculated by analyzing a heat dissipation rate of the transceivers, optionally based on a linear correlation between a difference in temperatures and the flow velocity.

In some embodiments, a current location of the catheter within the artery, for example the location of the catheter tip, is measured. Optionally, a distance between the catheter tip and one or more walls of the artery is determined, to deduce the spatial location of the catheter. In some embodiments, a diameter of the artery is estimated. Optionally, the diameter is calculated using at least two of the distances measured between the catheter tip and the artery walls. In some embodiments, a mean diameter of the artery (such as over time) is estimated. In some embodiments, a dynamic diameter of the artery is estimated, for example a diameter changing during heartbeat pulsations. In some embodiments, a cross sectional area of the artery is calculated based on the diameter estimation, and is used, for example, during indirect blood flow rate measurement, as described above.

In some embodiments, the method comprises an analysis of the pulsation waveform. Optionally, a diameter during systole and/or diastole is estimated, indicating the movement of the artery wall. In some embodiments, the arterial blood pressure is measured, for example using a pressure transducer. Optionally, the pressure transducer is configured on an ultrasonic catheter device. Optionally, the arterial blood pressure measurement and/or the pulsation waveform are incorporated in the detection of change in the sympathetic restraint of the renal artery.

Description of Methods for Direct Measurement of Blood Flow Rate

In some embodiments, a blood flow rate is measured directly, for example by tracking the propagation of an external liquid in the renal artery, as will be explained in the following figures. Optionally, the liquid is injected into the artery.

A Method for Measuring Blood Flow Rate Using Contrast Liquid

FIG. 84 is a flowchart of an exemplary method for measuring blood flow rate by tracking the flow of a contrast liquid, according to some embodiments of the invention. In some embodiments, contrast liquid such as iodine or gadolinium is injected (E401), for example through a catheter, into the location of the ostia of the renal artery in the aorta. In some embodiments, the flow of the contrast liquid is recorded continuously, for example recorded using x-ray angiography (E403). In some embodiments, the recorded data is processed (E405), for example automatically or semi-automatically analyzed using a MATLAB software. In some embodiments, the continuous recording is divided into frames.

In some embodiments, the analysis includes modeling the relevant artery segment, defining one or more regions of interests (ROI) along the artery segment, and detecting the attenuation of intensities of the x-rays in each of the ROIs (E407). In some embodiments, the analysis includes comparing pixel intensities between the frames. Optionally, the x-ray attenuation changes as the energy travels through the contrast liquid medium.

In some embodiments, the analysis includes detecting a flow onset for each of the ROIs (E409). In some embodiments, the flow onset is indicated by pixel intensities above a baseline intensity value, for example 20%, 50%, 40% and/or intermediate, smaller, or higher values above a baseline.

In some embodiments, the analysis includes a calculation of the flow rate (E411). In some embodiments, the calculation of the flow rate is based on measuring the relative time and/or distance that the contrast liquid passes, for example between two sequential ROIs. Optionally, if the flow onset of two sequential ROIs is detected during a relatively small time period (for example between 1-4 frames, or 40-160 ms), a higher flow rate is observed, for example in comparison to onsets that are detected with a longer time period between them.

Figure 85A:
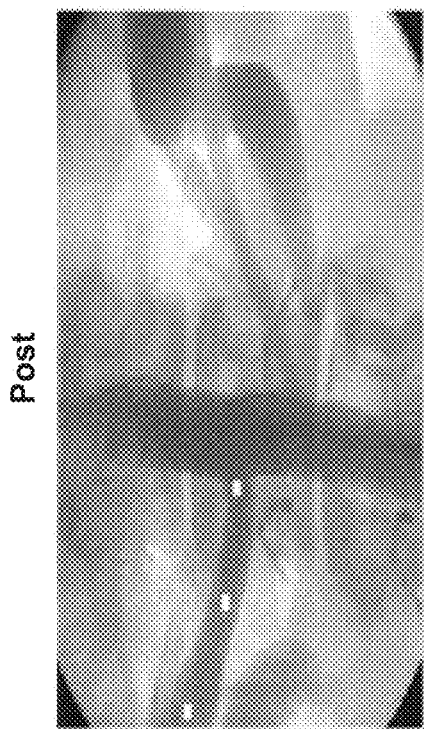
Figure 85B:
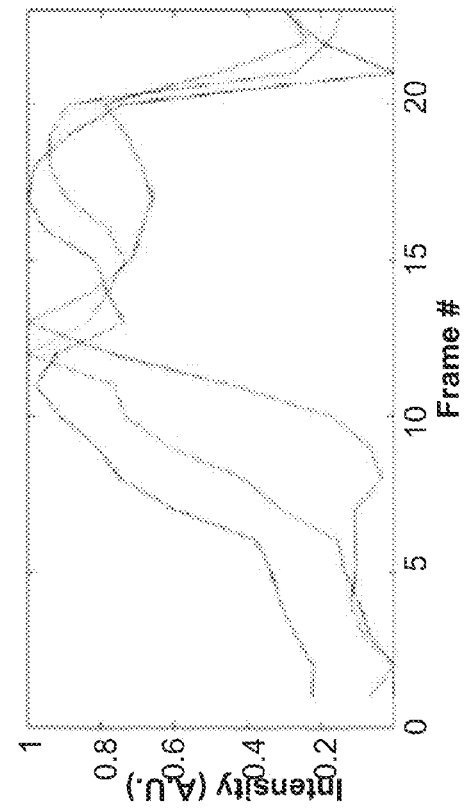
Figure 85C:
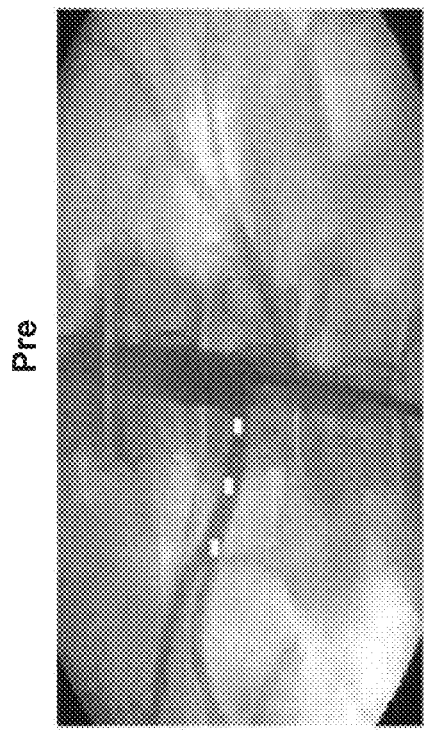
Figure 85D:
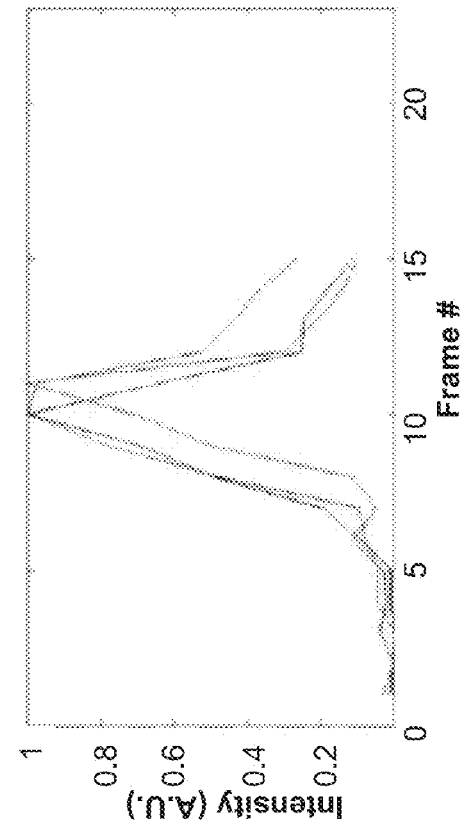

FIGS. 85A-D are experimental results of measuring blood flow rate by tracking contrast liquid in vivo, according to some embodiments of the invention. FIG. 85A is an x-ray angiography image of the aorta E501 and both renal arteries E503, after the injection of contrast liquid to the ostia of the renal artery in the aorta and before RSD treatment. FIG. 85B is a graphical analysis of the x-ray intensities measured in three selected ROIs E505, shown in FIG. 85A, before the RSD treatment. FIGS. 85C-D show an equivalent angiography image and graphical analysis, post RSD treatment.

A Method for Measuring Blood Flow Rate Using Cold Liquid

FIG. 86 is a flowchart of an exemplary method for measuring blood flow rate by tracking the flow of a cold liquid, according to some embodiments of the invention.

In some embodiments, the method includes positioning at least two thermistors at a distance from each other along a segment of the renal artery (E601). In some embodiments, a distance between the thermistors ranges between 0.5-8 cm, for example 0.6 cm, 2 cm, 4 cm, 5 cm, or intermediate, smaller or higher distances. Optionally, the thermistors are configured on catheter tips. In one example, a first thermistor is positioned at the renal artery ostium, and a second thermistor is positioned at a distance from the first thermistor, for example in the direction of the kidney.

In some embodiments, a cold liquid (such as cooled saline) is injected into the renal artery (E603), for example injected at the renal artery ostium. Optionally, the temperature of the cold liquid ranges between 4-25° Celsius.

In some embodiments, a temperature of the two or more thermistors is recorded (E605). Optionally, the temperature is recorded continuously. In some embodiments, the sampling rate is determined according to a predefined estimation of the flow velocity. In one example, the estimated flow velocity ranges between 10-100 cm/sec, and the sampling rate of the thermistors is 50 Hz.

Optionally, as the cold liquid flows through the artery and passes the location of the thermistors, a temperature of the thermistor decreases. Optionally, the temperature descends instantaneously upon the passing of the cold liquid.

In some embodiments, the recorded temperatures are analyzed to detect inter and/or intra thermistor temperature differences (E607). In some embodiments, a pre-defined threshold is applied to select specific temperature values and/or differences.

In some embodiments, the blood flow rate is calculated (E609). Optionally, the blood flow rate is calculated based on a parameters such as the distance and/or time duration of the cold liquid passing between the thermistors, and/or the inter and/or intra thermistor temperature differences. In one example, a decrease in temperature is detected in a first thermistor, and after a certain time period a decrease in temperature is detected in the second thermistor, which is located at a distance from the first thermistor within the artery segment. Optionally, using the distance between the thermistors and the time period between the two descents in temperatures, the blood flow rate is calculated.

Description of Methods for Indirect Measurement of Blood Flow Rate

In some embodiments, a blood flow rate is measured indirectly. Optionally, indirect measurement comprises measuring a cross-sectional area of the artery, and/or the blood flow velocity, to deduce the blood flow rate. Optionally, the measurement is based on the assumption that the blood flow rate is a function of the artery diameter. In some embodiments, blood flow rate is calculated by multiplying the cross sectional area of the artery times the blood flow velocity.

A Method for Determining Blood Flow Velocity Based on Heat Dissipation Rate

FIG. 87 is a flowchart of an exemplary method for determining renal blood flow velocity based on a heat dissipation rate of a transceiver, according to some embodiments of the invention. In some embodiments, one or more transceivers are inserted into the renal artery (E701). Optionally, the transceiver(s) are configured on a catheter tip. In some embodiments, the transceiver is equipped with a temperature sensor, such as a thermistor and/or a thermocouple. Optionally, the thermistor is configured in proximity to the transceiver so that a current temperature of the transceiver can be measured.

In some embodiments, the transceiver is excited by a series of short duration, low power excitations (E703). Optionally, the excitation power ranges between 5-20 Watt, for example 7, 10, 16 Watt or intermediate values. In some embodiments, the excitation is performed periodically, for example performed over a 10 seconds excitation period and a 10 seconds waiting interval between excitations.

In some embodiments, during the excitation and/or waiting interval, the temperature of the thermistor, indicating the temperature of the transceiver, is continuously recorded (E705).

In some embodiments, the recorded temperature is analyzed. Optionally, differences in measured temperature are detected (E707), for example by applying a predetermined threshold. Optionally, the flow velocity is determined using the temperature differences (E709), as explained below. In some embodiments, a heat dissipation rate is calculated using the measured temperature differences.

In some cases, as suggested by experiments conducted by the inventors, a linear relation exists between the heat dissipation rate of the transceiver (following the excitation) to the flow velocity. Optionally, as observed in the experiments, following the excitation period, the transceiver's temperature declines exponentially. A cooling time constant of the transceiver (calculated as the temperature drop to 1/e of the maximal temperature value) has been to shown to be linearly proportional to the flow velocity.

In some embodiments, the duration of excitation and/or waiting period is determined according to a heating time constant of the transceiver, and/or possible noise in the recorded temperature measurement.

FIGS. 88A-B show experimental results of an in vitro experiment to prove a linear relation between blood flow velocity and heat dissipation rate of the transceiver.

The experiment was performed in a 6-mm diameter pipe, simulating the renal artery. A glycerol solution having similar viscosity to blood at normal body temperature and having a flow velocity range similar to blood was used. The glycerol solution used in this experiment comprised 45% glycerol and 55% water. Optionally, in some embodiments, a different solution having similar viscosity and velocity range properties may be used.

FIG. 88A shows the measured heat dissipation rate of the transceiver as a function of predefined flow velocity values of the glycerol solution flowing through the pipe (shown by dots E801). The flow velocities were controlled by a peristaltic pump connected to a flow meter. A linear model E803 is fitted through the results.

FIG. 88B shows the cooling time constant of the transceiver (measured in seconds, calculated as the temperature drop to 1/e of the maximal temperature value) as a function of the flow velocity. As can be observed from the graph, the cooling time constant of the transceiver is shorter as the flow velocity increases.

FIGS. 89A-D show experimental results of an in vitro experiment for validating the linear relation between blood flow velocity and heat dissipation rate of the transceiver.

A similar experiment setup to the above was used, using two pipes to simulate the renal artery instead of one: one pipe having a diameter of 6 mm (marked by the blue markings), the other having a diameter of 8 mm (marked by the red markings). FIGS. 89A and 89C show the heat dissipation rate of the transceiver as a function of flow rate (89A) and flow velocity (89C). FIGS. 89B and 89D show the cooling time constant of the transceiver as a function of the flow rate (89B) and the flow velocity (89D).

A Method for Determining Blood Flow Velocity Based on Impulse Response Analysis

FIG. 90 is a flowchart of an exemplary method for determining blood flow velocity by analyzing an impulse response of a transceiver. In some embodiments, one more transceivers are inserted into the renal artery (E1001). In some embodiments, the transceiver is excited by a set of impulses (E1003). In some embodiments, the damping of the transceiver following the impulse is recorded (E1007).

In some embodiments, the flow velocity is determined (E1009). In some embodiments, the flow velocity is determined based on correlation between the measured impulse response variance and the flow velocity, as shown by the inventors in the following experiments. Optionally, a second correlation exists between arterial pulsation and the recorded impulse response variance.

FIGS. 91A-B show experimental results of an in vitro experiment to prove a correlation between a measured impulse response of the transceiver and the flow velocity.

The impulse response of a transceiver inserted into a pipe filled with water was measured at predetermined flow velocities. Using a "pulser-receiver" device, the transceiver was excited with a set of impulses, and the voltage tracing of the transceiver following the impulse was recorded. FIG. 91A shows the voltage tracing of the transceiver following an impulse. FIG. 91B shows the calculated voltage variance at four different predetermined flow velocities, suggesting a linear correlation between the voltage variance (the impulse response variance) and the velocity of the flow.

FIGS. 92A-B show experimental results of an in vivo experiment including an impulse response analysis.

The experiment setup included inserting a transceiver (configured on a catheter tip) into a renal artery of a swine, exciting the transceiver by a set of impulses, and recording the impulse response. FIG. 92A shows the recorded voltage trace of the transceiver following the impulse. FIG. 92B shows the variance of the measured voltage as a function of the time following an impulse (2.5 seconds). As previously suggested, the graph may show a correlation between the impulse response variance and the arterial pulsation.

Description of Methods for Measuring Sympathetic Artery Restraint

As previously described, a change in sympathetic restraint of the artery may indicate the effectiveness of an RSD treatment. Optionally, factors such as the movement of the artery walls during pulsation, and/or the pulsation force are indications of the artery restraint. Optionally, pulsation force is proportional to the blood pressure. Optionally, the movement of the artery walls changes a diameter of the artery.

The following methods relate to the measurement of arterial diameter and/or blood pressure, which may indicate a change in the artery restraint.

A Method for Measuring Arterial Blood Pressure

FIG. 93 is a flowchart of an exemplary method for measuring arterial blood flow. In some embodiments, a catheter connected to a pressure transducer is inserted into the aorta (E1301), for example near the renal artery ostium. Optionally, the pressure transducer is configured on an ultrasonic catheter device. Optionally, the ultrasonic catheter device is used for performing the RSD treatment and/or for assessing the blood pressure, for example immediately after the treatment. In some embodiments, the arterial systolic and/or diastolic arterial blood pressure is measured (E1303).

A Method for Determining a Diameter of an Artery

FIG. 94 is a flowchart of a method for analyzing a sequence of signals received from multiple sources and recorded through a single channel, according to some embodiments of the invention.

In some embodiments, the method is applied for acoustic location of walls of an artery, for example to determine a diameter of the artery using an ultrasonic catheter device. Optionally, the method is applied to determine a relative location of the catheter tip. Generally, the method can be applied to other signal processing implementations, which require separation of signals.

For clarification purposes, the method will be described in the context of measurement of an artery diameter using an ultrasonic catheter device comprising 3 transceivers arranged in a triangular configuration, as explained above in FIGS. 2A-C. In some embodiments, the transceivers receive narrow band energy. Optionally, the energy is transferred through a single channel. Optionally, the transceivers are excited simultaneously. Optionally, the transceivers are excited by a series of short pulses, for example 1 µs each.

In some embodiments, the ultrasonic energy emitted by the transceivers is reflected by one or more of the artery's walls, for example reflected in multiple directions. Optionally, the artery walls are moving, for example due to pulsation.

In some embodiments, the algorithm assumes the following conditions:

A. The signals are reflected (or, in some embodiments, emitted) from a known number of sources, or, alternatively, the number of receivers directed at different sources is known.

B. The sources move periodically, optionally in a non-synchronized manner

C. The width of the signals is larger than the inverse of the Eigen frequency of the receiver.

D. The signals are reflected (or, in some embodiments, emitted) simultaneously during at least one heartbeat period.

In some embodiments, the reflected echo signals are received by the transceiver. In some embodiments, the signals received through a single channel. Optionally, the signals may be received through multiple channels. In some embodiments, the signals are recorded (E1401). Optionally, the recording duration is defined as a few heartbeat periods, for example 2, 5, 20, 100 heartbeat periods.

In some embodiments, the recorded signals are arranged in a matrix (E1403). In one example, each column in the matrix contains recordings of one signal for the recorded sequence, and each row contains the identical recording-time samples (i.e. samples of different signals recorded at a specific time point).

In some embodiments, the mixed signals are separated. In some embodiments, separation includes determining a signal waveform energy during the recorded time course. Optionally, separation is based on a phase difference between the mixed signals, which may indicate a distance between the source and the receiver. However, in some cases, superposition of the signals and/or measurement noise may interfere with the separation of the signals according to their phase differences. Therefore, in some embodiments, separation of the mixed signals is performed by analyzing interference patterns (E1405).

In some embodiments, signals emitted from different sources are characterized by a different interference pattern. In some embodiments, the interference pattern is formed due to the passing of the echo signals through various mediums, for example through blood or through the artery wall tissue.

In some embodiments, a different interference pattern is observed for different signals along identical recording-time samples. Optionally, this may indicate that the signals were not reflected from the same source (i.e. artery wall). Optionally, signals reflected from the same source are characterized by a similar interference pattern. Optionally, these signals passed an equal distance from the source to the receiver.

In some embodiments, the method comprises measuring a correlation of the recorded signals. In one example, the signals are grouped using a correlation measure of the matrix rows, which include identical recording-time samples of a plurality of signals.

In some embodiments, a Pearson correlation coefficient is calculated, ranging between −1 for interference patterns with a negative correlation, and 1 for highly correlated interference patterns. In some embodiments, the correlations are calculated between wavelength spaced rows. Optionally, the results of the correlation computation are arranged in a symmetric matrix of correlations (E1407). In some embodiments, at this step, the correlation of each pattern to itself (which equals 1) is replaced by an average of adjacent correlation values.

In some embodiments, the correlation matrix is multiplied by −1, and normalized, so that the correlation values range between 0 and 1. Optionally, the new matrix is arranged as a "correlation distance" matrix, where uncorrelated patterns are distant from each other, and correlated patterns are close to each other.

In some embodiments, to associate each signal to its source, the calculated correlation coefficients are represented as points in a multidimensional space (E1409).

In some embodiments, a K-means algorithm is applied to cluster the points to groups (E1411). Optionally, the number of groups is predefined, for example it may be set to 4 groups: 3 groups being 3 source directions, such as the artery walls, and one group being noise. In some embodiments, a threshold is applied, for example to cluster points representing an energy level higher than the threshold, such as higher than one quarter of the average energy level.

In some embodiments, the K-means algorithm iteratively searches for centroids, for example 4 centroids, one for each group. Optionally, the centroids are artificial vectors which provide a minimal distance to the clustered points of a specific group, and/or a maximal distance to points belonging to a different group. Optionally, during each iteration, the centroids are recalculated for better fitting the clustered groups.

In some embodiments, the clustering is validated (E1413). Optionally, validating includes constructing a corresponding binary matrix, for example including a 0 to represent interference patterns from different groups, and 1 for interference patterns from the same group. Optionally, the normalized covariance of both matrices is a measure of their similarity, and is used to determine the quality of the clustering. For example, a normalized covariance above 0.5 indicates reliable clustering results.

In some embodiments, the noise group is identified. Optionally, a threshold is applied to the centroids to determine which of the groups represents noise. For example, a centroid with a maximal value below a threshold of 0.1 may be identified as the noise centroid.

In some embodiments, a distance of each of the sources, for example from the catheter tip, is calculated (E1415). In some embodiments, the distance is determined according to the centroid profile. In some embodiments, a maximal value of a centroid (representing a single group) is the mean distance of the source from the catheter. In some embodiments, a point (from the same group) that exceeds the median of the centroid is the minimal distance of the source from the catheter.

In some embodiments, the artery diameter is calculated according to the measured source distances.

In some embodiments, a movement profile of each wall is traced (E1417). In some embodiments, the movement profile is traced by finding a delay between successive time windows of the recording. Optionally, the delay is estimated by applying a cross correlation between the windows, and identifying a shift which maximizes the correlation. In some embodiments, the identified shifts are summed, for example starting from a mean distance of each signal, to yield the distances of the source during movement.

In some embodiments, a relative location of the catheter tip with respect to the artery walls is calculated. In some embodiments, to calculate the location of a center of the catheter tip (assuming a circular tip), the following equations are applied:

$$f_i = -(x_i^2 + y_i^2) \quad A = \begin{bmatrix} x_1 & y_1 & 1 \\ x_2 & y_2 & 1 \\ x_3 & y_3 & 1 \end{bmatrix}^{-1} \cdot \begin{bmatrix} f_1 \\ f_2 \\ f_3 \end{bmatrix}$$

$$R = \sqrt{\frac{A_1^2 + A_2^2}{4} - A_3} \quad (C_x, C_y) = (-0.5A_1, -0.5A_2)$$

$(x,y)_{1,2,3}$ are the Cartesian representation of the calculated distances to the artery walls, after adding an inner radius of the catheter tip, R is the calculated radius of the artery, $C_{x,y}$ are the catheter coordinates relative to the artery center, $A_{1,2,3}$ are the three dimensional coordinates of an intermediate vector.

In some embodiments, the method includes an algorithm for eliminating a ringing artifact of the recorded signal. Optionally, the ringing artifact appears mostly during the initial recording segment. Optionally, factors such as the excitation intensity and the damping of the transceivers affect the ringing artifact. In some embodiments, elimination of the artifact is based on the assumption that the artifact is a relatively constant signal, while a reflected echo signal varies in intensity, for example due to the movement of the artery wall. In some embodiments, eliminating the artifact comprises subtracting a mean value of samples of equal distance from the matrix, for example from the matrix columns.

In some embodiments, the method includes a sampling algorithm for correcting sampling irregularities. Optionally, the algorithm aligns the ringing artifact before its subtraction, as explained above. In some embodiments, the algorithm includes increasing a sampling rate (upsampling), for example during the initial segment, cross correlating the artifact with the first received signal, determining a shift which is required to achieve a maximal correlation between the artifact and the first signal, and decreasing the sampling rate (downsampling), for example back to the original rate.

FIGS. 95A-C are images of a typical recording of reflected echo signals from the artery wall. FIG. 95A is a recording of an echo signal reflected following one excitation pulse of the transceiver, showing the voltage tracing as a function of the distance. FIG. 95B is a recording of multiple echo signals reflected following a series of excitation pulses, showing multiple voltage tracings positioned on a time vs. distance axis (can be observed as a 90 degree rotation of the signal of FIG. 95A, accompanied by multiple signals). FIG. 95C is the recording of FIG. 95B, after a ringing artifact is suppressed from the recorded signal.

In some embodiments, as shown in FIG. 95C, the suppression of the ringing artifact, for example by the methods described above, reveals a clearer echo signal pattern E1501 for further analysis.

FIGS. 96A-C are graphical representations of a clustering process for separating signals according to interference patterns, for example according the methods described in FIG. 94.

FIG. 96A shows multiple echo signals that were reflected from one or more walls of an artery, and recorded. Optionally, the signals were received by one more transceivers, for example 3 transceivers.

FIG. 96B shows a symmetrical "correlation distance" matrix, where uncorrelated interference patterns are distant from each other, and correlated interference patterns are close to each other. Three areas having a correlation coefficient of approximately 1, marked by arrows E1601, indicate signals with a highly correlated interference pattern. Optionally, these signals were reflected from a similar source. FIG. 96C is a representation of the normalized correlation coefficients (representing the signals) as points E1602 in a multi dimensional space. In this example, the points are clustered, for example using a K-means algorithm, to 4 groups, each marked by a different color: 3 groups being 3 source directions, and one group being noise.

FIGS. 97A-D are graphical representations of a movement profile of an artery wall, according to some embodiments of the invention.

FIG. 97A shows changes in the correlation coefficients of the 3 identified groups (for example using the methods described in FIG. 94) as a function of the distance between the artery wall and the transceiver. The mean values of the three centroid profiles, one for each of the groups, are marked by red arrowheads E1701. Optionally, the mean value of a centroid profile represents a mean distance to an artery wall.

FIG. 97B shows an echo segment E1703 (marked by the dashed rectangle) used for computing the wall movement. Optionally, the echo segment is selected to cover a distance range above and below the calculated mean value of a centroid profile, for example 1 mm above and 1 mm below the mean value. In this example, the segment was selected around the smallest mean value of a centroid profile, (estimated at 2.1 mm).

FIG. 97C is an enlarged view of the selected segment of FIG. 97B.

FIG. 97D shows the traced movement of the artery wall, calculated using the selected segment. Optionally, the movement was calculated by summing the shifts required to increase the correlation between two sequential time windows, for example as described in FIG. 94.

FIGS. 98A-C are graphical representations of estimating a current location of the catheter tip with respect to the artery walls.

FIG. 98A shows a current position of the catheter tip E1801 in a cross section of the lumen of the artery, based on the calculated distances from the artery walls E1803. In some embodiments, the calculation assumes a circular shape of the artery. E1813 marks a center of the catheter tip, assuming a triangular configuration of the transceivers. In some embodiments, the location of the catheter tip is dynamically monitored. Optionally, the catheter tip is repositioned by the user according to a current indication of the location.

FIG. 98B shows fluctuations in the measured artery diameter as a function of the time, in this example during a 10 second time period. E1805 shows the original measured diameter pulsation waveform (marked by the red line). E1807 shows the diameter pulsation waveform after rectification. The diameters measured during systoles are marked by the red triangles E1809. The diameters measured during diastoles are marked by the green triangles E1811.

FIG. 98C shows the tracing of the location of the catheter tip with respect to the center of the artery lumen.

FIGS. 99A-C are graphical representations of a validation of the artery diameter estimation.

To validate the diameter estimation, the inventors compared the results of the estimated diameter to a diameter measured by analyzing angiograms of the artery. The diameter estimation and angiograms were taken from a renal artery of swine.

FIG. 99A shows a comparison between the estimated diameters E1901, marked by the red circles, to the diameters measured from the angiograms E1903, marked by the blue crosses and shown in increasing order.

FIG. 99B shows the comparison of FIG. 99A, after removing measurements in which: (1) the catheter tip was not centralized (with respect to the artery walls), such as cases where a minimal distance to an artery wall was smaller than 1.3 mm, (2) the artery diameter was narrower than 5 mm, and (3) an inner validation algorithm resulted in a value lower than a threshold of 0.5.

FIG. 99C shows the error rate for the comparisons of FIGS. 99A and 99B, where E1905 (blue line) indicates the error rates of the comparisons of 99B, and e1907 (red line) indicates the error rates of the comparisons of FIG. 99A, before the removal of specific measurements according to the predefined criteria.

In some embodiments, devices and/or systems and/or methods and/or components as described in one or more of the following applications may be used for renal denervation measurement and/or treatment:

PCT/IB2011/054634 filed on Oct. 18, 2011, entitled "THERAPEUTICS RESERVOIR", relating to a method of drug delivery and, more particularly, to a method for trapping drugs to form a drug reservoir in tissue;

PCT publication number WO2012/052921 filed on Oct. 18, 2011, entitled "ULTRASOUND EMISSION ELEMENT", showing, for example, an apparatus for generating relatively high efficiency ultrasound;

PCT publication number WO2012/052922 filed on Oct. 18, 2011, entitled "AN ULTRASOUND TRANSCEIVER AND USES THEREOF", showing for example, a method for feedback and control of the ultrasonic transducer;

PCT publication number WO2012/052927 filed on Oct. 18, 2011, entitled "AN ULTRASOUND TRANSCEIVER AND COOLING THEREOF", showing for example, a method for blood flow cooling of the ultrasonic transducer;

PCT publication number WO2012/052926 filed on Oct. 18, 2011, entitled "TISSUE TREATMENT", showing for example, a method of selective targeting and treating tissues using ultrasound;

PCT publication number WO2012/052924 filed on Oct. 18, 2011, entitled "SEPARATION DEVICE FOR ULTRASOUND ELEMENT", showing, for example, a device to prevent the transducer from touching the blood vessel wall; and PCT publication number WO2012/052925 filed on Oct. 18, 2011, entitled "AN ULTRASOUND TRANSCEIVER AND CONTROL OF A THERMAL DAMAGE PROCESS", showing, for example, an ultrasound transceiver and to control of an ablation or thermal damage process to a tissue.

The terms "comprises", "comprising", "includes", "including", "having" and their conjugates mean "including but not limited to".

The term "consisting of" means "including and limited to".

The term "consisting essentially or means that the composition, method or structure may include additional ingredients, steps and/or parts, but only if" the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. An intravascular catheter comprising an elongated shaft and a head for ultrasonic transmission, said head comprising:
a triangular chassis comprising three facets, each facet sized to receive a piezoelectric transceiver, each facet defining a flat outward facing surface along the length of the chassis;
three piezoelectric transceivers peripherally mounted onto said facets of said chassis, each transceiver being mounted onto a different facet, each transceiver comprising a flat radially-outward facing surface; all of said three piezoelectric transceivers positioned at a same axial position with respect to said chassis and being identical in length; wherein adjacent transceivers are spaced apart from each other in a circumferential direction, exposing the chassis therethrough, such that a space between adjacent transceivers extends along said chassis, said space being as long as each of said transceivers;
wherein said transceivers are configured to be electrically activated for emitting unfocused ultrasound energy suitable for tissue ablation, and for receiving echo signals; wherein each transceiver is positioned to face a different circumferential region of a blood vessel in which said catheter is positioned and wherein said transceivers are configured so that an outwardly facing angle α exists between beams emitted by adjacent transceivers.

2. The catheter according to claim 1, wherein said chassis is cannulated.

3. The catheter according to claim 2, wherein a central lumen of said cannulated chassis is configured to have blood flow therethrough.

4. The catheter according to claim 1, wherein a diameter of a circumscribing circle of said head is 2.2 mm or smaller.

5. The catheter according to claim 1, wherein said summed area of said outward facing surfaces of the transceivers covers at least 70% of said outward facing facets of the chassis.

6. The catheter according to claim 1, wherein said catheter further comprises a PCB configured between said chassis and at least one of said transceivers, said PCB comprising one or more vias for at least one of electrically and mechanically coupling between said PCB and said chassis.

7. The catheter according to claim 6, wherein said PCB comprises one or more bendable extensions in contact with transceivers different than the transceiver mounted on top of said PCB.

8. The catheter according to claim 1, wherein an electrically conductive strip folded to surround an exterior surface of said catheter head, contacting all of said at least three transceivers, serves as a current conducting electrode for activation of said transceivers.

9. The catheter according to claim 1, wherein said chassis is electrically conductive.

10. The catheter according to claim 1, wherein when said catheter is positioned within a vessel, said transceivers are configured to emit unfocused ultrasound energy suitable for ablating tissue when said transceivers are positioned a distance away from a vessel wall, said distance large enough to permit blood to flow between a transceiver and the wall to cool the wall.

11. The catheter according to claim 1, wherein said blood vessel is the renal artery and wherein tissue being ablated comprises nerve tissue.

12. The catheter according to claim 1, wherein said catheter comprises one or more temperature sensors positioned in proximity to said transceivers.

13. The catheter according to claim 1, wherein each of said transceivers is mounted onto said chassis using an array of electrically conductive glue drops, said glue drops equally distributed on each of said facets.

14. A system for operating an intravascular ultrasonic catheter by a physician, comprising:
a catheter according to claim 1;
a console connected on one end to said catheter;
a software installed on said console, said software configured for analyzing echo signals received by said plurality of piezoelectric transceivers; and
a foot pedal configured to be activated by said physician for generating excitation of said transceivers.

15. The system according to claim 14, wherein said console is configured for reading frequency and impedance data characteristics of said transceivers; and wherein said console is configured for providing an excitation having a sinusoidal waveform having a duration and power suitable to ablate tissue.

16. The catheter according to claim 1, wherein said angle α is defined between a central longitudinal axis of a beam emitted by a first transceiver and a central longitudinal axis of a beam emitted by an adjacent transceiver.

17. The catheter according to claim 1, wherein said angle α ranges between 115-130 degrees.

18. The catheter according to claim 1, wherein said transceivers are configured to emit energy towards multiple spaced apart tissue regions that are distributed circumferentially around the vessel.

19. The catheter according to claim 1, wherein said transceivers are arranged so that an overlap between said transceivers is avoided.

20. The catheter according to claim 1, further comprising a distancing element configured for positioning said catheter within a lumen of said blood vessel, said distancing element including a slotted cylinder having a plurality of expandable leaflets therebetween;
said transceivers configured to emit said unfocused ultrasound energy suitable for ablating tissue when said transceivers are positioned a distance away from a lumen wall by said distancing element;
said expandable leaflets of said distancing element configured to expand to position said catheter a large enough distance away from the lumen wall to provide a passageway for blood to flow between a transceiver and the wall to cool the wall.

21. The catheter according to claim 20, wherein said distancing device is configured for pushing said catheter head away from a lumen wall.

22. The catheter according to claim 20, wherein said distancing device is configured for centering said catheter head with respect to the lumen wall.

23. The catheter according to claim 20, wherein each of said expandable leaflets is positioned at a space between said spaced apart adjacent transceivers when said expandable leaflets are in a collapsed configuration.

24. The catheter according to claim 1, wherein a space between said spaced apart adjacent transceivers provides at least one of electrical and thermal insulation between said adjacent transceivers.

25. The catheter according to claim 1, wherein a beam of unfocused ultrasound emitted by each of said at least three transceivers diverges at an angle between 5-30° as measured between an edge of said beam and an axis parallel to the beam central long axis.

26. The catheter according to claim 25, wherein said beam cross section is trapezoidal.

27. The catheter according to claim 1, wherein said transceivers are rectangular, and wherein a space between said spaced apart adjacent transceivers extends along the length of said rectangular transceivers.

28. The catheter according to claim 1, wherein said catheter head is shaped as an equilateral triangle.

* * * * *